US008669370B2

(12) United States Patent
Ruf et al.

(10) Patent No.: US 8,669,370 B2
(45) Date of Patent: Mar. 11, 2014

(54) SUBSTITUTED 3-HETEROAROYLAMINO-PROPIONIC ACID DERIVATIVES AND THEIR USE AS PHARMACEUTICALS

(75) Inventors: Sven Ruf, Frankfurt am Main (DE); Thorsten Sadowski, Frankfurt am Main (DE); Klaus Wirth, Frankfurt am Main (DE); Herman Schreuder, Frankfurt am Main (DE); Christian Buning, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/357,245

(22) Filed: Jan. 24, 2012

(65) Prior Publication Data
US 2012/0252809 A1  Oct. 4, 2012

Related U.S. Application Data

(60) Provisional application No. 61/486,945, filed on May 17, 2011.

(30) Foreign Application Priority Data

Jan. 26, 2011  (EP) .................... 11305078

(51) Int. Cl.
A61K 31/44  (2006.01)
C07D 213/46  (2006.01)
(52) U.S. Cl.
USPC .......................... 546/314; 514/354
(58) Field of Classification Search
None
See application file for complete search history.

(56) References Cited

U.S. PATENT DOCUMENTS

2008/0045568 A1  2/2008  Deng et al.

FOREIGN PATENT DOCUMENTS

| WO | WO 03003008 A1 * | 1/2003 |
| WO | WO2007/035157 A1 | 3/2007 |
| WO | WO2008/080969 A1 | 7/2008 |
| WO | WO2009/153721 A1 | 12/2009 |

OTHER PUBLICATIONS

CAPLUS 2004:586832.*
Giardina, Giuseppe A. M. et al., "Discovery of a Novel Class of Selective Non-Peptide Antagonists for the Human Neurokinin-3-Receptor. 2. Identification of (S)-N-(1-Phenylpropyl)-3-hydroxy-2-phenylquinoline-4-carboxamide (SB 223412)," Journal of Medicinal Chemistry (1999), vol. 42, pp. 1053-1065.
European Search Report dated May 30, 2011 issued in EP11305078.

* cited by examiner

Primary Examiner — Janet L Andres
Assistant Examiner — Heidi Reese
(74) Attorney, Agent, or Firm — Scully, Scott, Murphy & Presser, P.C.

(57) ABSTRACT

The present invention relates to compounds of the formula I,

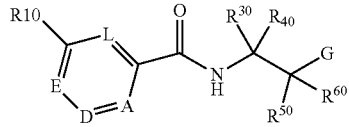

wherein A, D, E, L, G, $R^{10}$, $R^{30}$, $R^{40}$, $R^{50}$ and $R^{60}$ have the meanings indicated in the claims, which are valuable pharmaceutical active compounds. They are inhibitors of the protease cathepsin A, and are useful for the treatment of diseases such as atherosclerosis, heart failure, renal diseases, liver diseases or inflammatory diseases, for example. The invention furthermore relates to processes for the preparation of the compounds of the formula I, their use and pharmaceutical compositions comprising them.

13 Claims, No Drawings

SUBSTITUTED 3-HETEROAROYLAMINO-PROPIONIC ACID DERIVATIVES AND THEIR USE AS PHARMACEUTICALS

CROSS-REFERENCE TO RELATED APPLICATIONS

This application claims the benefit of U.S. Provisional Application No. 61/486,945 filed on May 17, 2011.

The present invention relates to compounds of the formula I,

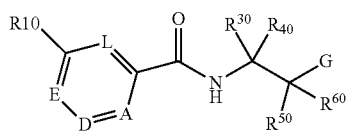

wherein A, D, E, L, G, $R^{10}$, $R^{30}$, $R^{40}$, $R^{50}$ and $R^{60}$ have the meanings indicated below, which are valuable pharmaceutical active compounds. They are inhibitors of the protease cathepsin A, and are useful for the treatment of diseases such as atherosclerosis, heart failure, renal diseases, liver diseases or inflammatory diseases, for example. The invention furthermore relates to processes for the preparation of the compounds of the formula I, their use and pharmaceutical compositions comprising them.

Cathepsin A (EC=3.4.16.5; gene symbol CTSA) is a protease also known as lysosomal carboxypeptidase A or protective protein. It belongs to a family of serine carboxypeptidases which contains only two other mammalian representatives, retinoid-inducible serine carboxypeptidase and vitellogenic carboxypeptidase-like protein. Within the cell cathepsin A resides in lysosomes where it forms a high molecular weight complex with beta-galactosidase and neuraminidase. The interaction of cathepsin A with these glycosidases is essential for their correct routing to the lysosome and protects them from intralysosomal proteolysis. A deficiency of cathepsin A resulting from various mutations in the ctsa gene leads to a secondary deficiency of beta-galactosidase and neuraminidase that is manifest as the autosomal recessive lysosomal storage disorder galactosialidosis (cf. A. d'Azzo et al., in "The Metabolic and Molecular Bases of Inherited Disease", vol. 2 (1995), 2835-2837). The majority of identified mutations in ctsa are missense mutations affecting the folding or the stability of the protein. None of them was shown to occur in the active site of the enzyme (G. Rudenko et al., Proc. Natl. Acad. Sci. USA 95 (1998), 621-625). Accordingly, the lysosomal storage disorder can be corrected with catalytically inactive cathepsin A mutants (N. J. Galjart et al., J. Biol. Chem. 266 (1991), 14754-14762). The structural function of cathepsin A is therefore separable from its catalytic activity. This is also underscored by the observation that in contrast to mice deficient in the ctsa gene, mice carrying a catalytically inactivating mutation in the ctsa gene do not develop signs of the human disease galactosialidosis (R. J. Rottier et al., Hum. Mol. Genet. 7 (1998), 1787-1794; V. Seyrantepe et al., Circulation 117 (2008), 1973-1981).

Cathepsin A displays carboxypeptidase activity at acidic pH and deamidase and esterase activities at neutral pH against various naturally occurring bioactive peptides. In vitro studies have indicated that cathepsin A converts angiotensin I to angiotensin 1-9 and bradykinin to bradykinin 1-8, which is the ligand for the bradykinin B1 receptor. It hydrolyzes endothelin-1, neurokinin and oxytocin, and deamidates substance P (cf. M. Hiraiwa, Cell. Mol. Life. Sci. 56 (1999), 894-907). High cathepsin A activity has been detected in urine, suggesting that it is responsible for tubular bradykinin degradation (M. Saito et al., Int. J. Tiss. Reac. 17 (1995), 181-190). However, the enzyme can also be released from platelets and lymphocytes and is expressed in antigen-presenting cells where it might be involved in antigen processing (W. L. Hanna et al., J. Immunol. 153 (1994), 4663-4672; H. Ostrowska, Thromb. Res. 86 (1997), 393-404; M. Reich et al., Immunol. Lett. (online Nov. 30, 2009)). Immunohistochemistry of human organs revealed prominent expression in renal tubular cells, bronchial epithelial cells, Leydig's cells of the testis and large neurons of the brain (O, Sohma et al., Pediatr. Neurol. 20 (1999), 210-214). It is upregulated during differentiation of monocytes to macrophages (N. M. Stamatos et al., FEBS J. 272 (2005), 2545-2556). Apart from structural and enzymatic functions, cathepsin A has been shown to associate with neuraminidase and an alternatively spliced beta-galactosidase to form the cell-surface laminin and elastin receptor complex expressed on fibroblasts, smooth muscle cells, chondroblasts, leukocytes and certain cancer cell types (A. Hinek, Biol. Chem. 377 (1996), 471-480).

The importance of cathepsin A for the regulation of local bradykinin levels has been demonstrated in animal models of hypertension. Pharmacological inhibition of cathepsin A activity increased renal bradykinin levels and prevented the development of salt-induced hypertension (H. I to et al., Br. J. Pharmacol. 126 (1999), 613-620). This could also be achieved by antisense oligonucleotides suppressing the expression of cathepsin A (I. Hajashi et al., Br. J. Pharmacol. 131 (2000), 820-826). Besides in hypertension, beneficial effects of bradykinin have been demonstrated in various further cardiovascular diseases and other diseases (cf. J. Chao et al., Biol. Chem. 387 (2006), 665-75; P. Madeddu et al., Nat. Clin. Pract. Nephrol. 3 (2007), 208-221). Key indications of cathepsin A inhibitors therefore include atherosclerosis, heart failure, cardiac infarction, cardiac hypertrophy, vascular hypertrophy, left ventricular dysfunction, in particular left ventricular dysfunction after myocardial infarction, renal diseases such as renal fibrosis, renal failure and kidney insufficiency; liver diseases such as liver fibrosis and liver cirrhosis, diabetes complications such as nephropathy, as well as organ protection of organs such as the heart and the kidney.

As indicated above, cathepsin A inhibitors can prevent the generation of the bradykinin B1 receptor ligand bradykinin 1-8 (M. Saito et al., Int. J. Tiss. Reac. 17 (1995), 181-190). This offers the opportunity to use cathepsin A inhibitors for the treatment of pain, in particular neuropathic pain, and inflammation, as has been shown for bradykinin B1 receptor antagonists (cf. F. Marceau et al., Nat. Rev. Drug Discov. 3 (2004), 845-852). Cathepsin A inhibitors can further be used as anti-platelet agents as has been demonstrated for the cathepsin A inhibitor ebelactone B, a propiolactone derivative, which suppresses platelet aggregation in hypertensive animals (H. Ostrowska et al., J. Cardiovasc. Pharmacol. 45 (2005), 348-353).

Further, like other serine proteases such as prostasin, elastase or matriptase, cathepsin A can stimulate the amiloride-sensitive epithelial sodium channel (ENaC) and is thereby involved in the regulation of fluid volumes across epithelial membranes (cf. C. Planes et al., Curr. Top. Dev. Biol. 78 (2007), 23-46). Thus, respiratory diseases can be ameliorated by the use of cathepsin A inhibitors, such as cystic fibrosis, chronic bronchitis, chronic obstructive pulmonary disease, asthma, respiratory tract infections and lung carcinoma. Cathepsin A modulation in the kidney could be used to promote diuresis and thereby induce a hypotensive effect.

Besides for the above-mentioned compound ebelactone B, an inhibitory effect on cathepsin A has been found for certain dipeptidic phenylalanine derivatives which are described in JP 2005/145839. There is a need for further compounds which inhibit cathepsin A and offer an opportunity for the treatment of the mentioned diseases and further diseases in which cathepsin A plays a role. The present invention satisfies this need by providing the oxygen-substituted 3-heteroaroylamino-propionic acid derivatives of the formula I defined below.

Certain compounds in which a 3-heteroaroylamino-propionic acid moiety can be present, have already been described. For example, in WO 2006/076202 amine derivatives, which modulate the activity of steroid nuclear receptors, are described which carry on the nitrogen atom of the amine function a heteroaroyl group and a further group which is defined very broadly. In US 2004/0072802 broadly-defined beta-amino acid derivatives are described which carry an acyl group on the beta-amino group and are inhibitors of matrix metalloproteases and/or tumor necrosis factor. In WO 2009/080226 and WO 2009/080227, which relate to antagonists of the platelet ADP receptor P2Y12 and inhibit platelet aggregation, pyrazoloylamino-substituted carboxylic acid derivatives are described which, however, additionally carry a carboxylic acid derivative group on the carbon atom carrying the pyrazoloylamino group. Other pyrazoloylamino-substituted compounds, in which the nitrogen atom of the amino group is connected to a ring system and which are inhibitors of the blood clotting enzymes factor Xa and/or factor VIIa, are described in WO 2004/056815.

A subject of the present invention is a compound of the formula I, in any of its stereoisomeric forms or a mixture of stereoisomeric forms in any ratio, or a physiologically acceptable salt thereof, or a physiologically acceptable solvate of any of them,

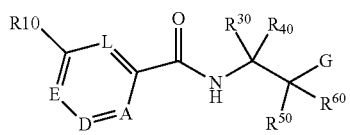

I wherein
A is chosen from the series consisting of $C(R^1)$ and N;
D is chosen from the series consisting of $C(R^2)$ and N;
E is chosen from the series consisting of $C(R^3)$ and N;
L is chosen from the series consisting of $C(R^4)$ and N;
where at least one and at most two of A, D, E or L is N;
G is chosen from the series consisting of $R^{71}$—O—C(O)—, $R^{72}$—N($R^{73}$)—C(O)— and tetrazol-5-yl;
$R^1$ is chosen from the series consisting of hydrogen, halogen, $(C_1-C_6)$-alkyl, HO—, $(C_1-C_6)$-alkyl-O—, $(C_1-C_6)$-alkyl-S$(O)_m$— and NC—;
$R^2$ is chosen from the series consisting of hydrogen, halogen, $(C_1-C_7)$-alkyl, $(C_1-C_6)$-alkyl-O—, $(C_1-C_6)$-alkyl-CO—, $(C_1-C_6)$-alkyl-CO—HN—, —$NR^{12}R^{13}$, $Het^2$, $(C_3-C_7)$-cycloalkyl-$C_sH_{2s}$— and Ar—$C_sH_{2s}$—, wherein s is an integer chosen from the series consisting of 0, 1, 2 and 3;
$R^3$ is chosen from the series consisting of hydrogen, halogen, $(C_1-C_6)$-alkyl, $(C_1-C_6)$-alkyl-S$(O)_m$—, $Het^4$-$(O)_t$—, —$NR^{12}R^{13}$, $Het^2$, $R^{11}$—O—, $R^{12}$—N($R^{13}$)—C(O)—O— and $Het^2$-C(O)—O— and NC—, wherein s is an integer chosen from the series consisting of 0, 1, 2 and 3 and wherein t is an integer chosen from the series consisting of 0 and 1;
$R^4$ is chosen from the series consisting of hydrogen, halogen, $(C_1-C_6)$-alkyl, $(C_1-C_6)$-alkyl-O—, HO—, $NR^{12}R^{13}$, $Het^2$;
$R^{10}$ is chosen from the series consisting hydrogen, halogen, $(C_1-C_6)$-alkyl, $(C_1-C_6)$-alkyl-O—, $(C_1-C_6)$-alkyl-S$(O)_m$—, HO—, —$NR^{12}R^{13}$, $Het^2$, phenyl-$C_sH_{2s}$—$(O)_t$—, wherein s is an integer chosen from the series consisting of 0, 1, 2 and 3 and wherein t is an integer chosen from the series consisting of 0 and 1;
or $R^1$ and $R^2$ or $R^2$ and $R^3$ or form pyridyl;
or $R^1$ and $R^2$ are —C(($C_1-C_3$)-alkyl)=N—N(($C_1-C_3$)-alkyl)-;
or $R^2$ and $R^3$ are —NH—CH=N—;
with the proviso that one of $R^1$, $R^2$, $R^3$, $R^4$ or $R^{10}$ is a cyclic substituent;
$R^{11}$ is chosen from the series consisting of hydrogen, $R^{14}$, $(C_3-C_7)$-cycloalkyl, Ar and $Het^3$;
$R^{12}$ and $R^{13}$ are independently of each other chosen from the series consisting of hydrogen and $R^{15}$;
$R^{14}$ is $(C_1-C_{10})$-alkyl which is optionally substituted by one or more identical or different substituents chosen from the series consisting of halogen, HO—, $R^{16}$—O—, oxo, $(C_3-C_7)$-cycloalkyl, Ar, $Het^1$, $Het^3$, NC—, $H_2N$—C(O)—, $(C_1-C_4)$-alkyl-NH—C(O)—, di(($C_1-C_4$)-alkyl)N—C(O)—, $Het^1$-C(O)—, $(C_1-C_4)$-alkyl-C(O)—NH— and $(C_1-C_4)$-alkyl-S$(O)_m$—;
$R^{15}$ is $(C_1-C_6)$-alkyl which is optionally substituted by one or more identical or different substituents chosen from the series consisting halogen, HO— and $(C_1-C_6)$-alkyl-O—;
$R^{16}$ is $(C_1-C_6)$-alkyl which is optionally substituted by one or more identical or different substituents chosen from the series consisting of HO—, $(C_1-C_4)$-alkyl-O— and NC—;
$R^{30}$ is chosen from the series consisting of $R^{31}$, $(C_3-C_7)$-cycloalkyl, $R^{32}$—$C_uH_{2u}$— and $Het^3$-$C_uH_{2u}$—, wherein u is an integer chosen from the series consisting of 0, 1, 2 and 3;
$R^{31}$ is $(C_1-C_{10})$-alkyl which is optionally substituted by one or more identical or different substituents chosen from the series consisting of halogen, $(C_3-C_7)$-cycloalkyl, HO—, $(C_1-C_6)$-alkyl-O—, $(C_1-C_6)$-alkyl-S$(O)_m$— and NC—;
$R^{32}$ is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1-C_6)$-alkyl, $(C_3-C_7)$-cycloalkyl, $R^{33}$, HO—, $(C_1-C_6)$-alkyl-O—, $R^{33}$—O—, $R^{33}$—$(C_1-C_4)$-alkyl-O—, —O—CH$_2$—O—, —O—CF$_2$—O—, $(C_1-C_6)$-alkyl-S$(O)_m$—, $H_2N$—S$(O)_2$—, $(C_1-C_4)$-alkyl-NH—S$(O)_2$—, di(($C_1-C_4$)-alkyl)N—S$(O)_2$—, $H_2N$—, $(C_1-C_6)$-alkyl-NH—, di(($C_1-C_6$)-alkyl)N—, $Het^1$, $(C_1-C_4)$-alkyl-C(O)—NH—, Ar—C(O)—NH—, $(C_1-C_4)$-alkyl-S$(O)_2$—NH— and NC—;
$R^{33}$ is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1-C_6)$-alkyl, $(C_3-C_7)$-cycloalkyl, HO—, $(C_1-C_6)$-alkyl-O—, $(C_1-C_6)$-alkyl-S$(O)_m$—, $H_2N$—S$(O)_2$—, $(C_1-C_4)$-alkyl-NH—S$(O)_2$—, di(($C_1-C_4$)-alkyl)N—S$(O)_2$— and NC—;

$R^{40}$ is chosen from the series consisting of hydrogen and $(C_1-C_4)$-alkyl;

or $R^{30}$ and $R^{40}$ together are $(CH_2)_x$, which is optionally substituted by one or more identical or different $(C_1-C_4)$-alkyl substituents, wherein x is an integer chosen from the series consisting of 2, 3, 4 and 5;

$R^{50}$ is chosen from the series consisting of hydrogen, $(C_1-C_6)$-alkyl, HO— and $(C_1-C_6)$-alkyl-O—, $R^{60}$ is chosen from the series consisting of hydrogen and $(C_1-C_6)$-alkyl;

or $R^{50}$ and $R^{60}$ together are $(CH_2)_y$ which is optionally substituted by one or more identical or different $(C_1-C_4)$-alkyl substituents, wherein y is an integer chosen from the series consisting of 2, 3, 4 and 5;

$R^{71}$ is chosen from the series consisting of hydrogen and $(C_1-C_8)$-alkyl which is optionally substituted by one or more identical or different substituents chosen from the series consisting $(C_1-C_6)$-alkyl-O— and $(C_1-C_6)$-alkyl-C(O)—O—;

$R^{72}$ is chosen from the series consisting of hydrogen, $(C_1-C_6)$-alkyl, $(C_3-C_6)$-cycloalkyl, —$CH_2$—$(CH_2)_b$—$(C_3-C_6)$-cycloalkyl, $Het^4$ and —$(CH_2)_b$-$Het^4$, where alkyl or cycloalkyl is optionally substituted by one or more identical or different substituents chosen from the series consisting of halogen, HO—, HOOC—, $(C_1-C_6)$-alkyl-O— and $(C_1-C_6)$-alkyl-C(O)—O—, NC—, $N((C_1-C_4)$-alkyl)$_2$ and b is 0, 1 or 2;

$R^{73}$ is chosen from the series consisting of hydrogen, $(C_1-C_6)$-alkyl;

or $R^{72}$ and $R^{73}$ together with the nitrogen atom to which they are bonded form a saturated 4-membered to 7-membered monocyclic heterocycle, which contain optionally one further ring heteroatom chosen from the series consisting of nitrogen, oxygen and sulfur, which is optionally substituted by one or more identical or different substituents chosen from the series consisting of halogen, $(C_1-C_4)$-alkyl, HO— and $(C_1-C_4)$-alkyl-O—;

Ar, independently of each other group Ar, is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1-C_6)$-alkyl, HO—$(C_1-C_6)$-alkyl, $Het^4$, —$(CH_2)_c$-Phenyl, $(C_1-C_6)$-alkyl-O—, $(C_3-C_7)$-cycloalkyl-$(CH_2)_x$—O—, —$CF_3$, —CO—$(C_1-C_6)$-alkyl, —$NR^{12}R^{13}$, $Het^2$, —CO—$NR^{12}R^{13}$, CO-$Het^2$, $(C_1-C_6)$-alkyl-$S(O)_m$—, $H_2N$—$S(O)_2$— and NC—;

and wherein phenyl may be substituted by —CH=CH—CH=CH—, —O—$CH_2$—O—, —O—$CH_2$—$CH_2$—O—, —O—$CF_2$—O— or —$N((C_1-C_3)$-alkyl)-CH=CH—;

$Het^1$, independently of each other group $Het^1$, is a saturated or unsaturated 4-membered to 8-membered monocyclic heterocycle which comprises a ring nitrogen atom via which $Het^1$ is bonded and optionally one or two identical or different further ring heteroatoms chosen from the series consisting of nitrogen, oxygen and sulfur, which is optionally substituted by one or more identical or different substituents chosen from the series consisting of halogen, $(C_1-C_4)$-alkyl, HO—, $(C_1-G_4)$-alkyl-O—, oxo and NC—;

$Het^2$ is a saturated 4-membered to 7-membered monocyclic heterocycle which comprises a ring nitrogen atom via which $Het^2$ is bonded and optionally one further ring heteroatom chosen from the series consisting of nitrogen, oxygen and sulfur, which is optionally substituted by one or more identical or different substituents chosen from the series consisting of halogen, $(C_1-C_4)$-alkyl, HO— and $(C_1-C_4)$-alkyl-O—;

$Het^3$, independently of each other group $Het^3$, is a saturated 4-membered to 7-membered monocyclic heterocycle which comprises one or two identical or different ring heteroatoms chosen from the series consisting of nitrogen, oxygen and sulfur and is bonded via a ring carbon atom, which is optionally substituted by one or more identical or different substituents chosen from the series consisting of fluorine, $(C_1-C_4)$-alkyl and oxo;

$Het^4$, independently of each other group $Het^4$, is a saturated or unsaturated 4-membered to 8-membered monocyclic heterocycle which comprises one to four ring heteroatoms chosen from the series consisting of nitrogen, oxygen and sulfur which is optionally substituted by one or more identical or different substituents chosen from the series consisting of halogen, $(C_1-C_4)$-alkyl, HO—, oxo and NC—;

m, independently of each other number m, is an integer chosen from the series consisting of 0, 1 and 2;

wherein all cycloalkyl groups, independently of each other, are optionally substituted by one or more identical or different substituents chosen from the series consisting of fluorine and $(C_1-C_4)$-alkyl;

wherein all alkyl, $C_sH_{2s}$, $C_uH_{2u}$, $(CH_2)_x$ and $(CH_2)_y$ groups, independently of each other, and independently of any other substituents, are optionally substituted by one or more fluorine substituents.

If structural elements such as groups, substituents or numbers, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear (straight-chain) or branched. This also applies if these groups are substituted or are part of another group, for example an alkyl-O— group (alkyloxy group, alkoxy group) or an HO-substituted alkyl group (hydroxyalkyl group). Depending on the respective definition, the number of carbon atoms in an alkyl group can be 1, 2, 3, 4, 5, 6, 7, 8, 9 or 10, or 1, 2, 3, 4, 5, 6, 7 or 8, or 1, 2, 3, 4, 5 or 6, or 1, 2, 3 or 4 or 1, 2 or 3, or 1 or 2, or 1, for example. In one embodiment of the invention, a $(C_1-C_{10})$-alkyl group present in the compounds of the formula I is a $(C_1-C_8)$-alkyl group, in another embodiment a $(C_1-C_6)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group. In one embodiment of the invention, a $(C_1-C_6)$-alkyl group present in any position of the compounds of the formula I is a $(C_1-C_6)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group, where any $(C_1-C_8)$-alkyl group present in the compounds of the formula I can independently of each other $(C_1-C_8)$-alkyl group be a group of any of these embodiments. In one embodiment of the invention, a $(C_1-C_6)$-alkyl group present in any position of the compounds of the formula I is a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group, where any $(C_1-C_6)$-alkyl group present in the compounds of the formula I can independently of each other $(C_1-C_6)$-alkyl group be a group of any of these embodiments. In one embodiment of the invention, a ($C_1$-$C_4$)-alkyl group present in any position of the compounds of the formula I is a ($C_1$-$C_3$)-alkyl group, in another embodiment a ($C_1$-$C_2$)-alkyl group, in another embodiment a ($C_2$-$C_3$)-alkyl group, in another embodiment a methyl group, where any ($C_1$-$C_4$)-alkyl group present in the compounds of the formula I can independently of each other ($C_1$-$C_4$)-alkyl group be a group of any of these embodiments. Examples of alkyl groups are methyl, ethyl, propyl groups including propyl (i.e. n-propyl) and isopropyl, butyl groups including butyl (i.e. n-butyl), sec-butyl, isobutyl and tert-butyl, pentyl groups including pentyl (i.e. n-pentyl), 1-methylbutyl, isopentyl, neopentyl and tert-pentyl, hexyl groups including hexyl (i.e. n-hexyl), 3,3-dimethylbutyl and isohexyl, heptyl groups including heptyl (i.e. n-heptyl), octyl groups including octyl (i.e. n-octyl), nonyl groups including nonyl (i.e. n-nonyl), and decyl groups including decyl (i.e. n-decyl). Examples of alkyl-O— groups are methoxy, ethoxy, propoxy (i.e. n-propoxy), isopropoxy, butoxy (i.e. n-butoxy), isobutoxy, tert-butoxy, pentoxy (i.e. n-pentoxy). Examples of alkyl-S(O)$_m$— are methylsulfanyl-($CH_3$—S—), methanesulfinyl-($CH_3$—S(O)—), methanesulfonyl ($CH_3$—S(O)$_2$—), ethylsulfanyl-($CH_3$—$CH_2$—S—), ethanesulfinyl-($CH_3$—$CH_2$—S(O)—), ethanesulfonyl ($CH_3$—$CH_2$—S(O)$_2$—), 1-methylethylsulfanyl-(($CH_3$)$_2$CH—S—), 1-methylethanesulfinyl-(($CH_3$)$_2$CH—S(O)—), 1-methylethanesulfonyl (($CH_3$)$_2$CH—S(O)$_2$—). In one embodiment of the invention the number m is chosen from 0 and 2, wherein all numbers m are independent of each other and can be identical or different. In another embodiment the number m in any of its occurrences is, independently of its meaning in other occurrences, 0. In another embodiment the number m in any of its occurrences is, independently of its meaning in other occurrences, 2.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I. In one embodiment of the invention, an individual carbon atom in any alkyl group in the compounds of the formula I, as well as in other groups such as cycloalkyl groups and heterocyclic groups, for example, independently of any other carbon atom does not carry more than one substituent which is bonded via an oxygen atom, nitrogen atom or sulfur atom, such as HO—, ($C_1$-$C_4$)-alkyl-O— or ($C_1$-$C_4$)-alkyl-S(O)$_m$— substituents, for example. An alkyl group which is optionally substituted by one or more fluorine substituents can be unsubstituted, i.e. not carry fluorine substituents, or substituted, for example by one, two, three, four, five, six, seven, eight, nine, ten or eleven fluorine substituents, or by one, two, three, four, five, six or seven fluorine substituents, or by one, two, three, four or five fluorine substituents, or by one, two or three fluorine substituents, which can be located in any positions. For example, in a fluoro-substituted alkyl group one or more methyl groups can carry three fluorine substituents each and be present as trifluoromethyl groups, and/or one or more methylene groups ($CH_2$) can carry two fluorine substituents each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-S(O)$_m$— groups are trifluoromethylsulfanyl-($CF_3$—S—), trifluoromethanesulfinyl-($CF_3$—S(O)—) and trifluoromethanesulfonyl ($CF_3$—S(O)$_2$—).

The above explanations with respect to alkyl groups apply correspondingly to alkanediyl groups (divalent alkyl groups) including the divalent groups $C_sH_{2s}$, $C_uH_{2u}$, ($CH_2$)$_x$ and ($CH_2$)$_y$. Also the alkyl part of a substituted alkyl group may be regarded as an alkanediyl group. Thus, alkanediyl groups can also be linear or branched, the bonds to the adjacent groups can be located in any positions and can start from the same carbon atom or from different carbon atoms, and they can be substituted by fluorine substituents. Examples of alkanediyl groups including the groups $C_sH_{2s}$ and $C_uH_{2u}$ and, as far they constitute polymethylene chains, the groups ($CH_2$)$_x$ are —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —CH($CH_3$)—, —C($CH_3$)$_2$—, —CH($CH_3$)—$CH_2$—, —$CH_2$—CH($CH_3$)—, —C($CH_3$)$_2$—$CH_2$—, —$CH_2$—C($CH_3$)$_2$—. Examples of fluoro-substituted alkanediyl groups, which can contain one, two, three, four, five or six fluorine substituents, or one, two, three or four fluorine substituents, or one or two fluorine substituents, for example, are —CHF—, —$CF_2$— —$CF_2$—$CH_2$—, —$CH_2$—$CF_2$—, —$CF_2$—$CF_2$—, —CF($CH_3$)—, —C($CF_3$)$_2$—, —C($CH_3$)$_2$—$CF_2$—, —$CF_2$—C($CH_3$)$_2$—.

The number of ring carbon atoms in a ($C_3$-$C_7$)-cycloalkyl group can be 3, 4, 5, 6 or 7. Examples of cycloalkyl are cyclopropyl, cyclobutyl, cyclopentyl, cyclohexyl and cycloheptyl. As regards the optional substitution of cycloalkyl groups by one or more ($C_1$-$C_4$)-alkyl substituents, they be unsubstituted, i.e. not carry alkyl substituents, or substituted, for example by one, two, three or four, or by one or two, identical or different ($C_1$-$C_4$)-alkyl substituents, for example by methyl groups, which substituents can be located in any positions. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl and 3,3,5,5-tetramethylcyclohexyl. As regards the optional substitution of cycloalkyl groups by one or more fluorine substituents, they can be unsubstituted, i.e. not carry fluorine substituents, or substituted, for example by one, two, three, four, five, six, seven, eight, nine, ten or eleven fluorine substituents, or by one, two, three, four, five or six fluorine substituents, or by one, two, three or four fluorine substituents, or by one or two fluorine substituents. The fluorine substituents can be located in any positions of the cycloalkyl group and can also be located in an alkyl substituent on the cycloalkyl group. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl and 3,3,4,4,5,5-hexafluorocyclohexyl. Cycloalkyl groups can also be substituted simultaneously by fluorine and alkyl. Examples of ($C_3$-$C_7$)-cycloalkyl-substituted alkyl groups, which can represent $R^{11}$ or $R^{30}$, for example, are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-. The explanations with respect cycloalkyl groups apply correspondingly to divalent cycloalkyl groups (cycloalkanediyl groups), which can occur in case the two groups $R^{30}$ and $R^{40}$ together are ($CH_2$)$_x$ or the two groups $R^{50}$ and $R^{60}$ together are $(CH_2)_y$. Also the cycloalkyl part of a substituted cycloalkyl group may be regarded as a cycloalkanediyl group. Thus, for example, the bonds through which a cycloalkanediyl group is connected to the adjacent groups, can be located in any positions and can start from the same ring carbon atom, as in the case of the cycloalkanediyl group which is present if $R^{30}$ and $R^{40}$ together are $(CH_2)_x$ or the two groups $R^{50}$ and $R^{60}$ together are $(CH_2)_y$, or from different ring carbon atoms.

In substituted phenyl groups the substituents can be located in any positions. In the case a the divalent substituents —O—CH$_2$—O— (methylenedioxy) and —O—CF$_2$—O— (difluoromethylenedioxy) which can be present on phenyl groups and aromatic heterocycles, the two oxygen atoms are bonded to adjacent ring carbon atoms of the phenyl group or the aromatic heterocycle and replace two hydrogen atoms of the parent system. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. If a phenyl group carries four substituents, some of which can be fluorine atoms, for example, the substituents can be located in 2,3,4,5-position, 2,3,4,6-position or 2,3,5,6-position. If a polysubstituted phenyl group carries different substituents, each substituent can be located in any suitable position, and the present invention comprises all positional isomers. The number of substituents in an optionally substituted phenyl group can be one, two, three, four or five. In one embodiment of the invention, an optionally substituted phenyl group, independently of any other optionally substituted phenyl group in a compound of the formula I, carries one, two, three or four, in another embodiment one, two or three, in another embodiment one or two, in another embodiment one, identical or different substituents, and in another embodiment it is unsubstituted.

Likewise, in substituted heterocyclic groups, including aromatic 5-membered and 6-membered monocyclic heterocycles which can represent $R^{32}$, $R^{33}$ and Ar, saturated and unsaturated 4-membered to 8-membered monocyclic heterocycles which can represent Het$^1$, and saturated 4-membered to 7-membered monocyclic heterocycles which can represent Het$^2$ and Het$^3$, the substituents can be located in any positions and can be present on ring carbon atoms and/or on suitable ring nitrogen atoms. The present invention comprises all positional isomers. The number of substituents which can be present on substituted heterocycles in the compounds of the formula I, depends on the ring size, the number and type of the ring heteroatoms and the degree of unsaturation. In one embodiment of the invention, the number of identical or different substituents on any of the heterocyclic groups in the compounds of the formula I, independently of the number of substituents in any other occurrence of this group and the number of substituents in any other heterocyclic group in the compounds of the formula I, is one, two, three, four or five, in another embodiment one, two, three or four, in another embodiment one, two or three, in another embodiment one or two, in another embodiment one. Ring nitrogen atoms which optionally carry a substituent, include ring nitrogen atoms in saturated heterocyclic rings other than those via which such a ring is bonded, and the ring nitrogen atom in 5-membered aromatic heterocycles such as pyrrole, imidazole or triazole, which in the parent heterocycle carry a hydrogen atom. In one embodiment of the invention, the substituents on any such ring nitrogen atoms in heterocyclic groups are chosen from those of the substituents specified in the definition of the respective group which are bonded via a carbon atom, for example from the series consisting of ($C_1$-$C_6$)-alkyl, ($C_3$-$C_7$)-cycloalkyl and $R^{33}$, in another embodiment from the series consisting of ($C_1$-$C_6$)-alkyl and ($C_3$-$C_7$)-cycloalkyl, in the case of the aromatic heterocycle which can represent $R^{32}$, from the series consisting of ($C_1$-$C_6$)-alkyl and ($C_3$-$C_7$)-cycloalkyl in the case of the aromatic heterocycle which can represent $R^{33}$, and are ($C_1$-$C_6$)-alkyl in the case of the aromatic heterocycle which can represent Ar and ($C_1$-$C_4$)-alkyl in the case of Het$^1$, Het$^2$ and Het$^3$. Generally, besides optionally carrying the substituents indicated in the definition of the respective group, suitable ring nitrogen atoms in heterocyclic groups in the compounds of the formula I, in particular aromatic heterocyclic groups such as the heterocyclic groups which can represent $R^{32}$, $R^{33}$ and Ar, for example the ring nitrogen atom in a pyridinyl group, can also carry an oxido substituent —O$^-$ and be present as an N-oxide.

The ring heteroatoms specified in the definitions of heterocyclic groups in the compounds of the formula I, including the aromatic 5-membered and 6-membered monocyclic heterocycles which can represent $R^{32}$, $R^{33}$ and Ar and the heterocycles which represent Het$^1$, Het$^2$, Het$^3$ and Het$^4$ can generally be present in any combination and located in any suitable ring positions, provided that the resulting group and the compound of the formula I are sufficiently stable and suitable as a pharmaceutical active compound, as mentioned above. In one embodiment of the invention, two oxygen atoms in any heterocyclic ring in the compounds of the formula I cannot be present in adjacent ring positions. In another embodiment, two ring heteroatoms in any non-aromatic heterocyclic ring in the compounds of the formula I cannot be present in adjacent ring positions. In another embodiment, two ring heteroatoms chosen from the series consisting of N atoms which carry a hydrogen atom or a substituent and are bonded to the adjacent ring atoms by single bonds, O atoms and S atoms in a non-aromatic heterocycle cannot be present in adjacent ring positions. In an aromatic heterocycle the choice of ring heteroatoms and their positions is limited by the prerequisite that the ring is aromatic, i.e., it comprises a cyclic system of six delocalized pi electrons. Thus, for example, in an aromatic monocyclic 6-membered heterocycle only nitrogen atoms can occur as ring heteroatoms, and in an aromatic monocyclic 5-membered heterocycle only one ring heteroatom chosen from the series consisting of O atoms, S atoms and N atoms carrying a hydrogen atom or a substituent, can be present. An unsaturated heterocycle which can represent Het$^1$, can be aromatic, for example in the case of a pyrrolyl, imidazolyl or triazolyl group which is bonded via a ring nitrogen atom and can represent Het$^1$, or non-aromatic and comprise one or two double bonds within the ring which can be present in any positions. In one embodiment, a 4-membered heterocycle representing Het$^1$ cannot be unsaturated. A heterocyclic group can be bonded via any ring carbon atom or via any suitable ring nitrogen atom, respectively, as indicated in the definition of the respective group. The group Het$^1$ can be 4-membered, 5-membered, 6-membered or 7-membered or 8-membered. The groups Het$^2$ and Het$^3$ can be 4-membered, 5-membered, 6-membered or 7-membered.

Examples of aromatic heterocycles, from any one or more of which the aromatic 5-membered and 6-membered monocyclic heterocycles which can represent $R^{32}$, $R^{33}$ and Ar and, as far as applicable, the group Het$^1$ are chosen in one embodiment of the invention, are pyrrole, furan, thiophene, imidazole, pyrazole, oxazole ([1,3]oxazole), isoxazole ([1,2]oxazole), thiazole ([1,3]thiazole), isothiazole ([1,2]thiazole), [1,2,3]triazole, [1,2,4]triazole, [1,3,4]oxadiazole, pyridine, pyridazine, pyrimidine and pyrazine, which can all be bonded via any ring carbon atom or via any suitable ring nitrogen atom, and which all are optionally substituted as indicated with respect to the compounds of formula I in general or in any embodiment specified above or below. Examples of specific residues of aromatic heterocycles, from any one or more of which the aromatic, 5-membered or 6-membered monocyclic heterocyclic residue which can represent $R^{32}$, $R^{33}$ or Ar and, as far as applicable, the group $Het^1$, are chosen in one embodiment of the invention, are pyrrol-1-yl, pyrrol-2-yl, pyrrol-3-yl, furan-2-yl, furan-3-yl, thiophen-2-yl(2-thienyl), thiophen-3-yl (3-thienyl), imidazol-1-yl, imidazol-2-yl, imidazol-4-yl, imidazol-5-yl, pyrazol-1-yl, pyrazol-3-yl, pyrazol-4-yl, pyrazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, [1,2,3]triazol-1-yl, [1,2,3]triazol-4-yl, [1,2,3]triazol-5-yl, [1,2,4]triazol-1-yl, [1,2,4]triazol-3-yl, [1,2,4]triazol-4-yl, [1,3,4]oxadiazol-2-yl, pyridin-2-yl (2-pyridyl), pyridin-3-yl (3-pyridyl), pyridin-4-yl (4-pyridyl), pyridazin-3-yl, pyridazin-4-yl, pyrimidin-2-yl, pyrimidin-4-yl, and pyrazin-2-yl, which all are optionally substituted as indicated with respect to the compounds of formula I in general or in any embodiment specified above or below.

Examples of saturated heterocycles and non-aromatic unsaturated heterocycles, from any one or more of which the groups $Het^1$, $Het^2$, $Het^3$ and $Het^4$ are independently of each other chosen in one embodiment of the invention, as far as applicable with regard to the ring size and the degree of saturation, are azetidine, oxetane, thietane, pyrrolidine, 2,5-dihydro-1H-pyrrole, tetrahydrofuran, tetrahydrothiophene, pyrazolidine, imidazolidine, 4,5-dihydro-1H-imidazole, [1,3]dioxolane, oxazolidine, thiazolidine, piperidine, 1,2,3,6-tetrahydropyridine, tetrahydropyran, tetrahydrothiopyran, piperazine, [1,3]dioxane, [1,4]dioxane, morpholine, thiomorpholine, azepane, oxepane, thiepane, [1,3]diazepane, [1,4]diazepane, [1,4]oxazepane, [1,4]thiazepane and azocane, which all are optionally substituted as indicated with respect to the compounds of formula I in general or in any embodiment specified above or below. Examples of specific residues of saturated and non-aromatic unsaturated heterocycles, from any one or more of which the groups $Het^1$, $Het^2$, $Het^3$ and $Het^4$ are independently of each other chosen in one embodiment of the invention, as far as applicable with regard to the ring size, the degree of saturation and the kind of the atom via which the residue is bonded are azetidin-1-yl, oxetan-3-yl, thietan-3-yl, pyrrolidin-1-yl, pyrrolidin-2-yl, pyrrolidin-3-yl, 2,5-dihydro-1H-pyrrol-1-yl, tetrahydrofuran-2-yl, tetrahydrofuran-3-yl, tetrahydrothiophen-2-yl, tetrahydrothiophen-3-yl, pyrazolidin-1-yl, pyrazolidin-4-yl, imidazolidin-1-yl, imidazolidin-2-yl, imidazolidin-4-yl, 4,5-dihydro-1H-imidazol-2-yl, 1,3-dioxolan-2-yl, 1,3-dioxolan-4-yl, oxazolidin-2-yl, oxazolidin-3-yl, oxazolidin-4-yl, oxazolidin-5-yl, thiazolidin-2-yl, thiazolidin-3-yl, thiazolidin-4-yl, thiazolidin-5-yl, piperidin-1-yl, piperidin-2-yl, piperidin-3-yl, piperidin-4-yl, 1,2,3,6-tetrahydropyridin-1-yl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, piperazin-1-yl, piperazin-2-yl, [1,3]dioxan-2-yl, [1,3]dioxan-4-yl, [1,3]dioxan-5-yl, [1,4]dioxan-2-yl, morpholin-2-yl, morpholin-3-yl, morpholin-4-yl, thiomorpholin-2-yl, thiomorpholin-3-yl, thiomorpholin-4-yl, azepan-1-yl, azepan-2-yl, azepan-3-yl, azepan-4-yl, oxepan-2-yl, oxepan-3-yl, oxepan-4-yl, [1,3]diazepan-1-yl, [1,4]diazepan-1-yl, [1,4]oxazepan-1-yl and [1,4]thiazepan-1-yl, which all are optionally substituted as indicated with respect to the compounds of formula I in general or in any embodiment specified above or below.

Halogen is fluorine, chlorine, bromine or iodine. In one embodiment of the invention, halogen in any occurrence in the compounds of the formula I, independently of all other occurrences, is fluorine, chlorine or bromine, in another embodiment fluorine or chlorine, in another embodiment fluorine.

An oxo substituent, i.e. an oxygen atom which is bonded via a double bond, when bonded to a carbon atom, replaces two hydrogen atoms on the carbon atom of the parent system to which it is bonded. Thus, if a $CH_2$ group is substituted by oxo, it becomes a carbonyl group (C(O), C=O). An oxo substituent cannot be present on a carbon atom in an aromatic ring. Besides on carbon atoms, oxo substituents can also be present on a ring sulfur atom in the group $Het^1$, in particular if the group $Het^1$ is saturated, and in the group $Het^3$, to give the ring member S(O) (S=O, i.e. a sulfoxide group), if one oxo substituent is present on the sulfur atom, or the ring member $S(O)_2$ ($S(=O)_2$, i.e. a sulfone group), if two oxo substituents are present on the sulfur atom. As examples of heterocycles which can represent $Het^1$ and $Het^3$ and which carry oxo substituent a ring sulfur atom, 1,1-dioxo-tetrahydrothiophene, 1-oxo-thiomorpholine and 1,1-dioxo-thiomorpholine may be mentioned, which all are optionally substituted by further substituents such as ($C_1$-$C_4$)-alkyl substituents as indicated with respect to the compounds of formula in general or in any embodiment specified above or below.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I, for example in unsubstituted or substituted alkyl groups, can all independently of each other have the S configuration or the R configuration. The invention relates to enantiomers, both the levorotatory and the dextrorotatory antipode, in enantiomerically pure form and essentially enantiomerically pure form, for example with a molar ratio of the two enantiomers of 99:1 or greater, and in the form of racemates and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, for example with a molar ratio of the cis/trans isomers of 99:1 or greater, and in the form of mixtures of the cis isomer and the trans isomer in all ratios. Cis/trans isomerism can occur in substituted rings. The preparation of individual stereoisomers, if desired, can be carried out by resolution of a mixture according to customary methods, for example, by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. The invention also comprises all tautomeric forms of the compounds of the formula I.

Physiologically acceptable salts, including pharmaceutically utilizable salts, of the compounds of the formula I generally comprise a nontoxic salt component. They can contain inorganic or organic salt components. Such salts can be formed, for example, from compounds of the formula I which contain an acidic group, for example a carboxylic acid group (hydroxycarbonyl group, HO—C(O)—), and nontoxic inorganic or organic bases. Suitable bases are, for example, alkali metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the formula I with bases for the preparation of the salts are in general carried out according to customary procedures in a solvent or diluent. Examples of salts of acidic groups thus are sodium, potassium, magnesium or calcium salts or ammonium salts which can also carry one or more organic groups on the nitrogen atom. Compounds of the formula I which contain a basic, i.e. protonatable, group, for example an amino group or a basic heterocycle, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the formula I by reaction with an acid in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange. The present invention also comprises all solvates of the compounds of the formula I and their salts, including physiologically acceptable solvates, such as hydrates, i.e. adducts with water, and adducts with alcohols like $(C_1-C_4)$-alkanols, as well as active metabolites of compounds of the formula I and prodrugs of the compounds of the formula I, i.e. compounds which in vitro may not necessarily exhibit pharmacological activity but which in vivo are converted into pharmacologically active compounds of the formula I, for example compounds which are converted by metabolic hydrolysis into a compound of the formula I, such as compounds in which a carboxylic acid group is present in esterified form or in the form of an amide.

In one embodiment of the invention, the group A is $C(R^1)$, in another embodiment A is N, in one embodiment of the invention, the group D is chosen from the series consisting of N, in another embodiment from the series consisting of $C(R^2)$, in one embodiment of the invention, the group E is chosen from the series consisting of N, in another embodiment from the series consisting of $C(R^3)$, in one embodiment of the invention, the group L is chosen from the series consisting of N, in another embodiment from the series consisting of $C(R^4)$, with the proviso that one or two of the groups A, D, E, L is N.

In another embodiment of the invention, the group A is N and the groups D, E and L are $C(R^2)$, $C(R^3)$ and $C(R^4)$.

In another embodiment of the invention, the group D is N and the groups A, E and L are $C(R^1)$, $C(R^3)$ and $C(R^4)$.

In another embodiment of the invention, the group E is N and the groups A, D and L are $C(R^1)$, $C(R^2)$ and $C(R^4)$.

In another embodiment of the invention, the group L is N and the groups A, D and E are $C(R^1)$, $C(R^2)$ and $C(R^3)$.

In another embodiment of the invention, the groups A and D are N and the groups E and L are $C(R^3)$ and $C(R^4)$.

In another embodiment of the invention, the group A and E is N and the groups D and L are $C(R^2)$ and $C(R^4)$.

In another embodiment of the invention, the group A and L is N and the groups D and E are $C(R^2)$ and $C(R^3)$.

In another embodiment of the invention, the group D and E is N and the groups A and L are $C(R^1)$ and $C(R^4)$.

In another embodiment of the invention, the group D and L is N and the groups A and E are $C(R^1)$ and $C(R^3)$.

In another embodiment of the invention, the group E and L is N and the groups A and D are $C(R^1)$ and $C(R^2)$.

In terms of formulae resulting from formula I by incorporation of meanings of A, D, E or L, in one embodiment of the invention a compound of the formula I is a compound of any one or more of formulae I-1 to I-7, for example a compound of formula I-1, or a compound of formula I-2, or a compound of formula I-3, or a compound of formula I-4, or a compound of formula I-5, or a compound of formula I-6, or a compound of formula I-7 in any of its stereoisomeric forms or a mixture of stereoisomeric forms in any ratio, or a physiologically acceptable salt thereof, or a physiologically acceptable solvate of any of them, wherein in the compounds of formulae I-1 to I-7 the groups A, D, E, G, $R^1$, $R^2$, $R^3$, $R^{10}$, $R^{30}$, $R^{40}$, $R^{50}$ and $R^{60}$ are defined as in the compounds of formula I in general or in any embodiment specified above or below.

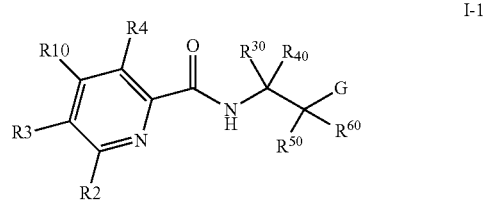

I-1

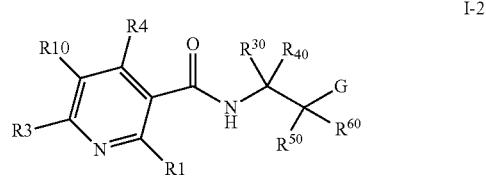

I-2

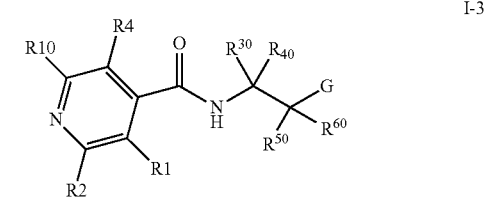

I-3

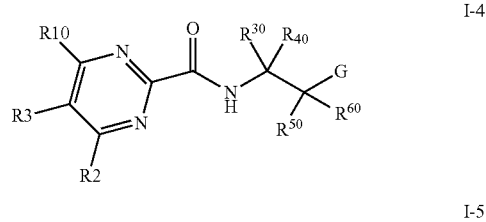

I-4

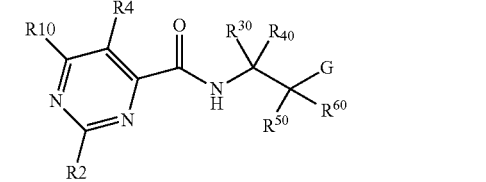

I-5

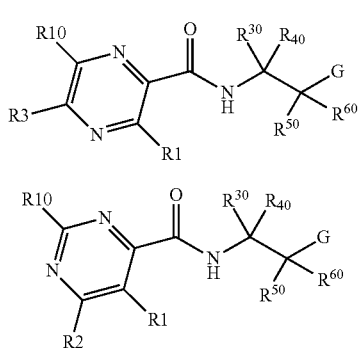

In one embodiment of the invention, the group G is chosen from the series consisting of $R^{71}$—O—C(O)—, $R^{72}$—N($R^{73}$)—C(O)— and tetrazol-5-yl, in another embodiment from the series consisting of $R^{71}$—O—C(O)— and $R^{72}$—N($R^{73}$)—C(O)—, in another embodiment G is $R^{71}$—O—C(O)—, and in another embodiment G is $R^{72}$—N($R^{73}$)—C(O)—.

In one embodiment of the invention, the group $R^1$ is chosen from the series consisting of hydrogen, halogen, ($C_1$-$C_6$)-alkyl, HO—, ($C_1$-$C_6$)-alkyl-O—, and NC—, in another embodiment from the series consisting of hydrogen, halogen, ($C_1$-$C_6$)-alkyl, ($C_1$-$C_6$)-alkyl-O— and NC—, in another embodiment from the series consisting of hydrogen, halogen, ($C_1$-$C_6$)-alkyl and NC—, in another embodiment from the series consisting of hydrogen, halogen, ($C_1$-$C_6$)-alkyl, HO— and ($C_1$-$C_6$)-alkyl-O—, in another embodiment from the series consisting of hydrogen, halogen, ($C_1$-$C_6$)-alkyl and ($C_1$-$C_6$)-alkyl-O—, in another embodiment from the series consisting of hydrogen, halogen and ($C_1$-$C_6$)-alkyl, in another embodiment from the series consisting of hydrogen and halogen, in another embodiment from the series consisting of hydrogen, fluorine and chlorine, and in another embodiment $R^1$ is hydrogen. In one embodiment of the invention, a ($C_1$-$C_6$)-alkyl group occurring in $R^1$ is a ($C_1$-$C_4$)-alkyl group, in another embodiment a ($C_1$-$C_2$)-alkyl group, in another embodiment it is methyl.

In one embodiment of the invention, the group $R^2$ is chosen from the series consisting of ($C_1$-$C_7$)-alkyl and ($C_3$-$C_7$)-cycloalkyl-$C_sH_{2s}$—, in another embodiment from the series consisting of ($C_3$-$C_7$)-cycloalkyl-$C_sH_{2s}$— and Ar—$C_sH_{2s}$—, in another embodiment $R^2$ is ($C_1$-$C_7$)-alkyl, in another embodiment $R^2$ is ($C_3$-$C_7$)-cycloalkyl-$C_sH_{2s}$—, and in another embodiment $R^2$ is Ar—$C_sH_{2s}$—. In one embodiment, s is an integer chosen from the series consisting of 0, 1 and 2, in another embodiment from the series consisting of 0 and 1, in another embodiment from the series consisting of 1 and 2, in another embodiment s is 0, and in another embodiment s is 1. In one embodiment of the invention, $R^2$ is Ar—$C_sH_{2s}$— and s is 0, i.e., $R^2$ is the group Ar and the group D thus is the group N(Ar). In one embodiment, the divalent alkanediyl group $C_sH_{2s}$ is a linear group. In one embodiment, a ($C_1$-$C_7$)-alkyl group representing $R^2$ is a ($C_3$-$C_7$)-alkyl group, in another embodiment a ($C_3$-$C_6$)-alkyl group. In one embodiment, a ($C_3$-$C_7$)-cycloalkyl group occurring in $R^2$ is a ($C_3$-$C_6$)-cycloalkyl group, in another embodiment a ($C_5$-$C_6$)-cycloalkyl group, in another embodiment a cyclopropyl group. In one embodiment, a group Ar occurring in $R^2$ is chosen from the series consisting of phenyl and an aromatic 5-membered or 6-membered heterocycle which comprises one or two identical or different ring heteroatoms chosen from the series consisting of nitrogen, oxygen and sulfur, which is bonded via a ring carbon atom, in another embodiment from the series consisting of phenyl and an aromatic 6-membered heterocycle which comprises one or two nitrogen atoms as ring heteroatoms, in another embodiment from the series consisting of phenyl, thiophenyl, pyridinyl and pyrimidinyl, in another embodiment from the series consisting of phenyl and thiophenyl, in another embodiment from the series consisting of phenyl, pyridinyl and pyrimidinyl, in another embodiment from the series consisting of phenyl and pyridinyl, and in another embodiment a group Ar occurring in $R^2$ is phenyl, which groups all are optionally substituted as indicated with respect to the compounds of formula I in general or in any embodiment specified above or below. In one embodiment, a group Ar occurring in $R^2$ is optionally substituted by one, two or three identical or different substituents, in another embodiment it is optionally substituted by one or two identical or different substituents, in another embodiment it is optionally substituted by one substituent, in another embodiment it is substituted by one, two or three identical or different substituents, in another embodiment it is substituted by one or two identical or different substituents, and in another embodiment it is substituted by one substituent. In one embodiment, the substituents which are optionally present on a group Ar occurring in $R^2$, are chosen from the series consisting of halogen, ($C_1$-$C_6$)-alkyl, ($C_1$-$C_6$)-alkyl-S(O)$_m$— and NC—, in another embodiment from the series consisting of halogen, ($C_1$-$C_6$)-alkyl, ($C_1$-$C_6$)-alkyl-O— and ($C_1$-$C_6$)-alkyl-S(O)$_m$—, in another embodiment from the series consisting of halogen, ($C_1$-$C_6$)-alkyl and ($C_1$-$C_6$)-alkyl-S(O)$_m$—, in another embodiment from the series consisting of halogen and ($C_1$-$C_6$)-alkyl, in another embodiment from the series consisting of halogen, in another embodiment from the series consisting of fluorine and chlorine, in another embodiment from the series consisting of fluorine, chlorine and methyl. In one embodiment of the invention, a ($C_1$-$C_6$)-alkyl group occurring in $R^2$ is a ($C_1$-$C_4$)-alkyl group, in another embodiment a ($C_1$-$C_2$)-alkyl group, in another embodiment it is methyl.

Examples of groups Ar which can occur in $R^2$, and from any one or more of which a group Ar occurring in $R^2$ is chosen in one embodiment of the invention, are phenyl, 2-fluoro-phenyl, 3-fluoro-phenyl, 4-fluoro-phenyl, 2-chloro-phenyl, 3-chloro-phenyl, 4-chloro-phenyl, 3-bromo-phenyl, 4-bromo-phenyl, 2,3-dichloro-phenyl, 2,4-dichloro-phenyl, 2,5-dichloro-phenyl, 2,6-dichloro-phenyl, 3,4-dichloro-phenyl, 2,3-difluoro-phenyl, 2,4-difluoro-phenyl, 2,5-difluoro-phenyl, 2,6-difluoro-phenyl, 3,4-difluoro-phenyl, 2-chloro-6-fluoro-phenyl, 3,4,5-trifluoro-phenyl, 2-methyl-phenyl (o-tolyl), 3-methyl-phenyl (m-tolyl), 4-methyl-phenyl (p-tolyl), 2,3-dimethyl-phenyl, 2,4-dimethyl-phenyl, 2,5-dimethyl-phenyl, 2,6-dimethyl-phenyl, 3,4-dimethyl-phenyl, 2-ethyl-phenyl, 3-ethyl-phenyl, 4-ethyl-phenyl, 3-isopropyl-phenyl, 3-tert-butyl-phenyl, 4-tert-butyl-phenyl, 3-trifluoromethyl-phenyl, 4-trifluoromethyl-phenyl, 2-fluoro-5-methyl-phenyl, 3-chloro-2-methyl-phenyl, 5-chloro-2-methyl-phenyl, 5-chloro-2-fluoro-3-methyl-phenyl, 2-fluoro-3-trifluoromethyl-phenyl, 2-fluoro-5-trifluoromethyl-phenyl, 4-fluoro-3-trifluoromethyl-phenyl, 5-fluoro-3-trifluoromethyl-phenyl, 3-chloro-4-trifluoromethyl-phenyl, 5-chloro-2-trifluoromethyl-phenyl, 5-chloro-3-trifluoromethyl-phenyl, 2-methoxy-phenyl, 3-methoxy-phenyl, 4-methoxy-phenyl, 3-ethoxy-phenyl, 3-propoxy-phenyl, 3-isopropoxy-phenyl, 4-tert-butoxy-phenyl, 3-trifluoromethoxy-phenyl, 4-trifluoromethoxy-phenyl, 3-(2,2,2-trifluoroethoxy)-phenyl, 5-chloro-2-methoxy-phenyl, 3-chloro-4-methoxy-phenyl, 5-fluoro-3-isopropoxy-phenyl, 2-fluoro-3-trifluoromethoxy-phenyl, 4-methoxy-3,5-dimethyl-phenyl, 3-methoxy-5-trifluoromethyl-phenyl, 2,3-methylenedioxyphenyl, 2,3-difluoromethylenedioxy-phenyl, 3,4-methylenedioxy-phenyl, 3,4-difluoromethylenedioxy-phenyl, 3-methylsulfanyl-phenyl, 3-ethylsulfanyl-phenyl, 3-trifluoromethylsulfanyl-phenyl, 3-methanesulfonyl-phenyl, 3-ethanesulfonyl-phenyl, 3-sulfamoyl-phenyl, 2-cyano-phenyl, 3-cyano-phenyl, 4-cyano-phenyl, thiophen-2-yl, thiophen-3-yl, 3-chloro-thiophen-2-yl, 4-chloro-thiophen-2-yl, 5-chloro-thiophen-2-yl, 4,5-dichloro-thiophen-2-yl, 5-chloro-thiophen-3-yl, 2,5-dichloro-thiophen-3-yl, 4-methyl-thiophen-2-yl, 5-methyl-thiophen-3-yl, 4,5-dimethyl-thiophen-2-yl, pyridin-2-yl, pyridin-3-yl, pyridin-4-yl, 2-chloro-pyridin-3-yl, 5-chloro-pyridin-2-yl, 6-chloro-pyridin-3-yl, 2-chloro-pyridin-4-yl, 2,6-dichloro-pyridin-3-yl, 6-methoxy-pyridin-3-yl, 2-chloro-6-methoxy-pyridin-3-yl.

In one embodiment of the invention, the group $R^3$ is chosen from the series consisting of hydrogen, halogen, $(C_1-C_6)$-alkyl, $(C_1-C_6)$-alkyl-O—, and NC—, in another embodiment from the series consisting of hydrogen, halogen, $(C_1-C_6)$-alkyl and NC—, in another embodiment from the series consisting of hydrogen, halogen, $(C_1-C_6)$-alkyl and $(C_1-C_6)$-alkyl-O—, in another embodiment from the series consisting of hydrogen, halogen and $(C_1-C_6)$-alkyl, in another embodiment from the series consisting of hydrogen and halogen, in another embodiment from the series consisting of hydrogen and $(C_1-C_6)$-alkyl, in another embodiment from the series consisting of hydrogen, fluorine and chlorine, in another embodiment $R^3$ is hydrogen, and in another embodiment $R^3$ is $(C_1-C_6)$-alkyl. In one embodiment of the invention, a $(C_1-C_6)$-alkyl group occurring in $R^3$ is a $(C_1-C_4)$-alkyl group, in another embodiment a $(C_1-C_2)$-alkyl group, in another embodiment it is methyl.

In one embodiment of the invention, the group $R^{10}$ is chosen from the series consisting of $R^{11}$—O— and $R^{12}$—N($R^{13}$)—C(O)—O—, in another embodiment from the series consisting of $R^{12}$—N($R^{13}$)—C(O)—O— and Het$^2$-C(O)—O—, and in another embodiment $R^{10}$ is $R^{11}$—O—.

In one embodiment, the group Het$^2$ which can occur in the group $R^2$, $R^3$, $R^4$ or $R^{10}$, is a saturated 4-membered to 6-membered, in another embodiment a 5-membered or 6-membered, in another embodiment a 5-membered, monocyclic heterocycle which, besides the ring nitrogen via which Het$^2$ is bonded, optionally comprises one further ring heteroatom chosen from the series nitrogen, oxygen and sulfur. In one embodiment, the group Het$^2$ which can occur in the group $R^2$, $R^3$, $R^4$ or $R^{10}$, does not comprise a further ring heteroatom besides the ring nitrogen atom via which Het$^2$ is bonded. In one embodiment, the group Het$^2$ which can occur in the group $R^2$, $R^3$, $R^4$ or $R^{10}$ is selected from the series pyrrolidine, piperidine and morpholine. In one embodiment, the number of substituents which are optionally present on a group Het$^2$ which can occur in group $R^2$, $R^3$, $R^4$ or $R^{10}$, is one, two, three or four, in another embodiment one, two or three, in another embodiment one or two, in another embodiment one, and in another embodiment such a group Het$^2$ is unsubstituted. In one embodiment, the substituents which are optionally present on a group Het$^2$ which can occur in the group $R^2$, $R^3$, $R^4$ or $R^{10}$, are chosen from the series consisting of fluorine, $(C_1-C_4)$-alkyl, HO— and $(C_1-C_4)$-alkyl-O—, in another embodiment from the series consisting of $(C_1-C_4)$-alkyl, HO— and $(C_1-C_4)$-alkyl-O—, in another embodiment from the series consisting of $(C_1-C_4)$-alkyl and HO— and $(C_1-C_4)$-alkyl-O—, in another embodiment they are $(C_1-C_4)$-alkyl substituents, and in another embodiment they are HO— substituents.

In one embodiment of the invention, the group $R^{11}$ is chosen from the series consisting of hydrogen, $R^{14}$, $(C_3-C_7)$-cycloalkyl and Het$^3$, in another embodiment from the series consisting of hydrogen and $R^{14}$, in another embodiment from the series consisting of hydrogen, $R^{14}$ and $(C_3-C_7)$-cycloalkyl, in another embodiment from the series consisting of $(C_3-C_7)$-cycloalkyl, Ar and Het$^3$, in another embodiment from the series consisting of $(C_3-C_7)$-cycloalkyl and Het$^3$, in another embodiment $R^{11}$ is hydrogen, in another embodiment $R^{11}$ is $R^{14}$, and in another embodiment $R^{11}$ is Ar. In one embodiment, a group Ar representing $R^{11}$ is phenyl which is optionally substituted as indicated with respect to the compounds of formula I in general or in any embodiment specified above or below. In one embodiment, a group Ar representing $R^{11}$ is optionally substituted by one, two or three identical or different substituents, in another embodiment it is optionally substituted by one or two identical or different substituents, in another embodiment it is optionally substituted by one substituent. In one embodiment, the substituents which are optionally present on a group Ar representing $R^{11}$, are chosen from the series consisting of halogen, $(C_1-C_4)$-alkyl, $(C_1-C_4)$-alkyl-O— and NC—, in another embodiment from the series consisting of halogen, $(C_1-C_4)$-alkyl and $(C_1-C_4)$-alkyl-O—, in another embodiment from the series consisting of halogen and $(C_1-C_4)$-alkyl. In one embodiment, a $(C_3-C_7)$-cycloalkyl group representing $R^{11}$ is a $(C_3-C_6)$-cycloalkyl group. In one embodiment, a group Het$^3$ representing $R^{11}$ is a saturated 4-membered to 6-membered monocyclic heterocycle which comprises one or two identical or different ring heteroatoms, in another embodiment one ring heteroatom, which are chosen from the series consisting of nitrogen, oxygen and sulfur, in another embodiment it comprises one ring heteroatom chosen from the series consisting of nitrogen and oxygen, in another embodiment one ring heteroatom chosen from the series consisting of oxygen and sulfur, and in another embodiment it comprises one oxygen atom as ring heteroatom, wherein the heterocycle is bonded via a ring carbon atom and is optionally substituted by one, two, three or four, in another embodiment by one or two, identical or different substituents chosen from the series consisting of fluorine, $(C_1-C_4)$-alkyl and oxo, in another embodiment from the series consisting of fluorine and $(C_1-C_4)$-alkyl.

In one embodiment of the invention, the groups $R^{12}$ and $R^{13}$ are independently of each other chosen from the series consisting of hydrogen and $R^{15}$, in another embodiment from the series consisting of $R^{15}$ and Ar, and in another embodiment they are identical or different groups $R^{15}$. In one embodiment, one of the groups $R^{12}$ and $R^{13}$ is chosen from the series consisting of $R^{15}$ and Ar, and the other is a group $R^{15}$. In one embodiment, a group Ar representing $R^{12}$ or $R^{13}$ is phenyl which is optionally substituted by one or two, in another embodiment by one, identical or different substituents chosen from the series consisting of halogen and $(C_1-C_4)$-alkyl, and in another embodiment it is unsubstituted phenyl.

In one embodiment of the invention, the $(C_1-C_{10})$-alkyl group representing the group $R^{14}$ is a $(C_1-C_8)$-alkyl group, in another embodiment a $(C_1-C_7)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a methyl group, in another embodiment a $(C_4-C_8)$-alkyl group, in another embodiment a $(C_4-C_7)$-alkyl group, in another embodiment a $(C_5-C_7)$-alkyl group, in another embodiment a $C_6$-alkyl group, wherein all these alkyl groups are linear or branched as applies to alkyl groups in the compounds of the formula I in general, and are optionally substituted by one or more identical or different substituents as indicated with respect to the compounds of formula I in general or in any embodiment specified above or below. In one embodiment of the invention, the number of optional substituents in an alkyl group representing $R^{14}$ is one, two, three or four, in another embodiment one, two or three, in another embodiment one or two, in another embodiment one. In one embodiment, an alkyl group representing $R^{14}$ is unsubstituted, and in another embodiment it is substituted by one, two, three or four, in another embodiment by one, two or three, in another embodiment by one or two, in another embodiment by one substituent as indicated.

In one embodiment, a $(C_3-C_7)$-cycloalkyl group occurring as a substituent on an alkyl group representing $R^{14}$ is a $(C_3-C_6)$-cycloalkyl group, in another embodiment it is a cyclopropyl group. In one embodiment, a group Ar occurring as a substituent on an alkyl group representing $R^{14}$ is phenyl or an aromatic 5-membered or 6-membered monocyclic heterocycle which comprises one or two identical or different ring heteroatoms chosen from the series consisting of nitrogen, oxygen and sulfur, and in another embodiment comprises one nitrogen atom as ring heteroatom and in the case of a 5-membered heterocycle one additional ring heteroatom chosen from the series consisting of nitrogen, oxygen and sulfur, and in another embodiment a group Ar occurring as a substituent in an alkyl group representing $R^{14}$ is chosen from phenyl, pyrazolyl, isoxazolyl and thiazolyl, wherein all these groups Ar are optionally substituted by one or more identical or different substituents as indicated with respect to the compounds of formula I in general or in any embodiment specified above or below. In one embodiment, the number of optional substituents on a group Ar occurring as a substituent in an alkyl group representing $R^{14}$ is one, two or three, in another embodiment one or two, in another embodiment one. In one embodiment, the substituents which are optionally present on a group Ar occurring as a substituent in an alkyl group representing $R^{14}$, are chosen from the series consisting of halogen, $(C_1-C_4)$-alkyl, $(C_1-C_4)$-alkyl-O— and NC—, in another embodiment from the series consisting of halogen, $(C_1-C_4)$-alkyl and $(C_1-C_4)$-alkyl-O—, in another embodiment from the series consisting of halogen and $(C_1-C_4)$-alkyl, and in another embodiment they are $(C_1-C_4)$-alkyl groups.

In one embodiment, a group $Het^1$ occurring as a substituent on an alkyl group representing $R^{14}$ is a saturated or unsaturated 4-membered to 6-membered heterocycle, in another embodiment a 5-membered or 6-membered heterocycle, which comprises a ring nitrogen atom via which $Het^1$ is bonded and optionally one further ring heteroatom chosen from the series consisting of nitrogen, oxygen and sulfur, which is optionally substituted as indicated with respect to the compounds of formula I in general or in any embodiment specified above or below. In one embodiment, a group $Het^1$ occurring as a substituent on an alkyl group representing $R^{14}$ does not comprise any further ring heteroatom besides the ring nitrogen atom via which $Het^1$ is bonded. In one embodiment, a group $Het^1$ occurring as a substituent on an alkyl group representing $R^{14}$ is saturated, in another embodiment it is unsaturated. In one embodiment, the number of substituents which are optionally present on a group $Het^1$ occurring as a substituent on an alkyl group representing $R^{14}$ is one, two, three or four, in another embodiment one, two or three, in another embodiment one or two, in another embodiment one. In one embodiment, the substituents which are optionally present on a group $Het^1$ occurring as a substituent on an alkyl group representing $R^{14}$ are chosen from the series consisting of halogen, $(C_1-C_4)$-alkyl, HO—, $(C_1-C_4)$-alkyl-O— and oxo, in another embodiment from the series consisting of fluorine, $(C_1-C_4)$-alkyl, HO— and oxo, in another embodiment from the series consisting of fluorine, $(C_1-C_4)$-alkyl and oxo, in another embodiment from the series consisting of $(C_1-C_4)$-alkyl and oxo, and in another embodiment they are oxo substituents. In one embodiment, the number of oxo substituents which are optionally present on a group $Het^1$ occurring as a substituent on an alkyl group representing $R^{14}$, is not greater than two, and in another embodiment it is not greater than one.

In one embodiment, a group $Het^1$ occurring in the substituent $Het^1$-C(O)— on an alkyl group representing $R^{14}$ is a 4-membered to 6-membered heterocycle, in another embodiment a 5-membered or 6-membered heterocycle, which is saturated or unsaturated and comprises a ring nitrogen atom via which $Het^1$ is bonded and optionally one further ring heteroatom chosen from the series consisting of nitrogen, oxygen and sulfur, and which is optionally substituted as indicated with respect to the compounds of formula I in general or in any embodiment specified above or below. In one embodiment, a group $Het^1$ occurring in the substituent $Het^1$-C(O)— on an alkyl group representing $R^{14}$ does not comprise any further ring heteroatom besides the ring nitrogen atom via which $Het^1$ is bonded. In one embodiment, a group $Het^1$ occurring in the substituent $Het^1$-C(O)— on an alkyl group representing $R^{14}$ is saturated or comprises one double bond within the ring, and in another embodiment it is saturated. In one embodiment, the number of substituents which are optionally present on a group $Het^1$ occurring in the substituent $Het^1$-C(O)— on an alkyl group representing $R^{14}$ is one, two, three or four, in another embodiment one, two or three, in another embodiment one or two, in another embodiment one. In one embodiment, the substituents which are optionally present on a group $Het^1$ occurring in the substituent $Het^1$-C(O)— on an alkyl group representing $R^{14}$ are chosen from the series consisting of halogen, $(C_1-C_4)$-alkyl, HO—, $(C_1-C_4)$-alkyl-O— and oxo, in another embodiment from the series consisting of fluorine, $(C_1-C_4)$-alkyl, HO— and oxo, in another embodiment from the series consisting of fluorine, $(C_1-C_4)$-alkyl and oxo, in another embodiment from $(C_1-C_4)$-alkyl and oxo, in another embodiment they are oxo substituents, and in another embodiment they are $(C_1-C_4)$-alkyl substituents. In one embodiment, the number of oxo substituents which are optionally present on a group $Het^1$ occurring in the substituent $Het^1$-C(O)— on an alkyl group representing $R^{14}$, is not greater than two, and in another embodiment it is not greater than one, and in another embodiment no oxo substituents are present on such a group $Het^1$.

In one embodiment, a group $Het^3$ occurring as a substituent on an alkyl group representing $R^{14}$ is a saturated 4-membered to 6-membered monocyclic heterocycle which comprises one or two identical or different ring heteroatoms, and in another embodiment comprises one ring heteroatom, which are chosen from the series consisting of nitrogen, oxygen and sulfur, and is bonded via a ring carbon atom and is optionally substituted as indicated with respect to the compounds of formula I in general or in any embodiment specified above or below. In one embodiment, the ring heteroatoms in a group $Het^3$ occurring as a substituent on an alkyl group representing $R^{14}$ are chosen from the series consisting of nitrogen and oxygen, in another embodiment from the series consisting of oxygen and sulfur, in another embodiment they are nitrogen atoms, and in another embodiment they are oxygen atoms. In one embodiment, the number of substituents which are optionally present on a group $Het^3$ occurring as a substituent on an alkyl group representing $R^{14}$ is one, two, three or four, in another embodiment one, two or three, in another embodiment one or two, in another embodiment one. In one embodiment, the substituents which are optionally present on a group $Het^3$ occurring as a substituent on an alkyl group representing $R^{14}$ are chosen from the series consisting of fluorine and $(C_1-C_4)$-alkyl, in another embodiment from the series consisting of $(C_1-C_4)$-alkyl and oxo, in another embodiment they are $(C_1-C_4)$-alkyl substituents, and in another embodiment they are oxo substituents. In one embodiment, the number of oxo substituents which are optionally present on a group $Het^3$ occurring as a substituent on an alkyl group representing $R^{14}$, is not greater than two, and in another embodiment it is not greater than one.

In one embodiment, the substituents which are optionally present on an alkyl group representing $R^{14}$ are chosen from the series consisting of halogen, HO—, $R^{16}$—O—, oxo, $(C_3$-$C_7)$-cycloalkyl, Ar, $Het^1$, $Het^3$, $H_2N$—C(O)—, $(C_1-C_4)$-alkyl-NH—C(O)—, di(($C_1-C_4$)-alkyl)N—C(O)— and $Het^1$-C(O)—, in another embodiment from the series consisting of halogen, HO—, $R^{16}$—O—, oxo, $(C_3-C_7)$-cycloalkyl, $Het^1$, $Het^3$, $H_2N$—C(O)—, NH—C(O)—, di(($C_1-C_4$)-alkyl)N—C(O)— and $Het^1$-C(O)—, in another embodiment from the series consisting of halogen, HO—, $R^{16}$—O—, oxo, $(C_3-C_7)$-cycloalkyl, $Het^1$, $Het^3$, di(($C_1-C_4$)-alkyl)N—C(O)— and $Het^1$-C(O)—, in another embodiment from the series consisting of halogen, HO—, $R^{16}$—O—, oxo, $(C_3-C_7)$-cycloalkyl, $Het^1$ and $Het^3$, in another embodiment from the series consisting of halogen, HO—, $R^{16}$—O—, oxo, $(C_3-C_7)$-cycloalkyl, Ar, $Het^1$ and $Het^3$, in another embodiment from the series consisting of HO—, $R^{16}$—O—, oxo, $(C_3-C_7)$-cycloalkyl, Ar, $Het^1$, di(($C_1-C_4$)-alkyl)N—C(O)— and $Het^1$-C(O)—, in another embodiment from the series consisting of HO—, $R^{16}$—O—, oxo, $(C_3-C_7)$-cycloalkyl, Ar, di(($C_1-C_4$)-alkyl)N—C(O)— and $Het^1$-C(O)—, in another embodiment from the series consisting of HO—, $R^{16}$—O—, oxo, $(C_3-C_7)$-cycloalkyl and Ar, in another embodiment from the series consisting of HO—, $R^{16}$—O—, oxo, $(C_3-C_7)$-cycloalkyl, di(($C_1-C_4$)-alkyl)N—C(O)— and $Het^1$-C(O)—, in another embodiment from the series consisting of HO—, $R^{16}$—O—, oxo, $(C_3-C_7)$-cycloalkyl, $Het^1$ and $Het^3$, in another embodiment from the series consisting of HO—, oxo, $(C_3-C_7)$-cycloalkyl and $Het^3$, in another embodiment from the series consisting of HO—, oxo, $(C_3-C_7)$-cycloalkyl and $Het^3$, in another embodiment from the series consisting of HO—, oxo and $(C_3-C_7)$-cycloalkyl, in another embodiment from the series consisting of HO—, oxo and $Het^3$, in another embodiment from the series consisting of HO— and oxo, in another embodiment from the series consisting of HO—, $R^{16}$—O—, $(C_3-C_7)$-cycloalkyl and $Het^3$, in another embodiment from the series consisting of HO—, $(C_3-C_7)$-cycloalkyl and $Het^3$, in another embodiment from the series consisting of HO— and $(C_3-C_7)$-cycloalkyl, in another embodiment from the series consisting of HO— and $Het^3$, in another embodiment they are HO— substituents, and in another embodiment they are oxo substituents. In one embodiment, the number of oxo substituents which are optionally present on an alkyl group representing $R^{14}$, is not greater than two, and in another embodiment it is not greater than one. In one embodiment, halogen atoms occurring as substituents on an alkyl group representing $R^{14}$, are chosen from the series consisting of fluorine and chlorine atoms, and in another embodiment they are fluorine atoms and, besides being substituted by an other substituents, in this latter embodiment an alkyl group representing $R^{14}$ is thus optionally substituted by fluorine substituents as applies to alkyl groups in the compounds of the formula I in general.

Examples of groups which can represent $R^{14}$, and from any one or more of which $R^{14}$ is chosen in one embodiment of the invention, are methyl, ethyl, propyl, isopropyl, butyl, isobutyl, cyclopropylmethyl, benzyl, 2-hydroxy-ethyl, 2-hydroxy-propyl, 2-hydroxy-butyl, 2-hydroxy-2-methyl-propyl, 2-hydroxy-2-methyl-butyl, 2-hydroxy-3-methyl-butyl, 2-hydroxy-2,3-dimethyl-butyl, 2-hydroxy-3,3-dimethyl-butyl, 2-ethyl-2-hydroxy-butyl, 2-hydroxy-2,3,3-trimethyl-butyl, 2-ethyl-2-hydroxy-3-methyl-butyl, 2-ethyl-2-hydroxy-3,3-dimethyl-butyl, 2-cyclopropyl-2-hydroxy-ethyl, 2-cyclopropyl-2-hydroxy-propyl, 2-cyclopropyl-2-hydroxy-butyl, 2-oxo-propyl, 2-oxo-butyl, 3-methyl-2-oxo-butyl, 3,3-dimethyl-2-oxo-butyl, 2-cyclopropyl-2-oxo-ethyl.

In case the optionally substituted alkyl group representing $R^{14}$, including the examples of groups listed afore which can represent $R^{14}$, contains a chiral carbon atom, the compound of the formula I can be present with respect to this carbon atom in any of it stereoisomeric forms, i.e. in R configuration or in S configuration, or in the form of a mixture of the stereoisomeric forms in any ratio, for example as a mixture of the two stereoisomeric forms in a molar ratio of 1:1, as applies to all chiral carbon atoms in the compounds of the formula I. In one embodiment of the invention, the compound of the formula I has at a chiral carbon atom in $R^{14}$ pure stereochemical configuration, either R configuration or S configuration, or essentially pure stereochemical configuration, for example with a molar ratio of the two configurations of 99:1 or greater.

In one embodiment of the invention, the $(C_1-C_6)$-alkyl group representing the group $R^{15}$ is a $(C_1-C_4)$-alkyl group, in another embodiment a $(C_1-C_2)$-alkyl group, in another embodiment a methyl group, wherein all these alkyl groups are optionally substituted by one or more identical or different substituents as indicated with respect to the compounds of formula I in general or in any embodiment specified above or below. In one embodiment of the invention, the number of optional substituents in an alkyl group representing $R^{15}$ is one or two, in another embodiment one. In one embodiment, the alkyl group representing $R^{15}$ is unsubstituted. In one embodiment, the substituents which are optionally present on an alkyl group representing $R^{15}$ are chosen from the series consisting of HO— and $(C_1-C_4)$-alkyl-O—.

In one embodiment of the invention, the $(C_1-C_6)$-alkyl group representing the group $R^{16}$ is a $(C_1-C_4)$-alkyl group, in another embodiment a $(C_1-C_3)$-alkyl group, in another embodiment a $(C_2-C_3)$-alkyl group, in another embodiment an ethyl group, in another embodiment a methyl group, wherein all these alkyl groups are optionally substituted by one or more identical or different substituents as indicated with respect to the compounds of formula I in general or in any embodiment specified above or below. In one embodiment of the invention, the number of optional substituents in an alkyl group representing $R^{16}$ is one or two, in another embodiment one. In one embodiment, an alkyl group representing $R^{14}$ is unsubstituted, in another embodiment it is substituted by one or two identical or different substituents, in another embodiment it is substituted by one substituent. In one embodiment, the substituents which are optionally present on an alkyl group representing $R^{15}$ are chosen from the series consisting of HO— and $(C_1-C_4)$-alkyl-O—, in another embodiment they are HO— substituents, in another embodiment they are $(C_1-C_4)$-alkyl-O— substituents, and in another embodiment they are $(C_1-C_2)$-alkyl-O-substituents.

In one embodiment of the invention, the group $R^{30}$ is chosen from the series consisting of $R^{31}$, $(C_3-C_7)$-cycloalkyl and $Het^3-C_uH_{2u}$—, in another embodiment from the series consisting of $(C_3-C_7)$-cycloalkyl, $R^{32}$—$C_uH_{2u}$— and $Het^3$-$C_uH_{2u}$—, in another embodiment from the series consisting of $R^{32}$—$C_uH_{2u}$— and $Het^3$-$C_uH_{2u}$—, in another embodiment $R^{30}$ is $R^{32}$—$C_uH_{2u}$—, and in another embodiment $R^{30}$ is $R^{31}$. In one embodiment, u is an integer chosen from the series consisting of 0, 1 and 2, in another embodiment from the series consisting of 0 and 1, in another embodiment from the series consisting of 1 and 2, in another embodiment u is 0, and in another embodiment u is 1. In one embodiment, $R^{30}$ is $R^{32}$—$C_uH_{2u}$— and u is 0, i.e., in this embodiment $R^{30}$ is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted as indicated with respect to the compounds of formula I in general or in any embodiment specified above or below. In one embodiment, the divalent alkanediyl group $C_uH_{2u}$ is a linear group.

In one embodiment, the $(C_3-C_7)$-cycloalkyl group representing $R^{30}$ is a $(C_3-C_6)$-cycloalkyl group, in another embodiment a $(C_6-C_6)$-cycloalkyl group, in another embodiment a cyclopropyl group. In one embodiment, a group $Het^3$ occurring in $R^{30}$ is a saturated 4-membered to 6-membered monocyclic heterocycle, in another embodiment a saturated 5-membered or 6-membered heterocycle, in another embodiment a saturated 6-membered heterocycle, which comprises one or two identical or different ring heteroatoms, and in another embodiment comprises one ring heteroatom, which are chosen from the series consisting of nitrogen, oxygen and sulfur, and is bonded via a ring carbon atom and is optionally substituted as indicated with respect to the compounds of formula I in general or in any embodiment specified above or below. In one embodiment, the ring heteroatoms in a group $Het^3$ occurring in $R^{30}$ are chosen from the series consisting of nitrogen and oxygen, in another embodiment from the series consisting of oxygen and sulfur, in another embodiment they are nitrogen atoms, and in another embodiment they are oxygen atoms. In one embodiment, the number of substituents which are optionally present on a group $Het^3$ occurring in $R^{30}$ is one, two, three or four, in another embodiment one, two or three, in another embodiment one or two, in another embodiment one, and in another embodiment a group $Het^3$ occurring in $R^{30}$ is unsubstituted. In one embodiment, the substituents which are optionally present on a group $Het^3$ occurring in $R^{30}$ are chosen from the series consisting of fluorine and $(C_1-C_4)$-alkyl, in another embodiment they are $(C_1-C_4)$-alkyl substituents.

In one embodiment of the invention, the $(C_1-C_{10})$-alkyl group representing $R^{31}$ is a $(C_1-C_8)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a methyl group, in another embodiment a $(C_4-C_8)$-alkyl group, in another embodiment a $(C_5-C_8)$-alkyl group, wherein all these alkyl groups are optionally substituted by one or more identical or different substituents as indicated with respect to the compounds of formula I in general or in any embodiment specified above or below. In one embodiment of the invention, the number of optional substituents in an alkyl group representing $R^{31}$ is one, two or three, in another embodiment one or two, in another embodiment one. In one embodiment, an alkyl group representing $R^{31}$ is unsubstituted, and in another embodiment it is substituted by one, two or three, in another embodiment by one or two, in another embodiment by one substituent as indicated. In one embodiment, the optional substituents on an alkyl group representing $R^{31}$ are chosen from the series consisting of halogen, $(C_3-C_7)$-cycloalkyl, $(C_1-C_6)$-alkyl-O— and NC—, in another embodiment from the series consisting of halogen, $(C_3-C_7)$-cycloalkyl and $(C_1-C_6)$-alkyl-O—, in another embodiment from the series consisting of halogen and $(C_3-C_7)$-cycloalkyl, and in another embodiment they are $(C_3-C_7)$-cycloalkyl substituents. In one embodiment, halogen atoms occurring as substituents on an alkyl group representing $R^{31}$, are chosen from the series consisting of fluorine and chlorine atoms, and in another embodiment they are fluorine atoms and, besides being substituted by an other substituents, in this latter embodiment an alkyl group representing $R^{31}$ is thus optionally substituted by fluorine substituents as applies to alkyl groups in the compounds of the formula I in general. In one embodiment, a $(C_3-C_7)$-cycloalkyl group occurring as a substituent on an alkyl group representing $R^{30}$ is a $(C_3-C_6)$-cycloalkyl group, in another embodiment a $(C_5-C_6)$-cycloalkyl group, in another embodiment a cyclopropyl group.

In one embodiment of the invention, the group $R^{32}$ is chosen from the series consisting of phenyl and an aromatic 5-membered or 6-membered monocyclic heterocycle which comprises one or two identical or different ring heteroatoms, in another embodiment one ring heteroatom, which are chosen from the series consisting of nitrogen, oxygen and sulfur, and is bonded via a ring carbon atom, in another embodiment from the series consisting of phenyl and an aromatic 6-membered monocyclic heterocycle which comprises one or two nitrogen atoms as ring heteroatoms, wherein the phenyl and the heterocycle all are optionally substituted by one or more identical or different substituents as indicated with respect to the compounds of formula I in general or in any embodiment specified above or below. In one embodiment, the ring heteroatoms in an aromatic heterocycle representing $R^{32}$ are chosen from the series consisting of nitrogen and sulfur, in another embodiment they are nitrogen atoms. In one embodiment, $R^{32}$ is chosen from the series consisting of phenyl and an aromatic 6-membered heterocycle as defined, in another embodiment $R^{32}$ is a 6-membered monocyclic heterocycle as defined, in another embodiment $R^{32}$ is chosen from the series consisting of phenyl, thiophenyl and pyridinyl, in another embodiment from the series consisting of phenyl and pyridinyl, in another embodiment $R^{32}$ is phenyl, and in another embodiment $R^{32}$ is pyridinyl, all of which are optionally substituted by one or more identical or different substituents as indicated with respect to the compounds of formula I in general or in any embodiment specified above or below. In one embodiment, the number of substituents which are optionally present on a phenyl group and an aromatic heterocycle representing $R^{32}$ is one, two, three or four, in another embodiment one, two or three, in another embodiment one or two, in another embodiment one.

In one embodiment, the substituents which are optionally present on a phenyl group and an aromatic heterocycle representing $R^{32}$, in particular on a phenyl group, are chosen from the series the series consisting of from halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, $H_2N$—S(O)$_2$—, $(C_1-C_4)$-alkyl-NH—S(O)$_2$—, di(($C_1-C_4$)-alkyl)N—S(O)$_2$—, $(C_1-C_6)$-alkyl-NH—, di(($C_1-C_6$)-alkyl)N—, $Het^1$, $(C_1-C_4)$-alkyl-C(O)—NH—, Ar—C(O)—NH—, $(C_1-C_4)$-alkyl-S(O)$_2$—NH— and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, $H_2N$—S(O)$_2$—, $(C_1-C_4)$-alkyl-NH—S(O)$_2$—, di(($C_1-C_4$)-alkyl)N—S(O)$_2$—, $(C_1-C_6)$-alkyl-NH—, di(($C_1-C_6$)-alkyl)N—, $Het^1$ and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—$(C_1-C_6)$-alkyl-S(O)$_m$—, $(C_1-C_6)$-alkyl-NH—, di(($C_1-C_6$)-alkyl)N—, $Het^1$ and NC—, in another embodiment from the series consisting of halogen, $(C_1-C_6)$-alkyl, $R^{33}$, $(C_1-C_6)$-alkyl-O—, $R^{33}$—O—, —O—$CH_2$—O—, —O—$CF_2$—O—, $(C_1-C_6)$-alkyl-S(O)$_m$—, $Het^1$ and NC—, in another embodiment from the series consisting of halogen, $(C_1-C_6)$-alkyl, $R^{33}$, $(C_1-C_6)$-alkyl-O—, $R^{33}$—O—, —O—CH$_2$—O—, —O—CF$_2$—O— and NC—, in another embodiment from the series consisting of halogen, $(C_1-C_6)$-alkyl, $R^{33}$, $(C_1-C_6)$-alkyl-O—, $R^{33}$—O— and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—CH$_2$—O—, —O—CF$_2$—O—, $(C_1-C_6)$-alkyl-S(O)$_m$—, di(($C_1-C_4$)-alkyl)N—S(O)$_2$—, H$_2$N—, di(($C_1-C_6$)-alkyl)N—, Het$^1$, $(C_1-C_4)$-alkyl-C(O)—NH—, Ar—C(O)—NH— and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—CH$_2$—O—, —O—CF$_2$—O—, $(C_1-C_6)$-alkyl-S(O)$_m$—, di(($C_1-C_4$)-alkyl)N—S(O)$_2$—, H$_2$N—, di(($C_1-C_6$)-alkyl)N—, Het$^1$ and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—CH$_2$—O—, —O—CF$_2$—O—, $(C_1-C_6)$-alkyl-S(O)$_m$—, di(($C_1-C_4$)-alkyl)N—S(O)$_2$—, di(($C_1-C_6$)-alkyl)N—, Het$^1$ and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, $(C_1-C_6)$-alkyl-S(O)$_m$—, di(($C_1-C_4$)-alkyl)N—S(O)$_2$—, di(($C_1-C_6$)-alkyl)N—, Het$^1$ and NC—, in another embodiment from the series consisting of halogen, $(C_1-C_6)$-alkyl, $R^{33}$, $(C_1-C_6)$-alkyl-O— and $R^{33}$—O—, in another embodiment from the series consisting of halogen, $(C_1-C_6)$-alkyl, $R^{33}$ and $(C_1-C_6)$-alkyl-O—, in another embodiment from the series consisting of halogen, $(C_1-C_6)$-alkyl and $R^{33}$, in another embodiment from the series consisting of halogen and $(C_1-C_6)$-alkyl. In one embodiment, in case that substituents from the series consisting of $(C_3-C_7)$-cycloalkyl, $R^{33}$, $R^{33}$—O—, $R^{33}$—$(C_1-C_4)$-alkyl-O—, —O—CH$_2$—O—, —O—CF$_2$—O—, Het$^1$ and Ar—C(O)—NH— are present on a phenyl group and an aromatic heterocycle representing $R^{32}$, not more than two such substituents, in another embodiment not more than one such substituent, are present, either without any other substituents or together with any other substituents.

In one embodiment, a $(C_1-C_6)$-alkyl group occurring in a substituent on a phenyl group and an aromatic heterocycle representing $R^{32}$ is a $(C_1-C_4)$-alkyl group, in another embodiment a $(C_1-C_3)$-alkyl group, in another embodiment a $(C_1-C_2)$-alkyl group, in another embodiment a methyl group. In one embodiment, a $(C_3-C_7)$-cycloalkyl group occurring as a substituent on a phenyl group and an aromatic heterocycle representing $R^{32}$ is a $(C_3-C_6)$-cycloalkyl group, in another embodiment a $(C_3-C_5)$-cycloalkyl group, in another embodiment a $(C_3-C_4)$-cycloalkyl group, in another embodiment it is a cyclopropyl group. In one embodiment, a group Ar occurring in a substituent on a phenyl group and an aromatic heterocycle representing $R^{32}$ is chosen from the series consisting of phenyl and an aromatic 5-membered or 6-membered heterocycle which comprises one or two identical or different ring heteroatoms, in another embodiment one ring heteroatom, chosen from the series consisting of nitrogen, oxygen and sulfur, which is bonded via a ring carbon atom, and in another embodiment it is a phenyl group, which groups all are optionally substituted as indicated with respect to the compounds of formula I in general or in any embodiment specified above or below. In one embodiment, the number of optional substituents on a group Ar occurring in a substituent on a phenyl group and an aromatic heterocycle representing $R^{32}$ is one or two, in another embodiment one, and the optional substituents are chosen from the series consisting of halogen, $(C_1-C_4)$-alkyl, $(C_1-C_4)$-alkyl-S(O)$_m$— and NC—, in another embodiment from the series consisting of halogen, $(C_1-C_4)$-alkyl and $(C_1-C_4)$-alkyl-O—, in another embodiment from the series consisting of halogen and $(C_1-C_4)$-alkyl, and in another embodiment such a group Ar is unsubstituted.

In one embodiment, a group Het$^1$ occurring as a substituent on a phenyl group or an aromatic heterocycle representing $R^{32}$ is a saturated or unsaturated 4-membered to 6-membered monocyclic heterocycle, in another embodiment a 5-membered or 6-membered heterocycle, which comprises a ring nitrogen atom via which Het$^1$ is bonded and optionally one or two further ring heteroatoms, in another embodiment one further ring heteroatom, which are chosen from the series consisting of nitrogen, oxygen and sulfur, which is optionally substituted as indicated with respect to the compounds of formula I in general or in any embodiment specified above or below. In one embodiment, a group Het$^1$ occurring as a substituent on a phenyl group or an aromatic heterocycle representing $R^{32}$ does not comprise any further ring heteroatom besides the ring nitrogen atom via which Het$^1$ is bonded. In one embodiment, a group Het$^1$ occurring as a substituent on a phenyl group or an aromatic heterocycle representing $R^{32}$ is saturated, in another embodiment it is unsaturated. In one embodiment, the number of substituents which are optionally present on a group Het$^1$ occurring as a substituent on a phenyl group or an aromatic heterocycle representing $R^{32}$ is one, two, three or four, in another embodiment one, two or three, in another embodiment one or two, in another embodiment one, and in another embodiment such a group Het$^1$ is unsubstituted. In one embodiment, the substituents which are optionally present on a group Het$^1$ occurring as a substituent on a phenyl group or an aromatic heterocycle representing $R^{32}$ are chosen from the series consisting of halogen, $(C_1-C_4)$-alkyl, HO—, $(C_1-C_4)$-alkyl-O— and oxo, in another embodiment from the series consisting of fluorine, $(C_1-C_4)$-alkyl, HO— and oxo, in another embodiment from the series consisting of fluorine, $(C_1-C_4)$-alkyl and oxo, and in another embodiment they are $(C_1-C_4)$-alkyl substituents.

Examples of groups $R^{32}$ from any one or more of which $R^{32}$ is chosen in one embodiment of the invention, are phenyl, 2-fluoro-phenyl, 3-fluoro-phenyl, 4-fluoro-phenyl, 2-chloro-phenyl, 3-chloro-phenyl, 4-chloro-phenyl, 3-bromo-phenyl, 4-bromo-phenyl, 2,3-dichloro-phenyl, 2,4-dichloro-phenyl, 2,5-dichloro-phenyl, 2,6-dichloro-phenyl, 3,4-dichloro-phenyl, 2,3-difluoro-phenyl, 2,4-difluoro-phenyl, 2,5-difluoro-phenyl, 2,6-difluoro-phenyl, 3,4-difluoro-phenyl, 2-chloro-6-fluoro-phenyl, 3,4,5-trifluoro-phenyl, 2-methyl-phenyl (o-tolyl), 3-methyl-phenyl (m-tolyl), 4-methyl-phenyl (p-tolyl), 2,3-dimethyl-phenyl, 2,4-dimethyl-phenyl, 2,5-dimethyl-phenyl, 2,6-dimethyl-phenyl, 3,4-dimethyl-phenyl, 2-ethyl-phenyl, 3-ethyl-phenyl, 4-ethyl-phenyl, 3-isopropyl-phenyl, 3-tert-butyl-phenyl, 4-tert-butyl-phenyl, 3-trifluoromethyl-phenyl, 4-trifluoromethyl-phenyl, 2-fluoro-5-methyl-phenyl, 3-chloro-2-methyl-phenyl, 5-chloro-2-methyl-phenyl, 5-chloro-2-fluoro-3-methyl-phenyl, 2-fluoro-3-trifluoromethyl-phenyl, 2-fluoro-5-trifluoromethyl-phenyl, 4-fluoro-3-trifluoromethyl-phenyl, 5-fluoro-3-trifluoromethyl-phenyl, 3-chloro-4-trifluoromethyl-phenyl, 5-chloro-2-trifluoromethyl-phenyl, 5-chloro-3-trifluoromethyl-phenyl, 2-methoxy-phenyl, 3-methoxy-phenyl, 4-methoxy-phenyl, 3-ethoxy-phenyl, 3-propoxy-phenyl, 3-isopropoxy-phenyl, 4-tert-butoxy-phenyl, 3-trifluoromethoxy-phenyl, 4-trifluoromethoxy-phenyl, 3-(2,2,2-trifluoroethoxy)-phenyl, 5-chloro-2-methoxy-phenyl, 3-chloro-4-methoxy-phenyl, 5-fluoro-3-isopropoxy-phenyl, 2-fluoro-3-trifluoromethoxy-phenyl, 4-methoxy-3,5-dimethyl-phenyl, 3-methoxy-5-trifluoromethyl-phenyl, 2,3-methylenedioxy-phenyl, 2,3-difluoromethylenedioxy-phenyl, 3,4-methylenedioxy-phenyl, 3,4-difluoromethylenedioxy-phenyl, 3-methylsulfanyl-phenyl, 3-ethylsulfanyl-phenyl, 3-trifluoromethylsulfanyl-phenyl, 3-methanesulfonyl-phenyl, 3-ethanesulfonyl-phenyl, 3-sulfamoyl-phenyl, 2-cyanophenyl, 3-cyano-phenyl, 4-cyano-phenyl, thiophen-2-yl, thiophen-3-yl, 3-chloro-thiophen-2-yl, 4-chloro-thiophen-2-yl, 5-chloro-thiophen-2-yl, 4,5-dichloro-thiophen-2-yl, 5-chloro-thiophen-3-yl, 2,5-dichloro-thiophen-3-yl, 4-methyl-thiophen-2-yl, 5-methyl-thiophen-3-yl, 4,5-dimethyl-thiophen-2-yl, pyridin-2-yl, pyridin-3-yl, pyridin-4-yl, 2-chloro-pyridin-3-yl, 5-chloro-pyridin-2-yl, 6-chloro-pyridin-3-yl, 2-chloro-pyridin-4-yl, 2,6-dichloro-pyridin-3-yl, 6-methoxy-pyridin-3-yl, 2-chloro-6-methoxy-pyridin-3-yl.

In one embodiment of the invention, the group $R^{33}$ is chosen from the series consisting of phenyl and an aromatic 5-membered or 6-membered monocyclic heterocycle which comprises one or two identical or different ring heteroatoms, in another embodiment one ring heteroatom, which is chosen from the series consisting of nitrogen, oxygen and sulfur, and is bonded via a ring carbon atom, wherein the phenyl and the heterocycle all are optionally substituted by one or more identical or different substituents as indicated with respect to the compounds of formula I in general or in any embodiment specified above or below. In one embodiment, the ring heteroatoms in an aromatic heterocycle representing $R^{33}$ are chosen from the series consisting of nitrogen and sulfur, in another embodiment they are nitrogen atoms. In one embodiment, $R^{33}$ is chosen from the series consisting of phenyl and an aromatic 6-membered heterocycle as defined, in another embodiment from the series consisting of phenyl and an aromatic 6-membered heterocycle which comprises one or two nitrogen atoms as ring heteroatoms, in another embodiment $R^{33}$ is a 6-membered monocyclic heterocycle as defined, in another embodiment it is an aromatic 6-membered heterocycle which comprises one or two nitrogen atoms as ring heteroatoms, in another embodiment $R^{33}$ is chosen from the series consisting of phenyl, thiophenyl and pyridinyl, in another embodiment from the series consisting of phenyl and pyridinyl, in another embodiment $R^{33}$ is phenyl, and in another embodiment $R^{33}$ is pyridinyl, all of which are optionally substituted by one or more identical or different substituents as indicated with respect to the compounds of formula I in general or in any embodiment specified above or below. In one embodiment, the number of substituents which are optionally present on a phenyl group and an aromatic heterocycle representing $R^{33}$ is one, two or three, in another embodiment one or two, in another embodiment one.

In one embodiment, the substituents which are optionally present on a phenyl group and an aromatic heterocycle representing $R^{33}$, are chosen from the series consisting of halogen, $(C_1-C_6)$-alkyl, $(C_3-C_7)$-cycloalkyl, HO—, $(C_1-C_6)$-alkyl-O—, $(C_1-C_6)$-alkyl-S(O)$_m$—, $H_2N$—S(O)$_2$—, di(($C_1$-$C_4$)-alkyl)N—S(O)$_2$— and NC—, in another embodiment from the series consisting of halogen, $(C_1-C_6)$-alkyl, $(C_3-C_7)$-cycloalkyl, HO—, $(C_1-C_6)$-alkyl-$H_2N$—S(O)$_2$—, di(($C_1$-$C_4$)-alkyl)N—S(O)$_2$— and NC—, in another embodiment from the series consisting of halogen, $(C_1-C_6)$-alkyl, $(C_3-C_7)$-cycloalkyl, HO—, $(C_1-C_6)$-alkyl-O— and NC—, are chosen from the series the series consisting of halogen, $(C_1-C_4)$-alkyl, $(C_1-C_4)$-alkyl-O—, $(C_1-C_4)$-alkyl-S(O)$_m$— and NC—, in another embodiment from the series consisting of halogen, $(C_1-C_4)$-alkyl, $(C_1-C_4)$-alkyl-O— and NC—, in another embodiment from the series consisting of halogen, $(C_1-C_4)$-alkyl and $(C_1-C_4)$-alkyl-O—, in another embodiment from the series consisting of halogen and $(C_1-C_4)$-alkyl. In one embodiment, a $(C_1-C_6)$-alkyl group occurring in a substituent on a phenyl group and an aromatic heterocycle representing $R^{33}$ is a $(C_1-C_4)$-alkyl group, in another embodiment a $(C_1-C_3)$-alkyl group, in another embodiment a $(C_1-C_2)$-alkyl group, in another embodiment a methyl group. In one embodiment, a $(C_3-C_7)$-cycloalkyl group occurring as a substituent on a phenyl group and an aromatic heterocycle representing $R^{32}$ is a $(C_3-C_6)$-cycloalkyl group, in another embodiment a $(C_3-C_6)$-cycloalkyl group, in another embodiment a $(C_3-C_4)$-cycloalkyl group, in another embodiment it is a cyclopropyl group.

In one embodiment of the invention, the group $R^{40}$ is chosen from the series consisting of hydrogen and $(C_1-C_2)$-alkyl, in another embodiment from the series consisting of hydrogen and methyl, and in another embodiment $R^{40}$ is hydrogen. In case $R^{30}$ and $R^{40}$ are different and the carbon atom carrying $R^{30}$ and $R^{40}$ thus is chiral, in one embodiment of the invention the compound of the formula I has at this carbon atom pure stereochemical configuration, either R configuration or S configuration, or essentially pure stereochemical configuration, for example with a molar ratio of the two configurations of 99:1 or greater. In case $R^{30}$ is $R^{32}$—$C_uH_{2u}$— and u is 0, i.e. $R^{30}$ is phenyl or an aromatic heterocycle as defined, $R^{40}$ is hydrogen and $R^{50}$ is hydrogen, in one embodiment of the invention the compound of the formula I has at the carbon atom carrying $R^{30}$ and $R^{40}$ pure S configuration, or essentially pure S configuration, for example with a molar ratio of S configuration to R configuration of 99:1 or greater.

In case $R^{30}$ and $R^{40}$ together are a divalent group $(CH_2)_x$, the two groups $R^{30}$ and $R^{40}$ together with the carbon atom carrying them form a cycloalkane ring chosen from cyclopropane, cyclobutane, cyclopentane and cyclohexane, which carries the moieties —C(O)—NH— and —C($R^{50}$)($R^{60}$)-G depicted in formula I on the same ring carbon atom. In one embodiment of the invention, the number of $(C_1-C_4)$-alkyl substituents which are optionally present on the group $(CH_2)_x$, is one, two, three or four, in another embodiment one or two, and in another embodiment no alkyl substituents are present on the group $(CH_2)_x$. In one embodiment, a $(C_1-C_4)$-alkyl group occurring as a substituent on the group $(CH_2)_x$ is a methyl group. In one embodiment, the integer x is chosen from the series consisting of 2, 4 and 5, in another embodiment from 4 and 5, in another embodiment x is 2, and in another embodiment x is 4. In one embodiment of the invention, $R^{30}$ and $R^{40}$ together cannot be $(CH_2)_x$, and in this embodiment $R^{30}$ and $R^{40}$ thus only have their other meanings as defined.

In one embodiment of the invention, the group $R^{50}$ is chosen from the series consisting of hydrogen, $(C_1-C_4)$-alkyl and HO—, in another embodiment from the series consisting of hydrogen and $(C_1-C_4)$-alkyl, in another embodiment from the series consisting of hydrogen and $(C_1-C_2)$-alkyl, in another embodiment from the series consisting of hydrogen and methyl, in another embodiment from the series consisting of hydrogen and HO—, and in another embodiment $R^{50}$ is hydrogen.

In one embodiment of the invention, the group $R^{60}$ is chosen from the series consisting of hydrogen and $(C_1-C_4)$-alkyl, in another embodiment from the series consisting of hydrogen and $(C_1-C_3)$-alkyl, in another embodiment from the series consisting of hydrogen and $(C_1-C_2)$-alkyl, in another embodiment from the series consisting of hydrogen and methyl, and in another embodiment $R^{60}$ is hydrogen. In one embodiment of the invention, $R^{50}$ and $R^{60}$ both are hydrogen. In case $R^{50}$ and $R^{60}$ are different and the carbon atom carrying $R^{50}$ and $R^{60}$ thus is chiral, in one embodiment of the invention the compound of the formula I has at this carbon atom pure stereochemical configuration, either R configuration or S configuration, or essentially pure stereochemical configuration, for example with a molar ratio of the two configurations of 99:1 or greater.

In case $R^{50}$ and $R^{60}$ together are a divalent group $(CH_2)_y$, the two groups $R^{50}$ and $R^{60}$ together with the carbon atom carrying them form a cycloalkane ring chosen from cyclopropane, cyclobutane, cyclopentane and cyclohexane, which carries the moieties —C($R^{30}$)($R^{40}$)— and G depicted in formula I on the same ring carbon atom. In one embodiment of the invention, the number of ($C_1$-$C_4$)-alkyl substituents which are optionally present on the group $(CH_2)_y$, is one, two, three or four, in another embodiment one or two, and in another embodiment no alkyl substituents are present on the group $(CH_2)_y$. In one embodiment, a ($C_1$-$C_4$)-alkyl group occurring as a substituent on the group $(CH_2)_y$ is a methyl group. In one embodiment, the integer y is chosen from the series consisting of 2, 4 and 5, in another embodiment from 4 and 5, in another embodiment y is 2, and in another embodiment y is 4. In one embodiment of the invention, $R^{50}$ and $R^{60}$ together cannot be $(CH_2)_y$, and in this embodiment $R^{50}$ and $R^{60}$ thus only have their other meanings as defined. In one embodiment of the invention, $R^{50}$ and $R^{60}$ together cannot be $(CH_2)_y$ if simultaneously $R^{30}$ and $R^{40}$ together are $(CH_2)_x$.

In one embodiment of the invention, the group $R^{71}$ is chosen from the series consisting of hydrogen and ($C_1$-$C_6$)-alkyl, in another embodiment from the series consisting of hydrogen and ($C_1$-$C_4$)-alkyl, in another embodiment from the series consisting of hydrogen and ($C_1$-$C_3$)-alkyl, in another embodiment from the series consisting of hydrogen and ($C_1$-$C_2$)-alkyl, in another embodiment $R^{71}$ is hydrogen, in another embodiment $R^{71}$ is ($C_1$-$C_6$)-alkyl, in another embodiment $R^{71}$ is ($C_1$-$C_4$)-alkyl, in another embodiment $R^{71}$ is ($C_1$-$C_3$)-alkyl, and in another embodiment $R^{71}$ is ($C_1$-$C_2$)-alkyl, wherein all these alkyl groups are optionally substituted as indicated with respect to the compounds of formula I in general or in any embodiment specified above or below. In one embodiment, the number of substituents which are optionally present on an alkyl group representing $R^{71}$ is one or two, in another embodiment it is one, in another embodiment an alkyl group representing $R^{71}$ is unsubstituted. In one embodiment, substituents which are optionally present on an alkyl group representing $R^{71}$ are ($C_1$-$C_6$)-alkyl-O— substituents, in another embodiment ($C_1$-$C_4$)-alkyl-O— substituents, in another embodiment ($C_1$-$C_3$)-alkyl-O— substituents, in another embodiment ($C_1$-$C_6$)-alkyl-C(O)—O— substituents, in another embodiment ($C_1$-$C_4$)-alkyl-C(O)—O— substituents, in another embodiment ($C_1$-$C_3$)-alkyl-C(O)—O— substituents.

In one embodiment the group $R^{72}$ is chosen from the series consisting of hydrogen, ($C_1$-$C_6$)-alkyl, ($C_3$-$C_6$)-cycloalkyl —CH$_2$—(CH$_2$)$_b$—($C_3$-$C_6$)-cycloalkyl and —(CH$_2$)$_b$-Het$^4$, where alkyl or cycloalkyl is optionally substituted by one or more identical or different substituents chosen from the series consisting of halogen, HO—, HOOC—, ($C_1$-$C_6$)-alkyl-O— and ($C_1$-$C_6$)-alkyl-C(O)—O—, NC—, N(($C_1$-$C_4$)-alkyl)$_2$ and b is 0, 1 or 2 and the group $R^{73}$ is chosen from the series consisting hydrogen, ($C_1$-$C_6$)-alkyl. In another embodiment the groups $R^{72}$ and $R^{73}$ together with the nitrogen atom to which they are bonded form a saturated 4-membered to 7-membered monocyclic heterocycle, which contain optionally one further ring heteroatom chosen from the series consisting of nitrogen, oxygen and sulfur, which is optionally substituted by one or more identical or different substituents chosen from the series consisting of halogen, ($C_1$-$C_4$)-alkyl, HO— and ($C_1$-$C_4$)-alkyl-O—.

In another embodiment the group $R^{72}$ is chosen from the series consisting of hydrogen, ($C_1$-$C_6$)-alkyl, ($C_3$-$C_6$)-cycloalkyl, Het$^4$ and —CH$_2$-Het$^4$, where alkyl or cycloalkyl is optionally substituted by one or more identical or different substituents chosen from the series consisting of halogen, HO—, HOOC—, ($C_1$-$C_6$)-alkyl-O— and ($C_1$-$C_6$)-alkyl-C(O)—O—, NC—, N(($C_1$-$C_4$)-alkyl)$_2$ and the group $R^{73}$ is chosen from the series consisting hydrogen, ($C_1$-$C_6$)-alkyl.

In another embodiment the groups $R^{72}$ and $R^{73}$ together with the nitrogen atom to which they are bonded form a saturated 5-membered to 6-membered monocyclic heterocycle, which contain optionally one further ring heteroatom chosen from the series consisting of nitrogen, oxygen and sulfur, which is optionally substituted by one or more identical or different substituents chosen from the series consisting of halogen, ($C_1$-$C_4$)-alkyl, HO— and ($C_1$-$C_4$)-alkyl-O—.

In one embodiment the group $R^{72}$ is chosen from the series consisting of hydrogen, ($C_1$-$C_6$)-alkyl, ($C_3$-$C_6$)-cycloalkyl and —CH$_2$-Het$^4$, where alkyl or cycloalkyl is optionally substituted by one or more identical or different substituents chosen from the series consisting of halogen, HO—, HOOC—, ($C_1$-$C_6$)-alkyl-O— and ($C_1$-$C_6$)-alkyl-C(O)—O—, NC—, N(($C_1$-$C_4$)-alkyl)$_2$ and the group $R^{73}$ is chosen from the series consisting hydrogen and ($C_1$-$C_6$)-alkyl.

In another embodiment the groups $R^{72}$ and $R^{73}$ together with the nitrogen atom to which they are bonded form a saturated 5-membered to 6-membered monocyclic heterocycle, which contain no further ring heteroatoms, which is optionally substituted by one or more identical or different substituents chosen from the series consisting of halogen, ($C_1$-$C_4$)-alkyl, HO— and ($C_1$-$C_4$)-alkyl-O—.

In one embodiment the group $R^{72}$ is chosen from the series consisting of hydrogen, 2,2-dimethyl-butane-3yl, 2,2-dimethyl-propane-3yl, pentan-3yl, propane-2yl, 2-methyl-propane-2yl, butane-1 yl, butane-2yl, 2-methyl-butane-3yl, 2-methyl-butane-2-yl, —CH$_2$CHF$_2$, —CHCF$_3$, CH$_2$CN, —CH$_2$CH$_2$OCH$_3$, —CH(CH$_2$OH)CH(CH$_3$)$_2$, —CH$_2$C(CH$_3$)$_2$—CH$_2$OH, CH(C$_2$H$_5$)CH$_2$OCH$_3$, CH$_2$CH$_2$CH$_2$N(CH$_3$)$_2$, cyclopropane, cyclobutane, cyclopentane, cyclohexane and —CH$_2$-Het$^4$ and the group $R^{73}$ is hydrogen.

In another embodiment the groups $R^{72}$ and $R^{73}$ together with the nitrogen atom to which they are bonded form pyrrolidine, which is optionally substituted by HO—. In another embodiment the group $R^{72}$ is chosen from the series consisting of hydrogen, ($C_1$-$C_6$)-alkyl, where alkyl is substituted by one or more times by HO— and the group $R^{73}$ is hydrogen.

In one embodiment of the invention, the groups $R^{72}$ and $R^{73}$ are independently of each other chosen from the series consisting of hydrogen and ($C_1$-$C_2$)-alkyl, in another embodiment from the series consisting of hydrogen and methyl. In one embodiment, one of the groups $R^{72}$ and $R^{73}$ is hydrogen and the other is chosen from the series consisting of hydrogen and ($C_1$-$C_4$)-alkyl, in another embodiment from the series consisting of hydrogen and ($C_1$-$C_2$)-alkyl, in another embodiment from the series consisting of hydrogen an methyl, and in another embodiment both groups $R^{72}$ and $R^{73}$ are hydrogen.

In one embodiment of the invention the group Het$^4$, independently of each other group Het$^4$, is a saturated or unsaturated 4-membered to 8-membered monocyclic heterocycle which comprises one to four ring heteroatoms chosen from the series consisting of nitrogen, oxygen and sulfur which is optionally substituted by one or more identical or different substituents chosen from the series consisting of halogen, ($C_1$-$C_4$)-alkyl, HO—, oxo and NC—;

In another embodiment the group Het$^4$, independently of each other group Het$^4$, is a saturated or unsaturated 5-membered to 6-membered monocyclic heterocycle which comprises one to four ring heteroatoms chosen from the series consisting of nitrogen, oxygen and sulfur which is optionally substituted by one or more identical or different substituents chosen from the series consisting of halogen, $(C_1-C_4)$-alkyl, HO—, $(C_1-C_4)$-alkyl-O—, oxo and NC—;

In another embodiment the group $Het^4$, independently of each other group $Het^4$, is a unsaturated 5-membered to 6-membered monocyclic heterocycle which comprises one to four ring heteroatoms chosen from the series consisting of nitrogen, oxygen and sulfur which is optionally substituted by one or more identical or different substituents chosen from the series consisting of halogen, $(C_1-C_4)$-alkyl, HO—, $(C_1-C_4)$-alkyl-O— and NC—;

In another embodiment the group $Het^4$, independently of each other group $Het^4$, is selected from 1,2-oxadiazolyl, tetrazlolyl, pyrazolyl, furanyl, pyridinyl, pyriminyl, which is optionally substituted by methyl.

In one embodiment of the invention, a group Ar in any occurrence in the compounds of the formula I, independently of each other group Ar, is chosen from the series consisting of phenyl and an aromatic 5-membered or 6-membered monocyclic heterocycle which comprises one or two identical or different ring heteroatoms, in another embodiment one ring heteroatom, which is chosen from the series consisting of nitrogen, oxygen and sulfur, and which is bonded via a ring carbon atom, in another embodiment Ar is chosen from the series consisting of phenyl and an aromatic 6-membered heterocycle which comprises one or two nitrogen atoms as ring heteroatoms, in another embodiment Ar is chosen from the series consisting of phenyl, thiophenyl and pyridinyl, in another embodiment from the series consisting of phenyl and thiophenyl, in another embodiment from the series consisting of phenyl and pyridinyl, in another embodiment a group Ar is phenyl, and in another embodiment a group Ar is pyridinyl, wherein the phenyl and all heterocycles are optionally substituted as indicated with respect to the compounds of formula I in general or in any embodiment specified above or below. In one embodiment, the number of substituents which are optionally present on a group Ar, independently of each other group Ar, is one, two, three or four, in another embodiment one, two or three, in another embodiment one or two, in another embodiment one, and in another embodiment a group Ar is unsubstituted.

In one embodiment, in case that substituents from the series consisting of —CH═CH—CH═CH—, —O—CH$_2$—CH$_2$—O—, —N((C$_1$-C$_3$)-alkyl)-CH═CH—, —O—CH$_2$—O— and —O—CF$_2$—O— are present on a group Ar which is phenyl, not more than two such substituents, in another embodiment not more than one such substituent, are present, either without any other substituents or together with any other substituents. In one embodiment, the substituents which are optionally present on a group Ar, independently of each other group Ar, are chosen from the series consisting of halogen, $(C_1-C_6)$-alkyl, HO—$(C_1-C_6)$-alkyl, Het4, —(CH$_2$)$_x$-phenyl, $(C_1-C_6)$-alkyl-O—, $(C_3-C_7)$-cycloalkyl-(CH$_2$)$_x$—O—, —CF$_3$, —CO—$(C_1-C_6)$-alkyl, —NR$^{12}$R$^{13}$, Het$^2$, —CO—NR$^{12}$R$^{13}$, CO-Het$^2$, H$_2$N—S(O)$_2$— and NC—;

In another embodiment from the series consisting of halogen, $(C_1-C_6)$-alkyl, $(C_1-C_6)$-alkyl-O—, $(C_1-C_6)$-alkyl-S(O)$_m$— and NC—, in another embodiment from the series consisting of halogen, $(C_1-C_6)$-alkyl, $(C_1-C_6)$-alkyl-O— and NC—, in another embodiment from the series consisting of halogen, $(C_1-C_6)$-alkyl and $(C_1-C_6)$-alkyl-O—, in another embodiment from the series consisting of halogen, $(C_1-C_4)$-alkyl and $(C_1-C_4)$-alkyl-O—, in another embodiment from the series consisting of halogen and $(C_1-C_4)$-alkyl.

A subject of the invention are all compounds of the formula I wherein any one or more structural elements such as groups, substituents and numbers are defined as in any of the specified embodiments or definitions of the elements or have one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratios, and their physiologically acceptable salts, and the physiologically acceptable solvates of any of them, are a subject of the present invention.

As an example of compounds of the invention which with respect to any structural elements are defined as in specified embodiments of the invention or definitions of such elements, compounds of the formula I may be mentioned wherein G is chosen from the series consisting of $R^{71}$—O—C(O)— and $R^{72}$—N($R^{73}$)—C(O)—;

$R^{30}$ is $R^{32}$—C$_u$H$_{2u}$—, wherein u is an integer chosen from the series consisting of 0 and $R^{32}$ is chosen from the series consisting of phenyl and an aromatic 6-membered monocyclic heterocycle which comprises one or two nitrogen atoms as ring heteroatoms, wherein the phenyl and the heterocycle all are optionally substituted by one or more identical or different substituents chosen from the series consisting of halogen, $(C_1-C_6)$-alkyl, $(C_3-C_7)$-cycloalkyl, $R^{33}$, HO—, $(C_1-C_6)$-alkyl-O—, $R^{33}$—O—, $R^{33}$—$(C_1-C_4)$-alkyl-O—, —O—CH$_2$—O—, —O—CF$_2$—O—, $(C_1-C_6)$-alkyl-S(O)$_m$—, di(($C_1-C_4$)-alkyl)N—S(O)$_2$—, H$_2$N—, di(($C_1-C_6$)-alkyl)N—, Het$^1$, $(C_1-C_4)$-alkyl-C(O)—NH—, Ar—C(O)—NH— and NC—;

$R^{33}$ is chosen from the series consisting of phenyl and an aromatic 6-membered monocyclic heterocycle which comprises one or two nitrogen atoms as ring heteroatoms, wherein the phenyl and the heterocycle all are optionally substituted by one or more identical or different substituents chosen from the series consisting of halogen, $(C_1-C_6)$-alkyl, $(C_3-C_7)$-cycloalkyl, HO—, $(C_1-C_6)$-alkyl-O—, $(C_1-C_6)$-alkyl-S(O)$_m$—, H$_2$N—S(O)$_2$—, di(($C_1-C_4$)-alkyl)N—S(O)$_2$— and NC—;

$R^{40}$ is hydrogen.

As another such example of compounds of the invention which with respect to any structural elements are defined as in specified embodiments of the invention or definitions of such elements, compounds of the formula I may be mentioned wherein G is $R^{71}$—O—C(O)—;

$R^{30}$ is $R^{32}$—C$_u$H$_{2u}$—, wherein u is 0;

$R^{32}$ is chosen from the series consisting of phenyl, wherein the phenyl is optionally substituted by one or more identical or different substituents chosen from the series consisting of halogen, $(C_1-C_6)$-alkyl, $(C_3-C_7)$-cycloalkyl, $R^{33}$, HO—, $(C_1-C_6)$-alkyl-O—, $R^{33}$—O—, $R^{33}$—$(C_1-C_4)$-alkyl-O—, —O—CH$_2$—O—, —O—CF$_2$—O—, $(C_1-C_6)$-alkyl-S(O)$_m$—, di(($C_1-C_4$)-alkyl)N—S(O)$_2$—, H$_2$N—, di(($C_1-C_6$)-alkyl)N—, Het$^1$, $(C_1-C_4)$-alkyl-C(O)—NH—, Ar—C(O)—NH— and NC—;

$R^{33}$ is chosen from the series consisting of phenyl, wherein the phenyl is optionally substituted by one or more identical or different substituents chosen from the series consisting of halogen, $(C_1-C_6)$-alkyl, $(C_3-C_7)$-cycloalkyl, HO—, $(C_1-C_6)$-alkyl-O—, $(C_1-C_6)$-alkyl-S(O)$_m$—, H$_2$N—S(O)$_2$—, di(($C_1-C_4$)-alkyl)N—S(O)$_2$— and NC—;

$R^{40}$ is hydrogen.

As another such example of compounds of the invention which with respect to any structural elements are defined as in specified embodiments of the invention or definitions of such elements, compounds of the formula I may be mentioned wherein $R^{50}$ is hydrogen;
$R^{60}$ is hydrogen.

As another such example of compounds of the invention which with respect to any structural elements are defined as in specified embodiments of the invention or definitions of such elements, compounds of the formula I may be mentioned wherein formula I is selected from the series of subformulae I-1 to I-7

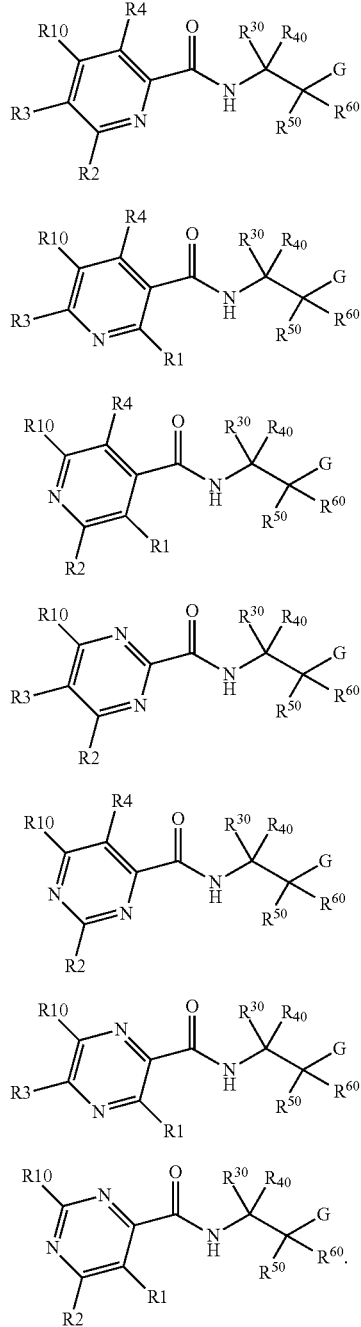

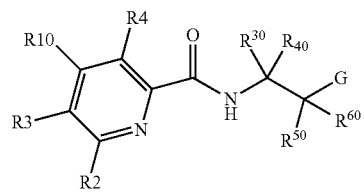

I-1 wherein
$R^2$ is Ar—$C_sH_{2s}$—, wherein s is an integer chosen from the series consisting of 0;
$R^3$ is chosen from the series consisting of hydrogen, halogen, $R^{11}$—O—, HO—, ($C_1$-$C_6$)-alkyl and ($C_1$-$C_6$)-alkyl-O—; preferred HO— and ($C_1$-$C_6$)-alkyl
$R^4$ is hydrogen;
$R^{10}$ is hydrogen;

As another such example of compounds of the invention which with respect to any structural elements are defined as in specified embodiments of the invention or definitions of such elements, compounds of the formula I-1

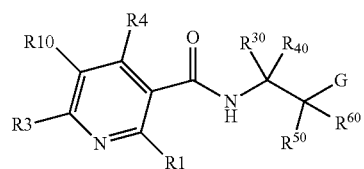

I-2 wherein
$R^1$ is hydrogen;
$R^3$ is chosen from the series consisting of hydrogen, halogen, ($C_1$-$C_6$)-alkyl, ($C_1$-$C_6$)-alkyl-S(O)$_m$—, Phenyl $C_sH_{2s}$—(O)$_t$—, Het$^4$-(O)$_t$—, —NR$^{12}$R$^{13}$, Het$^2$, R$^{11}$—O—, R$^{12}$—N(R$^{13}$)—C(O)—O— and Het$^2$-C(O)—O— and NC—, wherein s is an integer chosen from the series consisting of 0, 1, 2 and 3 and wherein t is an integer chosen from the series consisting of 0 and 1;
$R^4$ is hydrogen;
$R^{10}$ is chosen from the series consisting hydrogen, halogen, ($C_1$-$C_6$)-alkyl, ($C_1$-$C_6$)-alkyl-O—, ($C_1$-$C_6$)-alkyl-S(O)$_m$—, HO—, —NR$^{12}$R$^{13}$, Het$^2$, phenyl-$C_sH_{2s}$—(O)$_t$—, wherein s is an integer chosen from the series consisting of 0, 1, 2 and 3 and wherein t is an integer chosen from the series consisting of 0 and 1;

A subject of the invention also is a compound of the formula I which is chosen from any of the specific compounds of the formula I which are disclosed herein, or is any one of the specific compounds of the formula I which are disclosed herein, irrespective thereof whether they are disclosed as a free compound and/or as a specific salt, or a physiologically acceptable salt thereof, or a physiologically acceptable solvate of any of them, wherein the compound of the formula I is a subject of the invention in any of its stereoisomeric forms or a mixture of stereoisomeric forms in any ratio. For example, a subject of the invention is a compound of the formula I which is chosen from
(S)-3-[(5-Methoxy-6-phenyl-pyridine-2-carbonyl)-amino]-3-o-tolyl-propionic acid
(S)-3-(2,4-Dichloro-phenyl)-3-[(5-methoxy-6-phenyl-pyridine-2-carbonyl)-amino]-propionic acid
(S)-3-[(6-Chloro-5-methoxy-pyridine-2-carbonyl)-amino]-3-o-tolyl-propionic acid As another such example of compounds of the invention which with respect to any structural elements are defined as in specified embodiments of the invention or definitions of such elements, compounds of the formula I-1

(S)-3-{[3-(4,6-Dimethoxy-pyrimidin-2-yloxy)-pyridine-2-carbonyl]-amino}-3-o-tolyl-propionic acid
(S)-3-[(6-Bromo-5-methoxy-pyridine-2-carbonyl)-amino]-3-o-tolyl-propionic acid
(S)-3-{[4-(Pyrimidin-2-ylsulfanyl)-pyridine-2-carbonyl]-amino}-3-o-tolyl-propionic acid
(S)-3[(6-Phenyl-pyridine-2-carbonyl)-amino]-3-o-tolyl-propionic acid
(S)-3-[(5-Phenyl-pyridine-2-carbonyl)-amino]-3-o-tolyl-propionic acid
(S)-3-{[5-(2-Chloro-phenyl)-pyridine-3-carbonyl]-amino}-3-o-tolyl-propionic acid
(S)-3-{[5-(2,3-Dichloro-phenyl)-pyridine-3-carbonyl]-amino}-3-o-tolyl-propionic acid
(S)-3-{[5-(2,3-Dimethyl-phenyl)-pyridine-3-carbonyl]amino}-3-o-tolyl-propionic acid
(S)-3-o-Tolyl-3-[(6-m-tolyl-pyridine-2-carbonyl)-amino]-propionic acid
(S)-3-{[6-(2-Chloro-phenyl)-pyridine-2-carbonyl]-amino}-3-o-tolyl-propionic acid
(S)-3-{[6-(2-Fluoro-phenyl)-pyridine-2-carbonyl]-amino}-3-o-tolyl-propionic acid
(S)-3-{[6-(2,3-Difluoro-phenyl)-pyridine-2-carbonyl]-amino}-3-o-tolyl-propionic acid
(S)-3-{[6-(2,5-Difluoro-phenyl)-pyridine-2-carbonyl]-amino}-3-o-tolyl-propionic acid
(S)-3-{[6-(4-Fluoro-2-methyl-phenyl)-pyridine-2-carbonyl]-amino}-3-o-tolyl-propionic acid
(S)-3-{[6-(2,3-Dimethyl-phenyl)-pyridine-2-carbonyl]-amino}-3-o-tolyl-propionic acid
(S)-3-{[6-(5-Fluoro-2-methyl-phenyl)-pyridine-2-carbonyl]-amino}-3-o-tolyl-propionic acid
(S)-3-{[6-(2-Methoxy-4-trifluoromethyl-phenyl)-pyridine-2-carbonyl]-amino}-3-o-tolyl-propionic acid
(S)-3-{[6-(4-Chloro-2-methoxy-phenyl)-pyridine-2-carbonyl]-amino}-3-o-tolyl-propionic acid
(S)-3-{[6-(2-Fluoro-5-methoxy-phenyl)-pyridine-2-carbonyl]-amino}-3-o-tolyl-propionic acid
(S)-3-{[6-(2-Fluoro-phenyl)-5-methoxy-pyridine-2-carbonyl]-amino}-3-o-tolyl-propionic acid
(S)-3-{[6-(2-Fluoro-5-methyl-phenyl)-pyridine-2-carbonyl]-amino}-3-o-tolyl-propionic acid
(S)-3-[(5-Methoxy-6-phenyl-pyridine-2-carbonyl)-amino]-3-p-tolyl-propionic acid
(S)-3-[(5-Methoxy-6-o-tolyl-pyridine-2-carbonyl)-amino]-3-p-tolyl-propionic acid
(S)-3-{[5-Methoxy-6-(2-trifluoromethyl-phenyl)-pyridine-2-carbonyl]-amino}-3-p-tolyl-propionic acid
(S)-3-{[6-(3-Fluoro-phenyl)-5-methoxy-pyridine-2-carbonyl]-amino}-3-p-tolyl-propionic acid
(S)-3-{[5-Methoxy-6-(2-methoxy-phenyl)-pyridine-2-carbonyl]-amino}-3-p-tolyl-propionic acid
(S)-3-{[6-(2-Chloro-phenyl)-5-methoxy-pyridine-2-carbonyl]-amino}-3-p-tolyl-propionic acid
(S)-3-{[6-(2-Fluoro-phenyl)-5-methoxy-pyridine-2-carbonyl]-amino}-3-p-tolyl-propionic acid
(S)-3-{[6-(2,4-Difluoro-phenyl)-5-methoxy-pyridine-2-carbonyl]-amino}-3-p-tolyl-propionic acid
(S)-3-{[6-(2,3-Dichloro-phenyl)-5-methoxy-pyridine-2-carbonyl]-amino}-3-p-tolyl-propionic acid
(S)-3-{[6-(2-Chloro-5-trifluoromethyl-phenyl)-5-methoxy-pyridine-2-carbonyl]-amino}-3-p-tolyl-propionic acid
(S)-3-{[6-(3-Fluoro-2-methyl-phenyl)-5-methoxy-pyridine-2-carbonyl]-amino}-3-(2-fluoro-phenyl)-propionic acid
(S)-3-{[6-(2-Chloro-5-trifluoromethyl-phenyl)-5-methoxy-pyridine-2-carbonyl]-amino}-3-(2-fluoro-phenyl)-propionic acid
(S)-3-{[6-(2,3-Difluoro-phenyl)-5-methoxy-pyridine-2-carbonyl]-amino}-3-p-tolyl-propionic acid
(S)-3-{[6-(2,5-Difluoro-phenyl)-5-methoxy-pyridine-2-carbonyl]-amino}-3-p-tolyl-propionic acid
(S)-3-{[6-(2,5-Dichloro-phenyl)-5-methoxy-pyridine-2-carbonyl]-amino}-3-p-tolyl-propionic acid
(S)-3-{[6-(3,5-Dimethyl-isoxazol-4-yl)-5-methoxy-pyridine-2-carbonyl]-amino}-3-p-tolyl-propionic acid
(S)-3-{[6-(4-Fluoro-2-methyl-phenyl)-5-methoxy-pyridine-2-carbonyl]-amino}-3-p-tolyl-propionic acid
(S)-3-{[6-(2,3-Dimethyl-phenyl)-5-methoxy-pyridine-2-carbonyl]-amino}-3-p-tolyl-propionic acid
(S)-3-[(3,2'-Dimethoxy-[2,3']bipyridinyl-6-carbonyl)-amino]-3-p-tolyl-propionic acid
(S)-3-{[6-(5-Fluoro-2-methyl-phenyl)-5-methoxy-pyridine-2-carbonyl]-amino}-3-p-tolyl-propionic acid
(S)-3-{[6-(4-Fluoro-2-methoxy-phenyl)-5-methoxy-pyridine-2-carbonyl]-amino}-3-p-tolyl-propionic acid
(S)-3-{[6-(5-Fluoro-2-methoxy-phenyl)-5-methoxy-pyridine-2-carbonyl]-amino}-3-p-tolyl-propionic acid
(S)-3-{[6-(2-Fluoro-5-methyl-phenyl)-5-methoxy-pyridine-2-carbonyl]-amino}-3-p-tolyl-propionic acid
(S)-3-{[6-(3-Chloro-2-methyl-phenyl)-5-methoxy-pyridine-2-carbonyl]-amino}-3-p-tolyl-propionic acid
(S)-3-{[6-(3-Fluoro-2-methyl-phenyl)-5-methoxy-pyridine-2-carbonyl]-amino}-3-p-tolyl-propionic acid
(S)-3-{[6-(5-Chloro-2-fluoro-phenyl)-5-methoxy-pyridine-2-carbonyl]-amino}-3-p-tolyl-propionic acid
(S)-3-(2-Fluoro-phenyl)-3-[(5-methoxy-6-phenyl-pyridine-2-carbonyl)-amino]-propionic acid
(S)-3-{[6-(2,4-Dichloro-phenyl)-5-methoxy-pyridine-2-carbonyl]-amino}-3-(2-fluoro-phenyl)-propionic acid
(S)-3-(2-Fluoro-phenyl)-3-[(5-methoxy-6-o-tolyl-pyridine-2-carbonyl)-amino]-propionic acid
(S)-3-(2-Fluoro-phenyl)-3-{[5-methoxy-6-(2-trifluoromethyl-phenyl)-pyridine-2-carbonyl]-amino}-propionic acid
(S)-3-(2-Fluoro-phenyl)-3-{[5-methoxy-6-(2-methoxy-phenyl)-pyridine-2-carbonyl]-amino}-propionic acid
(S)-3-{[6-(2-Chloro-phenyl)-5-methoxy-pyridine-2-carbonyl]-amino}-3-(2-fluoro-phenyl)-propionic acid
(S)-3-(2-Fluoro-phenyl)-3-{[6-(2-fluoro-phenyl)-5-methoxy-pyridine-2-carbonyl]-amino}-propionic acid
(S)-3-{[6-(2,4-Difluoro-phenyl)-5-methoxy-pyridine-2-carbonyl]-amino}-3-(2-fluoro-phenyl)-propionic acid
(S)-3-{[6-(2,3-Dichloro-phenyl)-5-methoxy-pyridine-2-carbonyl]-amino}-3-(2-fluoro-phenyl)-propionic acid
(S)-3-{[6-(2,3-Difluoro-phenyl)-5-methoxy-pyridine-2-carbonyl]-amino}-3-(2-fluoro-phenyl)-propionic acid
(S)-3-{[6-(2,5-Difluoro-phenyl)-5-methoxy-pyridine-2-carbonyl]-amino}-3-(2-fluoro-phenyl)-propionic acid
(S)-3-{[6-(4-Fluoro-2-methyl-phenyl)-5-methoxy-pyridine-2-carbonyl]-amino}-3-(2-fluoro-phenyl)-propionic acid
(S)-3-{[6-(3,5-Dimethyl-isoxazol-4-yl)-5-methoxy-pyridine-2-carbonyl]-amino}-3-(2-fluoro-phenyl)-propionic acid
(S)-3-{[6-(2,3-Dimethyl-phenyl)-5-methoxy-pyridine-2-carbonyl]-amino}-3-(2-fluoro-phenyl)-propionic acid
(S)-3-[(3,2'-Dimethoxy-[2,3]bipyridinyl-6-carbonyl)-amino]-3-(2-fluoro-phenyl)-propionic acid
(S)-3-{[6-(5-Fluoro-2-methyl-phenyl)-5-methoxy-pyridine-2-carbonyl]-amino}-3-(2-fluoro-phenyl)-propionic acid
(S)-3-{[6-(4-Fluoro-2-methoxy-phenyl)-5-methoxy-pyridine-2-carbonyl]-amino}-3-(2-fluoro-phenyl)-propionic acid (S)-3-{[6-(5-Fluoro-2-methoxy-phenyl)-5-methoxy-pyridine-2-carbonyl]-amino}-3-(2-fluoro-phenyl)-propionic acid
(S)-3-{[6-(2-Fluoro-5-methyl-phenyl)-5-methoxy-pyridine-2-carbonyl]-amino}-3-(2-fluoro-phenyl)-propionic acid
(S)-3-{[6-(3-Chloro-2-methyl-phenyl)-5-methoxy-pyridine-2-carbonyl]-amino}-3-(2-fluoro-phenyl)-propionic acid
(S)-3-{[6-(5-Chloro-2-fluoro-phenyl)-5-methoxy-pyridine-2-carbonyl]-amino}-3-(2-fluoro-phenyl)-propionic acid
(S)-3-{[6-(3-Chloro-2-fluoro-phenyl)-5-methoxy-pyridine-2-carbonyl]-amino}-3-(2-fluoro-phenyl)-propionic acid
(S)-3-(2-Fluoro-phenyl)-3-{[5-methoxy-6-(2-methyl-furan-3-yl)-pyridine-2-carbonyl]-amino}-propionic acid
(S)-3-{[6-(2-Chloro-3-methyl-phenyl)-5-methoxy-pyridine-2-carbonyl]-amino}-3-(2-fluoro-phenyl)-propionic acid
(S)-3-(2-Chloro-phenyl)-3-[(5-methoxy-6-phenyl-pyridine-2-carbonyl)-amino]-propionic acid
(S)-3-(2-Chloro-phenyl)-3-{[6-(2,4-dichloro-phenyl)-5-methoxy-pyridine-2-carbonyl]-amino}-propionic acid
(S)-3-(2-Chloro-phenyl)-3-{[6-(4-fluoro-phenyl)-5-methoxy-pyridine-2-carbonyl]-amino}-propionic acid
(S)-3-{[5-Methoxy-6-(3-trifluoromethyl-phenyl)-pyridine-2-carbonyl]-amino}-3-o-tolyl-propionic acid
(S)-3-{[6-(2,4-Dichloro-phenyl)-5-methoxy-pyridine-2-carbonyl]-amino}-3-o-tolyl-propionic acid
(S)-3-{[6-(4-Fluoro-phenyl)-5-methoxy-pyridine-2-carbonyl]-amino}-3-o-tolyl-propionic acid
(S)-3-{[6-(4-Chloro-phenyl)-5-methoxy-pyridine-2-carbonyl]-amino}-3-o-tolyl-propionic acid
(S)-3-[(5-Methoxy-6-p-tolyl-pyridine-2-carbonyl)-amino]-3-o-tolyl-propionic acid
(S)-3-{[6-(3-Chloro-phenyl)-5-methoxy-pyridine-2-carbonyl]-amino}-3-o-tolyl-propionic acid
(S)-3-{[5-Methoxy-6-(2-methoxy-phenyl)-pyridine-2-carbonyl]-amino}-3-o-tolyl-propionic acid
(S)-3-[(5-Methoxy-6-m-tolyl-pyridine-2-carbonyl)-amino]-3-o-tolyl-propionic acid
(S)-3-{[6-(2-Chloro-phenyl)-5-methoxy-pyridine-2-carbonyl]-amino}-3-o-tolyl-propionic acid
(S)-3-{[6-(3,4-Difluoro-phenyl)-5-methoxy-pyridine-2-carbonyl]-amino}-3-o-tolyl-propionic acid
(S)-3-{[6-(2,5-Difluoro-phenyl)-5-methoxy-pyridine-2-carbonyl]-amino}-3-o-tolyl-propionic acid
(S)-3-{[6-(2,5-Dichloro-phenyl)-5-methoxy-pyridine-2-carbonyl]-amino}-3-o-tolyl-propionic acid
(S)-3-{[6-(3,5-Dimethyl-isoxazol-4-yl)-5-methoxy-pyridine-2-carbonyl]-amino}-3-o-tolyl-propionic acid
(S)-3-{[6-(2,3-Dimethyl-phenyl)-5-methoxy-pyridine-2-carbonyl]-amino}-3-o-tolyl-propionic acid
(S)-3-{[6-(2,4-Dimethyl-phenyl)-5-methoxy-pyridine-2-carbonyl]-amino}-3-o-tolyl-propionic acid
(S)-3-{[6-(4-Fluoro-2-methoxy-phenyl)-5-methoxy-pyridine-2-carbonyl]-amino}-3-o-tolyl-propionic acid
(S)-3-{[6-(2-Chloro-5-methyl-phenyl)-5-methoxy-pyridine-2-carbonyl]-amino}-3-o-tolyl-propionic acid
(S)-3-(2-Chloro-phenyl)-3-[(6-methoxy-5-o-tolyl-pyridine-3-carbonyl)-amino]-propionic acid
(S)-3-(2-Chloro-phenyl)-3-{[5-methoxy-6-(2-methoxy-phenyl)-pyridine-2-carbonyl]-amino}-propionic acid
(S)-3-(2-Chloro-phenyl)-3-[(5-methoxy-6-m-tolyl-pyridine-2-carbonyl)-amino]-propionic acid
(S)-3-(2-Chloro-phenyl)-3-{[6-(2-chloro-phenyl)-5-methoxy-pyridine-2-carbonyl]-amino}-propionic acid
(S)-3-(2-Chloro-phenyl)-3-{[6-(2-fluoro-phenyl)-5-methoxy-pyridine-2-carbonyl]-amino}-propionic acid
(S)-3-(2-Chloro-phenyl)-3-{[6-(2,4-difluoro-phenyl)-5-methoxy-pyridine-2-carbonyl]-amino}-propionic acid
(S)-3-(2-Chloro-phenyl)-3-{[6-(2,3-dichloro-phenyl)-5-methoxy-pyridine-2-carbonyl]-amino}-propionic acid
(S)-3-(2-Chloro-phenyl)-3-{[6-(2,3-difluoro-phenyl)-5-methoxy-pyridine-2-carbonyl]-amino}-propionic acid
(S)-3-(2-Chloro-phenyl)-3-{[6-(2,5-difluoro-phenyl)-5-methoxy-pyridine-2-carbonyl]-amino}-propionic acid
(S)-3-(2-Chloro-phenyl)-3-{[6-(4-fluoro-2-methyl-phenyl)-5-methoxy-pyridine-2-carbonyl]-amino}-propionic acid
(S)-3-(2-Chloro-phenyl)-3-{[6-(2,3-dimethyl-phenyl)-5-methoxy-pyridine-2-carbonyl]-amino}-propionic acid
(S)-3-(2-Chloro-phenyl)-3-[(3,2'-dimethoxy-[2,3']bipyridinyl-6-carbonyl)-amino]-propionic acid
(S)-3-(2-Chloro-phenyl)-3-{[6-(5-fluoro-2-methyl-phenyl)-5-methoxy-pyridine-2-carbonyl]-amino}-propionic acid
(S)-3-(2-Chloro-phenyl)-3-{[6-(4-fluoro-2-methoxy-phenyl)-5-methoxy-pyridine-2-carbonyl]-amino}-propionic acid
(S)-3-{[6-(4-Chloro-2-methoxy-phenyl)-5-methoxy-pyridine-2-carbonyl]-amino}-3-(2-chloro-phenyl)-propionic acid
(S)-3-(2-Chloro-phenyl)-3-{[6-(5-fluoro-2-methoxy-phenyl)-5-methoxy-pyridine-2-carbonyl]-amino}-propionic acid
(S)-3-(2-Chloro-phenyl)-3-{[6-(2-fluoro-5-trifluoromethyl-phenyl)-5-methoxy-pyridine-2-carbonyl]-amino}-propionic acid
(S)-3-{[5-Methoxy-6-(2-trifluoromethyl-phenyl)-pyridine-2-carbonyl]-amino}-3-o-tolyl-propionic acid
(S)-3-{[6-(2,4-Difluoro-phenyl)-5-methoxy-pyridine-2-carbonyl]-amino}-3-o-tolyl-propionic acid
(S)-3-{[6-(4-Fluoro-2-methyl-phenyl)-5-methoxy-pyridine-2-carbonyl]-amino}-3-o-tolyl-propionic acid
(S)-3-[(3,2'-Dimethoxy-[2,3']bipyridinyl-6-carbonyl)-amino]-3-o-tolyl-propionic acid
(S)-3-[(3'-Fluoro-3-methoxy-[2,4']bipyridinyl-6-carbonyl)-amino]-3-o-tolyl-propionic acid
(S)-3-{[5-Methoxy-6-(2-methyl-furan-3-yl)-pyridine-2-carbonyl]-amino}-3-o-tolyl-propionic acid
(S)-3-{[6-(4-Cyano-2-fluoro-phenyl)-5-methoxy-pyridine-2-carbonyl]-amino}-3-o-tolyl-propionic acid
(S)-3-(2-Chloro-phenyl)-3-{[6-(2-fluoro-5-methoxy-phenyl)-5-methoxy-pyridine-2-carbonyl]-amino}-propionic acid
(S)-3-(2-Chloro-phenyl)-3-{[6-(2-fluoro-5-methyl-phenyl)-5-methoxy-pyridine-2-carbonyl]-amino}-propionic acid
(S)-3-{[6-(3-Chloro-2-methyl-phenyl)-5-methoxy-pyridine-2-carbonyl]-amino}-3-(2-chloro-phenyl)-propionic acid
(S)-3-(2-Chloro-phenyl)-3-{[6-(3-fluoro-2-methyl-phenyl)-5-methoxy-pyridine-2-carbonyl]-amino}-propionic acid
(S)-3-{[6-(5-Chloro-2-fluoro-phenyl)-5-methoxy-pyridine-2-carbonyl]-amino}-3-(2-chloro-phenyl)-propionic acid
(S)-3-(2-Chloro-phenyl)-3-[(3'-fluoro-3-methoxy-[2,4']bipyridinyl-6-carbonyl)-amino]-propionic acid
(S)-3-(2-Chloro-phenyl)-3-[(5-methoxy-6-pyrazin-2-yl-pyridine-2-carbonyl)-amino]-propionic acid
(S)-3-{[6-(3-Chloro-2-fluoro-phenyl)-5-methoxy-pyridine-2-carbonyl]-amino}-3-(2-chloro-phenyl)-propionic acid
(S)-3-(2-Chloro-phenyl)-3-{[5-methoxy-6-(2-methyl-furan-3-yl)-pyridine-2-carbonyl]-amino}-propionic acid
(S)-3-{[6-(2-Chloro-3-fluoro-phenyl)-5-methoxy-pyridine-2-carbonyl]-amino}-3-(2-chloro-phenyl)-propionic acid
(S)-3-{[6-(2-Chloro-3-methyl-phenyl)-5-methoxy-pyridine-2-carbonyl]-amino}-3-(2-chloro-phenyl)-propionic acid
3-Biphenyl-4-yl-3-[(6-chloro-pyridine-2-carbonyl)-amino]-propionic acid
(S)-3-[(6-Chloro-pyridine-2-carbonyl)-amino]-3-o-tolyl-propionic acid (S)-3-[(3,5-Diamino-6-chloro-pyrazine-2-carbonyl)-amino]-3-o-tolyl-propionic acid
3-Biphenyl-4-yl-3-[(3,5-diamino-6-chloro-pyrazine-2-carbonyl)-amino]-propionic acid
(S)-3-{[6-(2-Fluoro-phenyl)-pyridine-2-carbonyl]-amino}-3-phenyl-propionic acid
(S)-3-(3-Fluoro-phenyl)-3-{[6-(2-fluoro-phenyl)-pyridine-2-carbonyl]-amino}-propionic acid
(S)-3-(2-Fluoro-phenyl)-3-{[6-(2-fluoro-phenyl)-pyridine-2-carbonyl]-amino}-propionic acid
(S)-3-(4-Fluoro-phenyl)-3-{[6-(2-fluoro-phenyl)-pyridine-2-carbonyl]-amino}-propionic acid
3-(2-Chloro-phenyl)-3-[(6-methoxy-quinoline-2-carbonyl)-amino]-propionic acid
(S)-3-[(6-Methoxy-biphenyl-3-carbonyl)-amino]-3-o-tolyl-propionic acid
(S)-3-{[6-(2-Chloro-phenyl)-pyridine-2-carbonyl]-amino}-3-m-tolyl-propionic acid
(S)-3-{[6-(2-Fluoro-phenyl)-pyridine-2-carbonyl]-amino}-3-(4-methoxy-phenyl)-propionic acid
(S)-3-{[6-(2-Chloro-phenyl)-pyridine-2-carbonyl]-amino}-3-(2-fluoro-phenyl)-propionic acid
(S)-3-{[6-(2-Chloro-phenyl)-pyridine-2-carbonyl]-amino}-3-(4-fluoro-phenyl)-propionic acid
(S)-3-(3-Chloro-phenyl)-3-{[6-(2-fluoro-phenyl)-pyridine-2-carbonyl]-amino}-propionic acid
(S)-3-(4-Chloro-phenyl)-3-{[6-(2-fluoro-phenyl)-pyridine-2-carbonyl]-amino}-propionic acid
(S)-3-(4-Chloro-phenyl)-3-{[6-(2-chloro-phenyl)-pyridine-2-carbonyl]-amino}-propionic acid
(S)-3-(3-Chloro-phenyl)-3-{[6-(2-chloro-phenyl)-pyridine-2-carbonyl]-amino}-propionic acid
3-(2-Chloro-phenyl)-3-{[6-(2-chloro-phenyl)-pyridine-2-carbonyl]-amino}-propionic acid
(S)-3-{[6-(2-Fluoro-phenyl)-pyridine-2-carbonyl]-amino}-3-(3-trifluoromethyl-phenyl)-propionic acid
(S)-3-{[6-(2-Chloro-phenyl)-pyridine-2-carbonyl]-amino}-3-(2,4-dichloro-phenyl)-propionic acid
(S)-3-{[6-(2-Chloro-phenyl)-pyridine-2-carbonyl]-amino}-3-(4-trifluoromethyl-phenyl)-propionic acid
(S)-3-{[6-(2-Chloro-phenyl)-pyridine-2-carbonyl]-amino}-3-(3-trifluoromethyl-phenyl)-propionic acid
(S)-3-{[6-Bromo-5-(3,3-dimethyl-2-oxo-butoxy)-pyridine-2-carbonyl]-amino}-3-O— tolyl-propionic acid.

For example, also a subject of the invention is a compound of the formula I which is chosen from
(S)-3-[(5-Methoxy-6-phenyl-pyridine-2-carbonyl)-amino]-3-o-tolyl-propionic acid
(S)-3-{[6-(2,3-Dimethyl-phenyl)-pyridine-2-carbonyl]-amino}-3-o-tolyl-propionic acid
(S)-3-{[6-(2-Chloro-phenyl)-pyridine-2-carbonyl]-amino}-3-o-tolyl-propionic acid
(S)-3-{[6-(2-Fluoro-phenyl)-pyridine-2-carbonyl]-amino}-3-o-tolyl-propionic acid
(S)-3-{[6-(5-Fluoro-2-methyl-phenyl)-pyridine-2-carbonyl]-amino}-3-o-tolyl-propionic acid
(S)-3-o-Tolyl-3-[(6-m-tolyl-pyridine-2-carbonyl)-amino]-propionic acid
(S)-3-({6-[3-(1-Hydroxy-1-methyl-ethyl)-phenyl]-pyridine-2-carbonyl}-amino)-3-o-tolyl-propionic acid
(S)-3-(2,4-Dichloro-phenyl)-3-[(5-methoxy-6-phenyl-pyridine-2-carbonyl)-amino]-propionic acid
(S)-3-[(2,6-Dimethoxy-pyrimidine-4-carbonyl)-amino]-3-o-tolyl-propionic acid
(S)-3-[(5-Phenyl-pyridine-2-carbonyl)-amino]-3-o-tolyl-propionic acid
(S)-3-{[3-(4,6-Dimethoxy-pyrimidin-2-yloxy)-pyridine-2-carbonyl]-amino}-3-o-tolyl-propionic acid
(S)-3-{[4-(Pyrimidin-2-ylsulfanyl)-pyridine-2-carbonyl]-amino}-3-o-tolyl-propionic acid
(S)-3-{[5-(2,3-Dichloro-phenyl)-pyridine-3-carbonyl]-amino}-3-o-tolyl-propionic acid
(S)-3-{[5-(2,3-Dimethyl-phenyl)-pyridine-3-carbonyl]-amino}-3-o-tolyl-propionic acid
(S)-3-{[5-(2-Chloro-phenyl)-pyridine-3-carbonyl]-amino}-3-o-tolyl-propionic acid
(S)-3-{[6-(2,3-Difluoro-phenyl)-pyridine-2-carbonyl]-amino}-3-o-tolyl-propionic acid
(S)-3-{[6-(2-Fluoro-5-methoxy-phenyl)-pyridine-2-carbonyl]-amino}-3-o-tolyl-propionic acid
(S)-3-{[6-(2-Fluoro-5-methyl-phenyl)-pyridine-2-carbonyl]-amino}-3-o-tolyl-propionic acid
(S)-3-{[6-(2-Methoxy-4-trifluoromethyl-phenyl)-pyridine-2-carbonyl]-amino}-3-o-tolyl-propionic acid
(S)-3-({5-Methoxy-6-[3-(5-methyl-[1,3,4]oxadiazol-2-yl)-phenyl]-pyridine-2-carbonyl}-amino)-3-o-tolyl-propionic acid
(S)-3-(2-Chloro-phenyl)-3-[(5-methoxy-6-naphthalen-2-yl-pyridine-2-carbonyl)-amino]-propionic acid
(S)-3-(2-Chloro-phenyl)-3-[(5-methoxy-6-pyrazin-2-yl-pyridine-2-carbonyl)-amino]-propionic acid
(S)-3-(2-Chloro-phenyl)-3-{[6-methoxy-5-naphthalen-2-yl-pyridine-3-carbonyl]-amino}-propionic acid
(S)-3-(2-Chloro-phenyl)-3-{[5-methoxy-6-(2-methyl-furan-3-yl)-pyridine-2-carbonyl]-amino}-propionic acid
(S)-3-(2-Chloro-phenyl)-3-{[6-(2,3-di methyl-phenyl)-5-methoxy-pyridine-2-carbonyl]-amino}-propionic acid
(S)-3-(2-Chloro-phenyl)-3-{[6-(2-chloro-phenyl)-5-methoxy-pyridine-2-carbonyl]-amino}-propionic acid
(S)-3-(2-Fluoro-phenyl)-3-{[5-methoxy-6-(1,3,5-trimethyl-1H-pyrazol-4-yl)-pyridine-2-carbonyl]-amino}-propionic acid
(S)-3-(2-Fluoro-phenyl)-3-{[5-methoxy-6-(1-methyl-1H-indol-5-yl)-pyridine-2-carbonyl]-amino}-propionic acid
(S)-3-[(5-Methoxy-6-m-tolyl-pyridine-2-carbonyl)-amino]-3-o-tolyl-propionic acid
(S)-3-{[6-(2-Chloro-phenyl)-5-methoxy-pyridine-2-carbonyl]-amino}-3-o-tolyl-propionic acid
(S)-3-{[6-(3,5-Dimethyl-isoxazol-4-yl)-5-methoxy-pyridine-2-carbonyl]-amino}-3-o-tolyl-propionic acid
(S)-3-{[6-(4-Chloro-phenyl)-5-methoxy-pyridine-2-carbonyl]-amino}-3-o-tolyl-propionic acid
(S)-3-{[6-(4-Chloro-phenyl)-5-methoxy-pyridine-2-carbonyl]-amino}-3-p-tolyl-propionic acid
(S)-3-{[6-(5-Acetyl-thiophen-2-yl)-5-methoxy-pyridine-2-carbonyl]-amino}-3-(2-chloro-phenyl)-propionic acid
(S)-3-{[6-(2-Fluoro-phenyl)-5-methoxy-pyridine-2-carbonyl]-amino}-3-o-tolyl-propionic acid
or which is any one of these compounds, or a physiologically acceptable salt thereof, or a physiologically acceptable solvate of any of them, wherein the compound of the formula I is a subject of the invention in any of its stereoisomeric forms or a mixture of stereoisomeric forms in any ratio, unless a specific stereoisomeric form is specified with respect to any carbon atoms in the respective compound.

Another subject of the present invention are processes for the preparation of the compounds of the formula I which are outlined below and by which the compounds are obtainable. For example, the preparation of the compounds of the formula I can be carried out by reacting a compound of the formula II with a compound of the formula III with formation of an amide bond. Various synthetic methods for the formation of the amide bond are described in C. A. G. N. Montalbetti et al., Tetrahedron 61 (2005), 10827-10852, for example.

In general the compounds described in this patent are synthesized according to the general scheme:

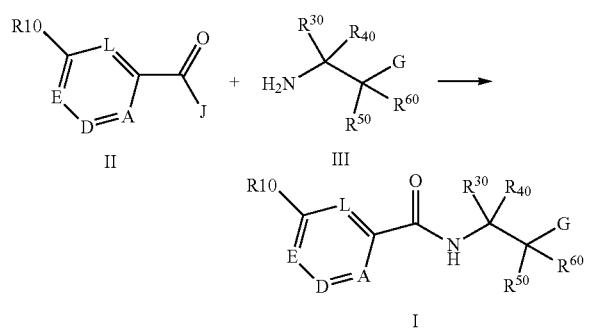

The formation of the amide bond between the carboxylic acid and the β-amino-acid can be done by the use of coupling agents well known to a person skilled in the art and described for example in Tetrahedron (2005), 61(46), 10827-10852. As alternatives instead of a carboxylic acid a carboxylic acid chloride and instead of the free β-amino acid a β-amino acid ester, especially methyl- or ethylester, may be used.

The β-amino-acids used within this work are either commercially available or prepared by methods described for example in JACS 1935, 1279 or by Rhodionow in Chem. Abstr. 1953, 1051. The Rhodionow scheme is depicted below:

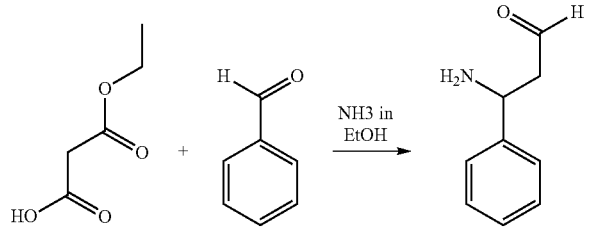

Enantiopure β-amino acids can either be obtained commercially or prepared from the racemic material by procedures described in Bioscience, Biotechnology and Biochemistry, 2006, 1941.

A general procedure for the coupling process using heterocyclic carboxylic acids is described below. The used carboxylic acids are commercially available.

Procedure A 0.25 mmol of the carboxylic acid is weighed into a reaction vial, 1.25 mmol N-ethyl morpholine in 1 ml DMF is added, followed by 0.245 mmol TOTU in 0.5 ml DMF. The mixture is allowed to react for 30 min at RT. 0.275 mmol of the amino acid suspended in 0.5 ml DMF is added, the vial is closed with a screw cap and shaken over night at RT. 0.2 ml TFA is added, the solution is filtered through syringe filters and directly submitted to prep HPLC.

Yield of the products: Between 5% and 80%

Another general procedure consists of the synthesis of amino acid derivatives with a functional group suitable for a subsequent Suzuki reaction as shown below.

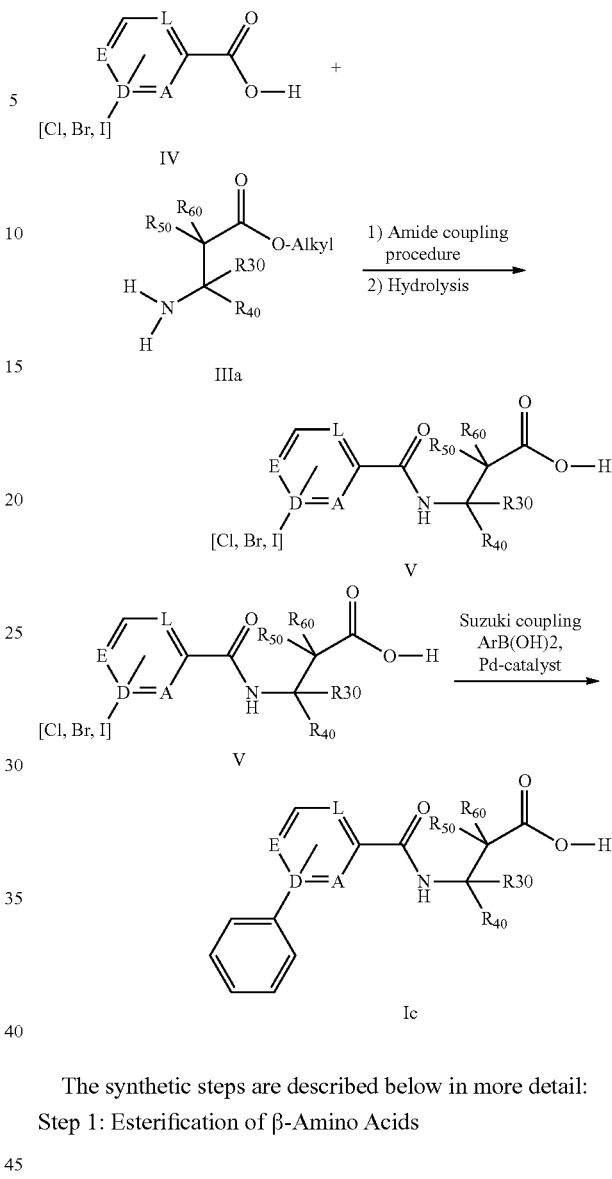

The synthetic steps are described below in more detail:

Step 1: Esterification of β-Amino Acids

Synthesis of (S)-3-Amino-3-(2-fluoro-phenyl)-propionic acid ethyl ester 5.0 g (27.3 mmol) (S)-3-Amino-3-(2-fluorophenyl)-propionic acid are suspended in 27 ml Methyl-THF and 16 ml ethanol and heated to 80° C.

2.45 ml (4.02; 33.8 mml; 1.24 eq) $SOCl_2$ are added and the resulting mixture is stirred for 2.5 h at 80° C. The mixture is allowed to reach RT and stirred overnight. The solvent is evaporated in vacuo and 9.2 g of crude material is obtained, which is washed several times with diisopropylether to obtain 6.34 g of pure material (Yield: 94%).

According to this procedure the following derivatives have been prepared:

(S)-3-Amino-3-(2-chloro-phenyl)-propionic acid ethyl ester (S)-3-Amino-3-o-tolyl-propionic acid ethyl ester (S)-3-Amino-3-p-tolyl-propionic acid ethyl ester Step 2: Coupling of Products from 1 to Heterocyclic Carboxylic Acids Substituted with Chlorine or Bromine Atoms:

Synthesis of (S)-3-[(6-Bromo-5-methoxy-pyridine-2-carbonyl)-amino]-3-(2-chloro-phenyl)-propionic acid ethyl ester 4.87 g (21 mmol) 6-Bromo-5-methoxy-pyridine-2-carboxylic acid and 4.17 g (25.2 mmol, 1.2 eq) CDI are suspended in 54 ml Me-THF and heated to 50° C. After stirring for 3.5 h at this temperature the mixture is cooled to 0° C. in an ice bath and 3.39 ml (24.2, 1.15 eq) triethyl-amine is added. After that 6.1 g (23.1 mmol, 1.1 eq) of (S)-3-Amino-3-(2-chloro-phenyl)-propionic acid ethyl ester are added within 20 minutes and the resulting mixture is allowed to reach RT and stirred overnight.

50 ml water is added, the phases are separated and the organic phase is washed several times with 50 ml of saturated NaHCO$_3$ solution followed by 50 ml of 1N HCl solution. The organic phase is evaporated in vacuo and 8.43 g of product are obtained. Yield: 89%.

According to this procedure the following derivatives have been prepared:
(S)-3-[(6-Bromo-5-methoxy-pyridine-2-carbonyl)-amino]-3-o-tolyl-propionic acid ethyl ester
(S)-3-[(6-Bromo-5-methoxy-pyridine-2-carbonyl)-amino]-3-p-tolyl-propionic acid ethyl ester
(S)-3-[(6-Bromo-5-methoxy-pyridine-2-carbonyl)-amino]-3-(2-fluoro-phenyl)-propionic acid ethyl ester
(S)-3-[(5-Chloro-6-methoxy-pyridine-3-carbonyl)-amino]-3-o-tolyl-propionic acid ethyl ester
(S)-3-[(5-Chloro-6-methoxy-pyridine-3-carbonyl)-amino]-3-(2-chloro-phenyl)-propionic acid ethyl ester
(S)-3-[(5-Bromo-pyridine-3-carbonyl)-amino]-3-o-tolyl-propionic acid ethyl ester
(S)-3-[(2-Chloro-6-methoxy-pyridine-4-carbonyl)-amino]-3-o-tolyl-propionic acid ethyl ester
(S)-3-[(2-Chloro-pyridine-4-carbonyl)-amino]-3-o-tolyl-propionic acid ethyl ester
(S)-3-[(6-Chloro-pyridine-2-carbonyl)-amino]-3-o-tolyl-propionic acid ethyl ester Step 3: Hydrolysis of Products from Step 2:

Synthesis of (S)-3-[(5-Chloro-6-methoxy-pyridine-3-carbonyl)-amino]-3-(2-chloro-phenyl)-propionic acid 8.03 g (20.21 mmol) (S)-3-[(5-Chloro-6-methoxy-pyridine-3-carbonyl)-amino]-3-(2-chloro-phenyl)-propionic acid ethyl ester are dissolved in 15.2 ml (30.32 mmol, 1.5 eq) 2N NaOH solution and stirred at 50° C. for 9 hours. The resulting mixture is stirred overnight at RT.

105 ml water and 30 ml isopropanol are added and the pH is adjusted to pH=3.0 with 2N HCl. The precipitate is separated and dried in vacuo to deliver 3.74 g of product (Yield: 50%).

According to this procedure the following derivatives have been prepared:
(S)-3-[(6-Bromo-5-methoxy-pyridine-2-carbonyl)-amino]-3-(2-chloro-phenyl)-propionic acid
(S)-3-[(6-Bromo-5-methoxy-pyridine-2-carbonyl)-amino]-3-o-tolyl-propionic acid
(S)-3-[(6-Bromo-5-methoxy-pyridine-2-carbonyl)-amino]-3-p-tolyl-propionic acid
(S)-3-[(6-Bromo-5-methoxy-pyridine-2-carbonyl)-amino]-3-(2-fluoro-phenyl)-propionic acid
(S)-3-[(5-Chloro-6-methoxy-pyridine-3-carbonyl)-amino]-3-o-tolyl-propionic acid
(S)-3-[(5-Bromo-pyridine-3-carbonyl)-amino]-3-o-tolyl-propionic acid
(S)-3-[(2-Chloro-6-methoxy-pyridine-4-carbonyl)-amino]-3-o-tolyl-propionic acid
(S)-3-[(2-Chloro-pyridine-4-carbonyl)-amino]-3-o-tolyl-propionic acid
(S)-3-[(6-Chloro-pyridine-2-carbonyl)-amino]-3-o-tolyl-propionic acid Procedures for Suzuki Couplings:
General Procedure B

Synthesis of (S)-3-(2-Fluoro-phenyl)-3-[(5-methoxy-6-phenyl-pyridine-2-carbonyl)-amino]-propionic acid (Example 263)

50 mg (0.12 mmol) of (S)-3-[(6-Bromo-5-methoxy-pyridine-2-carbonyl)-amino]-3-(2-fluoro-phenyl)-propionic acid are dissolved in 3 ml of DMF, 120 mg (0.16 mmol, 1.35 eq) phenylboronic acid, 10 mg of bis(triphenylphosphine)palladium(II)chloride as catalyst and 1 ml of 1N Na$_2$CO$_3$ solution are added and the resulting mixture is heated to 100° C. for 6 hours. The mixture is filtrated via a pad of celite and subjected to preparative HPLC chromatography to yield 15 mg (31%) of product.

General Procedure C

Synthesis of (S)-3-(2-Chloro-phenyl)-3-[(6-methoxy-5-phenyl-pyridine-3-carbonyl)-amino]-propionic acid (Example 353)

To a solution of 50 mg (0.13 mmol) of (S)-3-[(5-Chloro-6-methoxy-pyridine-3-carbonyl)-amino]-3-(2-chloro-phenyl)-propionic acid in 3 ml of DMF are added: 25 mg (0.21 mmol, 1.5 eq) phenylboronic acid, 60 mg Na$_2$CO$_3$ (0.56 mmol, 4.2 eq) and 10 mg (0.13 eq) DI-MICRO-CHLOROBIS [2-[(DIMETHYLAMINO)METHYL]PHENYL-C,N]DI-PAL as catalyst. After the addition of 1 ml of water the resulting mixture is heated to 100° C. for 6 hours, the reaction is filtered via a pad of celite and the resulting solution subjected to preparative HPLC chromatography yielding 16 mg of product (Yield: 29%).

The groups A, D, E, L, G, $R^{10}$, $R^{30}$, $R^{40}$, $R^{50}$ and $R^{60}$ in the compounds of the formulae II and III are defined as in the compounds of the formula I and additionally functional groups can be present in protected form or in the form of a precursor group which is later converted into the final group. The group J in the compounds of the formula II can be HO— (hydroxy), i.e. the compound of the formula II can thus be a carboxylic acid, or another group which can be replaced by the group NH in the compound of the formula III in a substitution reaction, for example an aryloxy group such as optionally substituted phenoxy or an alkyloxy group such as a $(C_1-C_4)$-alkyl-O— group, for example a $(C_1-C_3)$-alkyl-O— group like methoxy or ethoxy, or halogen, for example chlorine or bromine, and the compound of the formula II can thus be a reactive ester like an aryl ester or alkyl ester, for example a methyl ester or ethyl ester, or an acid halide, for example an acid chloride or acid bromide, of the respective carboxylic acid. The compounds of the formulae II and III can also be employed, and the compounds of the formula I obtained, in the form of a salt, for example an acid addition salt such as an hydrohalide, for example a hydrochloride, of the compound of the formula III and/or an alkaline metal salt, for example a sodium salt, of a compound of the formula II in which J is HO—. Likewise, in all other reactions in the preparation of the compounds of the formula I, including the preparation of starting compounds, compounds can also be employed and/or products obtained in the form a salt.

In case a compound of the formula II is employed in which J is HO—, the carboxylic acid group HO—C(O)— is generally activated in situ by means of a customary amide coupling reagent or converted into a reactive carboxylic acid derivative which can be prepared in situ or isolated. For example, the compound of the formula II in which J is HO— can be converted into an acid halide, such as the compound of the formula II in which J is chlorine or bromine, by treatment with thionyl chloride, phosphorus pentachloride, phosphorus tribromide or oxalyl chloride, or treated with an alkyl chloroformate like ethyl chloroformate or isobutyl chloroformate to give a mixed anhydride. In a favorable method for the conversion into the acid chloride, the acid is treated with oxalyl chloride in the presence of a catalytic amount of an amide such as N,N-dimethylformamide in an inert solvent such as a hydrocarbon or chlorinated hydrocarbon or an ether, at temperatures from about 0° C. to about 60° C., for example at room temperature. Customary amide coupling reagents which can be employed, are propanephosphonic anhydride, N,N'-carbonyldiazoles like N,N'-carbonyldiimidazole (CDI), carbodiimides like 1,3-diisopropylcarbodiimide (DIC), 1,3-dicyclohexylcarbodiimide (DCC) or 1-(3-dimethylaminopropyl)-3-ethylcarbodiimide hydrochloride (EDC), carbodiimides together with additives like 1-hydroxy-benzotriazole (HOBT) or 1-hydroxy-7-azabenzotriazole (HOAT), uronium-based coupling reagents like O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluroniurn tetrafluoroborate (TOTU), and phosphonium-based coupling reagents like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromotripyrrolidinophosphonium hexafluorophosphate (PyBroP).

The reaction conditions for the preparation of the compounds of the formula I from compounds of the formulae II and III depend on the particulars of the specific case, for example the meaning of the group J or the employed coupling reagent, and are familiar to a skilled person in view of the general knowledge in the art. For example, in case a compound of the formula II in which J is alkyl-O—, like methoxy or ethoxy, is reacted with a compound of the formula III, generally the reaction is carried out in an inert solvent, for example a hydrocarbon or chlorinated hydrocarbon like benzene, toluene, xylene, chlorobenzene, dichloromethane, chloroform or dichloroethane, an ether like tetrahydrofuran (THF), 2-methyltetrahydrofuran, dioxane, dibutyl ether, diisopropyl ether or dimethoxyethane (DME), or a mixture of solvents, at elevated temperatures, for example at temperatures from about 40° C. to about 140° C., in particular at temperatures from about 50° C. to about 120° C., for example at about the boiling temperature of the solvent. In case a compound of the formula II in which J is halogen, like chlorine or bromine, is reacted with a compound of the formula III, generally the reaction is likewise carried out in an inert solvent, for example a hydrocarbon or chlorinated hydrocarbon or ether like the aforementioned ones, an ester like ethyl acetate or butyl acetate, a nitrile like acetonitrile, or water, or a mixture of solvents including a mixture of water and an organic solvent which is miscible or immiscible with water, at temperatures from about −10° C. to about 100° C., in particular at temperatures from about 0° C. to about 80° C., for example at about room temperature. Favorably, the reaction of a compound of the formula II in which J is halogen with a compound of the formula III is carried out in the presence of a base such as a tertiary amine, like triethylamine, N-ethyldiisopropylamine (EDIA), N-methylmorpholine, N-ethylmorpholine or pyridine, or an inorganic base such as an alkaline metal hydroxide, carbonate or hydrogencarbonate, like sodium hydroxide, potassium hydroxide, sodium carbonate or sodium hydrogencarbonate.

In case a compound of the formula II in which J is HO— is reacted with a compound of the formula III and the carboxylic acid group is activated by means of an amide coupling reagent such as, for example, a carbodiimide or TOTU, the reaction is generally carried out under anhydrous conditions in an inert aprotic solvent, for example an ether like THF, dioxane or DME, an amide like N,N-dimethylformamide (DMF) or N-methylpyrrolidone (NMP), at temperatures from about −10° C. to about 40° C., in particular at temperatures from about 0° C. to about 30° C., for example at room temperature, in the presence of a base such as a tertiary amine, like triethylamine, EDIA, N-methylmorpholine or N-ethylmorpholine. In case the compound of the formula III is employed in the form of an acid addition salt in the reaction with the compound of the formula II, usually a sufficient amount of a base is added in order to liberate the free compound of the formula III.

As indicated above, during the formation of the amide bond between the compounds of the formulae II and III functional groups in the compounds of the formulae II and III can be present in protected form or in the form of a precursor group. Depending on the particulars of the specific case, it may be necessary or advisable for avoiding an undesired course of the reaction or side reactions to temporarily block any functional groups by protective groups and remove them later, or to let functional groups be present in the form of a precursor group which is later converted into the desired final group. This applies correspondingly to all reactions in the course of the synthesis of the compounds of the formula I including the synthesis of intermediates, starting compounds and building blocks. Respective synthetic strategies are commonly used in the art. Details about protective groups and their introduction and removal are described in P. G. M. Wuts and T. W. Greene, Greene's Protective Groups in Organic Synthesis, 4. ed. (2007), John Wiley & Sons, for example. Examples of protective groups which may be mentioned, are benzyl protective groups which may occur in the form of benzyl ethers of hydroxy groups and benzyl esters of carboxylic acid groups from which the benzyl group can be removed by catalytic hydrogenation in the presence of a palladium catalyst, tert-butyl protective groups which may occur in the form of tert-butyl esters of carboxylic acid groups from which the tert-butyl group can be removed by treatment with trifluoroacetic acid, acyl protective groups which may be used to protect hydroxy groups and amino groups in the form of esters and amides and which can be cleaved by acidic or basic hydrolysis, and alkyloxycarbonyl protective groups which may occur in the form of tert-butoxycarbonyl derivatives of amino groups which can be cleaved by treatment with trifluoroacetic acid. Undesired reactions of carboxylic acid groups, for example the carboxylic acid group present in the compound of the formula III in case G is a carboxylic acid group in the desired compound of the formula I, can also be avoided by employing them in the reaction with the compounds of the formula II in the form of other esters, for example in the form of alkyl esters like the methyl or ethyl ester which can be cleaved by hydrolysis, for example by means of an alkaline metal hydroxide like sodium hydroxide or lithium hydroxide. As examples of a precursor group, the cyano group (NC—, N≡C—) may be mentioned which can be converted into a carboxylic acid group, a carboxylic acid ester group and a carboxamide group under hydrolytic conditions or into a aminomethyl group by reduction, and the nitro group which can be converted into an amino group by reduction, for example by catalytic hydrogenation or by reduction with sodium dithionite, for example. A further example of a precursor group is an oxo group, which may initially be present in the course of the synthesis of compounds of the formula I containing a hydroxy group, and which can be reduced, for example with a complex hydride such as sodium borohydride, or reacted with an organometallic compound, for example a Grignard compound. If any protective groups or precursor groups are present in the compounds of the formulae II and III and the direct product of the reaction is not yet the desired final compound, the removal of the protective group or conversion into the desired compound can in general also be carried out in situ.

The starting compounds for the synthesis of the compounds of the formula I can generally be prepared according to procedures described in the literature or analogously to such procedures, or are commercially available.

The β-amino acids and derivatives of the formula III are commercially available or can be synthesized by well-known standard methods, or analogously to such methods, from readily available starting compounds. For example, for the preparation of β-amino acids and their alkyl esters of the formula III in which $R^{50}$ and $R^{60}$ are hydrogen, can carbonyl compounds of the formula $R^{30}$—C(O)—$R^{40}$, in particular aldehydes of the formula $R^{32}$—C(O)—H, be reacted with malonic acid mono-ethyl ester and ammonia in the presence of a base such as an alkaline metal hydroxide like potassium hydroxide in a solvent such as an alcohol like ethanol, as described in V. M. Rodionov et al., Izv. Akad. Nauk SSSR, Ser. Khim. (1952), 696-702 (Chem. Abstr. 47 (1953), abstr. no. 61888), or ammonia added to the double bond in the condensation product of the carbonyl compound with malonic acid or diethyl malonate and in the case of the condensation product with diethyl malonate the reaction product treated with an acid such as hydrochloric acid, as described in V. Scudi, J. Am. Chem. Soc. 57 (1935), 1279; or M. K. Tse et al., Chem. Eur. J. 12 (2006), 1855-1874, and in the obtained product an ester group hydrolyzed to the carboxylic acid, or a carboxylic acid group esterified, respectively, as desired and outlined above. Enantiomerically pure such compounds of the formula III, for example, can be obtained from the racemic compounds by crystallization of a salt with an optically active acid, such as tartaric acid, by stereoselective enzymatic or microbial degradation, for example as described in the mentioned article by M. K. Tse et al., or in J. Mano et al., Bioscience, Biotechnology and Biochemistry 70 (2006), 1941-1946. In another strategy for the synthesis of such compounds, in particular compounds in which $R^{40}$, $R^{50}$ and $R^{60}$ are hydrogen and $R^{30}$ is $R^{32}$, the respective 3-substituted acrylic acid, which can be obtained from the corresponding aldehyde, is converted into the acid chloride, for example with oxalyl chloride, and the acid chloride converted with an alcohol into an ester, for example into the tert-butyl ester using tert-butanol, and the amino group is then introduced by reaction with the lithium salt of an optically active amine, for example the lithium salt of (R)-(+)-N-benzyl-N-(1-phenylethyl)amine, and in the obtained 3-substituted tert-butyl 3-(N-benzyl-N-(1-phenylethyl)amino)propionate the benzyl group and the phenylethyl group is cleaved off by means of catalytic hydrogenation (cf. S. G. Davies et al., Tetrahedron: Asymmetry 2 (1991), 183-186); S. G. Davies et al., J. Chem. Soc. Perkin Trans. 1 (1994), 1129-1139).

The introduction of the structural moieties of the compounds of the formula in the course of the synthesis can also occur in another order than outlined above. For example, in the case of compounds of the formula I in which $R^{10}$ is another group than hydroxy, instead of preparing a compound of the formula II which contains the group $R^{10}$ and reacting it with a compound of the formula III, also a compound of the formula IIc, which specifically comprises a hydroxy group in place of the group $R^{10}$, can be reacted with a compound of the formula III, and the obtained compound of the formula Ia then modified on the hydroxy group by reaction with a compound of the formula VIII to give a compound of the formula I in which $R^{10}$ is different from hydroxy, i.e. a compound of the formula Ib. At the end, like in the compounds of the formula I when prepared as outlined above, any protective groups in the compounds of the formula Ib may still be deprotected and/or precursor group converted into the final groups.

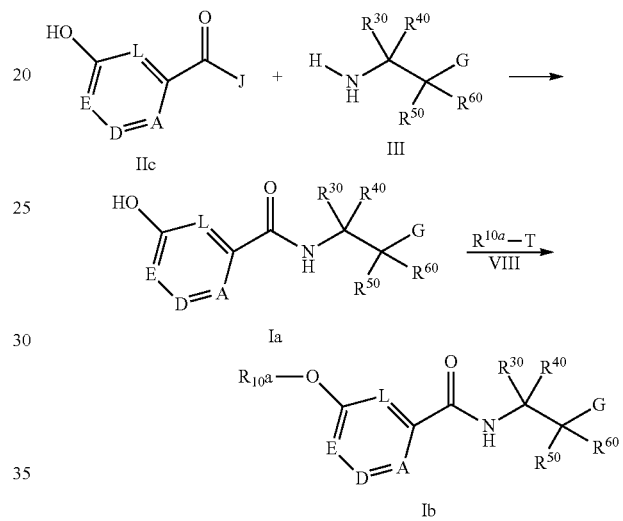

The groups A, D, E, L, G, $R^{30}$, $R^{40}$, $R^{50}$ and $R^{60}$ in the compounds of the formulae Ia, Ib and IIc are defined as in the compounds of the formula I and additionally functional groups can be present in protected form or in the form of a precursor group which is later converted into the final group. The group J in the compounds of the formula II is defined as in the compounds of the formula II. The group $R^{10a}$ in the compounds of the formula Ib is defined as in the compounds of the formulae IIb and VIII. The explanations given above on the reaction of the compounds of the formulae II and III and the reaction of the compounds of the formulae IIa and VIII apply correspondingly to the reaction of the compounds of the formulae IIc and III and the reaction of the compounds Ia and VIII, respectively.

For obtaining further compounds of the formula I, various transformations of functional groups can be carried out under standard conditions in compounds of the formula I or intermediates or starting compounds of the synthesis of the compounds of the formula I. For example, a hydroxy group, including a hydroxy group representing $R^{10}$ in a compound of the formula I, can be etherified, as outlined above, for example by alkylation with a halogen compound, for example a bromide or iodide, in the presence of a base such an alkali metal carbonate like potassium carbonate or cesium carbonate in an inert solvent such as an amide like DMF or NMP or a ketone like acetone or butan-2-one, or with the respective alcohol under the conditions of the Mitsunobu reaction referred to above. A hydroxy group can be esterified to give a carboxylic acid ester or a sulfonic acid ester, or converted into a halide by treatment with a halogenating agent. Halogen atoms can also be introduced by means of suitable halogenating agents which replace a hydrogen atom in the starting compound, for example by means of elemental bromine, sulfuryl chloride or 1-chloromethyl-4-fluoro-1,4-diazoniabicyclo[2.2.2]octane bis(tetrafluoroborate), which introduce a bromine, chlorine and fluorine substituent, respectively, for example in the 4-position of a compound of the formula IIb. A halogen atom can generally be replaced with a variety of groups in substitution reactions which may also be transition-metal catalyzed reactions. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with an activated carboxylic acid or a carboxylic acid derivate like an acid chloride or anhydride or a sulfonic acid chloride. A carboxylic ester group can be hydrolyzed under acidic or basic conditions to give a carboxylic acid. An acid group can be activated or converted into a reactive derivative as outlined above and reacted with an alcohol or an amine or ammonia to give an ester or amide. A primary amide can be dehydrated to give a nitrile. A sulfur atom in an alkyl-S— group or in a heterocyclic ring can be oxidized with a peroxide like hydrogen peroxide or a peracid to give a sulfoxide moiety S(O) or a sulfone moiety $S(O)_2$. A carboxylic acid group, carboxylic acid ester group and a ketone group can be reduced to an alcohol, for example with a complex hydride such al lithium aluminium hydride, lithium borohydride or sodium borohydride, or reacted with an organometallic compound or a Grignard compound to give an alcohol. Primary and secondary hydroxy groups can also be oxidized to the oxo groups. All reactions in the preparation of the compounds of the formula I are known per se and can be carried out in a manner familiar to a person skilled in the art according to, or analogously to, procedures which are described in the standard literature, for example in Houben-Weyl, Methods of Organic Chemistry, Thieme; or Organic Reactions, John Wiley & Sons; or R. C. Larock, Comprehensive Organic Transformations: A Guide to Functional Group Preparations, 2. ed. (1999), John Wiley & Sons, and the references quoted therein.

Another subject of the present invention are the novel starting compounds and intermediates occurring in the synthesis of the compounds of the formula I, including the compounds of the formulae Ia, Ib, Ic, II, IIc, III, IIIa, IV, V and VIII, wherein the groups A, D, E, L, G, J, T, $R^2$, $R^{10}$, $R^{10a}$, $R^{30}$, $R^{40}$, $R^{50}$ and $R^{60}$ are defined as above, in any of their stereoisomeric forms or a mixture of stereoisomeric forms in any ratio, and their salts, and solvates of any of them, and their use as synthetic intermediates or starting compounds. All general explanations, specifications of embodiments and definitions of numbers and groups given above with respect to the compounds of the formula I apply correspondingly to the said intermediates and starting compounds. A subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the formula I inhibit the protease cathepsin A as can be demonstrated in the pharmacological test described below and in other tests which are known to a person skilled in the art. The compounds of the formula I and their physiologically acceptable salts and solvates therefore are valuable pharmaceutical active compounds. The compounds of the formula I and their physiologically acceptable salts and solvates can be used for the treatment of cardiovascular diseases such as heart failure including systolic heart failure, diastolic heart failure, diabetic heart failure and heart failure with preserved ejection fraction, cardiomyopathy, myocardial infarction, left ventricular dysfunction including left ventricular dysfunction after myocardial infarction, cardiac hypertrophy, myocardial remodeling including myocardial remodeling after infarction or after cardiac surgery, valvular heart diseases, vascular hypertrophy, vascular remodeling including vascular stiffness, hypertension including pulmonary hypertension, portal hypertension and systolic hypertension, atherosclerosis, peripheral arterial occlusive disease (PAOD), restenosis, thrombosis and vascular permeability disorders, ischemia and/or reperfusion damage including ischemia and/or reperfusion damage of the heart and ischemia and/or reperfusion damage of the retina, inflammation and inflammatory diseases such as rheumatoid arthritis and osteoarthritis, renal diseases such as renal papillary necrosis and renal failure including renal failure after ischemia/reperfusion, pulmonary diseases such as cystic fibrosis, chronic bronchitis, chronic obstructive pulmonary disease (COPD), asthma, acute respiratory dystress syndrome (ARDS), respiratory tract infections and lung carcinoma, immunological diseases, diabetic complications including diabetic nephropathy and diabetic cardiomyopathy, fibrotic diseases such as pulmonary fibrosis including idiopathic lung fibrosis, cardiac fibrosis, vascular fibrosis, perivascular fibrosis, renal fibrosis including renal tubulointerstitial fibrosis, fibrosing skin conditions including keloid formation, collagenosis and scleroderma, and liver fibrosis, liver diseases such as liver cirrhosis, pain such as neuropathic pain, diabetic pain and inflammatory pain, macular degeneration, neurodegenerative diseases or psychiatric disorders, or for cardioprotection including cardioprotection after myocardial infarction and after cardiac surgery, or for renoprotection, for example. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial infarction, by means of the prophylactic or preventive medicinal treatment the occurrence or re-occurrence of a myocardial infarction can be prevented or its extent and sequelae decreased, or in patients who are susceptible to attacks of asthma, by means of the prophylactic or preventive medicinal treatment such attacks can be prevented or their severity decreased. The treatment of diseases can occur both in acute cases and in chronic cases. The efficacy of the compounds of the formula I can be demonstrated in the pharmacological test described below and in other tests which are known to a person skilled in the art. The compounds of the formula I with G selected from $R^{72}$—N($R^{73}$)—C(O)— and their physiologically acceptable salts and solvates can also be used as prodrugs.

The compounds of the formula I and their physiologically acceptable salts and solvates can therefore be used in animals, in particular in mammals and specifically in humans, as a pharmaceutical or medicament on their own, in mixtures with one another or in the form of pharmaceutical compositions. A subject of the present invention also are the compounds of the formula I and their physiologically acceptable salts and solvates for use as a pharmaceutical, as well as pharmaceutical compositions and medicaments which comprise an efficacious dose of at least one compound of the formula I and/or a physiologically acceptable salt thereof and/or solvate thereof as an active ingredient and a pharmaceutically acceptable carrier, i.e. one or more pharmaceutically innocuous, or non-hazardous, vehicles and/or excipients, and optionally one or more other pharmaceutical active compounds. A subject of the present invention furthermore are the compounds of the formula I and their physiologically acceptable salts and solvates for use in the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, the use of the compounds of the formula I and their physiologically acceptable salts and solvates for the manufacture of a medicament for the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, wherein the treatment of diseases comprises their therapy and prophylaxis as mentioned above, as well as their use for the manufacture of a medicament for the inhibition of cathepsin A. A subject of the invention also are methods for the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, which comprise administering an efficacious amount of at least one compound of the formula I and/or a physiologically acceptable salt thereof and/or solvate thereof to a human or an animal which is in need thereof. The compounds of the formula I and pharmaceutical compositions and medicaments comprising them can be administered enterally, for example by oral, sublingual or rectal administration, parenterally, for example by intravenous, intramuscular, subcutaneous or intraperitoneal injection or infusion, or by another type of administration such as topical, percutaneous, transdermal, intra-articular or intraocular administration.

The compounds of the formula I and their physiologically acceptable salts and solvates can also be used in combination with other pharmaceutical active compounds, wherein in such a combination use the compounds of the formula I and/or their physiologically acceptable salts and/or solvates and one or more other pharmaceutical active compounds can be present in one and the same pharmaceutical composition or in two or more pharmaceutical compositions for separate, simultaneous or sequential administration. Examples of such other pharmaceutical active compounds are diuretics, aquaretics, angiotensin converting enzyme (ACE) inhibitors, angiotensin receptor blockers, renin inhibitors, beta blockers, digoxin, aldosterone antagonists, NO donors, nitrates, hydralazines, ionotropes, vasopressin receptor antagonists, soluble guanylate cyclase activators, statins, peroxisome proliferator-activated receptor-alpha (PPAR-α) activators, peroxisome proliferator-activated receptor-gamma (PPAR-γ) activators, rosiglitazone, pioglitazone, metformin, sulfonylureas, glucagon-like peptide 1 (GLP-1) agonists, dipeptidyl peptidase IV (DPPIV) inhibitors, insulins, anti-arrhythmics, endothelin receptor antagonists, calcium antagonists, phosphodiesterase inhibitors, phosphodiesterase type 5 (PDE5) inhibitors, factor II/factor IIa inhibitors, factor IX/factor IXa inhibitors, factor X/factor Xa inhibitors, factor XIII/factor XIIIa inhibitors, heparins, glycoprotein IIb/IIIa antagonists, P2Y12 receptor antagonists, clopidogrel, coumarins, cyclooxygenase inhibitors, acetylsalicylic acid, RAF kinase inhibitors and p38 mitogen-activated protein kinase inhibitors. A subject of the present invention also is the said combination use of any one or more of the compounds of the formula I disclosed herein and their physiologically acceptable salts and solvates, with any one or more, for example one or two, of the mentioned other pharmaceutical active compounds.

The pharmaceutical compositions and medicaments according to the invention normally contain from about 0.5 to about 90 percent by weight of compounds of the formula I and/or physiologically acceptable salts and/or solvates thereof, and an amount of active ingredient of the formula I and/or its physiologically acceptable salt and/or solvate which in general is from about 0.2 mg to about 1.5 g, particularly from about 0.2 mg to about 1 g, more particularly from about 0.5 mg to about 0.5 g, for example from about 1 mg to about 0.3 g, per unit dose. Depending on the kind of the pharmaceutical composition and other particulars of the specific case, the amount may deviate from the indicated ones. The production of the pharmaceutical compositions and medicaments can be carried out in a manner known per se. For this, the compounds of the formula I and/or their physiologically acceptable salts and/or solvates are mixed together with one or more solid or liquid vehicles and/or excipients, if desired also in combination with one or more other pharmaceutical active compounds such as those mentioned above, and brought into a suitable form for dosage and administration, which can then be used in human medicine or veterinary medicine.

As vehicles, which may also be looked upon as diluents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of vehicles and excipients are water, vegetable oils, waxes, alcohols such as ethanol, isopropanol, 1,2-propanediol, benzyl alcohols, glycerol, polyols, polyethylene glycols or polypropylene glycols, glycerol triacetate, polyvinylpyrrolidone, gelatin, cellulose, carbohydrates such as lactose or starch like corn starch, sodium chloride, stearic acid and its salts such as magnesium stearate, talc, lanolin, petroleum jelly, or mixtures thereof, for example saline or mixtures of water with one or more organic solvents such as mixtures of water with alcohols. For oral and rectal use, pharmaceutical forms such as, for example, tablets, film-coated tablets, sugar-coated tablets, granules, hard and soft gelatin capsules, suppositories, solutions, including oily, alcoholic or aqueous solutions, syrups, juices or drops, furthermore suspensions or emulsions, can be used. For parenteral use, for example by injection or infusion, pharmaceutical forms such as solutions, for example aqueous solutions, can be used. For topical use, pharmaceutical forms such as ointments, creams, pastes, lotions, gels, sprays, foams, aerosols, solutions or powders can be used. Further suitable pharmaceutical forms are, for example, implants and patches and forms adapted to inhalation. The compounds of the formula I and their physiologically acceptable salts can also be lyophilized and the obtained lyophilizates used, for example, for the production of injectable compositions. In particular for topical application, also liposomal compositions are suitable. The pharmaceutical compositions and medicaments can also contain one or more other active ingredients and/or, for example, one or more vitamins.

As usual, the dosage of the compounds of the formula I depends on the circumstances of the specific case and is adjusted by the physician according to the customary rules and procedures. It depends, for example, on the compound of the formula I administered and its potency and duration of action, on the nature and severity of the individual syndrome, on the sex, age, weight and the individual responsiveness of the human or animal to be treated, on whether the treatment is acute or chronic or prophylactic, or on whether further pharmaceutical active compounds are administered in addition to a compound of the formula I. Normally, in the case of administration to an adult weighing about 75 kg, a dose from about 0.1 mg to about 100 mg per kg per day, in particular from about 1 mg to about 20 mg per kg per day, for example from about 1 mg to about 10 mg per kg per day (in each case in mg per kg of body weight), is administered. The daily dose can be administered in the form of a single dose or divided into a number of individual doses, for example two, three or four individual doses. The administration can also be carried out continuously, for example by continuous injection or infusion. Depending on the individual behavior in a specific case, it may be necessary to deviate upward or downward from the indicated dosages.

Besides as a pharmaceutical active compound in human medicine and veterinary medicine, the compounds of the formula I can also be employed as an aid in biochemical investigations or as a scientific tool or for diagnostic purposes, for example in in-vitro diagnoses of biological samples, if an inhibition of cathepsin A is intended. The compounds of the formula I and their salts can also be used as intermediates, for example for the preparation of further pharmaceutical active substances.

The following examples illustrate the invention.

ABBREVIATIONS

ACN acetonitrile
DCM dichloromethane
DMF N,N-dimethylformamide
DMSO dimethyl sulfoxide
EA ethyl acetate
EDIA N-ethyl-diisopropylamine
FA formic acid
MOH methanol
NEM N-ethyl-morpholine
TFA trifluoroacetic acid
THF tetrahydrofuran
TOTU O-(cyano(ethoxycarbonyl)methyleneamino)-N,N,N', N'-tetramethyluronium tetrafluoroborate When example compounds containing a basic group were purified by preparative high pressure liquid chromatography (HPLC) on reversed phase (RP) column material and, as customary, the eluent was a gradient mixture of water and acetonitrile containing trifluoroacetic acid, they were in part obtained in the form of their acid addition salts with trifluoroacetic acid, depending on the details of the work-up such as evaporation or lyophilization conditions. In the names of the example compounds and the structural formulae such contained trifluoroacetic acid is not specified. Likewise are other acid components of example compounds obtained in the form of an acid addition salt in general not specified in the name and the formula.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. Unless specified otherwise, $^1$H-NMR spectra were recorded at 500 MHz in $D_6$-DMSO as solvent at 298 K. In the NMR characterization, the chemical shift δ (in ppm), the number of hydrogen atoms (H), and the multiplicity (s: singlet, d: doublet, dd: doublet of doublets, t: triplet, q: quartet, m: multiplet) of the peaks as determined from the graphically depicted spectra are given. In the MS characterization, in general the mass number (m/z) of the peak of the molecular ion [M], for example [M$^+$], or of a related ion such as the ion [M+1], for example [(M+1)$^+$], i.e. the protonated molecular ion [(M+H)$^+$], or the ion [M−1], for example [(M−1)$^-$], i.e. the deprotonated molecular ion [(M−H)$^-$], which was formed depending on the ionization method used, is given. Generally, the ionization method was electrospray ionization (ES). The particulars of the LC/MS methods used are as follows.

Method LC1
  Column: YMC-Pack Jsphere H80, 33×2.1 mm, 4 µm; flow: 1.3 ml/min; room temperature; eluent A: water+0.05% TFA; eluent B: ACN+0.05% TFA; gradient: from 95% A+5% B to 5% A+95% B within 2.5 min; MS ionization method: ES$^+$ Method LC2
  Column: Waters XBridge C18, 50×4.6 mm, 2.5 µm; flow: 1.3 ml/min; room temperature; eluent A: water+0.1% FA; eluent B: ACN+0.08% FA; gradient: from 97% A+3% B to 40% A+60% B within 3.5 min, then to 2% A+98% B within 0.5 min, then 2% A+98% B for 1.0 min, then to 97% A+3% B within 0.2 min, then 97% A+3% B for 1.3 min; MS ionization method: ES$^-$ Method LC3
  Column: YMC-Pack Jsphere H80, 33×2.1 mm, 4 µm; flow: 1.0 ml/min; room temperature; eluent A: water+0.05% TFA; eluent B: ACN+0.05% TFA; gradient: 98% A+2% B for 1.0 min, then to 5% A+95% B within 4.0 min, then 5% A+95% B for 1.25 min; MS ionization method: ES$^+$ Method LC4
  Column: Waters XBridge C18, 50×4.6 mm, 2.5 µm; flow: 1.3 ml/min; 40° C.; eluent A: water+0.1% FA; eluent B: ACN+0.1% FA; gradient: from 97% A+3% B to 40% A+60% B within 3.5 min, then to 2% A+98% B within 0.5 min, then 2% A+98% B for 1.0 min, then to 97% A+3% B within 0.2 min, then 97% A+3% B for 1.3 min; MS ionization method: ES$^-$ Method LC5
  Column: Waters XBridge C18, 50×4.6 mm, 2.5 µm; flow: 1.7 ml/min; 40° C.; eluent A: water+0.05% TFA; eluent B: ACN+0.05% TFA; gradient: from 95% A+5% B to 5% A+95% B within 3.3 min, then 5% A+95% B for 0.55 min, then to 95% A+5% B within 0.15 min; MS ionization method: ES+

Method LC6
  Column: Waters XBridge C18, 50×4.6 mm, 2.5 µm; flow: 1.7 ml/min; 50° C.; eluent A: water+0.05% TFA; eluent B: ACN+0.05% TFA; gradient: 95% A+5% B for 0.2 min, then to 5% A+95% B within 2.2 min, then 5% A+95% B for 1.1 min, then to 95% A+5% B within 0.1 min, then 95% A+5% B for 0.9 min; MS ionization method: ES$^+$ Method LC7
Column: Waters XBridge C18, 50×4.6 mm, 2.5 μm; flow: 1.7 ml/min; 40° C.; eluent A: water+0.05% TFA; eluent B: ACN+0.05% TFA; gradient: 95% A+5% B for 0.2 min, then to 5% A+95% B within 2.2 min, then 5% A+95% B for 0.8 min, then to 95% A+5% B within 0.1 min, then 95% A+5% B for 0.7 min; MS ionization method: ES$^+$ Method LC8
Column: Waters XBridge C18, 50×4.6 mm, 2.5 μm; flow: 1.7 ml/min; 40° C.; eluent A: water+0.05% TFA; eluent B: ACN+0.05% TFA; gradient: 95% A+5% B for 0.3 min, then to 5% A+95% B within 3.2 min, then 5% A+95% B for 0.5 min; MS ionization method: ES$^+$ Method LC9
Column: Merck Chromolith FastGrad RP-18e, 50×2 mm; flow: 2.0 ml/min; room temperature; eluent A: water+0.05% TFA; eluent B: ACN+0.05% TFA; gradient: 98% A+2% B for 0.2 min, then to 2% A+98% B within 2.2 min, then 2% A+98% B for 0.8 min, then to 98% A+2% B within 0.1 min, then 98% A+2% B for 0.7 min; MS ionization method: ES$^+$ Method LC10
Column: Waters XBridge C18, 50×4.6 mm, 2.5 μm; flow: 1.3 ml/min; 45° C.; eluent A: water+0.1% FA; eluent B: ACN+0.1% FA; gradient: from 97% A+3% B to 40% A+60% B within 3.5 min, then to 2% A+98% B within 0.5 min, then 2% A+98% B for 1.0 min, then to 97% A+3% B within 0.2 min, then 97% A+3% B for 1.3 min; MS ionization method: ES$^+$ Method LC11
Column: Waters HPLC BEH C18, 50×2.1 mm, 1.7 μm; flow: 0.9 ml/min; 55° C.; eluent A: water+0.1% FA; eluent B: ACN+0.08% FA; gradient: from 95% A+5% B to 5% A+95% B within 1.1 min, then 5% A+95% B for 0.6 min, then to 95% A+5% B within 0.1 min, then 95% A+5% B for 0.2 min; MS ionization method: ES$^+$ Method LC11_2
Column: Waters HPLC BEH C18, 50×2.1 mm, 1.7 μm; flow: 0.9 ml/min; 55° C.; eluent A: water+0.05% FA; eluent B: ACN+0.035% FA; gradient: from 95% A+5% B to 5% A+95% B within 1.1 min, then 5% A+95% B for 0.6 min, then to 95% A+5% B within 0.1 min, then 95% A+5% B for 0.2 min; MS ionization method: ES$^+$ Method LC11_3
Column: Waters HPLC BEH C18, 50×2.1 mm, 1.7 μm; flow: 0.9 ml/min; 55° C.; eluent A: water+0.05% FA; eluent B: ACN+0.035% FA; gradient: from 95% A+5% B to 5% A+95% B within 1.1 min, then 5% A+95% B for 0.6 min, then to 95% A+5% B within 0.2 min, then 95% A+5% B for 0.1 min; MS ionization method: ES$^+$ Method LC11_X
Column: Waters HPLC BEH C18, 50×2.1 mm, 1.7 μm; flow: 0.9 ml/min; 55° C.; eluent A: water+0.05% TFA; eluent B: ACN+0.035% TFA; gradient: from 98% A+2% B to 5% A+95% B within 2.0 min, then 5% A+95% B for 0.6 min, then to 95% A+5% B within 0.1 min, then 95% A+5% B for 0.3 min; MS ionization method: ES$^+$ Method LC_X
Column: Waters XBridge C18, 50×4.6 mm, 2.5 μm; flow: 1.7 ml/min; 40° C.; eluent A: water+0.05% TFA; eluent B: ACN+0.05% TFA; gradient: from 95% A+5% B to 95% A+5% B within 0.2 min, then to 5% A+95% B within 2.2 min, then 5% A 95% B for 0.8 min, then to 95% A+5% B within 0.1 min, then 95% A+5% B for 0.7 min; MS ionization method: ES$^+$ Method LC12
Column: YMC-Pack Jsphere H80, 33×2.1 mm, 4 μm; flow: 1.0 ml/min; room temperature; eluent A: water+0.05% TFA; eluent B: MOH+0.05% TFA; gradient: 98% A+2% B for 1.0 min, then to 5% A+95% B within 4.0 min, then 5% A+95% B for 1.25 min; MS ionization method: ES$^+$ Method LC13.
Column: Waters XBridge C18, 50×4.6, 2.5 μm; flow: 1.3 mil/min; room temperature; eluent A: water+0.1% FA; eluent B: ACN+0.08% FA; gradient: from 97% A+3% B to 2% A+98% B within 18.0 min, then 2% A+98% B for 1.0 min, then to 97% A+3% B within 0.5 min, then 97% A+3% B for 0.5 min; MS ionization method: ES$^+$ Method LC14
Column: Waters XBridge C18 4.6*50 mm; 2.5 um, flow: 1.3 ml/min, eluent A H$_2$O+0.1% FA; eluent B: ACN+0.08% FA; gradient: from 97% A+3% B to 2% A+98% B within 18 min, then 2% A+98% B for 1 min, then to 97% A+3% B within 0.5 min then to 97:3 for 0.5 min.

Analogously as described in the synthesis examples, the example compounds of the formula I listed in Table 1 were prepared.

TABLE 1

Example compounds of the formula I

| Ex. No. | Compound name | m/z (1) | Rt (min) | LC/MS Method | Activity [μM] |
|---|---|---|---|---|---|
| 1 | (S)-3-[(5-Methoxy-6-phenyl-pyridine-2-carbonyl)-amino]-3-o-tolyl-propionic acid | 391.19 | 1.27 | LC11 | 0.1231 |
| 2 | (S)-3-(2,4-Dichloro-phenyl)-3-[(5-methoxy-6-phenyl-pyridine-2-carbonyl)-amino]-propionic acid | 445.1 | 1.33 | LC11 | 0.547 |
| 3 | (S)-3-[(6-Chloro-5-methoxy-pyridine-2-carbonyl)-amino]-3-o-tolyl-propionic acid | 349.09 | 1.06 | LC11 | 0.274 |
| 4 | (S)-3-{[3-(4,6-Dimethoxy-pyrimidin-2-yloxy)-pyridine-2-carbonyl]-amino}-3-o-tolyl-propionic acid | 439.17 | 1.19 | LC11 | 0.353 |
| 5 | (S)-3-[(Pyridine-2-carbonyl)-amino]-3-o-tolyl-propionic acid | 285.14 | 1.13 | LC11 | 3.98 |
| 6 | (S)-3-[(Pyridine-4-carbonyl)-amino]-3-o-tolyl-propionic acid | 285.16 | 0.97 | LC11 | |
| 7 | (S)-3-[(5-Bromo-pyridine-3-carbonyl)-amino]-3-o-tolyl-propionic acid | 363.04 | 1.14 | LC11 | >10.0 |

TABLE 1-continued

Example compounds of the formula I

| Ex. No. | Compound name | m/z (1) | Rt (min) | LC/MS Method | Activity [µM] |
|---|---|---|---|---|---|
| 8 | (S)-3-[(Pyridine-3-carbonyl)-amino]-3-o-tolyl-propionic acid | 285.16 | 0.99 | LC11 | 10.4 |
| 9 | (S)-3-[(3-Methoxy-pyridine-2-carbonyl)-amino]-3-o-tolyl-propionic acid | 315.18 | 1.04 | LC11 | 7.25 |
| 10 | (S)-3-[(6-Methyl-pyridine-2-carbonyl)-amino]-3-o-tolyl-propionic acid | 299.17 | 1.18 | LC11 | 1.24 |
| 11 | (S)-3-[(4,6-Dimethyl-pyridine-3-carbonyl)-amino]-3-o-tolyl-propionic acid | 313.2 | 0.92 | LC11 | >10.0 |
| 12 | (S)-3-[(6-Methylamino-pyrazine-2-carbonyl)-amino]-3-o-tolyl-propionic acid | 315.17 | 1.08 | LC11 | 7.32 |
| 13 | (S)-3-[(2,6-Bis-dimethylamino-pyrimidine-4-carbonyl)-amino]-3-o-tolyl-propionic acid | 372.24 | 3.25 | LC2 | 10.1 |
| 14 | (S)-3-[(4-Methyl-pyridine-2-carbonyl)-amino]-3-o-tolyl-propionic acid | 299.17 | 1.18 | LC11 | 4.35 |
| 15 | (S)-3-[(5-Phenyl-pyridine-3-carbonyl)-amino]-3-o-tolyl-propionic acid | 361.32 | 3.85 | LC2 | 2.16 |
| 16 | (S)-3-[(2,6-Dimethoxy-pyrimidine-4-carbonyl)-amino]-3-o-tolyl-propionic acid | 346.15 | 1.2 | LC11 | 1.05 |
| 17 | (S)-3-[([1,6]Naphthyridine-2-carbonyl)-amino]-3-o-tolyl-propionic acid | 336.16 | 1.09 | LC11 | 3.09 |
| 18 | (S)-3-[(4-Ethyl-pyridine-2-carbonyl)-amino]-3-o-tolyl-propionic acid | 313.2 | 1.22 | LC11 | 3.06 |
| 19 | (S)-3-[(2-Acetylamino-pyridine-4-carbonyl)-amino]-3-o-tolyl-propionic acid | 342.17 | 1.03 | LC11 | >10.0 |
| 20 | (S)-3-[(3,4,5,6-Tetrahydro-2H-[1,2']bipyridinyl-4'-carbonyl)-amino]-3-o-tolyl-propionic acid | 368.22 | 1.04 | LC11 | |
| 21 | (S)-3-[(2-Methoxy-pyridine-4-carbonyl)-amino]-3-o-tolyl-propionic acid | 315.17 | 1.12 | LC11 | |
| 22 | (S)-3-{[2-(2,2-Dimethyl-propionylamino)-pyridine-4-carbonyl]-amino}-3-o-tolyl-propionic acid | 384.2 | 1.17 | LC11 | |
| 23 | (S)-3-[(6-Bromo-5-methoxy-pyridine-2-carbonyl)-amino]-3-o-tolyl-propionic acid | 393.05 | 1.21 | LC11 | 0.564 |
| 24 | (S)-3-[(6-Methoxy-pyridine-3-carbonyl)-amino]-3-o-tolyl-propionic acid | 315.17 | 1.11 | LC11 | |
| 25 | (S)-3-[(6-Morpholin-4-yl-pyridine-2-carbonyl)-amino]-3-o-tolyl-propionic acid | 370.19 | 1.17 | LC11 | |
| 26 | (S)-3-[(2-Pyrrolidin-1-yl-pyridine-4-carbonyl)-amino]-3-o-tolyl-propionic acid | 354.22 | 0.97 | LC11 | |
| 27 | (S)-3-[(1-Ethyl-3,6-dimethyl-1H-pyrazolo[3,4-b]pyridine-4-carbonyl)-amino]-3-o-tolyl-propionic acid | 381.23 | 1.15 | LC11 | |
| 28 | (S)-3-[(6-Cyclopropyl-1,3-dimethyl-1H-pyrazolo[3,4-b]pyridine-4-carbonyl)-amino]-3-o-tolyl-propionic acid | 393.21 | 1.2 | LC11 | |
| 29 | (S)-3-[(2-Morpholin-4-yl-pyridine-4-carbonyl)-amino]-3-o-tolyl-propionic acid | 370.21 | 1.03 | LC11 | |
| 30 | (S)-3-[(4,6-Dimethoxy-pyrimidine-2-carbonyl)-amino]-3-o-tolyl-propionic acid | 344.27 | 1.15 | LC11 | 4.21 |
| 31 | (S)-3-[(6-Methoxy-pyridine-2-carbonyl)-amino]-3-o-tolyl-propionic acid | 315.17 | 1.19 | LC11 | 4.77 |

TABLE 1-continued

Example compounds of the formula I

| Ex. No. | Compound name | m/z (1) | Rt (min) | LC/MS Method | Activity [μM] |
|---|---|---|---|---|---|
| 32 | (S)-3-{[6-(Tetrahydro-pyran-4-yloxy)-pyridine-3-carbonyl]-amino}-3-o-tolyl-propionic acid | 385.18 | 1.14 | LC11 | |
| 33 | (S)-3-[(3-Fluoro-pyridine-2-carbonyl)-amino]-3-o-tolyl-propionic acid | 301.26 | 1.1 | LC11 | 3.42 |
| 34 | (S)-3-[(3H-Imidazo[4,5-b]pyridine-5-carbonyl)-amino]-3-o-tolyl-propionic acid; compound with trifluoro-acetic acid | 325.16 | 1 | LC11 | 5.07 |
| 35 | (S)-3-{[4-(Pyrimidin-2-ylsulfanyl)-pyridine-2-carbonyl]-amino}-3-o-tolyl-propionic acid | 395.13 | 1.19 | LC11 | 0.844 |
| 36 | (S)-3-[(2-Methyl-pyridine-4-carbonyl)-amino]-3-o-tolyl-propionic acid | 299.18 | 0.94 | LC11 | |
| 37 | (S)-3-[(6-Phenyl-pyridine-2-carbonyl)-amino]-3-o-tolyl-propionic acid | 361.2 | 1.14 | LC11_2 | 0.1302 |
| 38 | (S)-3-[(3-Phenyl-pyridine-2-carbonyl)-amino]-3-o-tolyl-propionic acid | 361.17 | 1.19 | LC11 | |
| 39 | (S)-3-[(4-Phenyl-pyridine-2-carbonyl)-amino]-3-o-tolyl-propionic acid | 361.19 | 1.28 | LC11 | 1.08 |
| 40 | (S)-3-[(5-Phenyl-pyridine-2-carbonyl)-amino]-3-o-tolyl-propionic acid | 361.18 | 1.28 | LC11 | 0.45 |
| 41 | (S)-3-[(5-Pyrrolidin-1-yl-pyridine-3-carbonyl)-amino]-3-o-tolyl-propionic acid; compound with trifluoro-acetic acid | 354.2 | 1.01 | LC11 | |
| 42 | (S)-3-[(5-Methyl-pyrazine-2-carbonyl)-amino]-3-o-tolyl-propionic acid | 298.26 | 1.1 | LC11 | |
| 43 | (S)-3-{[6-(3-Methoxy-phenyl)-pyridine-2-carbonyl]-amino}-3-o-tolyl-propionic acid | 391.19 | 1.14 | LC11_2 | 2.27 |
| 44 | (S)-3-{[6-(2-Methoxy-phenyl)-pyridine-2-carbonyl]-amino}-3-o-tolyl-propionic acid | 391.23 | 1.14 | LC11_2 | 1.192 |
| 45 | (S)-3-{[6-(4-Methoxy-phenyl)-pyridine-2-carbonyl]-amino}-3-o-tolyl-propionic acid | 391.18 | 1.26 | LC11 | 3.09 |
| 46 | (S)-3-[(6-Phenoxy-pyridine-3-carbonyl)-amino]-3-o-tolyl-propionic acid | 377.16 | 1.23 | LC11 | 9.94 |
| 47 | (S)-3-[(4-Hydroxy-pyridine-2-carbonyl)-amino]-3-o-tolyl-propionic acid | 301.14 | 0.97 | LC11 | |
| 48 | (S)-3-[(6-Fluoro-pyridine-2-carbonyl)-amino]-3-o-tolyl-propionic acid | 301.28 | 1.15 | LC11 | 1.67 |
| 49 | (S)-3-[(6-Pyrrolidin-1-yl-pyridine-3-carbonyl)-amino]-3-o-tolyl-propionic acid | 354.21 | 0.95 | LC11 | |
| 50 | (S)-3-[(4-Morpholin-4-yl-pyridine-2-carbonyl)-amino]-3-o-tolyl-propionic acid | 370.2 | 0.93 | LC11 | 7.73 |
| 51 | (S)-3-[(4,6-Dimethyl-pyridine-2-carbonyl)-amino]-3-o-tolyl-propionic acid | 313.19 | 1.2 | LC11 | 1.81 |
| 52 | (S)-3-[(2-Amino-6-isobutyl-pyrimidine-4-carbonyl)-amino]-3-o-tolyl-propionic acid; compound with trifluoro-acetic acid | 357.03 | 1.18 | LC11 | 3.68 |
| 53 | (S)-3-[(3,6-Difluoro-pyridine-2-carbonyl)-amino]-3-o-tolyl-propionic acid | 319.24 | 1.12 | LC11 | 2.83 |
| 54 | (S)-3-[(3,4,5,6-Tetrahydro-2H-[1,2']bipyridinyl-6'-carbonyl)-amino]-3-o-tolyl-propionic acid | 368.22 | 1.3 | LC11 | 8.93 |
| 55 | (S)-3-[(2,6-Dimethyl-pyrimidine-4-carbonyl)-amino]-3-o-tolyl-propionic acid | 314.19 | 1.11 | LC11 | 5.26 |

TABLE 1-continued

Example compounds of the formula I

| Ex. No. | Compound name | m/z (1) | Rt (min) | LC/MS Method | Activity [μM] |
|---|---|---|---|---|---|
| 56 | (S)-3-[(6-Imidazol-1-yl-pyridine-2-carbonyl)-amino]-3-o-tolyl-propionic acid | 351.16 | 0.95 | LC11 | 11.1 |
| 57 | (S)-3-{[5-(4-Methoxy-phenyl)-pyridine-3-carbonyl]-amino}-3-o-tolyl-propionic acid | 391.23 | 1.17 | LC11 | 11.46 |
| 58 | (S)-3-[(6-Methoxy-[2,4']bipyridinyl-4-carbonyl)-amino]-3-o-tolyl-propionic acid; compound with trifluoro-acetic acid | 392.24 | 0.91 | LC11_2 | >30.0 |
| 59 | (S)-3-[(6-Methoxy-[2,3']bipyridinyl-4-carbonyl)-amino]-3-o-tolyl-propionic acid; compound with trifluoro-acetic acid | 392.33 | 0.96 | LC11_2 | >30.0 |
| 60 | (S)-3-o-Tolyl-3-{[5-(3-trifluoromethyl-phenyl)-pyridine-3-carbonyl]-amino}-propionic acid | 429.41 | 4.36 | LC2 | |
| 61 | (S)-3-{[5-(2,4-Dichloro-phenyl)-pyridine-3-carbonyl]-amino}-3-o-tolyl-propionic acid | 429.17 | 1.14 | LC11_2 | 5.14 |
| 62 | (S)-3-{[5-(4-Fluoro-phenyl)-pyridine-3-carbonyl]-amino}-3-o-tolyl-propionic acid | 377.23 | 1.06 | LC11_2 | |
| 63 | (S)-3-o-Tolyl-3-[(5-p-tolyl-pyridine-3-carbonyl)-amino]-propionic acid | 375.39 | 4.09 | LC2 | |
| 64 | (S)-3-o-Tolyl-3-{[5-(4-trifluoromethyl-phenyl)-pyridine-3-carbonyl]-amino}-propionic acid | 429.41 | 4.4 | LC2 | |
| 65 | (S)-3-{[5-(3-Methoxy-phenyl)-pyridine-3-carbonyl]-amino}-3-o-tolyl-propionic acid | 391.41 | 3.91 | LC2 | |
| 66 | (S)-3-o-Tolyl-3-{[5-(2-trifluoromethyl-phenyl)-pyridine-3-carbonyl]-amino}-propionic acid | 429.34 | 4.21 | LC2 | 4.29 |
| 67 | (S)-3-{[5-(2-Methoxy-phenyl)-pyridine-3-carbonyl]-amino}-3-o-tolyl-propionic acid | 391.41 | 3.83 | LC2 | 4.97 |
| 68 | (S)-3-o-Tolyl-3-[(5-m-tolyl-pyridine-3-carbonyl)-amino]-propionic acid | 375.39 | 4.1 | LC2 | |
| 69 | (S)-3-{[5-(2-Fluoro-phenyl)-pyridine-3-carbonyl]-amino}-3-o-tolyl-propionic acid | 379.38 | 3.92 | LC2 | 1.4 |
| 70 | (S)-3-{[5-(3-Cyano-phenyl)-pyridine-3-carbonyl]-amino}-3-o-tolyl-propionic acid | 386.38 | 3.78 | LC2 | |
| 71 | (S)-3-{[5-(4-Cyano-phenyl)-pyridine-3-carbonyl]-amino}-3-o-tolyl-propionic acid | 386.26 | 1.03 | LC11_2 | |
| 72 | (S)-3-{[5-(3,4-Dimethoxy-phenyl)-pyridine-3-carbonyl]-amino}-3-o-tolyl-propionic acid | 421.44 | 3.59 | LC2 | |
| 73 | (S)-3-{[5-(2,4-Difluoro-phenyl)-pyridine-3-carbonyl]-amino}-3-o-tolyl-propionic acid | 395.21 | 1.07 | LC11_2 | 3.25 |
| 74 | (S)-3-{[5-(3,4-Difluoro-phenyl)-pyridine-3-carbonyl]-amino}-3-o-tolyl-propionic acid | 395.19 | 1.08 | LC11_2 | |
| 75 | (S)-3-{[5-(2,6-Difluoro-phenyl)-pyridine-3-carbonyl]-amino}-3-o-tolyl-propionic acid | 395.17 | 1.07 | LC11_2 | |
| 76 | (S)-3-[(5-Benzo[1,3]dioxol-5-yl-pyridine-3-carbonyl)-amino]-3-o-tolyl-propionic acid | 405.34 | 3.78 | LC2 | 8.04 |
| 77 | (S)-3-{[5-(3,4-Dimethyl-phenyl)-pyridine-3-carbonyl]-amino}-3-o-tolyl-propionic acid | 389.39 | 4.29 | LC2 | |
| 78 | (S)-3-o-Tolyl-3-{[5-(3,4,5-trimethoxy-phenyl)-pyridine-3-carbonyl]-amino}-propionic acid | 451.31 | 1.03 | LC11_2 | |
| 79 | (S)-3-{[5-(2,3-Difluoro-phenyl)-pyridine-3-carbonyl]-amino}-3-o-tolyl-propionic acid | 395.17 | 1.07 | LC11_2 | 5.01 |

TABLE 1-continued

Example compounds of the formula I

| Ex. No. | Compound name | m/z (1) | Rt (min) | LC/MS Method | Activity [μM] |
|---|---|---|---|---|---|
| 80 | (S)-3-{[5-(2-Cyano-phenyl)-pyridine-3-carbonyl]-amino}-3-o-tolyl-propionic acid | 386.23 | 1.02 | LC11_2 | |
| 81 | (S)-3-{[5-(3,5-Dimethyl-isoxazol-4-yl)-pyridine-3-carbonyl]-amino}-3-o-tolyl-propionic acid | 380.26 | 0.98 | LC11_2 | |
| 82 | (S)-3-{[5-(4-Fluoro-2-methyl-phenyl)-pyridine-3-carbonyl]-amino}-3-o-tolyl-propionic acid | 393.37 | 4.13 | LC2 | 3.08 |
| 83 | (S)-3-{[(5-Pyrimidin-5-yl-pyridine-3-carbonyl)-amino]-3-o-tolyl-propionic acid; compound with trifluoro-acetic acid | 363.22 | 0.88 | LC11_2 | |
| 84 | (S)-3-{[5-(2-Dimethylcarbamoyl-phenyl)-pyridine-3-carbonyl]-amino}-3-o-tolyl-propionic acid | 432.42 | 3.34 | LC2 | |
| 85 | (S)-3-{[5-(4-Fluoro-2-methoxy-phenyl)-pyridine-3-carbonyl]-amino}-3-o-tolyl-propionic acid | 409.4 | 3.96 | LC2 | 7.83 |
| 86 | (S)-3-{[5-(2-Methoxy-4-trifluoromethyl-phenyl)-pyridine-3-carbonyl]amino}-3-o-tolyl-propionic acid | 459.37 | 4.42 | LC2 | |
| 87 | (S)-3-{[5-(1-Benzyl-1H-pyrazol-4-yl)-pyridine-3-carbonyl]-amino}-3-o-tolyl-propionic acid | 441.45 | 3.78 | LC2 | |
| 88 | (S)-3-{[5-(2-Fluoro-5-methoxy-phenyl)-pyridine-3-carbonyl]-amino}-3-o-tolyl-propionic acid | 407.26 | 1.07 | LC11_2 | 8.51 |
| 89 | (S)-3-{[5-(2-Dimethylamino-pyrimidin-5-yl)-pyridine-3-carbonyl]-amino}-3-o-tolyl-propionic acid; compound with trifluoro-acetic acid | 406.32 | 0.99 | LC11_2 | |
| 90 | (S)-3-[(2'-Morpholin-4-yl-[3,4']bipyridinyl-5-carbonyl)-amino]-3-o-tolyl-propionic acid | 447.34 | 0.88 | LC11_2 | |
| 91 | (S)-3-[(5'-Fluoro-[3,3']bipyridinyl-5-carbonyl)-amino]-3-o-tolyl-propionic acid | 380.22 | 0.97 | LC11_2 | |
| 92 | (S)-3-{[2-(4-Methoxy-phenyl)-pyridine-4-carbonyl]-amino}-3-o-tolyl-propionic acid | 391.2 | 1.16 | LC11 | |
| 93 | (S)-3-o-Tolyl-3-{[2-(4-trifluoromethyl-phenyl)-pyridine-4-carbonyl]-amino}-propionic acid | 429.19 | 1.27 | LC11 | |
| 94 | (S)-3-{[2-(3-Methoxy-phenyl)-pyridine-4-carbonyl]-amino}-3-o-tolyl-propionic acid | 391.23 | 1.18 | LC11 | |
| 95 | (S)-3-{[2-(2-Methoxy-phenyl)-pyridine-4-carbonyl]-amino}-3-o-tolyl-propionic acid | 391.22 | 1.13 | LC11 | |
| 96 | (S)-3-o-Tolyl-3-[(2-m-tolyl-pyridine-4-carbonyl)-amino]-propionic acid | 375.23 | 1.22 | LC11 | |
| 97 | (S)-3-{[2-(2-Fluoro-phenyl)-pyridine-4-carbonyl]-amino}-3-o-tolyl-propionic acid | 379.2 | 1.17 | LC11 | 2.71 |
| 98 | (S)-3-{[2-(3,4-Dimethoxy-phenyl)-pyridine-4-carbonyl]-amino}-3-o-tolyl-propionic acid | 421.23 | 1.13 | LC11 | |
| 99 | (S)-3-{[2-(3,5-Difluoro-phenyl)-pyridine-4-carbonyl]-amino}-3-o-tolyl-propionic acid | 397.18 | 1.24 | LC11 | |
| 100 | (S)-3-{[2-(3,4-Difluoro-phenyl)-pyridine-4-carbonyl]-amino}-3-o-tolyl-propionic acid | 397.2 | 1.23 | LC11 | |
| 101 | (S)-3-[(2-Benzo[1,3]dioxol-5-yl-pyridine-4-carbonyl)-amino]-3-o-tolyl-propionic acid | 405.21 | 1.16 | LC11 | |
| 102 | (S)-3-o-Tolyl-3-{[2-(3,4,5-trimethoxy-phenyl)-pyridine-4-carbonyl]-amino}-propionic acid | 451.26 | 1.16 | LC11 | |

TABLE 1-continued

Example compounds of the formula I

| Ex. No. | Compound name | m/z (1) | Rt (min) | LC/MS Method | Activity [μM] |
|---|---|---|---|---|---|
| 103 | (S)-3-[([2,3']Bipyridinyl-4-carbonyl)-amino]-3-o-tolyl-propionic acid | 362.19 | 0.98 | LC11 | |
| 104 | (S)-3-{[2-(2,5-Dichloro-phenyl)-pyridine-4-carbonyl]-amino}-3-o-tolyl-propionic acid | 429.16 | 1.24 | LC11 | |
| 105 | (S)-3-{[2-(3,5-Dimethyl-isoxazol-4-yl)-pyridine-4-carbonyl]-amino}-3-o-tolyl-propionic acid | 380.2 | 1.11 | LC11 | |
| 106 | (S)-3-[(2'-Methyl-[2,4']bipyridinyl-4-carbonyl)-amino]-3-o-tolyl-propionic acid | 376.21 | 0.94 | LC11 | |
| 107 | (S)-3-{[2-(4-Fluoro-2-methoxy-phenyl)-pyridine-4-carbonyl]-amino}-3-o-tolyl-propionic acid | 409.21 | 1.16 | LC11 | |
| 108 | (S)-3-{[2-(1-Benzyl-1H-pyrazol-4-yl)-pyridine-4-carbonyl]-amino}-3-o-tolyl-propionic acid; compound with trifluoro-acetic acid | 441.27 | 1.16 | LC11 | |
| 109 | (S)-3-{[2-(2-Fluoro-5-methoxy-phenyl)-pyridine-4-carbonyl]-amino}-3-o-tolyl-propionic acid | 409.21 | 1.18 | LC11 | |
| 110 | (S)-3-{[2-(3-Cyclopropylmethoxy-phenyl)-pyridine-4-carbonyl]-amino}-3-o-tolyl-propionic acid | 431.27 | 1.25 | LC11 | |
| 111 | (S)-3-{[5-(3-Chloro-4-fluoro-phenyl)-pyridine-3-carbonyl]-amino}-3-o-tolyl-propionic acid | 413.23 | 1.11 | LC11_2 | |
| 112 | (S)-3-{[5-(2-Chloro-phenyl)-pyridine-3-carbonyl]-amino}-3-o-tolyl-propionic acid | 395.33 | 4.09 | LC2 | 0.826 |
| 113 | (S)-3-{[5-(4-tert-Butyl-phenyl)-pyridine-3-carbonyl]-amino}-3-o-tolyl-propionic acid | 417.45 | 4.66 | LC2 | |
| 114 | (S)-3-{[5-(2,3-Dichloro-phenyl)-pyridine-3-carbonyl]-amino}-3-o-tolyl-propionic acid | 429.21 | 1.13 | LC11_2 | 0.95 |
| 115 | (S)-3-[([3,4']Bipyridinyl-5-carbonyl)-amino]-3-o-tolyl-propionic acid | 362.21 | 0.8 | LC11_2 | |
| 116 | (S)-3-{[5-(2,3-Dimethyl-phenyl)-pyridine-3-carbonyl]-amino}-3-o-tolyl-propionic acid | 389.39 | 4.24 | LC2 | 1.01 |
| 117 | (S)-3-{[5-(2,4-Dimethyl-phenyl)-pyridine-3-carbonyl]-amino}-3-o-tolyl-propionic acid | 389.39 | 4.29 | LC2 | 5.27 |
| 118 | (S)-3-[(2'-Methyl-[3,4']bipyridinyl-5-carbonyl)-amino]-3-o-tolyl-propionic acid | 376.26 | 0.79 | LC11_2 | |
| 119 | (S)-3-{[5-(4-Chloro-2-methoxy-phenyl)-pyridine-3-carbonyl]-amino}-3-o-tolyl-propionic acid | 425.24 | 1.11 | LC11_2 | |
| 120 | (S)-3-({5-[3-(5-Methyl-[1,3,4]oxadiazol-2-yl)-phenyl]-pyridine-3-carbonyl}-amino)-3-o-tolyl-propionic acid | 443.3 | 1 | LC11_2 | |
| 121 | (S)-3-{[5-(3-Chloro-4-dimethylcarbamoyl-phenyl)-pyridine-3-carbonyl]-amino}-3-o-tolyl-propionic acid | 466.27 | 0.99 | LC11_2 | |
| 122 | (S)-3-[(2-Biphenyl-3-yl-pyridine-4-carbonyl)-amino]-3-o-tolyl-propionic acid | 437.27 | 1.29 | LC11 | |
| 123 | (S)-3-{[2-(2,3-Dichloro-phenyl)-pyridine-4-carbonyl]-amino}-3-o-tolyl-propionic acid | 429.12 | 1.23 | LC11 | 3.7 |
| 124 | (S)-3-{[2-(3,4-Dimethyl-phenyl)-pyridine-4-carbonyl]-amino}-3-o-tolyl-propionic acid | 389.23 | 1.24 | LC11 | |
| 125 | (S)-3-{[2-(2,3-Difluoro-phenyl)-pyridine-4-carbonyl]-amino}-3-o-tolyl-propionic acid | 397.18 | 1.19 | LC11 | |
| 126 | (S)-3-{[2-(2-Cyano-phenyl)-pyridine-4-carbonyl]-amino}-3-o-tolyl-propionic acid | 386.18 | 1.14 | LC11 | |

TABLE 1-continued

Example compounds of the formula I

| Ex. No. | Compound name | m/z (1) | Rt (min) | LC/MS Method | Activity [μM] |
|---|---|---|---|---|---|
| 127 | (S)-3-{[2-(4-Fluoro-2-methyl-phenyl)-pyridine-4-carbonyl]-amino}-3-o-tolyl-propionic acid | 393.2 | 1.2 | LC11 | |
| 128 | (S)-3-{[2-(2-Methoxy-4-trifluoromethyl-phenyl)-pyridine-4-carbonyl]-amino}-3-o-tolyl-propionic acid | 459.22 | 1.25 | LC11 | |
| 129 | (S)-3-{[2-(4-Chloro-2-methoxy-phenyl)-pyridine-4-carbonyl]-amino}-3-o-tolyl-propionic acid | 425.17 | 1.21 | LC11 | |
| 130 | (S)-3-[(2'-Morpholin-4-yl-[2,4']bipyridinyl-4-carbonyl)-amino]-3-o-tolyl-propionic acid | 447.27 | 1 | LC11 | |
| 131 | (S)-3-[(5'-Fluoro-[2,3']bipyridinyl-4-carbonyl)-amino]-3-o-tolyl-propionic acid | 380.18 | 1.12 | LC11 | |
| 132 | (S)-3-({2-[3-(1-Hydroxy-1-methyl-ethyl)-phenyl]-pyridine-4-carbonyl}-amino)-3-o-tolyl-propionic acid | 419.25 | 1.13 | LC11 | |
| 133 | (S)-3-o-Tolyl-3-{[6-(3-trifluoromethyl-phenyl)-pyridine-2-carbonyl]-amino}-propionic acid | 429.18 | 1.19 | LC11_2 | 5.76 |
| 134 | (S)-3-{[6-(3-Chloro-4-fluoro-phenyl)-pyridine-2-carbonyl]-amino}-3-o-tolyl-propionic acid | 413.14 | 1.19 | LC11_2 | 3.62 |
| 135 | (S)-3-{[6-(4-Fluoro-phenyl)-pyridine-2-carbonyl]-amino}-3-o-tolyl-propionic acid | 379.17 | 1.15 | LC11_2 | 1.18 |
| 136 | (S)-3-{[6-(4-Chloro-phenyl)-pyridine-2-carbonyl]-amino}-3-o-tolyl-propionic acid | 395.13 | 1.19 | LC11_2 | 4.85 |
| 137 | (S)-3-o-Tolyl-3-[(6-p-tolyl-pyridine-2-carbonyl)-amino]-propionic acid | 375.21 | 1.18 | LC11_2 | 1.24 |
| 138 | (S)-3-o-Tolyl-3-{[6-(4-trifluoromethyl-phenyl)-pyridine-2-carbonyl]-amino}-propionic acid | 429.19 | 1.2 | LC11_2 | 6.83 |
| 139 | (S)-3-o-Tolyl-3-{[6-(2-trifluoromethyl-phenyl)-pyridine-2-carbonyl]-amino}-propionic acid | 429.19 | 1.16 | LC11_2 | 1.09 |
| 140 | (S)-3-{[6-(3-Chloro-phenyl)-pyridine-2-carbonyl]-amino}-3-o-tolyl-propionic acid | 395.18 | 1.18 | LC11_2 | 1.57 |
| 141 | (S)-3-o-Tolyl-3-[(6-m-tolyl-pyridine-2-carbonyl)-amino]-propionic acid | 375.21 | 1.18 | LC11_2 | 0.1608 |
| 142 | (S)-3-{[6-(2-Chloro-phenyl)-pyridine-2-carbonyl]-amino}-3-o-tolyl-propionic acid | 395.14 | 1.16 | LC11_2 | 0.05 |
| 143 | (S)-3-{[6-(2-Fluoro-phenyl)-pyridine-2-carbonyl]-amino}-3-o-tolyl-propionic acid | 379.16 | 1.15 | LC11_2 | 0.0733 |
| 144 | (S)-3-{[6-(4-tert-Butyl-phenyl)-pyridine-2-carbonyl]-amino}-3-o-tolyl-propionic acid | 417.29 | 1.26 | LC11_2 | |
| 145 | (S)-3-{[6-(3-Cyano-phenyl)-pyridine-2-carbonyl]-amino}-3-o-tolyl-propionic acid | 386.21 | 1.11 | LC11_2 | 7.46 |
| 146 | (S)-3-{[6-(4-Cyano-phenyl)-pyridine-2-carbonyl]-amino}-3-o-tolyl-propionic acid | 386.17 | 1.11 | LC11_2 | 2.16 |
| 147 | (S)-3-[(6-Biphenyl-3-yl-pyridine-2-carbonyl)-amino]-3-o-tolyl-propionic acid | 437.26 | 1.24 | LC11_2 | 3.16 |
| 148 | (S)-3-{[6-(3,4-Dimethoxy-phenyl)-pyridine-2-carbonyl]-amino}-3-o-tolyl-propionic acid | 421.22 | 1.1 | LC11_2 | |
| 149 | (S)-3-{[6-(2,4-Difluoro-phenyl)-pyridine-2-carbonyl]-amino}-3-o-tolyl-propionic acid | 397.16 | 1.16 | LC11_2 | 4.4 |
| 150 | (S)-3-{[6-(3,5-Difluoro-phenyl)-pyridine-2-carbonyl]-amino}-3-o-tolyl-propionic acid | 397.15 | 1.16 | LC11_2 | 1.02 |

TABLE 1-continued

Example compounds of the formula I

| Ex. No. | Compound name | m/z (1) | Rt (min) | LC/MS Method | Activity [μM] |
|---|---|---|---|---|---|
| 151 | (S)-3-{[6-(3,4-Difluoro-phenyl)-pyridine-2-carbonyl]-amino}-3-o-tolyl-propionic acid | 397.18 | 1.16 | LC11_2 | 1.18 |
| 152 | (S)-3-[(6-Benzo[1,3]dioxol-5-yl-pyridine-2-carbonyl)-amino]-3-o-tolyl-propionic acid | 405.19 | 1.12 | LC11_2 | 1.55 |
| 153 | (S)-3-{[6-(3,4-Dimethyl-phenyl)-pyridine-2-carbonyl]-amino}-3-o-tolyl-propionic acid | 389.23 | 1.21 | LC11_2 | 1.19 |
| 154 | (S)-3-o-Tolyl-3-{[6-(3,4,5-trimethoxy-phenyl)-pyridine-2-carbonyl]-amino}-propionic acid | 451.24 | 1.12 | LC11_2 | |
| 155 | (S)-3-[([2,3']Bipyridinyl-6-carbonyl)-amino]-3-o-tolyl-propionic acid | 362.17 | 0.93 | LC11_2 | |
| 156 | (S)-3-{[6-(2,3-Difluoro-phenyl)-pyridine-2-carbonyl]-amino}-3-o-tolyl-propionic acid | 397.18 | 1.16 | LC11_2 | 0.272 |
| 157 | (S)-3-{[6-(2-Cyano-phenyl)-pyridine-2-carbonyl]-amino}-3-o-tolyl-propionic acid | 386.14 | 1.1 | LC11_2 | 2.46 |
| 158 | (S)-3-{[6-(2,5-Difluoro-phenyl)-pyridine-2-carbonyl]-amino}-3-o-tolyl-propionic acid | 397.15 | 1.27 | LC11 | 0.126 |
| 159 | (S)-3-{[6-(3,5-Dimethyl-isoxazol-4-yl)-pyridine-2-carbonyl]-amino}-3-o-tolyl-propionic acid | 380.15 | 1.18 | LC11 | 14.4 |
| 160 | (S)-3-{[6-(4-Fluoro-2-methyl-phenyl)-pyridine-2-carbonyl]-amino}-3-o-tolyl-propionic acid | 393.16 | 1.29 | LC11 | 0.472 |
| 161 | (S)-3-{[6-(2,3-Dimethyl-phenyl)-pyridine-2-carbonyl]-amino}-3-o-tolyl-propionic acid | 389.19 | 1.31 | LC11 | 0.0294 |
| 162 | (S)-3-{[6-(2,4-Dimethyl-phenyl)-pyridine-2-carbonyl]-amino}-3-o-tolyl-propionic acid | 389.17 | 1.32 | LC11 | 1.43 |
| 163 | (S)-3-[(2'-Methyl-[2,4']bipyridinyl-6-carbonyl)-amino]-3-o-tolyl-propionic acid | 376.17 | 0.96 | LC11 | |
| 164 | (S)-3-[(6-Pyrimidin-5-yl-pyridine-2-carbonyl)-amino]-3-o-tolyl-propionic acid; compound with trifluoro-acetic acid | 363.15 | 1.09 | LC11 | |
| 165 | (S)-3-{[6-(5-Fluoro-2-methyl-phenyl)-pyridine-2-carbonyl]-amino}-3-o-tolyl-propionic acid | 393.16 | 1.29 | LC11 | 0.0944 |
| 166 | (S)-3-{[6-(4-Fluoro-2-methoxy-phenyl)-pyridine-2-carbonyl]-amino}-3-o-tolyl-propionic acid | 409.16 | 1.27 | LC11 | |
| 167 | (S)-3-{[6-(2-Methoxy-4-trifluoromethyl-phenyl)-pyridine-2-carbonyl]-amino}-3-o-tolyl-propionic acid | 459.18 | 1.32 | LC11 | 0.963 |
| 168 | (S)-3-{[6-(4-Chloro-2-methoxy-phenyl)-pyridine-2-carbonyl]-amino}-3-o-tolyl-propionic acid | 425.13 | 1.31 | LC11 | 0.425 |
| 169 | (S)-3-{[6-(1-Benzyl-1H-pyrazol-4-yl)-pyridine-2-carbonyl]-amino}-3-o-tolyl-propionic acid; compound with trifluoro-acetic acid | 441.19 | 1.23 | LC11 | |
| 170 | (S)-3-{[6-(2-Fluoro-5-methoxy-phenyl)-pyridine-2-carbonyl]-amino}-3-o-tolyl-propionic acid | 409.16 | 1.28 | LC11 | 0.815 |
| 171 | (S)-3-{[6-(3-Cyclopropylmethoxy-phenyl)-pyridine-2-carbonyl]-amino}-3-o-tolyl-propionic acid | 431.22 | 1.33 | LC11 | 6.98 |
| 172 | (S)-3-{[6-(3-Fluoro-2-methyl-phenyl)-pyridine-2-carbonyl]-amino}-3-o-tolyl-propionic acid | 393.17 | 1.29 | LC11 | 3.21 |
| 173 | (S)-3-{[6-(2-Dimethylamino-pyrimidin-5-yl)-pyridine-2-carbonyl]-amino}-3-o-tolyl-propionic acid; compound with trifluoro-acetic acid | 406.21 | 1.2 | LC11 | |

TABLE 1-continued

Example compounds of the formula I

| Ex. No. | Compound name | m/z (1) | Rt (min) | LC/MS Method | Activity [µM] |
|---|---|---|---|---|---|
| 174 | (S)-3-{[6-(3-Chloro-4-dimethylcarbamoyl-phenyl)-pyridine-2-carbonyl]-amino}-3-o-tolyl-propionic acid | 464.31 | 1.18 | LC11 | 1.59 |
| 175 | (S)-3-{[6-(5-Chloro-2-fluoro-4-methyl-phenyl)-pyridine-2-carbonyl]-amino}-3-o-tolyl-propionic acid | 427.13 | 1.34 | LC11 | 2.36 |
| 176 | (S)-3-({6-[3-(1-Hydroxy-1-methyl-ethyl)-phenyl]-pyridine-2-carbonyl}-amino)-3-o-tolyl-propionic acid | 419.2 | 1.2 | LC11 | 3.32 |
| 177 | (S)-3-{[2-(2-Dimethylamino-pyrimidin-5-yl)-pyridine-4-carbonyl]-amino}-3-o-tolyl-propionic acid; compound with trifluoro-acetic acid | 406.25 | 1.12 | LC11 | |
| 178 | (S)-3-{[6-(2-Fluoro-phenyl)-5-methoxy-pyridine-2-carbonyl]-amino}-3-o-tolyl-propionic acid | 409.1 | 1.12 | LC11_2 | 0.0683 |
| 179 | (S)-3-{[2-(3-Chloro-phenyl)-pyridine-4-carbonyl]-amino}-3-o-tolyl-propionic acid | 395.23 | 4.51 | LC2 | |
| 180 | (S)-3-{[6-(2-Fluoro-5-methyl-phenyl)-pyridine-2-carbonyl]-amino}-3-o-tolyl-propionic acid | 393.16 | 1.3 | LC11 | 0.289 |
| 181 | (S)-3-{[5-Methoxy-6-(3-trifluoromethyl-phenyl)-pyridine-2-carbonyl]-amino}-3-p-tolyl-propionic acid | 459.28 | 1.19 | LC11_2 | 5 |
| 182 | (S)-3-[(5-Methoxy-6-phenyl-pyridine-2-carbonyl)-amino]-3-p-tolyl-propionic acid | 389.28 | 1.14 | LC11_2 | 0.232 |
| 183 | (S)-3-{[6-(2,4-Dichloro-phenyl)-5-methoxy-pyridine-2-carbonyl]-amino}-3-p-tolyl-propionic acid | 459.21 | 1.2 | LC11_2 | 1.009 |
| 184 | (S)-3-{[6-(3-Chloro-4-fluoro-phenyl)-5-methoxy-pyridine-2-carbonyl]-amino}-3-p-tolyl-propionic acid | 443.23 | 1.19 | LC11_2 | >10.0 |
| 185 | (S)-3-{[6-(4-Fluoro-phenyl)-5-methoxy-pyridine-2-carbonyl]-amino}-3-p-tolyl-propionic acid | 409.23 | 1.15 | LC11_2 | 1.289 |
| 186 | (S)-3-{[6-(4-Chloro-phenyl)-5-methoxy-pyridine-2-carbonyl]-amino}-3-p-tolyl-propionic acid | 425.25 | 1.18 | LC11_2 | 3.56 |
| 187 | (S)-3-{[5-Methoxy-6-(4-methoxy-phenyl)-pyridine-2-carbonyl]-amino}-3-p-tolyl-propionic acid | 419.32 | 1.13 | LC11_2 | 4.85 |
| 188 | (S)-3-[(5-Methoxy-6-p-tolyl-pyridine-2-carbonyl)-amino]-3-p-tolyl-propionic acid | 403.31 | 1.17 | LC11_2 | 4.45 |
| 189 | (S)-3-{[5-Methoxy-6-(4-trifluoromethyl-phenyl)-pyridine-2-carbonyl]-amino}-3-p-tolyl-propionic acid | 457.35 | 1.2 | LC11_2 | >10.0 |
| 190 | (S)-3-[(5-Methoxy-6-o-tolyl-pyridine-2-carbonyl)-amino]-3-p-tolyl-propionic acid | 403.33 | 1.14 | LC11_2 | 0.0813 |
| 191 | (S)-3-{[5-Methoxy-6-(3-methoxy-phenyl)-pyridine-2-carbonyl]-amino}-3-p-tolyl-propionic acid | 419.34 | 1.14 | LC11_2 | 4.57 |
| 192 | (S)-3-{[5-Methoxy-6-(2-trifluoromethyl-phenyl)-pyridine-2-carbonyl]-amino}-3-p-tolyl-propionic acid | 457.33 | 1.15 | LC11_2 | 0.1457 |
| 193 | (S)-3-{[6-(3-Chloro-phenyl)-5-methoxy-pyridine-2-carbonyl]-amino}-3-p-tolyl-propionic acid | 425.17 | 1.18 | LC11_2 | 2.74 |
| 194 | (S)-3-{[6-(3-Fluoro-phenyl)-5-methoxy-pyridine-2-carbonyl]-amino}-3-p-tolyl-propionic acid | 407.29 | 1.15 | LC11_2 | 0.725 |
| 195 | (S)-3-[(5-Methoxy-6-naphthalen-2-yl-pyridine-2-carbonyl)-amino]-3-p-tolyl-propionic acid | 441 | 1.2 | LC11_2 | 8.83 |

TABLE 1-continued

Example compounds of the formula I

| Ex. No. | Compound name | m/z (1) | Rt (min) | LC/MS Method | Activity [µM] |
|---|---|---|---|---|---|
| 196 | (S)-3-{[5-Methoxy-6-(2-methoxy-phenyl)-pyridine-2-carbonyl]-amino}-3-p-tolyl-propionic acid | 419.33 | 1.11 | LC11_2 | 0.1191 |
| 197 | (S)-3-[(5-Methoxy-6-m-tolyl-pyridine-2-carbonyl)-amino]-3-p-tolyl-propionic acid | 404.68 | 1.17 | LC11_2 | 1.71 |
| 198 | (S)-3-{[6-(2-Chloro-phenyl)-5-methoxy-pyridine-2-carbonyl]-amino}-3-p-tolyl-propionic acid | 423.24 | 1.14 | LC11_2 | 0.159 |
| 199 | (S)-3-{[6-(2-Fluoro-phenyl)-5-methoxy-pyridine-2-carbonyl]-amino}-3-p-tolyl-propionic acid | 407.28 | 1.12 | LC11_2 | 0.228 |
| 200 | (S)-3-{[6-(4-tert-Butyl-phenyl)-5-methoxy-pyridine-2-carbonyl]-amino}-3-p-tolyl-propionic acid | 445.39 | 1.25 | LC11_2 | >10.0 |
| 201 | (S)-3-{[6-(3-Cyano-phenyl)-5-methoxy-pyridine-2-carbonyl]-amino}-3-p-tolyl-propionic acid | 415.81 | 1.12 | LC11_2 | >10.0 |
| 202 | (S)-3-{[6-(4-Cyano-phenyl)-5-methoxy-pyridine-2-carbonyl]-amino}-3-p-tolyl-propionic acid | 416.24 | 1.11 | LC11_2 | >10.0 |
| 203 | (S)-3-{[6-(3-Acetyl-phenyl)-5-methoxy-pyridine-2-carbonyl]-amino}-3-p-tolyl-propionic acid | 433.31 | 1.1 | LC11_2 | 8.35 |
| 204 | (S)-3-[(6-Biphenyl-3-yl-5-methoxy-pyridine-2-carbonyl)-amino]-3-p-tolyl-propionic acid | 465.32 | 1.22 | LC11_2 | 1.402 |
| 205 | (S)-3-{[6-(4-Acetyl-phenyl)-5-methoxy-pyridine-2-carbonyl]-amino}-3-p-tolyl-propionic acid | 431.43 | 1.1 | LC11_2 | >10.0 |
| 206 | (S)-3-{[6-(2,4-Difluoro-phenyl)-5-methoxy-pyridine-2-carbonyl]-amino}-3-p-tolyl-propionic acid | 425.26 | 1.14 | LC11_2 | 0.1556 |
| 207 | (S)-3-{[6-(3,5-Difluoro-phenyl)-5-methoxy-pyridine-2-carbonyl]-amino}-3-p-tolyl-propionic acid | 425.28 | 1.16 | LC11_2 | 2.65 |
| 208 | (S)-3-{[6-(3,4-Difluoro-phenyl)-5-methoxy-pyridine-2-carbonyl]-amino}-3-p-tolyl-propionic acid | 425.31 | 1.16 | LC11_2 | 7.42 |
| 209 | (S)-3-{[6-(2,3-Dichloro-phenyl)-5-methoxy-pyridine-2-carbonyl]-amino}-3-p-tolyl-propionic acid | 457.27 | 1.18 | LC11_2 | 0.0696 |
| 210 | (S)-3-{[6-(5-Acetyl-thiophen-2-yl)-5-methoxy-pyridine-2-carbonyl]-amino}-3-p-tolyl-propionic acid | 437.3 | 1.1 | LC11_2 | 7.52 |
| 211 | (S)-3-{[6-(2-Chloro-5-trifluoromethyl-phenyl)-5-methoxy-pyridine-2-carbonyl]-amino}-3-p-tolyl-propionic acid | 493.24 | 1.19 | LC11_2 | 0.421 |
| 212 | (S)-3-{[6-(3-Fluoro-2-methyl-phenyl)-5-methoxy-pyridine-2-carbonyl]-amino}-3-(2-fluoro-phenyl)-propionic acid | 427.27 | 1.13 | LC11_2 | 0.1497 |
| 213 | (S)-3-{[6-(2-Chloro-5-trifluoromethyl-phenyl)-5-methoxy-pyridine-2-carbonyl]-amino}-3-(2-fluoro-phenyl)-propionic acid | 497.2 | 1.17 | LC11_2 | 0.887 |
| 214 | (S)-3-(2-Chloro-phenyl)-3-{[6-(2-fluoro-4-trifluoromethyl-phenyl)-5-methoxy-pyridine-2-carbonyl]-amino}-propionic acid | 497.21 | 1.19 | LC11_2 | 7.02 |
| 215 | (S)-3-[(3-Methoxy-[2,4']bipyridinyl-6-carbonyl)-amino]-3-p-tolyl-propionic acid | 390.2 | 0.88 | LC11_2 | 9.66 |
| 216 | (S)-3-[(3-Methoxy-[2,3']bipyridinyl-6-carbonyl)-amino]-3-p-tolyl-propionic acid | 390.25 | 0.93 | LC11_2 | >10.0 |
| 217 | (S)-3-{[6-(2,3-Difluoro-phenyl)-5-methoxy-pyridine-2-carbonyl]-amino}-3-p-tolyl-propionic acid | 425.32 | 1.13 | LC11_2 | 0.0902 |
| 218 | (S)-3-{[6-(2,5-Difluoro-phenyl)-5-methoxy-pyridine-2-carbonyl]-amino}-3-p-tolyl-propionic acid | 425.31 | 1.13 | LC11_2 | 0.0998 |

TABLE 1-continued

Example compounds of the formula I

| Ex. No. | Compound name | m/z (1) | Rt (min) | LC/MS Method | Activity [μM] |
|---|---|---|---|---|---|
| 219 | (S)-3-{[6-(2,5-Dichloro-phenyl)-5-methoxy-pyridine-2-carbonyl]-amino}-3-p-tolyl-propionic acid | 457.25 | 1.18 | LC11_2 | 0.91 |
| 220 | (S)-3-{[6-(3,5-Dimethyl-isoxazol-4-yl)-5-methoxy-pyridine-2-carbonyl]-amino}-3-p-tolyl-propionic acid | 408.28 | 1.07 | LC11_2 | 0.143 |
| 221 | (S)-3-{[6-(4-Fluoro-2-methyl-phenyl)-5-methoxy-pyridine-2-carbonyl]-amino}-3-p-tolyl-propionic acid | 421.35 | 1.15 | LC11_2 | 0.239 |
| 222 | (S)-3-{[6-(2,3-Dimethyl-phenyl)-5-methoxy-pyridine-2-carbonyl]-amino}-3-p-tolyl-propionic acid | 417.34 | 1.17 | LC11_2 | 0.037 |
| 223 | (S)-3-{[6-(3-Fluoro-4-methyl-phenyl)-5-methoxy-pyridine-2-carbonyl]-amino}-3-p-tolyl-propionic acid | 423.27 | 1.18 | LC11_2 | 1.294 |
| 224 | (S)-3-{[6-(2,4-Dimethyl-phenyl)-5-methoxy-pyridine-2-carbonyl]-amino}-3-p-tolyl-propionic acid | 417.36 | 1.18 | LC11_2 | 3.39 |
| 225 | (S)-3-{[6-(4-Fluoro-3-methyl-phenyl)-5-methoxy-pyridine-2-carbonyl]-amino}-3-p-tolyl-propionic acid | 421.33 | 1.18 | LC11_2 | 3.26 |
| 226 | (S)-3-[(5-Methoxy-6-pyrimidin-5-yl-pyridine-2-carbonyl)-amino]-3-p-tolyl-propionic acid | 391.29 | 1 | LC11_2 | >10.0 |
| 227 | (S)-3-[(6'-Fluoro-3-methoxy-[2,3']bipyridinyl-6-carbonyl)-amino]-3-p-tolyl-propionic acid | 408.28 | 1.09 | LC11_2 | 7.63 |
| 228 | (S)-3-{[6-(2-Dimethylcarbamoyl-phenyl)-5-methoxy-pyridine-2-carbonyl]-amino}-3-p-tolyl-propionic acid | 462.31 | 1.06 | LC11_2 | 3.96 |
| 229 | (S)-3-[(3,2'-Dimethoxy-[2,3']bipyridinyl-6-carbonyl)-amino]-3-p-tolyl-propionic acid | 422.29 | 1.07 | LC11_2 | 0.609 |
| 230 | (S)-3-{[6-(5-Fluoro-2-methyl-phenyl)-5-methoxy-pyridine-2-carbonyl]-amino}-3-p-tolyl-propionic acid | 423.27 | 1.15 | LC11_2 | 0.1113 |
| 231 | (S)-3-{[6-(4-Fluoro-2-methoxy-phenyl)-5-methoxy-pyridine-2-carbonyl]-amino}-3-p-tolyl-propionic acid | 439.27 | 1.12 | LC11_2 | 0.305 |
| 232 | (S)-3-{[6-(4-Chloro-2-methoxy-phenyl)-5-methoxy-pyridine-2-carbonyl]-amino}-3-p-tolyl-propionic acid | 455.26 | 1.16 | LC11_2 | 2.33 |
| 233 | (S)-3-{[6-(5-Chloro-2-methoxy-phenyl)-5-methoxy-pyridine-2-carbonyl]-amino}-3-p-tolyl-propionic acid | 455.25 | 1.15 | LC11_2 | 2.24 |
| 234 | (S)-3-{[6-(5-Fluoro-2-methoxy-phenyl)-5-methoxy-pyridine-2-carbonyl]-amino}-3-p-tolyl-propionic acid | 439.28 | 1.12 | LC11_2 | 0.51 |
| 235 | (S)-3-{[6-(2,5-Dimethoxy-phenyl)-5-methoxy-pyridine-2-carbonyl]-amino}-3-p-tolyl-propionic acid | 451.3 | 1.1 | LC11_2 | >10.0 |
| 236 | (S)-3-{[6-(2-Fluoro-5-trifluoromethyl-phenyl)-5-methoxy-pyridine-2-carbonyl]-amino}-3-p-tolyl-propionic acid | 477.27 | 1.18 | LC11_2 | 3.57 |
| 237 | (S)-3-{[5-Methoxy-6-(5-methyl-furan-2-yl)-pyridine-2-carbonyl]-amino}-3-p-tolyl-propionic acid | 395.25 | 1.11 | LC11_2 | 3.54 |
| 238 | (S)-3-{[5-Methoxy-6-(1-methyl-1H-pyrazol-4-yl)-pyridine-2-carbonyl]-amino}-3-p-tolyl-propionic acid | 395.26 | 1.02 | LC11_2 | >10.0 |

TABLE 1-continued

Example compounds of the formula I

| Ex. No. | Compound name | m/z (1) | Rt (min) | LC/MS Method | Activity [μM] |
|---|---|---|---|---|---|
| 239 | (S)-3-{[6-(2-Fluoro-5-methoxy-phenyl)-5-methoxy-pyridine-2-carbonyl]-amino}-3-p-tolyl-propionic acid | 439.28 | 1.12 | LC11_2 | 1.16 |
| 240 | (S)-3-{[6-(5-tert-Butyl-2-methoxy-phenyl)-5-methoxy-pyridine-2-carbonyl]-amino}-3-p-tolyl-propionic acid | 477.37 | 1.22 | LC11_2 | >10.0 |
| 241 | (S)-3-{[6-(2-Fluoro-4-trifluoromethyl-phenyl)-5-methoxy-pyridine-2-carbonyl]-amino}-3-p-tolyl-propionic acid | 477.27 | 1.19 | LC11_2 | >10.0 |
| 242 | (S)-3-{[6-(2-Fluoro-5-methyl-phenyl)-5-methoxy-pyridine-2-carbonyl]-amino}-3-p-tolyl-propionic acid | 423.29 | 1.15 | LC11_2 | 0.278 |
| 243 | (S)-3-{[6-(3-Chloro-2-methyl-phenyl)-5-methoxy-pyridine-2-carbonyl]-amino}-3-p-tolyl-propionic acid | 439.27 | 1.19 | LC11_2 | 0.2027 |
| 244 | (S)-3-{[6-(3-Fluoro-2-methyl-phenyl)-5-methoxy-pyridine-2-carbonyl]-amino}-3-p-tolyl-propionic acid | 423.29 | 1.15 | LC11_2 | 0.0901 |
| 245 | (S)-3-{[6-(5-Chloro-2-fluoro-phenyl)-5-methoxy-pyridine-2-carbonyl]-amino}-3-p-tolyl-propionic acid | 443.24 | 1.17 | LC11_2 | 0.44 |
| 246 | (S)-3-{[6-(4-Chloro-3-fluoro-phenyl)-5-methoxy-pyridine-2-carbonyl]-amino}-3-p-tolyl-propionic acid | 443.22 | 1.2 | LC11_2 | 4.48 |
| 247 | (S)-3-[(2'-Chloro-3-methoxy-5'-methyl-[2,3']bipyridinyl-6-carbonyl)-amino]-3-p-tolyl-propionic acid | 440.27 | 1.09 | LC11_2 | 8.43 |
| 248 | (S)-3-{[6-(3-Chloro-5-methyl-phenyl)-5-methoxy-pyridine-2-carbonyl]-amino}-3-p-tolyl-propionic acid | 439.25 | 1.21 | LC11_2 | >10.0 |
| 249 | (S)-3-({5-Methoxy-6-[3-(5-methyl-[1,3,4]oxadiazol-2-yl)-phenyl]-pyridine-2-carbonyl}-amino)-3-p-tolyl-propionic acid | 473.29 | 1.08 | LC11_2 | 8.71 |
| 250 | (S)-3-{[5-Methoxy-6-(1,3,5-trimethyl-1H-pyrazol-4-yl)-pyridine-2-carbonyl]-amino}-3-p-tolyl-propionic acid | 423.32 | 1.02 | LC11_2 | >10.0 |
| 251 | (S)-3-{[5-Methoxy-6-(1-methyl-1H-indol-6-yl)-pyridine-2-carbonyl]-amino}-3-p-tolyl-propionic acid | 444.31 | 1.16 | LC11_2 | 8.94 |
| 252 | (S)-3-{[6-(4-Chloro-3-methoxy-phenyl)-5-methoxy-pyridine-2-carbonyl]-amino}-3-p-tolyl-propionic acid | 455.26 | 1.18 | LC11_2 | >10.0 |
| 253 | (S)-3-(2-Fluoro-phenyl)-3-{[5-methoxy-6-(3-trifluoromethyl-phenyl)-pyridine-2-carbonyl]-amino}-propionic acid | 461.3 | 1.17 | LC11_2 | 4.06 |
| 254 | (S)-3-(2-Fluoro-phenyl)-3-[(5-methoxy-6-phenyl-pyridine-2-carbonyl)-amino]-propionic acid | 395.25 | 1.11 | LC11_2 | 0.1818 |
| 255 | (S)-3-{[6-(2,4-Dichloro-phenyl)-5-methoxy-pyridine-2-carbonyl]-amino}-3-(2-fluoro-phenyl)-propionic acid | 463.18 | 1.18 | LC11_2 | 0.879 |
| 256 | (S)-3-{[6-(3-Chloro-4-fluoro-phenyl)-5-methoxy-pyridine-2-carbonyl]-amino}-3-(2-fluoro-phenyl)-propionic acid | 447.21 | 1.17 | LC11_2 | >10.0 |
| 257 | (S)-3-(2-Fluoro-phenyl)-3-{[6-(4-fluoro-phenyl)-5-methoxy-pyridine-2-carbonyl]-amino}-propionic acid | 413.21 | 1.12 | LC11_2 | 1.263 |

TABLE 1-continued

Example compounds of the formula I

| Ex. No. | Compound name | m/z (1) | Rt (min) | LC/MS Method | Activity [µM] |
|---|---|---|---|---|---|
| 258 | (S)-3-{[6-(4-Chloro-phenyl)-5-methoxy-pyridine-2-carbonyl]-amino}-3-(2-fluoro-phenyl)-propionic acid | 429.24 | 1.17 | LC11_2 | 5.27 |
| 259 | (S)-3-(2-Fluoro-phenyl)-3-{[5-methoxy-6-(4-methoxy-phenyl)-pyridine-2-carbonyl]-amino}-propionic acid | 425.27 | 1.11 | LC11_2 | 5.01 |
| 260 | (S)-3-(2-Fluoro-phenyl)-3-[(5-methoxy-6-p-tolyl-pyridine-2-carbonyl)-amino]-propionic acid | 409.27 | 1.15 | LC11_2 | 5.18 |
| 261 | (S)-3-(2-Fluoro-phenyl)-3-{[5-methoxy-6-(4-trifluoromethyl-phenyl)-pyridine-2-carbonyl]-amino}-propionic acid | 463.27 | 1.18 | LC11_2 | >10.0 |
| 262 | (S)-3-(2-Fluoro-phenyl)-3-[(5-methoxy-6-o-tolyl-pyridine-2-carbonyl)-amino]-propionic acid | 407.26 | 1.12 | LC11_2 | 0.0819 |
| 263 | (S)-3-(2-Fluoro-phenyl)-3-{[5-methoxy-6-(3-methoxy-phenyl)-pyridine-2-carbonyl]-amino}-propionic acid | 425.27 | 1.11 | LC11_2 | 5.06 |
| 264 | (S)-3-(2-Fluoro-phenyl)-3-{[5-methoxy-6-(2-trifluoromethyl-phenyl)-pyridine-2-carbonyl]-amino}-propionic acid | 463.25 | 1.12 | LC11_2 | 0.179 |
| 265 | (S)-3-{[6-(3-Chloro-phenyl)-5-methoxy-pyridine-2-carbonyl]-amino}-3-(2-fluoro-phenyl)-propionic acid | 429.23 | 1.16 | LC11_2 | 1.719 |
| 266 | (S)-3-(2-Fluoro-phenyl)-3-{[6-(3-fluoro-phenyl)-5-methoxy-pyridine-2-carbonyl]-amino}-propionic acid | 413.23 | 1.13 | LC11_2 | 1.26 |
| 267 | (S)-3-(2-Fluoro-phenyl)-3-[(5-methoxy-6-naphthalen-2-yl-pyridine-2-carbonyl)-amino]-propionic acid | 445.3 | 1.18 | LC11_2 | >10.0 |
| 268 | (S)-3-(2-Fluoro-phenyl)-3-{[5-methoxy-6-(2-methoxy-phenyl)-pyridine-2-carbonyl]-amino}-propionic acid | 425.25 | 1.08 | LC11_2 | 0.102 |
| 269 | (S)-3-(2-Fluoro-phenyl)-3-[(5-methoxy-6-m-tolyl-pyridine-2-carbonyl)-amino]-propionic acid | 409.26 | 1.15 | LC11_2 | 1.015 |
| 270 | (S)-3-{[6-(2-Chloro-phenyl)-5-methoxy-pyridine-2-carbonyl]-amino}-3-(2-fluoro-phenyl)-propionic acid | 429.23 | 1.11 | LC11_2 | 0.9178 |
| 271 | (S)-3-(2-Fluoro-phenyl)-3-{[6-(2-fluoro-phenyl)-5-methoxy-pyridine-2-carbonyl]-amino}-propionic acid | 413.23 | 1.1 | LC11_2 | 0.0418 |
| 272 | (S)-3-{[6-(4-tert-Butyl-phenyl)-5-methoxy-pyridine-2-carbonyl]-amino}-3-(2-fluoro-phenyl)-propionic acid | 451.34 | 1.23 | LC11_2 | >10.0 |
| 273 | (S)-3-{[6-(3-Cyano-phenyl)-5-methoxy-pyridine-2-carbonyl]-amino}-3-(2-fluoro-phenyl)-propionic acid | 420.25 | 1.09 | LC11_2 | 9.57 |
| 274 | (S)-3-{[6-(4-Cyano-phenyl)-5-methoxy-pyridine-2-carbonyl]-amino}-3-(2-fluoro-phenyl)-propionic acid | 420.23 | 1.09 | LC11_2 | >10.0 |
| 275 | (S)-3-{[6-(3-Acetyl-phenyl)-5-methoxy-pyridine-2-carbonyl]-amino}-3-(2-fluoro-phenyl)-propionic acid | 437.25 | 1.08 | LC11_2 | 8.54 |
| 276 | (S)-3-[(6-Biphenyl-3-yl-5-methoxy-pyridine-2-carbonyl)-amino]-3-(2-fluoro-phenyl)-propionic acid | 471.33 | 1.21 | LC11_2 | 2.16 |

TABLE 1-continued

Example compounds of the formula I

| Ex. No. | Compound name | m/z (1) | Rt (min) | LC/MS Method | Activity [μM] |
|---|---|---|---|---|---|
| 277 | (S)-3-{[6-(4-Acetyl-phenyl)-5-methoxy-pyridine-2-carbonyl]-amino}-3-(2-fluoro-phenyl)-propionic acid | 437.27 | 1.07 | LC11_2 | >10.0 |
| 278 | (S)-3-{[6-(2,4-Difluoro-phenyl)-5-methoxy-pyridine-2-carbonyl]-amino}-3-(2-fluoro-phenyl)-propionic acid | 431.24 | 1.12 | LC11_2 | 0.1201 |
| 279 | (S)-3-{[6-(3,5-Difluoro-phenyl)-5-methoxy-pyridine-2-carbonyl]-amino}-3-(2-fluoro-phenyl)-propionic acid | 431.21 | 1.15 | LC11_2 | 3.85 |
| 280 | (S)-3-{[6-(3,4-Difluoro-phenyl)-5-methoxy-pyridine-2-carbonyl]-amino}-3-(2-fluoro-phenyl)-propionic acid | 431.23 | 1.14 | LC11_2 | 3.12 |
| 281 | (S)-3-{[6-(2,3-Dichloro-phenyl)-5-methoxy-pyridine-2-carbonyl]-amino}-3-(2-fluoro-phenyl)-propionic acid | 463.16 | 1.15 | LC11_2 | 0.114 |
| 282 | (S)-3-(2-Fluoro-phenyl)-3-[(3-methoxy-[2,4']bipyridinyl-6-carbonyl)-amino]-propionic acid | 396.21 | 0.84 | LC11_2 | >10.0 |
| 283 | (S)-3-{[6-(5-Cyano-thiophen-2-yl)-5-methoxy-pyridine-2-carbonyl]-amino}-3-(2-fluoro-phenyl)-propionic acid | 426.15 | 1.1 | LC11_2 | 5.4 |
| 284 | (S)-3-(2-Fluoro-phenyl)-3-[(3-methoxy-[2,3']bipyridinyl-6-carbonyl)-amino]-propionic acid | 396.22 | 0.88 | LC11_2 | >10.0 |
| 285 | (S)-3-{[6-(2,3-Difluoro-phenyl)-5-methoxy-pyridine-2-carbonyl]-amino}-3-(2-fluoro-phenyl)-propionic acid | 431.25 | 1.11 | LC11_2 | 0.234 |
| 286 | (S)-3-{[6-(2,5-Difluoro-phenyl)-5-methoxy-pyridine-2-carbonyl]-amino}-3-(2-fluoro-phenyl)-propionic acid | 431.23 | 1.11 | LC11_2 | 0.171 |
| 287 | (S)-3-{[6-(3,5-Dimethyl-isoxazol-4-yl)-5-methoxy-pyridine-2-carbonyl]-amino}-3-(2-fluoro-phenyl)-propionic acid | 414.25 | 1.04 | LC11_2 | 0.645 |
| 288 | (S)-3-{[6-(4-Fluoro-2-methyl-phenyl)-5-methoxy-pyridine-2-carbonyl]-amino}-3-(2-fluoro-phenyl)-propionic acid | 427.27 | 1.13 | LC11_2 | 0.394 |
| 289 | (S)-3-{[6-(2,3-Dimethyl-phenyl)-5-methoxy-pyridine-2-carbonyl]-amino}-3-(2-fluoro-phenyl)-propionic acid | 423.29 | 1.14 | LC11_2 | 0.0528 |
| 290 | (S)-3-{[6-(3-Fluoro-4-methyl-phenyl)-5-methoxy-pyridine-2-carbonyl]-amino}-3-(2-fluoro-phenyl)-propionic acid | 427.26 | 1.16 | LC11_2 | 3.81 |
| 291 | (S)-3-{[6-(2,4-Dimethyl-phenyl)-5-methoxy-pyridine-2-carbonyl]-amino}-3-(2-fluoro-phenyl)-propionic acid | 423.29 | 1.15 | LC11_2 | 4.02 |
| 292 | (S)-3-{[6-(4-Fluoro-3-methyl-phenyl)-5-methoxy-pyridine-2-carbonyl]-amino}-3-(2-fluoro-phenyl)-propionic acid | 427.25 | 1.16 | LC11_2 | 4.13 |
| 293 | (S)-3-(2-Fluoro-phenyl)-3-[(5-methoxy-6-pyrimidin-5-yl-pyridine-2-carbonyl)-amino]-propionic acid | 397.2 | 0.96 | LC11_2 | >10.0 |
| 294 | (S)-3-[(6'-Fluoro-3-methoxy-[2,3']bipyridinyl-6-carbonyl)-amino]-3-(2-fluoro-phenyl)-propionic acid | 414.22 | 1.06 | LC11_2 | >10.0 |
| 295 | (S)-3-{[6-(2-Dimethylcarbamoyl-phenyl)-5-methoxy-pyridine-2-carbonyl]-amino}-3-(2-fluoro-phenyl)-propionic acid | 464.38 | 1.02 | LC11_2 | 4.51 |

TABLE 1-continued

Example compounds of the formula I

| Ex. No. | Compound name | m/z (1) | Rt (min) | LC/MS Method | Activity [μM] |
|---|---|---|---|---|---|
| 296 | (S)-3-[(3,2'-Dimethoxy-[2,3']bipyridinyl-6-carbonyl)-amino]-3-(2-fluoro-phenyl)-propionic acid | 426.26 | 1.04 | LC11_2 | 0.756 |
| 297 | (S)-3-{[6-(5-Fluoro-2-methyl-phenyl)-5-methoxy-pyridine-2-carbonyl]-amino}-3-(2-fluoro-phenyl)-propionic acid | 427.25 | 1.13 | LC11_2 | 0.475 |
| 298 | (S)-3-{[6-(4-Fluoro-2-methoxy-phenyl)-5-methoxy-pyridine-2-carbonyl]-amino}-3-(2-fluoro-phenyl)-propionic acid | 443.26 | 1.1 | LC11_2 | 0.389 |
| 299 | (S)-3-{[6-(4-Chloro-2-methoxy-phenyl)-5-methoxy-pyridine-2-carbonyl]-amino}-3-(2-fluoro-phenyl)-propionic acid | 459.24 | 1.14 | LC11_2 | 1.83 |
| 300 | (S)-3-{[6-(5-Chloro-2-methoxy-phenyl)-5-methoxy-pyridine-2-carbonyl]-amino}-3-(2-fluoro-phenyl)-propionic acid | 459.25 | 1.13 | LC11_2 | 4.11 |
| 301 | (S)-3-{[6-(5-Fluoro-2-methoxy-phenyl)-5-methoxy-pyridine-2-carbonyl]-amino}-3-(2-fluoro-phenyl)-propionic acid | 443.26 | 1.1 | LC11_2 | 0.0737 |
| 302 | (S)-3-(2-Fluoro-phenyl)-3-{[5-methoxy-6-(1-methyl-1H-indol-5-yl)-pyridine-2-carbonyl]-amino}-propionic acid | 448.3 | 1.12 | LC11_2 | >10.0 |
| 303 | (S)-3-{[6-(2,5-Dimethoxy-phenyl)-5-methoxy-pyridine-2-carbonyl]-amino}-3-(2-fluoro-phenyl)-propionic acid | 455.29 | 1.08 | LC11_2 | >10.0 |
| 304 | (S)-3-(2-Fluoro-phenyl)-3-{[6-(2-fluoro-5-trifluoromethyl-phenyl)-5-methoxy-pyridine-2-carbonyl]-amino}-propionic acid | 481.23 | 1.16 | LC11_2 | 3.99 |
| 305 | (S)-3-(2-Fluoro-phenyl)-3-{[5-methoxy-6-(5-methyl-furan-2-yl)-pyridine-2-carbonyl]-amino}-propionic acid | 399.23 | 1.09 | LC11_2 | >10.0 |
| 306 | (S)-3-(2-Fluoro-phenyl)-3-{[5-methoxy-6-(1-methyl-1H-pyrazol-4-yl)-pyridine-2-carbonyl]-amino}-propionic acid | 399.22 | 0.99 | LC11_2 | >10.0 |
| 307 | (S)-3-{[6-(2-Fluoro-5-methoxy-phenyl)-5-methoxy-pyridine-2-carbonyl]-amino}-3-(2-fluoro-phenyl)-propionic acid | 443.26 | 1.1 | LC11_2 | 2.92 |
| 308 | (S)-3-{[6-(5-tert-Butyl-2-methoxy-phenyl)-5-methoxy-pyridine-2-carbonyl]-amino}-3-(2-fluoro-phenyl)-propionic acid | 481.44 | 1.2 | LC11_2 | >10.0 |
| 309 | (S)-3-(2-Fluoro-phenyl)-3-{[6-(2-fluoro-4-trifluoromethyl-phenyl)-5-methoxy-pyridine-2-carbonyl]-amino}-propionic acid | 481.25 | 1.17 | LC11_2 | >10.0 |
| 310 | (S)-3-{[6-(2-Fluoro-5-methyl-phenyl)-5-methoxy-pyridine-2-carbonyl]-amino}-3-(2-fluoro-phenyl)-propionic acid | 427.26 | 1.13 | LC11_2 | 0.262 |
| 311 | (S)-3-{[6-(3-Chloro-2-methyl-phenyl)-5-methoxy-pyridine-2-carbonyl]-amino}-3-(2-fluoro-phenyl)-propionic acid | 443.25 | 1.16 | LC11_2 | 0.2019 |
| 312 | (S)-3-{[6-(5-Chloro-2-fluoro-phenyl)-5-methoxy-pyridine-2-carbonyl]-amino}-3-(2-fluoro-phenyl)-propionic acid | 447.19 | 1.14 | LC11_2 | 0.481 |
| 313 | (S)-3-{[6-(4-Chloro-3-fluoro-phenyl)-5-methoxy-pyridine-2-carbonyl]-amino}-3-(2-fluoro-phenyl)-propionic acid | 447.21 | 1.18 | LC11_2 | 3.55 |

TABLE 1-continued

Example compounds of the formula I

| Ex. No. | Compound name | m/z (1) | Rt (min) | LC/MS Method | Activity [μM] |
|---|---|---|---|---|---|
| 314 | (S)-3-[(2'-Chloro-3-methoxy-5'-methyl-[2,3']bipyridinyl-6-carbonyl)-amino]-3-(2-fluoro-phenyl)-propionic acid | 444.23 | 1.06 | LC11_2 | >10.0 |
| 315 | (S)-3-{[6-(3-Chloro-5-methyl-phenyl)-5-methoxy-pyridine-2-carbonyl]-amino}-3-(2-fluoro-phenyl)-propionic acid | 443.25 | 1.19 | LC11_2 | >10.0 |
| 316 | (S)-3-(2-Fluoro-phenyl)-3-({5-methoxy-6-[3-(5-methyl-[1,3,4]oxadiazol-2-yl)-phenyl]-pyridine-2-carbonyl}-amino)-propionic acid | 477.31 | 1.06 | LC11_2 | >10.0 |
| 317 | (S)-3-(2-Fluoro-phenyl)-3-{[5-methoxy-6-(1,3,5-trimethyl-1H-pyrazol-4-yl)-pyridine-2-carbonyl]-amino}-propionic acid | 427.27 | 0.99 | LC11_2 | >10.0 |
| 318 | (S)-3-(2-Fluoro-phenyl)-3-{[5-methoxy-6-(1-methyl-1H-indol-6-yl)-pyridine-2-carbonyl]-amino}-propionic acid | 448.3 | 1.13 | LC11_2 | >10.0 |
| 319 | (S)-3-{[6-(4-Chloro-3-methoxy-phenyl)-5-methoxy-pyridine-2-carbonyl]-amino}-3-(2-fluoro-phenyl)-propionic acid | 459.22 | 1.16 | LC11_2 | >10.0 |
| 320 | (S)-3-{[6-(3-Chloro-2-fluoro-phenyl)-5-methoxy-pyridine-2-carbonyl]-amino}-3-(2-fluoro-phenyl)-propionic acid | 447.22 | 1.14 | LC11_2 | 0.0484 |
| 321 | (S)-3-(2-Fluoro-phenyl)-3-[(3-methoxy-2'-morpholin-4-yl-[2,4']bipyridinyl-6-carbonyl)-amino]-propionic acid | 481.33 | 0.91 | LC11_2 | >10.0 |
| 322 | (S)-3-(2-Fluoro-phenyl)-3-{[5-methoxy-6-(2-methyl-furan-3-yl)-pyridine-2-carbonyl]-amino}-propionic acid | 399.21 | 1.11 | LC11_2 | 0.0813 |
| 323 | (S)-3-{[6-(2-Chloro-5-methyl-phenyl)-5-methoxy-pyridine-2-carbonyl]-amino}-3-(2-fluoro-phenyl)-propionic acid | 443.18 | 1.14 | LC11_2 | 2.31 |
| 324 | (S)-3-{[6-(2-Chloro-3-fluoro-phenyl)-5-methoxy-pyridine-2-carbonyl]-amino}-3-(2-fluoro-phenyl)-propionic acid | 447.2 | 1.12 | LC11_2 | 1.266 |
| 325 | (S)-3-{[6-(4-Cyano-2-fluoro-phenyl)-5-methoxy-pyridine-2-carbonyl]-amino}-3-(2-fluoro-phenyl)-propionic acid | 438.23 | 1.08 | LC11_2 | 3.58 |
| 326 | (S)-3-(2-Fluoro-phenyl)-3-({6-[3-(3-hydroxy-oxetan-3-yl)-phenyl]-5-methoxy-pyridine-2-carbonyl}-amino)-propionic acid | 467.29 | 1 | LC11_2 | 8.46 |
| 327 | (S)-3-(2-Fluoro-phenyl)-3-({6-[3-(1-hydroxy-1-methyl-ethyl)-phenyl]-5-methoxy-pyridine-2-carbonyl}-amino)-propionic acid | 453.32 | 1.07 | LC11_2 | 7.32 |
| 328 | (S)-3-{[6-(2-Chloro-3-methyl-phenyl)-5-methoxy-pyridine-2-carbonyl]-amino}-3-(2-fluoro-phenyl)-propionic acid | 443.24 | 1.14 | LC11_2 | 0.1192 |
| 329 | (S)-3-(2-Chloro-phenyl)-3-{[5-methoxy-6-(3-trifluoromethyl-phenyl)-pyridine-2-carbonyl]-amino}-propionic acid | 479.11 | 1.21 | LC11_3 | 3.74 |
| 330 | (S)-3-(2-Chloro-phenyl)-3-[(5-methoxy-6-phenyl-pyridine-2-carbonyl)-amino]-propionic acid | 411.12 | 1.14 | LC11_3 | 0.0751 |
| 331 | (S)-3-(2-Chloro-phenyl)-3-{[6-(2,4-dichloro-phenyl)-5-methoxy-pyridine-2-carbonyl]-amino}-propionic acid | 479.05 | 1.21 | LC11_3 | 0.589 |

TABLE 1-continued

Example compounds of the formula I

| Ex. No. | Compound name | m/z (1) | Rt (min) | LC/MS Method | Activity [µM] |
|---|---|---|---|---|---|
| 332 | (S)-3-{[6-(3-Chloro-4-fluoro-phenyl)-5-methoxy-pyridine-2-carbonyl]-amino}-3-(2-chloro-phenyl)-propionic acid | 463.07 | 1.2 | LC11_3 | 5.24 |
| 333 | (S)-3-(2-Chloro-phenyl)-3-{[6-(4-fluoro-phenyl)-5-methoxy-pyridine-2-carbonyl]-amino}-propionic acid | 429.12 | 1.16 | LC11_3 | 0.909 |
| 334 | (S)-3-(2-Chloro-phenyl)-3-{[6-(4-chloro-phenyl)-5-methoxy-pyridine-2-carbonyl]-amino}-propionic acid | 445.09 | 1.2 | LC11_3 | 1.81 |
| 335 | (S)-3-(2-Chloro-phenyl)-3-{[5-methoxy-6-(4-methoxy-phenyl)-pyridine-2-carbonyl]-amino}-propionic acid | 441.13 | 1.14 | LC11_3 | 2.25 |
| 336 | (S)-3-(2-Chloro-phenyl)-3-[(5-methoxy-6-p-tolyl-pyridine-2-carbonyl)-amino]-propionic acid | 425.14 | 1.18 | LC11_3 | 3.13 |
| 337 | (S)-3-(2-Chloro-phenyl)-3-{[5-methoxy-6-(4-trifluoromethyl-phenyl)-pyridine-2-carbonyl]-amino}-propionic acid | 479.11 | 1.21 | LC11_3 | 9.5 |
| 338 | (S)-3-(2-Chloro-phenyl)-3-[(5-methoxy-6-o-tolyl-pyridine-2-carbonyl)-amino]-propionic acid | 425.14 | 1.15 | LC11_3 | >10.0 |
| 339 | (S)-3-(2-Chloro-phenyl)-3-{[5-methoxy-6-(3-methoxy-phenyl)-pyridine-2-carbonyl]-amino}-propionic acid | 441.13 | 1.14 | LC11_3 | 2.78 |
| 340 | (S)-3-(2-Chloro-phenyl)-3-{[6-(3-chloro-phenyl)-5-methoxy-pyridine-2-carbonyl]-amino}-propionic acid | 445.09 | 1.19 | LC11_3 | 1.51 |
| 341 | (S)-3-(2-Chloro-phenyl)-3-{[5-(3-fluoro-phenyl)-6-methoxy-pyridine-3-carbonyl]-amino}-propionic acid | 429.22 | 1.13 | LC11_2 | 9.86 |
| 342 | (S)-3-{[6-Methoxy-5-(4-trifluoromethyl-phenyl)-pyridine-3-carbonyl]-amino}-3-o-tolyl-propionic acid | 459.27 | 1.18 | LC11_2 | >10.0 |
| 343 | (S)-3-(2-Chloro-phenyl)-3-{[6-methoxy-5-(3-trifluoromethyl-phenyl)-pyridine-3-carbonyl]-amino}-propionic acid | 479.22 | 1.18 | LC11_2 | >10.0 |
| 344 | (S)-3-(2-Chloro-phenyl)-3-[(6-methoxy-5-phenyl-pyridine-3-carbonyl)-amino]-propionic acid | 411.23 | 1.12 | LC11_2 | 3.49 |
| 345 | (S)-3-{[5-(3-Chloro-4-fluoro-phenyl)-6-methoxy-pyridine-3-carbonyl]-amino}-3-(2-chloro-phenyl)-propionic acid | 463.16 | 1.17 | LC11_2 | >10.0 |
| 346 | (S)-3-(2-Chloro-phenyl)-3-{[5-(4-fluoro-phenyl)-6-methoxy-pyridine-3-carbonyl]-amino}-propionic acid | 429.2 | 1.13 | LC11_2 | 8.26 |
| 347 | (S)-3-{[5-Methoxy-6-(3-trifluoromethyl-phenyl)-pyridine-2-carbonyl]-amino}-3-o-tolyl-propionic acid | 459.08 | 1.19 | LC11_2 | 0.981 |
| 348 | (S)-3-{[6-(2,4-Dichloro-phenyl)-5-methoxy-pyridine-2-carbonyl]-amino}-3-o-tolyl-propionic acid | 459.01 | 1.19 | LC11_2 | 0.161 |
| 349 | (S)-3-{[6-(3-Chloro-4-fluoro-phenyl)-5-methoxy-pyridine-2-carbonyl]-amino}-3-o-tolyl-propionic acid | 443.03 | 1.19 | LC11_2 | 1.458 |
| 350 | (S)-3-{[6-(4-Fluoro-phenyl)-5-methoxy-pyridine-2-carbonyl]-amino}-3-o-tolyl-propionic acid | 409.08 | 1.14 | LC11_2 | 0.267 |
| 351 | (S)-3-{[6-(4-Chloro-phenyl)-5-methoxy-pyridine-2-carbonyl]-amino}-3-o-tolyl-propionic acid | 425.04 | 1.18 | LC11_2 | 0.501 |

TABLE 1-continued

Example compounds of the formula I

| Ex. No. | Compound name | m/z (1) | Rt (min) | LC/MS Method | Activity [μM] |
|---|---|---|---|---|---|
| 352 | (S)-3-[(5-Methoxy-6-p-tolyl-pyridine-2-carbonyl)-amino]-3-o-tolyl-propionic acid | 405.12 | 1.17 | LC11_2 | 0.586 |
| 353 | (S)-3-{[5-Methoxy-6-(4-trifluoromethyl-phenyl)-pyridine-2-carbonyl]-amino}-3-o-tolyl-propionic acid | 459.08 | 1.19 | LC11_2 | >10.0 |
| 354 | (S)-3-{[6-(3-Chloro-phenyl)-5-methoxy-pyridine-2-carbonyl]-amino}-3-o-tolyl-propionic acid | 425.05 | 1.18 | LC11_2 | 0.53 |
| 355 | (S)-3-{[5-Methoxy-6-(2-methoxy-phenyl)-pyridine-2-carbonyl]-amino}-3-o-tolyl-propionic acid | 421.13 | 1.1 | LC11_2 | 0.0833 |
| 356 | (S)-3-[(5-Methoxy-6-m-tolyl-pyridine-2-carbonyl)-amino]-3-o-tolyl-propionic acid | 405.09 | 1.16 | LC11_2 | 0.152 |
| 357 | (S)-3-{[6-(2-Chloro-phenyl)-5-methoxy-pyridine-2-carbonyl]-amino}-3-o-tolyl-propionic acid | 425.06 | 1.13 | LC11_2 | 0.223 |
| 358 | (S)-3-{[6-(4-tert-Butyl-phenyl)-5-methoxy-pyridine-2-carbonyl]-amino}-3-o-tolyl-propionic acid | 447.19 | 1.25 | LC11_2 | >10.0 |
| 359 | (S)-3-{[6-(3-Cyano-phenyl)-5-methoxy-pyridine-2-carbonyl]-amino}-3-o-tolyl-propionic acid | 416.1 | 1.11 | LC11_2 | 4.49 |
| 360 | (S)-3-{[6-(3-Acetyl-phenyl)-5-methoxy-pyridine-2-carbonyl]-amino}-3-o-tolyl-propionic acid | 433.13 | 1.1 | LC11_2 | 2.42 |
| 361 | (S)-3-{[6-(4-Acetyl-phenyl)-5-methoxy-pyridine-2-carbonyl]-amino}-3-o-tolyl-propionic acid | 433.12 | 1.09 | LC11_2 | 9.24 |
| 362 | (S)-3-{[6-(3,5-Difluoro-phenyl)-5-methoxy-pyridine-2-carbonyl]-amino}-3-o-tolyl-propionic acid | 427.08 | 1.16 | LC11_2 | 1.43 |
| 363 | (S)-3-{[6-(3,4-Difluoro-phenyl)-5-methoxy-pyridine-2-carbonyl]-amino}-3-o-tolyl-propionic acid | 427.11 | 1.16 | LC11_2 | 0.258 |
| 364 | (S)-3-{[6-(5-Acetyl-thiophen-2-yl)-5-methoxy-pyridine-2-carbonyl]-amino}-3-o-tolyl-propionic acid | 439.09 | 1.1 | LC11_2 | 9.25 |
| 365 | (S)-3-[(3-Methoxy-[2,4']bipyridinyl-6-carbonyl)-amino]-3-o-tolyl-propionic acid | 392.13 | 0.87 | LC11_2 | 5.45 |
| 366 | (S)-3-{[6-(2,5-Difluoro-phenyl)-5-methoxy-pyridine-2-carbonyl]-amino}-3-o-tolyl-propionic acid | 427.09 | 1.13 | LC11_2 | 0.121 |
| 367 | (S)-3-{[6-(2,5-Dichloro-phenyl)-5-methoxy-pyridine-2-carbonyl]-amino}-3-o-tolyl-propionic acid | 459.01 | 1.18 | LC11_2 | 0.385 |
| 368 | (S)-3-{[6-(3,5-Dimethyl-isoxazol-4-yl)-5-methoxy-pyridine-2-carbonyl]-amino}-3-o-tolyl-propionic acid | 410.24 | 4 | LC2 | 0.1873 |
| 369 | (S)-3-{[6-(2,3-Dimethyl-phenyl)-5-methoxy-pyridine-2-carbonyl]-amino}-3-o-tolyl-propionic acid | 419.14 | 1.16 | LC11_2 | 0.1318 |
| 370 | (S)-3-{[6-(3-Fluoro-4-methyl-phenyl)-5-methoxy-pyridine-2-carbonyl]-amino}-3-o-tolyl-propionic acid | 423.11 | 1.18 | LC11_2 | 1.585 |
| 371 | (S)-3-{[6-(2,4-Dimethyl-phenyl)-5-methoxy-pyridine-2-carbonyl]-amino}-3-o-tolyl-propionic acid | 419.16 | 1.17 | LC11_2 | 0.457 |
| 372 | (S)-3-[(5-Methoxy-6-pyrimidin-5-yl-pyridine-2-carbonyl)-amino]-3-o-tolyl-propionic acid | 393.11 | 0.98 | LC11_2 | 8.88 |
| 373 | (S)-3-[(6'-Fluoro-3-methoxy-[2,3']bipyridinyl-6-carbonyl)-amino]-3-o-tolyl-propionic acid | 410.1 | 1.08 | LC11_2 | 1.6 |
| 374 | (S)-3-{[6-(2-Dimethylcarbamoyl-phenyl)-5-methoxy-pyridine-2-carbonyl]-amino}-3-o-tolyl-propionic acid | 460.12 | 1.04 | LC11_2 | 2.48 |

TABLE 1-continued

Example compounds of the formula I

| Ex. No. | Compound name | m/z (1) | Rt (min) | LC/MS Method | Activity [µM] |
|---|---|---|---|---|---|
| 375 | (S)-3-{[6-(4-Fluoro-2-methoxy-phenyl)-5-methoxy-pyridine-2-carbonyl]-amino}-3-o-tolyl-propionic acid | 439.13 | 1.12 | LC11_2 | 0.216 |
| 376 | (S)-3-{[5-Methoxy-6-(5-methyl-furan-2-yl)-pyridine-2-carbonyl]-amino}-3-o-tolyl-propionic acid | 395.11 | 1.11 | LC11_2 | 6.1 |
| 377 | (S)-3-{[5-Methoxy-6-(1-methyl-1H-pyrazol-4-yl)-pyridine-2-carbonyl]-amino}-3-o-tolyl-propionic acid | 395.13 | 1.01 | LC11_2 | >10.0 |
| 378 | (S)-3-{[6-(3-Chloro-5-methyl-phenyl)-5-methoxy-pyridine-2-carbonyl]-amino}-3-o-tolyl-propionic acid | 439.1 | 1.21 | LC11_2 | 7.49 |
| 379 | (S)-3-{[5-Methoxy-6-(1,3,5-trimethyl-1H-pyrazol-4-yl)-pyridine-2-carbonyl]-amino}-3-o-tolyl-propionic acid | 421.13 | 1 | LC11_2 | >10.0 |
| 380 | (S)-3-{[5-Methoxy-6-(1-methyl-1H-indol-6-yl)-pyridine-2-carbonyl]-amino}-3-o-tolyl-propionic acid | 444.15 | 1.15 | LC11_2 | 5.33 |
| 381 | (S)-3-[(3-Methoxy-2'-morpholin-4-yl-[2,4']bipyridinyl-6-carbonyl)-amino]-3-o-tolyl-propionic acid | 477.16 | 0.93 | LC11_2 | >10.0 |
| 382 | (S)-3-{[6-(2-Chloro-5-methyl-phenyl)-5-methoxy-pyridine-2-carbonyl]-amino}-3-o-tolyl-propionic acid | 439.13 | 1.16 | LC11_2 | 0.497 |
| 383 | (S)-3-{[6-(2-Chloro-3-fluoro-phenyl)-5-methoxy-pyridine-2-carbonyl]-amino}-3-o-tolyl-propionic acid | 443.06 | 1.14 | LC11_2 | 1.635 |
| 384 | (S)-3-({6-[3-(3-Hydroxy-oxetan-3-yl)-phenyl]-5-methoxy-pyridine-2-carbonyl}-amino)-3-o-tolyl-propionic acid | 463.15 | 1.02 | LC11_2 | 2.39 |
| 385 | (S)-3-({6-[3-(1-Hydroxy-1-methyl-ethyl)-phenyl]-5-methoxy-pyridine-2-carbonyl}-amino)-3-o-tolyl-propionic acid | 449.17 | 1.08 | LC11_2 | 1.15 |
| 386 | (S)-3-(2-Chloro-phenyl)-3-{[5-(4-chloro-phenyl)-6-methoxy-pyridine-3-carbonyl]-amino}-propionic acid | 445.17 | 1.17 | LC11_2 | 10.4 |
| 387 | (S)-3-(2-Chloro-phenyl)-3-{[6-methoxy-5-(4-methoxy-phenyl)-pyridine-3-carbonyl]-amino}-propionic acid | 441.24 | 1.11 | LC11_2 | 9.43 |
| 388 | (S)-3-(2-Chloro-phenyl)-3-[(6-methoxy-5-p-tolyl-pyridine-3-carbonyl)-amino]-propionic acid | 425.24 | 1.15 | LC11_2 | 7.12 |
| 389 | (S)-3-(2-Chloro-phenyl)-3-{[6-methoxy-5-(4-trifluoromethyl-phenyl)-pyridine-3-carbonyl]-amino}-propionic acid | 479.21 | 1.18 | LC11_2 | >10.0 |
| 390 | (S)-3-(2-Chloro-phenyl)-3-[(6-methoxy-5-o-tolyl-pyridine-3-carbonyl)-amino]-propionic acid | 425.25 | 1.13 | LC11_2 | 0.702 |
| 391 | (S)-3-(2-Chloro-phenyl)-3-{[6-methoxy-5-(3-methoxy-phenyl)-pyridine-3-carbonyl]-amino}-propionic acid | 441.24 | 1.12 | LC11_2 | 10.6 |
| 392 | (S)-3-(2-Chloro-phenyl)-3-{[5-(3-chloro-phenyl)-6-methoxy-pyridine-3-carbonyl]-amino}-propionic acid | 445.2 | 1.16 | LC11_2 | 10.3 |
| 393 | (S)-3-(2-Chloro-phenyl)-3-[(6-methoxy-5-naphthalen-2-yl-pyridine-3-carbonyl)-amino]-propionic acid | 461.25 | 1.18 | LC11_2 | >10.0 |

TABLE 1-continued

Example compounds of the formula I

| Ex. No. | Compound name | m/z (1) | Rt (min) | LC/MS Method | Activity [μM] |
|---|---|---|---|---|---|
| 394 | (S)-3-(2-Chloro-phenyl)-3-{[6-methoxy-5-(2-methoxy-phenyl)-pyridine-3-carbonyl]-amino}-propionic acid | 441.25 | 1.1 | LC11_2 | 3.76 |
| 395 | (S)-3-(2-Chloro-phenyl)-3-[(6-methoxy-5-m-tolyl-pyridine-3-carbonyl)-amino]-propionic acid | 425.24 | 1.15 | LC11_2 | 6.57 |
| 396 | (S)-3-{[5-(4-tert-Butyl-phenyl)-6-methoxy-pyridine-3-carbonyl]-amino}-3-(2-chloro-phenyl)-propionic acid | 467.31 | 1.24 | LC11_2 | >10.0 |
| 397 | (S)-3-(2-Chloro-phenyl)-3-{[5-(3-cyano-phenyl)-6-methoxy-pyridine-3-carbonyl]-amino}-propionic acid | 436.23 | 1.09 | LC11_2 | >10.0 |
| 398 | (S)-3-(2-Chloro-phenyl)-3-{[5-(4-cyano-phenyl)-6-methoxy-pyridine-3-carbonyl]-amino}-propionic acid | 436.23 | 1.09 | LC11_2 | >10.0 |
| 399 | (S)-3-{[5-(3-Acetyl-phenyl)-6-methoxy-pyridine-3-carbonyl]-amino}-3-(2-chloro-phenyl)-propionic acid | 453.25 | 1.08 | LC11_2 | >10.0 |
| 400 | (S)-3-[(5-Biphenyl-3-yl-6-methoxy-pyridine-3-carbonyl)-amino]-3-(2-chloro-phenyl)-propionic acid | 487.27 | 1.21 | LC11_2 | >10.0 |
| 401 | (S)-3-{[5-(4-Acetyl-phenyl)-6-methoxy-pyridine-3-carbonyl]-amino}-3-(2-chloro-phenyl)-propionic acid | 453.25 | 1.08 | LC11_2 | >10.0 |
| 402 | (S)-3-(2-Chloro-phenyl)-3-{[5-(3,5-difluoro-phenyl)-6-methoxy-pyridine-3-carbonyl]-amino}-propionic acid | 447.2 | 1.15 | LC11_2 | >10.0 |
| 403 | (S)-3-(2-Chloro-phenyl)-3-{[5-(3,4-difluoro-phenyl)-6-methoxy-pyridine-3-carbonyl]-amino}-propionic acid | 447.2 | 1.14 | LC11_2 | >10.0 |
| 404 | (S)-3-(2-Chloro-phenyl)-3-{[5-(4-fluoro-2-methyl-phenyl)-6-methoxy-pyridine-3-carbonyl]-amino}-propionic acid | 443.26 | 1.14 | LC11_2 | 7.14 |
| 405 | (S)-3-[(6-Methoxy-5-phenyl-pyridine-3-carbonyl)-amino]-3-o-tolyl-propionic acid | 391.28 | 1.12 | LC11_2 | 3.9 |
| 406 | (S)-3-{[5-(3-Chloro-4-fluoro-phenyl)-6-methoxy-pyridine-3-carbonyl]-amino}-3-o-tolyl-propionic acid | 443.22 | 1.17 | LC11_2 | 10 |
| 407 | (S)-3-{[5-(4-Fluoro-phenyl)-6-methoxy-pyridine-3-carbonyl]-amino}-3-o-tolyl-propionic acid | 409.24 | 1.13 | LC11_2 | 4.39 |
| 408 | (S)-3-{[5-(4-Chloro-phenyl)-6-methoxy-pyridine-3-carbonyl]-amino}-3-o-tolyl-propionic acid | 425.22 | 1.17 | LC11_2 | 5.73 |
| 409 | (S)-3-{[6-Methoxy-5-(4-methoxy-phenyl)-pyridine-3-carbonyl]-amino}-3-o-tolyl-propionic acid | 421.3 | 1.11 | LC11_2 | 9.04 |
| 410 | (S)-3-[(6-Methoxy-5-p-tolyl-pyridine-3-carbonyl)-amino]-3-o-tolyl-propionic acid | 405.26 | 1.15 | LC11_2 | 5.38 |
| 411 | (S)-3-[(6-Methoxy-5-o-tolyl-pyridine-3-carbonyl)-amino]-3-o-tolyl-propionic acid | 405.27 | 1.13 | LC11_2 | 1.186 |
| 412 | (S)-3-{[6-Methoxy-5-(3-methoxy-phenyl)-pyridine-3-carbonyl]-amino}-3-o-tolyl-propionic acid | 421.27 | 1.12 | LC11_2 | 8.36 |
| 413 | (S)-3-{[5-(3-Chloro-phenyl)-6-methoxy-pyridine-3-carbonyl]-amino}-3-o-tolyl-propionic acid | 425.21 | 1.16 | LC11_2 | 6.24 |
| 414 | (S)-3-{[5-(3-Fluoro-phenyl)-6-methoxy-pyridine-3-carbonyl]-amino}-3-o-tolyl-propionic acid | 409.22 | 1.13 | LC11_2 | 8.07 |

TABLE 1-continued

Example compounds of the formula I

| Ex. No. | Compound name | m/z (1) | Rt (min) | LC/MS Method | Activity [μM] |
|---|---|---|---|---|---|
| 415 | (S)-3-[(6-Methoxy-5-naphthalen-2-yl-pyridine-3-carbonyl)-amino]-3-o-tolyl-propionic acid | 441.33 | 1.18 | LC11_2 | >10.0 |
| 416 | (S)-3-{[6-Methoxy-5-(2-methoxy-phenyl)-pyridine-3-carbonyl]-amino}-3-o-tolyl-propionic acid | 421.31 | 1.1 | LC11_2 | 3.42 |
| 417 | (S)-3-[(6-Methoxy-5-m-tolyl-pyridine-3-carbonyl)-amino]-3-o-tolyl-propionic acid | 405.28 | 1.15 | LC11_2 | 4.86 |
| 418 | (S)-3-{[5-(2-Fluoro-phenyl)-6-methoxy-pyridine-3-carbonyl]-amino}-3-o-tolyl-propionic acid | 409.23 | 1.11 | LC11_2 | 1.083 |
| 419 | (S)-3-{[5-(4-tert-Butyl-phenyl)-6-methoxy-pyridine-3-carbonyl]-amino}-3-o-tolyl-propionic acid | 447.38 | 1.24 | LC11_2 | >10.0 |
| 420 | (S)-3-{[5-(3-Cyano-phenyl)-6-methoxy-pyridine-3-carbonyl]-amino}-3-o-tolyl-propionic acid | 416.25 | 1.09 | LC11_2 | >10.0 |
| 421 | (S)-3-{[5-(4-Cyano-phenyl)-6-methoxy-pyridine-3-carbonyl]-amino}-3-o-tolyl-propionic acid | 416.29 | 1.09 | LC11_2 | 10.4 |
| 422 | (S)-3-{[5-(3-Acetyl-phenyl)-6-methoxy-pyridine-3-carbonyl]-amino}-3-o-tolyl-propionic acid | 433.28 | 1.08 | LC11_2 | >10.0 |
| 423 | (S)-3-[(5-Biphenyl-3-yl-6-methoxy-pyridine-3-carbonyl)-amino]-3-o-tolyl-propionic acid | 467.34 | 1.21 | LC11_2 | >10.0 |
| 424 | (S)-3-{[5-(4-Acetyl-phenyl)-6-methoxy-pyridine-3-carbonyl]-amino}-3-o-tolyl-propionic acid | 433.28 | 1.08 | LC11_2 | >10.0 |
| 425 | (S)-3-{[5-(3,4-Difluoro-phenyl)-6-methoxy-pyridine-3-carbonyl]-amino}-3-o-tolyl-propionic acid | 427.25 | 1.15 | LC11_2 | 8.84 |
| 426 | (S)-3-(2-Chloro-phenyl)-3-{[6-(3-fluoro-phenyl)-5-methoxy-pyridine-2-carbonyl]-amino}-propionic acid | 429.12 | 1.16 | LC11_3 | 1.54 |
| 427 | (S)-3-(2-Chloro-phenyl)-3-[(5-methoxy-6-naphthalen-2-yl-pyridine-2-carbonyl)-amino]-propionic acid | 461.14 | 1.21 | LC11_3 | 7.11 |
| 428 | (S)-3-(2-Chloro-phenyl)-3-{[5-methoxy-6-(2-methoxy-phenyl)-pyridine-2-carbonyl]-amino}-propionic acid | 441.14 | 1.11 | LC11_3 | 0.1161 |
| 429 | (S)-3-(2-Chloro-phenyl)-3-[(5-methoxy-6-m-tolyl-pyridine-2-carbonyl)-amino]-propionic acid | 425.14 | 1.18 | LC11_3 | 0.335 |
| 430 | (S)-3-(2-Chloro-phenyl)-3-{[6-(2-chloro-phenyl)-5-methoxy-pyridine-2-carbonyl]-amino}-propionic acid | 445.09 | 1.14 | LC11_3 | 0.147 |
| 431 | (S)-3-(2-Chloro-phenyl)-3-{[6-(2-fluoro-phenyl)-5-methoxy-pyridine-2-carbonyl]-amino}-propionic acid | 429.11 | 1.13 | LC11_3 | 0.132 |
| 432 | (S)-3-{[6-(4-tert-Butyl-phenyl)-5-methoxy-pyridine-2-carbonyl]-amino}-3-(2-chloro-phenyl)-propionic acid | 467.18 | 1.26 | LC11_3 | >10.0 |
| 433 | (S)-3-(2-Chloro-phenyl)-3-{[6-(3-cyano-phenyl)-5-methoxy-pyridine-2-carbonyl]-amino}-propionic acid | 436.12 | 1.12 | LC11_3 | 8.26 |
| 434 | (S)-3-(2-Chloro-phenyl)-3-{[6-(4-cyano-phenyl)-5-methoxy-pyridine-2-carbonyl]-amino}-propionic acid | 436.12 | 1.12 | LC11_3 | >10.0 |
| 435 | (S)-3-{[6-(3-Acetyl-phenyl)-5-methoxy-pyridine-2-carbonyl]-amino}-3-(2-chloro-phenyl)-propionic acid | 453.13 | 1.11 | LC11_3 | 4.2 |

TABLE 1-continued

Example compounds of the formula I

| Ex. No. | Compound name | m/z (1) | Rt (min) | LC/MS Method | Activity [μM] |
|---|---|---|---|---|---|
| 436 | (S)-3-[(6-Biphenyl-3-yl-5-methoxy-pyridine-2-carbonyl)-amino]-3-(2-chloro-phenyl)-propionic acid | 487.16 | 1.24 | LC11_3 | 2.97 |
| 437 | (S)-3-{[6-(4-Acetyl-phenyl)-5-methoxy-pyridine-2-carbonyl]-amino}-3-(2-chloro-phenyl)-propionic acid | 453.13 | 1.1 | LC11_3 | >10.0 |
| 438 | (S)-3-(2-Chloro-phenyl)-3-{[6-(2,4-difluoro-phenyl)-5-methoxy-pyridine-2-carbonyl]-amino}-propionic acid | 447.19 | 1.13 | LC11_2 | 0.0491 |
| 439 | (S)-3-(2-Chloro-phenyl)-3-{[6-(3,5-difluoro-phenyl)-5-methoxy-pyridine-2-carbonyl]-amino}-propionic acid | 447.11 | 1.18 | LC11_3 | 2.39 |
| 440 | (S)-3-(2-Chloro-phenyl)-3-{[6-(3,4-difluoro-phenyl)-5-methoxy-pyridine-2-carbonyl]-amino}-propionic acid | 447.11 | 1.17 | LC11_3 | 1.96 |
| 441 | (S)-3-(2-Chloro-phenyl)-3-{[6-(2,3-dichloro-phenyl)-5-methoxy-pyridine-2-carbonyl]-amino}-propionic acid | 479.05 | 1.18 | LC11_3 | 0.2352 |
| 442 | (S)-3-{[6-(5-Acetyl-thiophen-2-yl)-5-methoxy-pyridine-2-carbonyl]-amino}-3-(2-chloro-phenyl)-propionic acid | 459.09 | 1.11 | LC11_3 | >10.0 |
| 443 | (S)-3-(2-Chloro-phenyl)-3-[(3-methoxy-[2,4']bipyridinyl-6-carbonyl)-amino]-propionic acid | 412.12 | 0.86 | LC11_3 | 8.04 |
| 444 | (S)-3-(2-Chloro-phenyl)-3-[(3-methoxy-[2,3']bipyridinyl-6-carbonyl)-amino]-propionic acid | 412.12 | 0.91 | LC11_3 | 10.1 |
| 445 | (S)-3-(2-Chloro-phenyl)-3-{[6-(2,3-difluoro-phenyl)-5-methoxy-pyridine-2-carbonyl]-amino}-propionic acid | 447.11 | 1.14 | LC11_3 | 0.1505 |
| 446 | (S)-3-(2-Chloro-phenyl)-3-{[6-(2,5-difluoro-phenyl)-5-methoxy-pyridine-2-carbonyl]-amino}-propionic acid | 447.1 | 1.14 | LC11_3 | 0.0571 |
| 447 | (S)-3-(2-Chloro-phenyl)-3-{[6-(4-fluoro-2-methyl-phenyl)-5-methoxy-pyridine-2-carbonyl]-amino}-propionic acid | 443.13 | 1.16 | LC11_3 | 0.1106 |
| 448 | (S)-3-(2-Chloro-phenyl)-3-{[6-(2,3-dimethyl-phenyl)-5-methoxy-pyridine-2-carbonyl]-amino}-propionic acid | 439.15 | 1.17 | LC11_3 | 0.1393 |
| 449 | (S)-3-(2-Chloro-phenyl)-3-{[6-(3-fluoro-4-methyl-phenyl)-5-methoxy-pyridine-2-carbonyl]-amino}-propionic acid | 443.13 | 1.2 | LC11_3 | 2.016 |
| 450 | (S)-3-(2-Chloro-phenyl)-3-{[6-(2,4-dimethyl-phenyl)-5-methoxy-pyridine-2-carbonyl]-amino}-propionic acid | 439.15 | 1.18 | LC11_3 | 1.6 |
| 451 | (S)-3-(2-Chloro-phenyl)-3-{[6-(4-fluoro-3-methyl-phenyl)-5-methoxy-pyridine-2-carbonyl]-amino}-propionic acid | 443.13 | 1.19 | LC11_3 | 3.79 |
| 452 | (S)-3-(2-Chloro-phenyl)-3-[(5-methoxy-6-pyrimidin-5-yl-pyridine-2-carbonyl)-amino]-propionic acid | 413.11 | 0.99 | LC11_3 | >10.0 |
| 453 | (S)-3-(2-Chloro-phenyl)-3-[(6'-fluoro-3-methoxy-[2,3']bipyridinyl-6-carbonyl)-amino]-propionic acid | 430.11 | 1.09 | LC11_3 | 6.49 |
| 454 | (S)-3-(2-Chloro-phenyl)-3-{[6-(2-dimethylcarbamoyl-phenyl)-5-methoxy-pyridine-2-carbonyl]-amino}-propionic acid | 482.3 | 1.04 | LC11_2 | 2.5 |
| 455 | (S)-3-(2-Chloro-phenyl)-3-[(3,2'-dimethoxy-[2,3']bipyridinyl-6-carbonyl)-amino]-propionic acid | 442.13 | 1.07 | LC11_3 | 0.185 |

TABLE 1-continued

Example compounds of the formula I

| Ex. No. | Compound name | m/z (1) | Rt (min) | LC/MS Method | Activity [μM] |
|---|---|---|---|---|---|
| 456 | (S)-3-(2-Chloro-phenyl)-3-{[6-(5-fluoro-2-methyl-phenyl)-5-methoxy-pyridine-2-carbonyl]-amino}-propionic acid | 443.13 | 1.16 | LC11_3 | 0.1193 |
| 457 | (S)-3-(2-Chloro-phenyl)-3-{[6-(4-fluoro-2-methoxy-phenyl)-5-methoxy-pyridine-2-carbonyl]-amino}-propionic acid | 459.13 | 1.13 | LC11_3 | 0.1072 |
| 458 | (S)-3-{[6-(4-Chloro-2-methoxy-phenyl)-5-methoxy-pyridine-2-carbonyl]-amino}-3-(2-chloro-phenyl)-propionic acid | 475.1 | 1.17 | LC11_3 | 0.415 |
| 459 | (S)-3-{[6-(5-Chloro-2-methoxy-phenyl)-5-methoxy-pyridine-2-carbonyl]-amino}-3-(2-chloro-phenyl)-propionic acid | 475.1 | 1.16 | LC11_3 | 1.147 |
| 460 | (S)-3-(2-Chloro-phenyl)-3-{[6-(5-fluoro-2-methoxy-phenyl)-5-methoxy-pyridine-2-carbonyl]-amino}-propionic acid | 459.12 | 1.12 | LC11_3 | 0.1073 |
| 461 | (S)-3-(2-Chloro-phenyl)-3-{[6-(2,5-dimethoxy-phenyl)-5-methoxy-pyridine-2-carbonyl]-amino}-propionic acid | 471.14 | 1.11 | LC11_3 | 8.31 |
| 462 | (S)-3-(2-Chloro-phenyl)-3-{[6-(2-fluoro-5-trifluoromethyl-phenyl)-5-methoxy-pyridine-2-carbonyl]-amino}-propionic acid | 497.2 | 1.18 | LC11_2 | 0.597 |
| 463 | (S)-3-(2-Chloro-phenyl)-3-{[5-methoxy-6-(5-methyl-furan-2-yl)-pyridine-2-carbonyl]-amino}-propionic acid | 415.15 | 1.11 | LC11_2 | >10.0 |
| 464 | (S)-3-{[5-Methoxy-6-(2-trifluoromethyl-phenyl)-pyridine-2-carbonyl]-amino}-3-o-tolyl-propionic acid | 459.1 | 1.14 | LC11_2 | 0.0993 |
| 465 | (S)-3-{[6-(4-Cyano-phenyl)-5-methoxy-pyridine-2-carbonyl]-amino}-3-o-tolyl-propionic acid | 416.1 | 1.1 | LC11_2 | 6.8 |
| 466 | (S)-3-{[6-(2,4-Difluoro-phenyl)-5-methoxy-pyridine-2-carbonyl]-amino}-3-o-tolyl-propionic acid | 427.09 | 1.13 | LC11_2 | 0.0463 |
| 467 | (S)-3-{[6-(4-Fluoro-2-methyl-phenyl)-5-methoxy-pyridine-2-carbonyl]-amino}-3-o-tolyl-propionic acid | 423.09 | 1.14 | LC11_2 | 0.1768 |
| 468 | (S)-3-[(3,2'-Dimethoxy-[2,3']bipyridinyl-6-carbonyl)-amino]-3-o-tolyl-propionic acid | 422.12 | 1.06 | LC11_2 | 0.347 |
| 469 | (S)-3-[(2'-Chloro-3-methoxy-5'-methyl-[2,3']bipyridinyl-6-carbonyl)-amino]-3-o-tolyl-propionic acid | 440.1 | 1.08 | LC11_2 | 5.63 |
| 470 | (S)-3-[(3'-Fluoro-3-methoxy-[2,4']bipyridinyl-6-carbonyl)-amino]-3-o-tolyl-propionic acid | 410.06 | 1.06 | LC11_2 | 0.1182 |
| 471 | (S)-3-({5-Methoxy-6-[3-(5-methyl-[1,3,4]oxadiazol-2-yl)-phenyl]-pyridine-2-carbonyl}-amino)-3-o-tolyl-propionic acid | 473.13 | 1.07 | LC11_2 | 4.23 |
| 472 | (S)-3-{[5-Methoxy-6-(2-methyl-furan-3-yl)-pyridine-2-carbonyl]-amino}-3-o-tolyl-propionic acid | 395.04 | 1.13 | LC11_2 | 0.096 |
| 473 | (S)-3-{[6-(4-Cyano-2-fluoro-phenyl)-5-methoxy-pyridine-2-carbonyl]-amino}-3-o-tolyl-propionic acid | 434.13 | 1.1 | LC11_2 | 0.288 |
| 474 | (S)-3-(2-Chloro-phenyl)-3-{[6-(2-fluoro-5-methoxy-phenyl)-5-methoxy-pyridine-2-carbonyl]-amino}-propionic acid | 459.12 | 1.13 | LC11_3 | 0.58 |
| 475 | (S)-3-{[6-(5-tert-Butyl-2-methoxy-phenyl)-5-methoxy-pyridine-2-carbonyl]-amino}-3-(2-chloro-phenyl)-propionic acid | 497.2 | 1.23 | LC11_3 | >10.0 |

TABLE 1-continued

Example compounds of the formula I

| Ex. No. | Compound name | m/z (1) | Rt (min) | LC/MS Method | Activity [µM] |
|---|---|---|---|---|---|
| 476 | (S)-3-(2-Chloro-phenyl)-3-{[6-(2-fluoro-5-methyl-phenyl)-5-methoxy-pyridine-2-carbonyl]-amino}-propionic acid | 443.13 | 1.16 | LC11_3 | 0.3695 |
| 477 | (S)-3-{[6-(3-Chloro-2-methyl-phenyl)-5-methoxy-pyridine-2-carbonyl]-amino}-3-(2-chloro-phenyl)-propionic acid | 459.1 | 1.19 | LC11_3 | 0.11 |
| 478 | (S)-3-(2-Chloro-phenyl)-3-{[6-(3-fluoro-2-methyl-phenyl)-5-methoxy-pyridine-2-carbonyl]-amino}-propionic acid | 443.13 | 1.16 | LC11_3 | 0.192 |
| 479 | (S)-3-{[6-(5-Chloro-2-fluoro-phenyl)-5-methoxy-pyridine-2-carbonyl]-amino}-3-(2-chloro-phenyl)-propionic acid | 463.08 | 1.17 | LC11_3 | 0.262 |
| 480 | (S)-3-{[6-(4-Chloro-3-fluoro-phenyl)-5-methoxy-pyridine-2-carbonyl]-amino}-3-(2-chloro-phenyl)-propionic acid | 463.07 | 1.21 | LC11_3 | 4.37 |
| 481 | (S)-3-[(2'-Chloro-3-methoxy-5'-methyl-[2,3']bipyridinyl-6-carbonyl)-amino]-3-(2-chloro-phenyl)-propionic acid | 460.1 | 1.09 | LC11_3 | 8.77 |
| 482 | (S)-3-(2'-Chloro-phenyl)-3-[(3'-fluoro-3-methoxy-[2,4']bipyridinyl-6-carbonyl)-amino]-propionic acid | 430.2 | 1.03 | LC11_2 | 0.1153 |
| 483 | (S)-3-{[6-(3-Chloro-5-methyl-phenyl)-5-methoxy-pyridine-2-carbonyl]-amino}-3-(2-chloro-phenyl)-propionic acid | 459.1 | 1.22 | LC11_3 | 9.49 |
| 484 | (S)-3-(2-Chloro-phenyl)-3-({5-methoxy-6-[3-(5-methyl-[1,3,4]oxadiazol-2-yl)-phenyl]-pyridine-2-carbonyl}-amino)-propionic acid | 493.14 | 1.09 | LC11_3 | 6.69 |
| 485 | (S)-3-(2-Chloro-phenyl)-3-[(5-methoxy-6-pyrazin-2-yl-pyridine-2-carbonyl)-amino]-propionic acid | 413 | 1.07 | LC11_3 | 0.1588 |
| 486 | (S)-3-(2-Chloro-phenyl)-3-{[5-methoxy-6-(1,3,5-trimethyl-1H-pyrazol-4-yl)-pyridine-2-carbonyl]-amino}-propionic acid | 443.16 | 1.02 | LC11_3 | 4.95 |
| 487 | (S)-3-(2-Chloro-phenyl)-3-{[5-methoxy-6-(1-methyl-1H-indol-6-yl)-pyridine-2-carbonyl]-amino}-propionic acid | 464.15 | 1.17 | LC11_3 | >10.0 |
| 488 | (S)-3-{[6-(4-Chloro-3-methoxy-phenyl)-5-methoxy-pyridine-2-carbonyl]-amino}-3-(2-chloro-phenyl)-propionic acid | 475.09 | 1.19 | LC11_3 | >10.0 |
| 489 | (S)-3-{[6-(3-Chloro-2-fluoro-phenyl)-5-methoxy-pyridine-2-carbonyl]-amino}-3-(2-chloro-phenyl)-propionic acid | 463.08 | 1.17 | LC11_3 | 0.1314 |
| 490 | (S)-3-(2-Chloro-phenyl)-3-[(3-methoxy-2'-morpholin-4-yl-[2,4']bipyridinyl-6-carbonyl)-amino]-propionic acid | 497.17 | 0.92 | LC11_3 | 9.08 |
| 491 | (S)-3-(2-Chloro-phenyl)-3-{[5-methoxy-6-(2-methyl-furan-3-yl)-pyridine-2-carbonyl]-amino}-propionic acid | 415.12 | 1.14 | LC11_3 | 0.199 |
| 492 | (S)-3-{[6-(2-Chloro-5-methyl-phenyl)-5-methoxy-pyridine-2-carbonyl]-amino}-3-(2-chloro-phenyl)-propionic acid | 459.1 | 1.17 | LC11_3 | 1.053 |
| 493 | (S)-3-{[6-(2-Chloro-3-fluoro-phenyl)-5-methoxy-pyridine-2-carbonyl]-amino}-3-(2-chloro-phenyl)-propionic acid | 463.07 | 1.15 | LC11_3 | 0.05065 |
| 494 | (S)-3-(2-Chloro-phenyl)-3-{[6-(4-cyano-2-fluoro-phenyl)-5-methoxy-pyridine-2-carbonyl]-amino}-propionic acid | 454.11 | 1.11 | LC11_3 | 11.4 |

TABLE 1-continued

Example compounds of the formula I

| Ex. No. | Compound name | m/z (1) | Rt (min) | LC/MS Method | Activity [μM] |
|---|---|---|---|---|---|
| 495 | (S)-3-(2-Chloro-phenyl)-3-({6-[3-(3-hydroxy-oxetan-3-yl)-phenyl]-5-methoxy-pyridine-2-carbonyl}-amino)-propionic acid | 483.14 | 1.04 | LC11_3 | 3.89 |
| 496 | (S)-3-(2-Chloro-phenyl)-3-({6-[3-(1-hydroxy-1-methyl-ethyl)-phenyl]-5-methoxy-pyridine-2-carbonyl}-amino)-propionic acid | 469.16 | 1.1 | LC11_3 | 2.86 |
| 497 | (S)-3-{[6-(2-Chloro-3-methyl-phenyl)-5-methoxy-pyridine-2-carbonyl]-amino}-3-(2-chloro-phenyl)-propionic acid | 459.1 | 1.17 | LC11_3 | 0.0678 |
| 498 | 3-Biphenyl-4-yl-3-[(3,6-dichloro-pyridine-2-carbonyl)-amino]-propionic acid | 413.24 | 1.13 | LC11_2 | 8.55 |
| 499 | 3-Biphenyl-4-yl-3-[(4-chloro-3-methoxy-pyridine-2-carbonyl)-amino]-propionic acid | 409.23 | 1.11 | LC11_2 | >10.0 |
| 500 | 3-Biphenyl-4-yl-3-[(2-chloro-6-methyl-pyridine-4-carbonyl)-amino]-propionic acid | 395.22 | 1.12 | LC11_2 | >10.0 |
| 501 | 3-Biphenyl-4-yl-3-[(6-chloro-pyridine-2-carbonyl)-amino]-propionic acid | 381.18 | 1.13 | LC11_2 | 0.463 |
| 502 | 3-Biphenyl-4-yl-3-[(5-chloro-6-hydroxy-pyridine-3-carbonyl)-amino]-propionic acid | 397.18 | 1.01 | LC11_2 | >10.0 |
| 503 | 3-Biphenyl-4-yl-3-[(2-chloro-pyridine-4-carbonyl)-amino]-propionic acid | 381.18 | 1.09 | LC11_2 | >10.0 |
| 504 | 3-Biphenyl-4-yl-3-[(5-chloro-pyridine-3-carbonyl)-amino]-propionic acid | 381.45 | 1.09 | LC11_2 | >10.0 |
| 505 | 3-Biphenyl-4-yl-3-[(5-chloro-6-methoxy-pyridine-3-carbonyl)-amino]-propionic acid | 411.2 | 1.14 | LC11_2 | >10.0 |
| 506 | (S)-3-[(3,6-Dichloro-pyridine-2-carbonyl)-amino]-3-o-tolyl-propionic acid | 353.11 | 1.03 | LC11_2 | 8.48 |
| 507 | (S)-3-[(2-Chloro-6-methyl-pyridine-4-carbonyl)-amino]-3-o-tolyl-propionic acid | 331.17 | 1.02 | LC11_2 | >10.0 |
| 508 | (S)-3-[(2-Chloro-6-methoxy-pyridine-4-carbonyl)-amino]-3-o-tolyl-propionic acid | 349.18 | 1.07 | LC11_2 | >10.0 |
| 509 | (S)-3-[(2,6-Dichloro-pyridine-4-carbonyl)-amino]-3-o-tolyl-propionic acid | 353.12 | 1.08 | LC11_2 | >10.0 |
| 510 | (S)-3-[(6-Chloro-pyridine-2-carbonyl)-amino]-3-o-tolyl-propionic acid | 319.16 | 1.05 | LC11_2 | 0.2049 |
| 511 | (S)-3-[(5-Chloro-6-hydroxy-pyridine-3-carbonyl)-amino]-3-o-tolyl-propionic acid | 333.14 | 0.88 | LC11_2 | >10.0 |
| 512 | (S)-3-[(2-Chloro-pyridine-4-carbonyl)-amino]-3-o-tolyl-propionic acid | 317.16 | 0.99 | LC11_2 | >10.0 |
| 513 | (S)-3-[(5-Chloro-pyridine-3-carbonyl)-amino]-3-o-tolyl-propionic acid | 319.17 | 0.98 | LC11_2 | >10.0 |
| 514 | (S)-3-[(6-Chloro-pyrazine-2-carbonyl)-amino]-3-o-tolyl-propionic acid | 320.03 | 3.67 | LC2 | 1.21 |
| 515 | (S)-3-[(3,5-Diamino-6-chloro-pyrazine-2-carbonyl)-amino]-3-o-tolyl-propionic acid | 350.16 | 0.97 | LC11_2 | 0.0871 |
| 516 | 3-Biphenyl-4-yl-3-{[5-chloro-6-(2-hydroxy-ethylamino)-pyridine-3-carbonyl]-amino}-propionic acid | 438.29 | 1.04 | LC11_2 | >10.0 |
| 517 | (S)-3-[(5-Chloro-6-methoxy-pyridine-3-carbonyl)-amino]-3-o-tolyl-propionic acid | 347.15 | 1.05 | LC11_2 | >10.0 |
| 518 | (S)-3-[(2,5-Dichloro-pyridine-3-carbonyl)-amino]-3-o-tolyl-propionic acid | 351.11 | 1.01 | LC11_2 | >10.0 |

TABLE 1-continued

Example compounds of the formula I

| Ex. No. | Compound name | m/z (1) | Rt (min) | LC/MS Method | Activity [µM] |
|---|---|---|---|---|---|
| 519 | 3-Biphenyl-4-yl-3-[(3,5-diamino-6-chloro-pyrazine-2-carbonyl)-amino]-propionic acid | 412.19 | 1.07 | LC11_2 | 0.563 |
| 520 | (S)-3-[(4-Chloro-3-methoxy-pyridine-2-carbonyl)-amino]-3-o-tolyl-propionic acid | 347.16 | 1.01 | LC11_2 | >10.0 |
| 521 | 3-(2-Chloro-phenyl)-3-[(pyrazine-2-carbonyl)-amino]-propionic acid | 304.19 | 1.05 | LC11_2 | 12.8 |
| 522 | 3-(2-Chloro-phenyl)-3-[(pyridine-3-carbonyl)-amino]-propionic acid | 305.07 | 0.98 | LC11_2 | |
| 523 | 3-(2-Chloro-phenyl)-3-[(pyridine-2-carbonyl)-amino]-propionic acid | 305.08 | 1.12 | LC11_2 | |
| 524 | 3-(2-Chloro-phenyl)-3-[(pyridine-4-carbonyl)-amino]-propionic acid | 305.08 | 0.97 | LC11_2 | 10.2 |
| 525 | 3-(2-Chloro-phenyl)-3-[(5-methyl-pyrazine-2-carbonyl)-amino]-propionic acid | 318.17 | 1.09 | LC11_2 | |
| 526 | 3-(2-Chloro-phenyl)-3-[(2-methyl-pyridine-4-carbonyl)-amino]-propionic acid | 319.09 | 0.94 | LC11_2 | |
| 527 | 3-(2-Chloro-phenyl)-3-[(6-methyl-pyridine-2-carbonyl)-amino]-propionic acid | 319.1 | 1.16 | LC11_2 | 4.96 |
| 528 | 3-(2-Chloro-phenyl)-3-[(4-methyl-pyridine-2-carbonyl)-amino]-propionic acid | 319.1 | 1.16 | LC11_2 | 5.81 |
| 529 | 3-(2-Chloro-phenyl)-3-[(4-hydroxy-pyridine-2-carbonyl)-amino]-propionic acid | 321.06 | 0.97 | LC11_2 | 5.12 |
| 530 | 3-(2-Chloro-phenyl)-3-[(3-fluoro-pyridine-2-carbonyl)-amino]-propionic acid | 321.14 | 1.09 | LC11_2 | 5.27 |
| 531 | 3-(2-Chloro-phenyl)-3-[(6-fluoro-pyridine-2-carbonyl)-amino]-propionic acid | 323.06 | 1.15 | LC11_2 | 7.65 |
| 532 | 3-(2-Chloro-phenyl)-3-[(4-ethyl-pyridine-2-carbonyl)-amino]-propionic acid | 331.22 | 1.21 | LC11_2 | 10.2 |
| 533 | 3-(2-Chloro-phenyl)-3-[(4,6-dimethyl-pyridine-2-carbonyl)-amino]-propionic acid | 331.22 | 1.2 | LC11_2 | 6.29 |
| 534 | 3-(2-Chloro-phenyl)-3-[(4,6-dimethyl-pyridine-3-carbonyl)-amino]-propionic acid | 333.11 | 0.92 | LC11_2 | |
| 535 | 3-(2-Chloro-phenyl)-3-[(6-methylamino-pyrazine-2-carbonyl)-amino]-propionic acid | 335.08 | 1.07 | LC11_2 | |
| 536 | 3-(2-Chloro-phenyl)-3-[(2-methoxy-pyridine-4-carbonyl)-amino]-propionic acid | 335.08 | 1.11 | LC11_2 | 5.08 |
| 537 | 3-(2-Chloro-phenyl)-3-[(6-methoxy-pyridine-3-carbonyl)-amino]-propionic acid | 335.08 | 1.1 | LC11_2 | |
| 538 | 3-(2-Chloro-phenyl)-3-[(6-methoxy-pyridine-2-carbonyl)-amino]-propionic acid | 335.08 | 1.18 | LC11_2 | |
| 539 | 3-(2-Chloro-phenyl)-3-[(3-methoxy-pyridine-2-carbonyl)-amino]-propionic acid | 335.09 | 1.03 | LC11_2 | >10.0 |
| 540 | 3-(2-Chloro-phenyl)-3-[(6-chloro-pyridine-2-carbonyl)-amino]-propionic acid | 339.02 | 1.18 | LC11_2 | 1.6 |
| 541 | 3-(2-Chloro-phenyl)-3-[(3,6-difluoro-pyridine-2-carbonyl)-amino]-propionic acid | 339.14 | 1.12 | LC11_2 | |
| 542 | 3-(2-Chloro-phenyl)-3-[(3H-imidazo[4,5-b]pyridine-5-carbonyl)-amino]-propionic acid; compound with trifluoro-acetic acid | 345.06 | 1.0 | LC11_2 | 10.8 |
| 543 | 3-(2-Chloro-phenyl)-3-[([1,8]naphthyridine-2-carbonyl)-amino]-propionic acid | 356.07 | 1.09 | LC11_2 | |

TABLE 1-continued

Example compounds of the formula I

| Ex. No. | Compound name | m/z (1) | Rt (min) | LC/MS Method | Activity [μM] |
|---|---|---|---|---|---|
| 544 | 3-(2-Chloro-phenyl)-3-[([1,6]naphthyridine-2-carbonyl)-amino]-propionic acid | 356.07 | 1.08 | LC11_2 | 11.1 |
| 545 | 3-[(2-Acetylamino-pyridine-4-carbonyl)-amino]-3-(2-chloro-phenyl)-propionic acid | 362.08 | 1.02 | LC11_2 | |
| 546 | 3-[(2-Amino-6-isopropyl-pyrimidine-4-carbonyl)-amino]-3-(2-chloro-phenyl)-propionic acid; compound with trifluoro-acetic acid | 363.12 | 1.15 | LC11_2 | |
| 547 | (S)-3-{[6-(2-Fluoro-phenyl)-pyridine-2-carbonyl]-amino}-3-phenyl-propionic acid | 365.29 | 1.75 | LC X | 0.345 |
| 548 | 3-(2-Chloro-phenyl)-3-[(4,6-dimethoxy-pyrimidine-2-carbonyl)-amino]-propionic acid | 366.07 | 1.24 | LC X | |
| 549 | 3-(2-Chloro-phenyl)-3-[(2,6-dimethoxy-pyrimidine-4-carbonyl)-amino]-propionic acid | 366.08 | 1.19 | LC X | |
| 550 | 3-[(6-Chloro-5-methoxy-pyridine-2-carbonyl)-amino]-3-(2-chloro-phenyl)-propionic acid | 369.03 | 1.19 | LC X | 1.08 |
| 551 | 3-(2-Chloro-phenyl)-3-[(6-imidazol-1-yl-pyridine-2-carbonyl)-amino]-propionic acid | 371.08 | 0.96 | LC X | |
| 552 | 3-(2-Chloro-phenyl)-3-[(3,6-dichloro-pyridine-2-carbonyl)-amino]-propionic acid | 371.1 | 1.18 | LC X | |
| 553 | 3-(2-Chloro-phenyl)-3-[(2-pyrrolidin-1-yl-pyridine-4-carbonyl)-amino]-propionic acid; compound with trifluoro-acetic acid | 374.11 | 0.96 | LC X | 11.1 |
| 554 | 3-(2-Chloro-phenyl)-3-[(6-pyrrolidin-1-yl-pyridine-3-carbonyl)-amino]-propionic acid; compound with trifluoro-acetic acid | 374.11 | 0.95 | LC X | |
| 555 | 3-(2-Chloro-phenyl)-3-[(5-pyrrolidin-1-yl-pyridine-3-carbonyl)-amino]-propionic acid; compound with trifluoro-acetic acid | 374.13 | 1.01 | LC11_2 | >10.0 |
| 556 | (S)-3-{[5-Chloro-6-(2-hydroxy-ethylamino)-pyridine-3-carbonyl]-amino}-3-o-tolyl-propionic acid | 376.22 | 0.92 | LC11_2 | >10.0 |
| 557 | 3-[(2-Amino-6-isobutyl-pyrimidine-4-carbonyl)-amino]-3-(2-chloro-phenyl)-propionic acid | 377.12 | 1.19 | LC11_2 | 14 |
| 558 | (S)-3-{[6-(2-Fluoro-phenyl)-pyridine-2-carbonyl]-amino}-3-phenyl-butyric acid | 379.33 | 1.8 | LC X | |
| 559 | (S)-3-{[6-(2-Fluoro-phenyl)-pyridine-2-carbonyl]-amino}-3-p-tolyl-propionic acid | 379.33 | 1.81 | LC X | 4.38 |
| 560 | (S)-3-{[6-(2-Fluoro-phenyl)-pyridine-2-carbonyl]-amino}-3-m-tolyl-propionic acid | 379.33 | 1.81 | LC X | 12.9 |
| 561 | (R)-3-{[6-(2-Fluoro-phenyl)-pyridine-2-carbonyl]-amino}-4-phenyl-butyric acid | 379.34 | 1.79 | LC X | 5.33 |
| 562 | 3-[(6-Bromo-pyridine-2-carbonyl)-amino]-3-(2-chloro-phenyl)-propionic acid | 381.04 | 1.2 | LC11_2 | 2.1 |
| 563 | 3-(2-Chloro-phenyl)-3-[(6-phenyl-pyridine-2-carbonyl)-amino]-propionic acid | 381.1 | 1.27 | LC11_2 | 3.09 |
| 564 | 3-(2-Chloro-phenyl)-3-[(3-phenyl-pyridine-2-carbonyl)-amino]-propionic acid | 381.1 | 1.18 | LC11_2 | |
| 565 | 3-(2-Chloro-phenyl)-3-[(4-phenyl-pyridine-2-carbonyl)-amino]-propionic acid | 381.1 | 1.27 | LC11_2 | 4.07 |

TABLE 1-continued

Example compounds of the formula I

| Ex. No. | Compound name | m/z (1) | Rt (min) | LC/MS Method | Activity [μM] |
|---|---|---|---|---|---|
| 566 | 3-(2-Chloro-phenyl)-3-[(5-phenyl-pyridine-3-carbonyl)-amino]-propionic acid | 381.11 | 1.18 | LC11_2 | 11.7 |
| 567 | (S)-3-{[6-(2-Chloro-phenyl)-pyridine-2-carbonyl]-amino}-3-phenyl-propionic acid | 381.27 | 1.77 | LC X | 2.18 |
| 568 | 3-[(5-Bromo-pyridine-3-carbonyl)-amino]-3-(2-chloro-phenyl)-propionic acid | 382.97 | 1.13 | LC11_2 | |
| 569 | (S)-3-(3-Fluoro-phenyl)-3-{[6-(2-fluoro-phenyl)-pyridine-2-carbonyl]-amino}-propionic acid | 383.29 | 1.77 | LC11_X | 0.429 |
| 570 | (S)-3-(2-Fluoro-phenyl)-3-{[6-(2-fluoro-phenyl)-pyridine-2-carbonyl]-amino}-propionic acid | 383.3 | 1.76 | LC11_X | 0.195 |
| 571 | (S)-3-(4-Fluoro-phenyl)-3-{[6-(2-fluoro-phenyl)-pyridine-2-carbonyl]-amino}-propionic acid | 383.3 | 1.77 | LC11_X | 0.514 |
| 572 | 3-(2-Chloro-phenyl)-3-[(3,4,5,6-tetrahydro-2H-[1,2']bipyridinyl-4'-carbonyl)-amino]-propionic acid; compound with trifluoro-acetic acid | 388.15 | 1.03 | LC11_2 | >10.0 |
| 573 | 3-(2-Chloro-phenyl)-3-[(3,4,5,6-tetrahydro-2H-[1,2']bipyridinyl-6'-carbonyl)-amino]-propionic acid; compound with trifluoro-acetic acid | 388.16 | 1.29 | LC11_2 | |
| 574 | 3-(2-Chloro-phenyl)-3-[(6-morpholin-4-yl-pyridine-2-carbonyl)-amino]-propionic acid; compound with trifluoro-acetic acid | 390.12 | 1.16 | LC11_2 | |
| 575 | 3-(2-Chloro-phenyl)-3-[(4-morpholin-4-yl-pyridine-2-carbonyl)-amino]-propionic acid; compound with trifluoro-acetic acid | 390.12 | 0.93 | LC11_2 | |
| 576 | 3-(2-Chloro-phenyl)-3-[(2-morpholin-4-yl-pyridine-4-carbonyl)-amino]-propionic acid; compound with trifluoro-acetic acid | 390.13 | 1.03 | LC11_2 | |
| 577 | (S)-3-[(6-Methoxy-biphenyl-3-carbonyl)-amino]-3-o-tolyl-propionic acid | 390.2 | 1.26 | LC11_ | 0.414 |
| 578 | (S)-3-[(3-Methoxy-[2,3']bipyridinyl-6-carbonyl)-amino]-3-o-tolyl-propionic acid | 392.08 | 0.91 | LC11_ | 7.54 |
| 579 | 3-[(2,6-Bis-dimethylamino-pyrimidine-4-carbonyl)-amino]-3-(2-chloro-phenyl)-propionic acid; compound with trifluoro-acetic acid | 392.14 | 1.01 | LC11_2 | |
| 580 | (S)-3-{[6-(2-Chloro-phenyl)-pyridine-2-carbonyl]-amino}-3-p-tolyl-propionic acid | 393.19 | 1.95 | LC 11_X | 15.6 |
| 581 | (S)-3-{[6-(2-Chloro-phenyl)-pyridine-2-carbonyl]-amino}-3-phenyl-butyric acid | 395.17 | 1.94 | LC 11_X | 5.76 |
| 582 | (S)-3-{[6-(2-Chloro-phenyl)-pyridine-2-carbonyl]-amino}-3-m-tolyl-propionic acid | 395.18 | 1.96 | LC 11_X | 0.16 |
| 583 | (R)-3-{[6-(2-Chloro-phenyl)-pyridine-2-carbonyl]-amino}-4-phenyl-butyric acid | 395.29 | 1.81 | LC 11_X | >30.0 |
| 584 | (S)-3-{[6-(2-Fluoro-phenyl)-pyridine-2-carbonyl]-amino}-3-(4-methoxy-phenyl)-propionic acid | 395.31 | 1.74 | LC X | 0.54 |
| 585 | 3-(2-Chloro-phenyl)-3-[(6-phenoxy-pyridine-3-carbonyl)-amino]-propionic acid | 397.08 | 1.21 | LC 11 | 8.67 |
| 586 | (S)-3-{[6-(2-Chloro-phenyl)-pyridine-2-carbonyl]-amino}-3-(2-fluoro-phenyl)-propionic acid | 399.13 | 1.92 | LC 11_X | 0.339 |

TABLE 1-continued

Example compounds of the formula I

| Ex. No. | Compound name | m/z (1) | Rt (min) | LC/MS Method | Activity [µM] |
|---|---|---|---|---|---|
| 587 | (S)-3-{[6-(2-Chloro-phenyl)-pyridine-2-carbonyl]-amino}-3-(3-fluoro-phenyl)-propionic acid | 399.15 | 1.92 | LC 11_X | 7.35 |
| 588 | (S)-3-{[6-(2-Chloro-phenyl)-pyridine-2-carbonyl]-amino}-3-(4-fluoro-phenyl)-propionic acid | 399.23 | 4.49 | LC 11_X | 0.107 |
| 589 | 3-(2-Chloro-phenyl)-3-{[6-(2-fluoro-phenyl)-pyridine-2-carbonyl]-amino}-propionic acid | 399.26 | 1.8 | LC X | 4.89 |
| 590 | (S)-3-(3-Chloro-phenyl)-3-{[6-(2-fluoro-phenyl)-pyridine-2-carbonyl]-amino}-propionic acid | 399.26 | 1.83 | LC 11_X | 0.339 |
| 591 | (S)-3-(4-Chloro-phenyl)-3-{[6-(2-fluoro-phenyl)-pyridine-2-carbonyl]-amino}-propionic acid | 399.27 | 1.83 | LC 11_X | 0.322 |
| 592 | 3-(2-Chloro-phenyl)-3-[(1-ethyl-3,6-dimethyl-1H-pyrazolo[3,4-b]pyridine-4-carbonyl)-amino]-propionic acid | 401.13 | 1.14 | LC 11_2 | |
| 593 | 3-(2-Chloro-phenyl)-3-{[2-(2,2-dimethyl-propionylamino)-pyridine-4-carbonyl]-amino}-propionic acid | 404.14 | 1.17 | LC 11_2 | |
| 594 | 3-(2-Chloro-phenyl)-3-{[6-(tetrahydro-pyran-4-yloxy)-pyridine-3-carbonyl]-amino}-propionic acid | 405.1 | 1.14 | LC 11_2 | |
| 595 | 3-(2-Chloro-phenyl)-3-{[6-(4-methoxy-phenyl)-pyridine-2-carbonyl]-amino}-propionic acid | 409.3 | 1.27 | LC 11_2 | 1.42 |
| 596 | 3-(2-Chloro-phenyl)-3-{[6-(3-methoxy-phenyl)-pyridine-2-carbonyl]-amino}-propionic acid | 411.1 | 1.27 | LC 11_2 | 5.77 |
| 597 | 3-(2-Chloro-phenyl)-3-{[6-(2-methoxy-phenyl)-pyridine-2-carbonyl]-amino}-propionic acid | 411.1 | 1.27 | LC 11_2 | 1.45 |
| 598 | 3-[(6-Bromo-5-methoxy-pyridine-2-carbonyl)-amino]-3-(2-chloro-phenyl)-propionic acid | 411.18 | 1.2 | LC 11_2 | 1.46 |
| 599 | (S)-3-{[6-(2-Chloro-phenyl)-pyridine-2-carbonyl]-amino}-3-(4-methoxy-phenyl)-propionic acid | 411.29 | 1.77 | LC 11_X | 2.83 |
| 600 | 3-(2-Chloro-phenyl)-3-[(6-cyclopropyl-1,3-dimethyl-1H-pyrazolo[3,4-b]pyridine-4-carbonyl)-amino]-propionic acid | 413.14 | 1.19 | LC 11_2 | |
| 601 | 3-(2-Chloro-phenyl)-3-{[4-(pyrimidin-2-ylsulfanyl)-pyridine-2-carbonyl]-amino}-propionic acid | 415.05 | 1.18 | LC 11_2 | 3.85 |
| 602 | (S)-3-(4-Chloro-phenyl)-3-{[6-(2-chloro-phenyl)-pyridine-2-carbonyl]-amino}-propionic acid | 415.09 | 1.94 | LC 11_X | 0.0623 |
| 603 | (S)-3-(3-Chloro-phenyl)-3-{[6-(2-chloro-phenyl)-pyridine-2-carbonyl]-amino}-propionic acid | 415.12 | 1.98 | LC 11_2 | 0.0803 |
| 604 | 3-(2-Chloro-phenyl)-3-{[6-(2-chloro-phenyl)-pyridine-2-carbonyl]-amino}-propionic acid | 415.25 | 1.83 | LC_X | 0.345 |
| 605 | (S)-3-(2,4-Dichloro-phenyl)-3-{[6-(2-fluoro-phenyl)-pyridine-2-carbonyl]-amino}-propionic acid | 433.24 | 1.9 | LC 11_X | 2.28 |
| 606 | (S)-3-(2,3-Dichloro-phenyl)-3-{[6-(2-fluoro-phenyl)-pyridine-2-carbonyl]-amino}-propionic acid | 433.25 | 1.87 | LC 11_X | 3.93 |
| 607 | (S)-3-{[6-(2-Fluoro-phenyl)-pyridine-2-carbonyl]-amino}-3-(2-trifluoromethyl-phenyl)-propionic acid | 433.31 | 1.83 | LC_X | 0.88 |
| 608 | (S)-3-{[6-(2-Fluoro-phenyl)-pyridine-2-carbonyl]-amino}-3-(4-trifluoromethyl-phenyl)-propionic acid | 433.31 | 1.87 | LC_X | 6.27 |

TABLE 1-continued

Example compounds of the formula I

| Ex. No. | Compound name | m/z (1) | Rt (min) | LC/MS Method | Activity [μM] |
|---|---|---|---|---|---|
| 609 | (S)-3-{[6-(2-Fluoro-phenyl)-pyridine-2-carbonyl]-amino}-3-(3-trifluoromethyl-phenyl)-propionic acid | 433.32 | 1.85 | LC_X | 0.902 |
| 610 | (S)-3-{[6-(2-Chloro-phenyl)-pyridine-2-carbonyl]-amino}-3-(2,3-dichloro-phenyl)-propionic acid | 449.07 | 2.01 | LC 11_X | 2.32 |
| 611 | (S)-3-{[6-(2-Chloro-phenyl)-pyridine-2-carbonyl]-amino}-3-(2,4-dichloro-phenyl)-propionic acid | 449.09 | 2.05 | LC 11_X | 0.27 |
| 612 | (S)-3-{[6-(2-Chloro-phenyl)-pyridine-2-carbonyl]-amino}-3-(2-trifluoromethyl-phenyl)-propionic acid | 449.13 | 1.98 | LC 11_X | 1.66 |
| 613 | (S)-3-{[6-(2-Chloro-phenyl)-pyridine-2-carbonyl]-amino}-3-(4-trifluoromethyl-phenyl)-propionic acid | 449.16 | 2.02 | LC 11_X | 0.406 |
| 614 | (S)-3-{[6-(2-Chloro-phenyl)-pyridine-2-carbonyl]-amino}-3-(3-trifluoromethyl-phenyl)-propionic acid | 449.16 | 2.0 | LC 11_X | 0.315 |
| 615 | 3-(2-Chloro-phenyl)-3-{[3-(4,6-dimethoxy-pyrimidin-2-yloxy)-pyridine-2-carbonyl]-amino}-propionic acid | 459.13 | 1.06 | LC 11_2 | 3.58 |
| 616 | 3-(2-Chloro-phenyl)-3-[(6-phenyl-2-piperidin-1-yl-pyrimidine-4-carbonyl)-amino]-propionic acid; compound with trifluoro-acetic acid | 465.21 | 5.02 | LC 11_2 | 10.4 |
| 617 | (S)-3-{[6-Bromo-5-(3,3-dimethyl-2-oxo-butoxy)-pyridine-2-carbonyl]-amino}-3-o-tolyl-propionic acid | 477.03 | 1.25 | LC 11 | 0.1568 |
| 618 | (S)-3-{[5-(3,3-Dimethyl-2-oxo-butoxy)-6-phenyl-pyridine-2-carbonyl]-amino}-3-o-tolyl-propionic acid | | 1.19 | LC 11_2 | |

(1) Mass spectroscopic characterization; observed mass number of the ion [(M + H)$^+$], unless specified otherwise
(2) Cathepsin A inhibitory activity determined in the pharmacological test "Cathepsin A inhibitory activity" described below.

Pharmacological Tests
a) Cathepsin A Inhibitory Activity

Recombinant human cathepsin A (residues 29-480, with a C-terminal 10-His tag; R&D Systems, #1049-SE) was proteolytically activated with recombinant human cathepsin L (R&D Systems, #952-CY). Briefly, cathepsin A was incubated at 10 μg/ml with cathepsin L at 1 μg/ml in activation buffer (25 mM 2-(morpholin-4-yl)-ethanesulfonic acid (MES), pH 6.0, containing 5 mM dithiothreitol (DTT)) for 15 min at 37° C. Cathepsin L activity was then stopped by the addition of the cysteine protease inhibitor E-64 (N-(trans-epoxysuccinyl)-L-leucine-4-guanidinobutylamide; Sigma-Aldrich, # E3132; dissolved in activation buffer/DMSO) to a final concentration of 10 μM.

The activated cathepsin A was diluted in assay buffer (25 mM MES, pH 5.5, containing 5 mM DTT) and mixed with the test compound (dissolved in assay buffer containing (v/v) 3% DMSO) or, in the control experiments, with the vehicle in a multiple assay plate. After incubation for 15 min at room temperature, as substrate then bradykinin carrying an N-terminal® Bodipy FL (4,4-difluoro-5,7-dimethyl-4-bora-3a,4a-diaza-s-indacene-3-propionyl) label (JPT Peptide Technologies GmbH; dissolved in assay buffer) was added to the mixture. The final concentration of cathepsin A was 833 ng/ml and the final concentration of labeled bradykinin 2 μM. After incubation for 15 min at room temperature the reaction was stopped by the addition of stop buffer (130 mM 2-(4-(2-hydroxy-ethyl)-piperazin-1-yl)-ethanesulfonic acid, pH 7.4, containing (v/v) 0.013%®Triton X-100, 0.13% Coating Reagent 3 (Caliper Life Sciences), 6.5% DMSO and 20 μM ebelactone B (Sigma, # E0886)).

Uncleaved substrate and product were then separated by a microfluidic capillary electrophoresis on a LabChip® 3000 Drug Discovery System (12-Sipper-Chip; Caliper Life Sciences) and quantified by determination of the respective peak areas. Substrate turnover was calculated by dividing product peak area by the sum of substrate and product peak areas, and the enzyme activity and the inhibitory effect of the test compound thus quantified. From the percentage of inhibition of cathepsin A activity observed with the test compound at several concentrations, the inhibitory concentration $IC_{50}$, i.e. the concentration which effects 50% inhibition of enzyme activity was, calculated. $IC_{50}$ values of various example compounds are given in Table 1 in μM.

B) In Vivo Antihypertrophic and Renoprotective Activity

The in vivo pharmacological activity of the compounds of the invention can be investigated, for example, in the model of DOCA-salt sensitive rats with unilateral nephrectomy. Briefly, in this model unilateral nephrectomy of the left kidney (UNX) is performed on Sprague Dawley rats of 150 g to 200 g of body weight. After the operation as well as at the beginning of each of the following weeks 30 mg/kg of body weight of DOCA (desoxycorticosterone acetate) are administered to the rats by subcutaneous injection. The nephrectomized rats treated with DOCA are supplied with drinking water containing 1% of sodium chloride (UNX/DOCA rats). The UNX/DOCA rats develop high blood pressure, endothelial dysfunction, myocardial hypertrophy and fibrosis as well as renal dysfunction. In the test group (UNX/DOCA Test) and the placebo group (UNX/DOCA Placebo), which consist of randomized UNX/DOCA rats, the rats are treated orally by gavage in two part administrations at 6 a.m. and 6 p.m. with the daily dose of the test compound (for example 10 mg/kg of body weight dissolved in vehicle) or with vehicle only, respectively. In a control group (control), which consists of animals which have not been subjected to UNX and DOCA administration, the animals receive normal drinking water and are treated with vehicle only. After five weeks of treatment, systolic blood pressure (SBP) and heart rate (HR) are measured non-invasively via the tail cuff method. For determination of albuminuria and creatinine, 24 h urine is collected on metabolic cages. Endothelial function is assessed in excised rings of the thoracic aorta as described previously (W. Linz et al., JRAAS (Journal of the renin-angiotensin-aldosterone system) 7 (2006), 155-161). As a measure of myocardial hypertrophy and fibrosis, heart weight, left ventricular weight and the relation of hydroxyproline and proline are determined in excised hearts.

The invention claimed is:

1. A compound of the formula I, in any of its stereoisomeric forms or a mixture of stereoisomeric forms in any ratio, or a physiologically acceptable salt thereof, or a physiologically acceptable solvate of any of them,

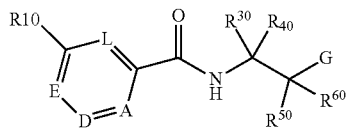

I wherein

A is selected from the group consisting of $C(R^1)$ and N;
D is selected from the group consisting of $C(R^2)$ and N;
E is $C(R^3)$;
L is selected from the group consisting of $C(R^4)$ and N;
wherein one of A, D, and L is N;
G is selected from the group consisting of $R^{71}$—O—C(O)—, $R^{72}$—N($R^{73}$)—C(O)— and tetrazol-5-yl;
$R^1$ is selected from the group consisting of hydrogen, halogen, $(C_1-C_6)$-alkyl, HO—, $(C_1-C_6)$-alkyl-O—, $(C_1-C_6)$-alkyl-S(O)$_m$— and NC—;
$R^2$ is selected from the group consisting of hydrogen, halogen, $(C_1-C_7)$-alkyl, $(C_1-C_6)$-alkyl-O—, $(C_1-C_6)$-alkyl-CO—, $(C_1-C_6)$-alkyl-CO—HN—, —$NR^{12}R^{13}$, $Het^{2t}$ $(C_3-C_7)$-cycloalkyl-$C_sH_{2s}$— and Ar—$C_sH_{2s}$—, wherein s is 0, 1, 2 or 3;
$R^3$ is $R^{11}$—O—;
$R^4$ is selected from the group consisting of hydrogen, halogen, $(C_1-C_6)$-alkyl, $(C_1-C_6)$-alkyl-O—, HO—, $NR^{12}R^{13}$, $Het^2$;
$R^{10}$ is selected from the group consisting hydrogen, halogen, $(C_1-C_6)$-alkyl, $(C_1-C_6)$-alkyl-O—, $(C_1-C_6)$-alkyl-S(O)$_m$—, HO—, —$NR^{12}R^{13}$, $Het^2$, phenyl-$C_sH_{2s}$—(O)$_t$—, wherein s is 0, 1, 2 or 3, and t is 0 or 1;
with the proviso that one of $R^1$, $R^2$, $R^4$ or $R^{10}$ is a cyclic substituent;
$R^{11}$ is selected from the group consisting of hydrogen, $R^{14}$, $(C_3-C_7)$-cycloalkyl, Ar and $Het^3$;
$R^{12}$ and $R^{13}$ are independently selected from the group consisting of hydrogen and $R^{15}$;
$R^{14}$ is $(C_1-C_{10})$-alkyl, which is optionally substituted by one or more identical or different substituents selected from the group consisting of halogen, HO—, $R^{16}$—O—, oxo, $(C_3-C_7)$-cycloalkyl, Ar, $Het^1$, $Het^3$, NC—, $H_2N$—C(O)—, $(C_1-C_4)$-alkyl-NH—C(O)—, di(($C_1-C_4)$-alkyl)N—C(O)—, $Het^1$-C(O)—, $(C_1-C_4)$-alkyl-C(O)—NH— and $(C_1-C_4)$-alkyl-S(O)$_m$—;
$R^{15}$ is $(C_1-C_6)$-alkyl which is optionally substituted by one or more identical or different substituents selected from the group consisting halogen, HO— and $(C_1-C_6)$-alkyl-O—;
$R^{16}$ is $(C_1-C_6)$-alkyl which is optionally substituted by one or more identical or different substituents selected from the group consisting of HO—, $(C_1-C_4)$-alkyl-O— and NC—;
$R^{30}$ is selected from the group consisting of $R^{31}$, $(C_3-C_7)$-cycloalkyl, $R^{32}$—$C_uH_{2u}$— and $Het^3$-$C_uH_{2u}$—, wherein u is an integer selected from the group consisting of 0, 1, 2 and 3;
$R^{31}$ is $(C_1-C_{10})$-alkyl, which is optionally substituted by one or two identical or different substituents selected from the group consisting of halogen, $(C_3-C_7)$-cycloalkyl, HO—, $(C_1-C_6)$-alkyl-O—, $(C_1-C_6)$-alkyl-S(O)$_m$— and NC—;
$R^{32}$ is selected from the group consisting of phenyl and an aromatic 5-membered or 6-membered monocyclic heterocycle containing one, two or three identical or different ring heteroatoms selected from the group consisting of nitrogen, oxygen and sulfur and is bonded via a ring carbon atom, wherein the phenyl and the heterocycle are optionally substituted by one or more identical or different substituents selected from the group consisting of halogen, $(C_1-C_6)$-alkyl, HO—, $(C_1-C_6)$-alkyl-O—, —O—$CH_2$—O—, —O—$CF_2$—O—, $(C_4-C_6)$-alkyl-S(O)$_m$—, $H_2N$—S(O)$_2$—, $(C_1-C_4)$-alkyl-NH—S(O)$_2$—, di(($C_1-C_4)$-alkyl)N—S(O)$_2$—, $H_2N$—, $(C_1-C_6)$-alkyl-NH—, di(($C_1-C_6)$-alkyl)N—, $(C_1-C_4)$-alkyl-C(O)—NH—, $(C_1-C_4)$-alkyl-S(O)$_2$—NH— and NC—, or substituted once by a phenyl ring or $(C_3-C_7)$-cycloalkyl ring;
$R^{40}$ is selected from the group consisting of hydrogen and $(C_1-C_4)$-alkyl;
or $R^{30}$ and $R^{40}$ together are $(CH_2)_x$ which is optionally substituted by one or more identical or different $(C_1-C_4)$-alkyl substituents, wherein x is 2, 3, 4 or 5;
$R^{50}$ is selected from the group consisting of hydrogen, $(C_1-C_6)$-alkyl, HO— and $(C_1-C_6)$-alkyl-O—;
$R^{60}$ is selected from the group consisting of hydrogen and $(C_1-C_6)$-alkyl;
or $R^{50}$ and $R^{60}$ together are $(CH_2)_y$ which is optionally substituted by one or more identical or different $(C_1-C_4)$-alkyl substituents, wherein y is 2, 3, 4 or 5;
$R^{71}$ is selected from the group consisting of hydrogen and $(C_1-C_8)$-alkyl, which is optionally substituted by one or more identical or different substituents selected from the group consisting $(C_1-C_6)$-alkyl-O— and $(C_1-C_6)$-alkyl-C(O)—O—;
$R^{72}$ is selected from the group consisting of hydrogen, $(C_1-C_6)$-alkyl, $(C_3-C_6)$-cycloalkyl, —$CH_2$—$(CH_2)_b$—

$(C_3-C_6)$-cycloalkyl, Het$^4$ and $-(CH_2)_b$-Het$^4$, where alkyl or cycloalkyl is optionally substituted by one or more identical or different substituents selected from the group consisting of halogen, HO—, HOOC—, $(C_1-C_6)$-alkyl-O— and $(C_1-C_6)$-alkyl-C(O)—O—, NC—, $N((C_1-C_4)$-alkyl)$_2$, and b is 0, 1 or 2;

$R^{73}$ is selected from the group consisting of hydrogen and $(C_1-C_6)$-alkyl;

or $R^{72}$ and $R^{73}$, together with the nitrogen atom to which they are bonded, form a saturated 4-membered to 7-membered monocyclic heterocycle, which contain optionally one further ring heteroatom selected from the group consisting of nitrogen, oxygen and sulfur, which is optionally substituted by one or more identical or different substituents selected from the group consisting of halogen, $(C_1-C_4)$-alkyl, HO— and $(C_1-C_4)$-alkyl-O—;

Ar, independently of each other group Ar, is selected from the group consisting of phenyl and an aromatic 5-membered or 6-membered monocyclic heterocycle containing one, two or three identical or different ring heteroatoms selected from the group consisting of nitrogen, oxygen and sulfur and is bonded via a ring carbon atom, wherein the phenyl and the heterocycle all are optionally substituted by one or more identical or different substituents selected from the group consisting of halogen, $(C_1-C_6)$-alkyl, HO—$(C_1-C_6)$-alkyl, Het$^4$, $-(CH_2)_x$-Phenyl, $(C_1-C_6)$-alkyl-O—, $(C_3-C_7)$-cycloalkyl-$(CH_2)_x$—O—, —CF$_3$, —CO—$(C_1-C_6)$-alkyl, —NR$^{12}$R$^{13}$, Het$^2$, —CO—NR$^{12}$R$^{13}$, CO-Het$^2$, $(C_1-C_6)$-alkyl-S(O)$_m$—, H$_2$N—S(O)$_2$— and NC—; and wherein phenyl may be substituted by —CH═CH—CH═CH—, —O—CH$_2$—O—, —O—CH$_2$—CH$_2$—O—, —O—CF$_2$—O— or —N($(C_1-C_3)$-alkyl)-CH═CH—;

Het$^1$, independently of each other group Het$^1$, is a saturated or unsaturated 4-membered to 8-membered monocyclic heterocycle containing a ring nitrogen atom via which Het$^1$ is bonded, and optionally, one or two identical or different further ring heteroatoms selected from the group consisting of nitrogen, oxygen and sulfur, which is optionally substituted by one or more identical or different substituents selected from the group consisting of halogen, $(C_1-C_4)$-alkyl, HO—, $(C_1-C_4)$-alkyl-O—, oxo and NC—;

Het$^2$ is a saturated 4-membered to 7-membered monocyclic heterocycle containing a ring nitrogen atom via which Het$^2$ is bonded and optionally one further ring heteroatom selected from the group consisting of nitrogen, oxygen and sulfur, which is optionally substituted by one or more identical or different substituents selected from the group consisting of halogen, $(C_1-C_4)$-alkyl, HO— and $(C_1-C_4)$-alkyl-O—;

Het$^3$, independently of each other group Het$^3$, is a saturated 4-membered to 7-membered monocyclic heterocycle containing one or two identical or different ring heteroatoms selected from the group consisting of nitrogen, oxygen and sulfur and is bonded via a ring carbon atom, which is optionally substituted by one or more identical or different substituents selected from the group consisting of fluorine, $(C_1-C_4)$-alkyl and oxo;

Het$^4$, independently of each other group Het$^4$, is a saturated or unsaturated 4-membered to 8-membered monocyclic heterocycle containing one to four ring heteroatoms selected from the group consisting of nitrogen, oxygen and sulfur which is optionally substituted by one or more identical or different substituents selected from the group consisting of halogen, $(C_1-C_4)$-alkyl, HO—, $(C_1-C_4)$-alkyl-O—, oxo and NC—;

m, independently of each other number m, is 0, 1 or 2;

wherein all cycloalkyl groups, independently of each other, are optionally substituted by one or more identical or different substituents selected from the group consisting of fluorine and $(C_1-C_4)$-alkyl;

wherein all alkyl, $C_sH_{2s}$, $C_uH_{2u}$, $(CH_2)_x$ and $(CH_2)_y$ groups, independently of each other, and independently of any other substituents, are optionally substituted by one or more fluorine substituents.

2. A compound of the formula I in any of its stereoisomeric forms or a mixture of stereoisomeric forms in any ratio, or a physiologically acceptable salt thereof, or a physiologically acceptable solvate of any of them, as claimed in claim 1, wherein G is selected from the group consisting of $R^{71}$—O—C(O)— and $R^{72}$—N(R$^{73}$)—C(O)—;

$R^{30}$ is $R^{32}$—$C_uH_{2u}$—, wherein u is 0 or 1;

$R^{32}$ is selected from the group consisting of phenyl and an aromatic 6-membered monocyclic heterocycle containing one or two nitrogen atoms as ring heteroatoms, wherein the phenyl and the heterocycle are optionally substituted by one or more identical or different substituents selected from the group consisting of halogen, $(C_1-C_6)$-alkyl, HO—, $(C_1-C_6)$-alkyl-O—, —O—CH$_2$—O—, —O—CF$_2$—O—, di($(C_1-C_4)$-alkyl)N—S(O)$_2$—, H$_2$N—, di($(C_1-C_6)$-alkyl)N—, $(C_1-C_4)$-alkyl-C(O)—NH—, and NC—, or substituted once by a phenyl ring or $(C_3-C_7)$-cycloalkyl ring;

$R^{40}$ is hydrogen.

3. A compound of the formula I in any of its stereoisomeric forms or a mixture of stereoisomeric forms in any ratio, or a physiologically acceptable salt thereof, or a physiologically acceptable solvate of any of them, as claimed in claim 1, wherein G is $R^{71}$—O—C(O)—;

$R^{30}$ is $R^{32}$—$C_uH_{2u}$—, wherein u is 0;

$R^{32}$ is phenyl, wherein the phenyl is optionally substituted by one or more identical or different substituents selected from the group consisting of halogen, $(C_1-C_6)$-alkyl, HO—, $(C_1-C_6)$-alkyl-O—, —O—CH$_2$—O—, —O—CF$_2$—O—, $(C_1-C_6)$-alkyl-S(O)$_m$—, di($(C_1-C_4)$-alkyl)N—S(O)$_2$—, H$_2$N—, di($(C_1-C_6)$-alkyl)N—, $(C_1-C_4)$-alkyl-C(O)—NH—, and NC—, or substituted once by a phenyl ring or $(C_3-C_2)$-cycloalkyl ring;

and $R^{40}$ is hydrogen.

4. A compound of the formula I in any of its stereoisomeric forms or a mixture of stereoisomeric forms in any ratio, or a physiologically acceptable salt thereof, or a physiologically acceptable solvate of any of them, as claimed in claim 1, wherein $R^{50}$ and $R^{60}$ are both hydrogen.

5. A compound of the formula I in any of its stereoisomeric forms or a mixture of stereoisomeric forms in any ratio, or a physiologically acceptable salt thereof, or a physiologically acceptable solvate of any of them, as claimed in claim 1, selected from the subformulae:

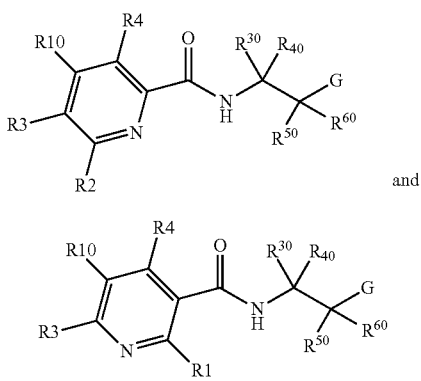

wherein $R^1$, $R^2$, $R^3$, $R^4$, $R^{10}$, $R^{30}$, $R^{40}$, $R^{50}$, and $R^{60}$ are as defined in claim 1.

6. A compound of the formula I-1, in any of its stereoisomeric forms or a mixture of stereoisomeric forms in any ratio, or a physiologically acceptable salt thereof, or a physiologically acceptable solvate of any of them, as claimed in claim 5, wherein $R^2$ is Ar—$C_sH_{2s}$—, wherein s is 0;
$R^4$ is hydrogen; and
$R^{10}$ is hydrogen.

7. A compound of the formula I in any of its stereoisomeric forms or a mixture of stereoisomeric forms in any ratio, or a physiologically acceptable salt thereof, or a physiologically acceptable solvate of any of them, as claimed in claim 1, wherein $R^{11}$ is hydrogen or $(C_1\text{-}C_{10})$-alkyl.

8. A compound of the formula I in any of its stereoisomeric forms or a mixture of stereoisomeric forms in any ratio, or a physiologically acceptable salt thereof, or a physiologically acceptable solvate of any of them, as claimed in claim 1, wherein $R^3$ is —O—$CH_3$.

9. A compound of the formula I, or a physiologically acceptable salt thereof, or a physiologically acceptable solvate of any of them, as claimed in claim 1, selected from:

(S)-3-[(5-Methoxy-6-phenyl-pyridine-2-carbonyl)-amino]-3-o-tolyl-propionic acid
(S)-3-(2,4-Dichloro-phenyl)-3-[(5-methoxy-6-phenyl-pyridine-2-carbonyl)-amino]-propionic acid
(S)-3-[(6-Chloro-5-methoxy-pyridine-2-carbonyl)-amino]-3-o-tolyl-propionic acid
(S)-3-[(6-Bromo-5-methoxy-pyridine-2-carbonyl)-amino]-3-o-tolyl-propionic acid
(S)-3-{[6-(2-Fluoro-phenyl)-5-methoxy-pyridine-2-carbonyl]-amino}-3-o-tolyl-propionic acid
(S)-3-[(5-Methoxy-6-phenyl-pyridine-2-carbonyl)-amino]-3-p-tolyl-propionic acid
(S)-3-[(5-Methoxy-6-o-tolyl-pyridine-2-carbonyl)-amino]-3-p-tolyl-propionic acid
(S)-3-{[5-Methoxy-6-(2-trifluoromethyl-phenyl)-pyridine-2-carbonyl]-amino}-3-p-tolyl-propionic acid
(S)-3-{[6-(3-Fluoro-phenyl)-5-methoxy-pyridine-2-carbonyl]-amino}-3-p-tolyl-propionic acid
(S)-3-{[5-Methoxy-6-(2-methoxy-phenyl)-pyridine-2-carbonyl]-amino}-3-p-tolyl-propionic acid
(S)-3-{[6-(2-Chloro-phenyl)-5-methoxy-pyridine-2-carbonyl]-amino}-3-p-tolyl-propionic acid
(S)-3-{[6-(2-Fluoro-phenyl)-5-methoxy-pyridine-2-carbonyl]-amino}-3-p-tolyl-propionic acid
(S)-3-{[6-(2,4-Difluoro-phenyl)-5-methoxy-pyridine-2-carbonyl]-amino}-3-p-tolyl-propionic acid
(S)-3-{[6-(2,3-Dichloro-phenyl)-5-methoxy-pyridine-2-carbonyl]-amino}-3-p-tolyl-propionic acid
(S)-3-{[6-(2-Chloro-5-trifluoromethyl-phenyl)-5-methoxy-pyridine-2-carbonyl]-amino}-3-p-tolyl-propionic acid
(S)-3-{[6-(3-Fluoro-2-methyl-phenyl)-5-methoxy-pyridine-2-carbonyl]-amino}-3-(2-fluoro-phenyl)-propionic acid
(S)-3-{[6-(2-Chloro-5-trifluoromethyl-phenyl)-5-methoxy-pyridine-2-carbonyl]-amino}-3-(2-fluoro-phenyl)-propionic acid
(S)-3-{[6-(2,3-Difluoro-phenyl)-5-methoxy-pyridine-2-carbonyl]-amino}-3-p-tolyl-propionic acid
(S)-3-{[6-(2,5-Difluoro-phenyl)-5-methoxy-pyridine-2-carbonyl]-amino}-3-p-tolyl-propionic acid
(S)-3-{[6-(2,5-Dichloro-phenyl)-5-methoxy-pyridine-2-carbonyl]-amino}-3-p-tolyl-propionic acid
(S)-3-{[6-(3,5-Dimethyl-isoxazol-4-yl)-5-methoxy-pyridine-2-carbonyl]-amino}-3-p-tolyl-propionic acid
(S)-3-{[6-(4-Fluoro-2-methyl-phenyl)-5-methoxy-pyridine-2-carbonyl]-amino}-3-p-tolyl-propionic acid
(S)-3-{[6-(2,3-Dimethyl-phenyl)-5-methoxy-pyridine-2-carbonyl]-amino}-3-p-tolyl-propionic acid
(S)-3-{[6-(5-Fluoro-2-methyl-phenyl)-5-methoxy-pyridine-2-carbonyl]-amino}-3-p-tolyl-propionic acid
(S)-3-{[6-(4-Fluoro-2-methoxy-phenyl)-5-methoxy-pyridine-2-carbonyl]-amino}-3-p-tolyl-propionic acid
(S)-3-{[6-(5-Fluoro-2-methoxy-phenyl)-5-methoxy-pyridine-2-carbonyl]-amino}-3-p-tolyl-propionic acid
(S)-3-{[6-(2-Fluoro-5-methyl-phenyl)-5-methoxy-pyridine-2-carbonyl]-amino}-3-p-tolyl-propionic acid
(S)-3-{[6-(3-Chloro-2-methyl-phenyl)-5-methoxy-pyridine-2-carbonyl]-amino}-3-p-tolyl-propionic acid
(S)-3-{[6-(3-Fluoro-2-methyl-phenyl)-5-methoxy-pyridine-2-carbonyl]-amino}-3-p-tolyl-propionic acid
(S)-3-{[6-(5-Chloro-2-fluoro-phenyl)-5-methoxy-pyridine-2-carbonyl]-amino}-3-p-tolyl-propionic acid
(S)-3-(2-Fluoro-phenyl)-3-[(5-methoxy-6-phenyl-pyridine-2-carbonyl)-amino]-propionic acid
(S)-3-{[6-(2,4-Dichloro-phenyl)-5-methoxy-pyridine-2-carbonyl]-amino}-3-(2-fluoro-phenyl)-propionic acid
(S)-3-(2-Fluoro-phenyl)-3-[(5-methoxy-6-o-tolyl-pyridine-2-carbonyl)-amino]-propionic acid
(S)-3-(2-Fluoro-phenyl)-3-{[5-methoxy-6-(2-trifluoromethyl-phenyl)-pyridine-2-carbonyl]-amino}-propionic acid
(S)-3-(2-Fluoro-phenyl)-3-{[5-methoxy-6-(2-methoxy-phenyl)-pyridine-2-carbonyl]-amino}-propionic acid
(S)-3-{[6-(2-Chloro-phenyl)-5-methoxy-pyridine-2-carbonyl]-amino}-3-(2-fluoro-phenyl)-propionic acid
(S)-3-(2-Fluoro-phenyl)-3-{[6-(2-fluoro-phenyl)-5-methoxy-pyridine-2-carbonyl]-amino}-propionic acid
(S)-3-{[6-(2,4-Difluoro-phenyl)-5-methoxy-pyridine-2-carbonyl]-amino}-3-(2-fluoro-phenyl)-propionic acid
(S)-3-{[6-(2,3-Dichloro-phenyl)-5-methoxy-pyridine-2-carbonyl]-amino}-3-(2-fluoro-phenyl)-propionic acid
(S)-3-{[6-(2,3-Difluoro-phenyl)-5-methoxy-pyridine-2-carbonyl]-amino}-3-(2-fluoro-phenyl)-propionic acid
(S)-3-{[6-(2,5-Difluoro-phenyl)-5-methoxy-pyridine-2-carbonyl]-amino}-3-(2-fluoro-phenyl)-propionic acid
(S)-3-{[6-(4-Fluoro-2-methyl-phenyl)-5-methoxy-pyridine-2-carbonyl]-amino}-3-(2-fluoro-phenyl)-propionic acid (S)-3-{[6-(3,5-Dimethyl-isoxazol-4-yl)-5-methoxy-pyridine-2-carbonyl]-amino}-3-(2-fluoro-phenyl)-propionic acid
(S)-3-{[6-(2,3-Dimethyl-phenyl)-5-methoxy-pyridine-2-carbonyl]-amino}-3-(2-fluoro-phenyl)-propionic acid
(S)-3-[(3,2'-Dimethoxy-[2,3]bipyridinyl-6-carbonyl)-amino]-3-(2-fluoro-phenyl)-propionic acid
(S)-3-{[6-(5-Fluoro-2-methyl-phenyl)-5-methoxy-pyridine-2-carbonyl]-amino}-3-(2-fluoro-phenyl)-propionic acid
(S)-3-{[6-(4-Fluoro-2-methoxy-phenyl)-5-methoxy-pyridine-2-carbonyl]-amino}-3-(2-fluoro-phenyl)-propionic acid
(S)-3-{[6-(5-Fluoro-2-methoxy-phenyl)-5-methoxy-pyridine-2-carbonyl]-amino}-3-(2-fluoro-phenyl)-propionic acid
(S)-3-{[6-(2-Fluoro-5-methyl-phenyl)-5-methoxy-pyridine-2-carbonyl]-amino}-3-(2-fluoro-phenyl)-propionic acid
(S)-3-{[6-(3-Chloro-2-methyl-phenyl)-5-methoxy-pyridine-2-carbonyl]-amino}-3-(2-fluoro-phenyl)-propionic acid
(S)-3-{[6-(5-Chloro-2-fluoro-phenyl)-5-methoxy-pyridine-2-carbonyl]-amino}-3-(2-fluoro-phenyl)-propionic acid
(S)-3-{[6-(3-Chloro-2-fluoro-phenyl)-5-methoxy-pyridine-2-carbonyl]-amino}-3-(2-fluoro-phenyl)-propionic acid
(S)-3-(2-Fluoro-phenyl)-3-{[5-methoxy-6-(2-methyl-furan-3-yl)-pyridine-2-carbonyl]-amino}-propionic acid
(S)-3-{[6-(2-Chloro-3-methyl-phenyl)-5-methoxy-pyridine-2-carbonyl]-amino}-3-(2-fluoro-phenyl)-propionic acid
(S)-3-(2-Chloro-phenyl)-3-[(5-methoxy-6-phenyl-pyridine-2-carbonyl)-amino]-propionic acid
(S)-3-(2-Chloro-phenyl)-3-{[6-(2,4-dichloro-phenyl)-5-methoxy-pyridine-2-carbonyl]-amino}-propionic acid
(S)-3-(2-Chloro-phenyl)-3-{[6-(4-fluoro-phenyl)-5-methoxy-pyridine-2-carbonyl]-amino}-propionic acid
(S)-3-{[5-Methoxy-6-(3-trifluoromethyl-phenyl)-pyridine-2-carbonyl]-amino}-3-o-tolyl-propionic acid
(S)-3-{[6-(2,4-Dichloro-phenyl)-5-methoxy-pyridine-2-carbonyl]-amino}-3-o-tolyl-propionic acid
(S)-3-{[6-(4-Fluoro-phenyl)-5-methoxy-pyridine-2-carbonyl]-amino}-3-o-tolyl-propionic acid
(S)-3-{[6-(4-Chloro-phenyl)-5-methoxy-pyridine-2-carbonyl]}-3-o-tolyl-propionic acid
(S)-3-[(5-Methoxy-6-p-tolyl-pyridine-2-carbonyl)-amino]-3-o-tolyl-propionic acid
(S)-3-{[6-(3-Chloro-phenyl)-5-methoxy-pyridine-2-carbonyl]-amino}-3-o-tolyl-propionic acid
(S)-3-{[5-Methoxy-6-(2-methoxy-phenyl)-pyridine-2-carbonyl]-amino}-3-o-tolyl-propionic acid
(S)-3-[(5-Methoxy-6-m-tolyl-pyridine-2-carbonyl)-amino]-3-o-tolyl-propionic acid
(S)-3-{[6-(2-Chloro-phenyl)-5-methoxy-pyridine-2-carbonyl]-amino}-3-o-tolyl-propionic acid
(S)-3-{[6-(3,4-Difluoro-phenyl)-5-methoxy-pyridine-2-carbonyl]-amino}-3-o-tolyl-propionic acid
(S)-3-{[6-(2,5-Difluoro-phenyl)-5-methoxy-pyridine-2-carbonyl]-amino}-3-o-tolyl-propionic acid
(S)-3-{[6-(2,5-Dichloro-phenyl)-5-methoxy-pyridine-2-carbonyl]-amino}-3-o-tolyl-propionic acid
(S)-3-{[6-(3,5-Dimethyl-isoxazol-4-yl)-5-methoxy-pyridine-2-carbonyl]-amino}-3-o-tolyl-propionic acid
(S)-3-{[6-(2,3-Dimethyl-phenyl)-5-methoxy-pyridine-2-carbonyl]-amino}-3-o-tolyl-propionic acid
(S)-3-{[6-(2,4-Dimethyl-phenyl)-5-methoxy-pyridine-2-carbonyl]-amino}-3-o-tolyl-propionic acid
(S)-3-{[6-(4-Fluoro-2-methoxy-phenyl)-5-methoxy-pyridine-2-carbonyl]-amino}-3-o-tolyl-propionic acid
(S)-3-{[6-(2-Chloro-5-methyl-phenyl)-5-methoxy-pyridine-2-carbonyl]-amino}-3-o-tolyl-propionic acid
(S)-3-(2-Chloro-phenyl)-3-[(6-methoxy-5-o-tolyl-pyridine-3-carbonyl)-amino]-propionic acid
(S)-3-(2-Chloro-phenyl)-3-{[5-methoxy-6-(2-methoxy-phenyl)-pyridine-2-carbonyl]-amino}-propionic acid
(S)-3-(2-Chloro-phenyl)-3-[(5-methoxy-6-m-tolyl-pyridine-2-carbonyl)-amino]-propionic acid
(S)-3-(2-Chloro-phenyl)-3-{[6-(2-chloro-phenyl)-5-methoxy-pyridine-2-carbonyl]-amino}-propionic acid
(S)-3-(2-Chloro-phenyl)-3-{[6-(2-fluoro-phenyl)-5-methoxy-pyridine-2-carbonyl]-amino}-propionic acid
(S)-3-(2-Chloro-phenyl)-3-{[6-(2,4-difluoro-phenyl)-5-methoxy-pyridine-2-carbonyl]-amino}-propionic acid
(S)-3-(2-Chloro-phenyl)-3-{[6-(2,3-dichloro-phenyl)-5-methoxy-pyridine-2-carbonyl]-amino}-propionic acid
(S)-3-(2-Chloro-phenyl)-3-{[6-(2,3-difluoro-phenyl)-5-methoxy-pyridine-2-carbonyl]-amino}-propionic acid
(S)-3-(2-Chloro-phenyl)-3-{[6-(2,5-difluoro-phenyl)-5-methoxy-pyridine-2-carbonyl]-amino}-propionic acid
(S)-3-(2-Chloro-phenyl)-3-{[6-(4-fluoro-2-methyl-phenyl)-5-methoxy-pyridine-2-carbonyl]-amino}-propionic acid
(S)-3-(2-Chloro-phenyl)-3-{[6-(2,3-dimethyl-phenyl)-5-methoxy-pyridine-2-carbonyl]-amino}-propionic acid
(S)-3-(2-Chloro-phenyl)-3-[(3,2'-dimethoxy-[2,3']bipyridinyl-6-carbonyl)-amino]-propionic acid
(S)-3-(2-Chloro-phenyl)-3-{[6-(5-fluoro-2-methyl-phenyl)-5-methoxy-pyridine-2-carbonyl]-amino}-propionic acid
(S)-3-(2-Chloro-phenyl)-3-{[6-(4-fluoro-2-methoxy-phenyl)-5-methoxy-pyridine-2-carbonyl]-amino}-propionic acid
(S)-3-{[6-(4-Chloro-2-methoxy-phenyl)-5-methoxy-pyridine-2-carbonyl]-amino}-3-(2-chloro-phenyl)-propionic acid
(S)-3-(2-Chloro-phenyl)-3-{[6-(5-fluoro-2-methoxy-phenyl)-5-methoxy-pyridine-2-carbonyl]-amino}-propionic acid
(S)-3-(2-Chloro-phenyl)-3-{[6-(2-fluoro-5-trifluoromethyl-phenyl)-5-methoxy-pyridine-2-carbonyl]-amino}-propionic acid
(S)-3-{[5-Methoxy-6-(2-trifluoromethyl-phenyl)-pyridine-2-carbonyl]-amino}-3-o-tolyl-propionic acid
(S)-3-{[6-(2,4-Difluoro-phenyl)-5-methoxy-pyridine-2-carbonyl]-amino}-3-o-tolyl-propionic acid
(S)-3-{[6-(4-Fluoro-2-methyl-phenyl)-5-methoxy-pyridine-2-carbonyl]-amino}-3-o-tolyl-propionic acid
(S)-3-[(3,2'-Dimethoxy-[2,3']bipyridinyl-6-carbonyl)-amino]-3-o-tolyl-propionic acid
(S)-3-[(3'-Fluoro-3-methoxy-[2,4']bipyridinyl-6-carbonyl)-amino]-3-o-tolyl-propionic acid
(S)-3-{[5-Methoxy-6-(2-methyl-furan-3-yl)-pyridine-2-carbonyl]-amino}-3-o-tolyl-propionic acid
(S)-3-{[6-(4-Cyano-2-fluoro-phenyl)-5-methoxy-pyridine-2-carbonyl]-amino}-3-o-tolyl-propionic acid
(S)-3-(2-Chloro-phenyl)-3-{[6-(2-fluoro-5-methoxy-phenyl)-5-methoxy-pyridine-2-carbonyl]-amino}-propionic acid
(S)-3-(2-Chloro-phenyl)-3-{[6-(2-fluoro-5-methyl-phenyl)-5-methoxy-pyridine-2-carbonyl]-amino}-propionic acid (S)-3-{[6-(3-Chloro-2-methyl-phenyl)-5-methoxy-pyridine-2-carbonyl]-amino}-3-(2-chloro-phenyl)-propionic acid (S)-3-(2-Chloro-phenyl)-3-{[6-(3-fluoro-2-methyl-phenyl)-5-methoxy-pyridine-2-carbonyl]-amino}-propionic acid (S)-3-{[6-(5-Chloro-2-fluoro-phenyl)-5-methoxy-pyridine-2-carbonyl]amino}-3-(2-chloro-phenyl)-propionic acid (S)-3-(2-Chloro-phenyl)-3-[(3'-fluoro-3-methoxy-[2,4]bipyridinyl-6-carbonyl)-amino]-propionic acid (S)-3-(2-Chloro-phenyl)-3-[(5-methoxy-6-pyrazin-2-yl-pyridine-2-carbonyl)-amino]-propionic acid (S)-3-{[6-(3-Chloro-2-fluoro-phenyl)-5-methoxy-pyridine-2-carbonyl]-amino}-3-(2-chloro-phenyl)-propionic acid (S)-3-(2-Chloro-phenyl)-3-{[5-methoxy-6-(2-methyl-furan-3-yl)-pyridine-2-carbonyl]-amino}-propionic acid (S)-3-{[6-(2-Chloro-3-fluoro-phenyl)-5-methoxy-pyridine-2-carbonyl]-amino}-3-(2-chloro-phenyl)-propionic acid, and (S)-3-{[6-(2-Chloro-3-methyl-phenyl)-5-methoxy-pyridine-2-carbonyl]-amino}-3-(2-chloro-phenyl)-propionic acid.

10. A compound of the formula I, or a physiologically acceptable salt thereof, or a physiologically acceptable solvate of any of them, as claimed in claim 1, selected from:

(S)-3-[(5-Methoxy-6-phenyl-pyridine-2-carbonyl)-amino]-3-o-tolyl-propionic acid (S)-3-(2,4-Dichloro-phenyl)-3-[(5-methoxy-6-phenyl-pyridine-2-carbonyl)-amino]-propionic acid (S)-3-({5-Methoxy-6-[3-(5-methyl-[1,3,4]oxadiazol-2-yl)-phenyl]-pyridine-2-carbonyl}-amino)-3-o-tolyl-propionic acid (S)-3-(2-Chloro-phenyl)-3-[(5-methoxy-6-naphthalen-2-yl-pyridine-2-carbonyl)-amino]-propionic acid (S)-3-(2-Chloro-phenyl)-3-[(5-methoxy-6-pyrazin-2-yl-pyridine-2-carbonyl)-amino]-propionic acid (S)-3-(2-Chloro-phenyl)-3-[(6-methoxy-5-naphthalen-2-yl-pyridine-3-carbonyl)-amino]-propionic acid (S)-3-(2-Chloro-phenyl)-3-{[5-methoxy-6-(2-methyl-furan-3-yl)-pyridine-2-carbonyl]-amino}-propionic acid (S)-3-(2-Chloro-phenyl)-3-{[6-(2,3-dimethyl-phenyl)-5-methoxy-pyridine-2-carbonyl]-amino}-propionic acid (S)-3-(2-Chloro-phenyl)-3-{[6-(2-chloro-phenyl)-5-methoxy-pyridine-2-carbonyl]-amino}-propionic acid (S)-3-(2-Fluoro-phenyl)-3-{[5-methoxy-6-(1,3,5-trimethyl-1H-pyrazol-4-yl)-pyridine-2-carbonyl]-amino}-propionic acid (S)-3-(2-Fluoro-phenyl)-3-{[5-methoxy-6-(1-methyl-1H-indol-5-yl)-pyridine-2-carbonyl]-amino}-propionic acid (S)-3-[(5-Methoxy-6-m-tolyl-pyridine-2-carbonyl)-amino]-3-o-tolyl-propionic acid (S)-3-{[6-(2-Chloro-phenyl)-5-methoxy-pyridine-2-carbonyl]-amino}-3-o-tolyl-propionic acid (S)-3-{[6-(3,5-Dimethyl-isoxazol-4-yl)-5-methoxy-pyridine-2-carbonyl]-amino}-3-o-tolyl-propionic acid (S)-3-{[6-(4-Chloro-phenyl)-5-methoxy-pyridine-2-carbonyl]amino}-3-o-tolyl-propionic acid (S)-3-{[6-(4-Chloro-phenyl)-5-methoxy-pyridine-2-carbonyl]amino}-3-p-tolyl-propionic acid (S)-3-{[6-(5-Acetyl-thiophen-2-yl)-5-methoxy-pyridine-2-carbonyl]-amino}-3-(2-chloro-phenyl)-propionic acid, and (S)-3-{[6-(2-Fluoro-phenyl)-5-methoxy-pyridine-2-carbonyl]-amino}-3-o-tolyl-propionic acid.

11. A process for preparing the compound of formula I or a physiologically acceptable salt thereof or a physiologically solvate of any of them as claimed in claim 1, comprising reacting a compound of the formula II with a compound of the formula III,

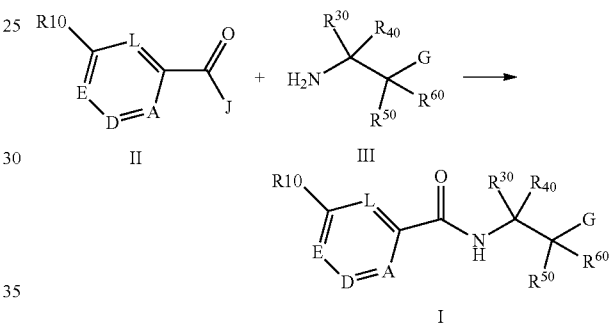

wherein the groups A, D, E, L, G, $R^{10}$, $R^{30}$, $R^{40}$, $R^{50}$ and $R^{60}$ in the compounds of the formulae II and III are defined as in the compounds of the formula I and additionally functional groups can be present in protected form or in the form of a precursor group, and the group 3 in the compound of the formula II is HO—, $(C_1\text{-}C_4)$-alkyl-O— or halogen.

12. A pharmaceutical composition comprising the compound of claim 1 or a physiologically acceptable salt thereof or a physiologically acceptable solvate of any of them.

13. The pharmaceutical composition of claim 12, further comprising a pharmaceutically acceptable carrier.

\* \* \* \* \*

UNITED STATES PATENT AND TRADEMARK OFFICE
CERTIFICATE OF CORRECTION

PATENT NO. : 8,669,370 B2  
APPLICATION NO. : 13/357245  
DATED : March 11, 2014  
INVENTOR(S) : Sven Ruf et al.

Page 1 of 4

It is certified that error appears in the above-identified patent and that said Letters Patent is hereby corrected as shown below:

On the Title Page:

In the abstract, in item (57), please replace

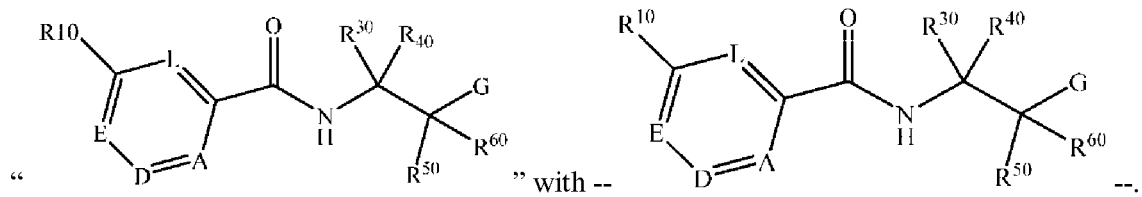

" with --  --.

In the Claims:

At column 115, claim number 1, line 59: please replace "$Het^2$," with --$Het^2$,--;

At column 115, claim number 1, line 65: please replace "$NR^{12}R^{13}$, $Het^2$," with --$NR^{12}R^{13}$, and $Het^2$--;

At column 115, claim number 1, line 66: please replace "from the group consisting hydrogen" with --from the group consisting of hydrogen--;

At column 116, claim number 1, lines 1-2: please replace "$Het^2$, phenyl-$C_sH_{2s}$—(O)$_t$—," with --$Het^2$, and phenyl-$C_sH_{2s}$—(O)$_t$—,--;

At column 116, claim number 1, line 9: please replace "$R^{14}$ is ($C_1$-$C_{10}$-alkyl" with --$R^{14}$ is ($C_1$-$C_{10}$)-alkyl--;

Signed and Sealed this  
Eighth Day of March, 2016

Michelle K. Lee  
*Director of the United States Patent and Trademark Office*

CERTIFICATE OF CORRECTION (continued)

In the Claims:

At column 116, claim number 1, line 18: please replace "the group consisting halogen" with --the group consisting of halogen--;

At column 116, claim number 1, lines 42-43: please replace "$(C_4-C_6)$-alkyl-$S(O)_m$—," with --$(C_1-C_6)$-alkyl-$S(O)_m$—,--;

At column 116, claim number 1, line 64: please replace "group consisting $(C_1-C_6)$-alkyl-O—" with --group consisting of $(C_1-C_6)$-alkyl-O— --;

At column 117, claim number 1, lines 1-2: please replace "—$(CH_2)_b$-Het$^4$, where alkyl" with -- —$(CH_2)_b$-Het$^4$, where the alkyl--;

At column 117, claim number 1, lines 27-28: please replace "—$(CH_2)_x$-Phenyl" with -- —$(CH_2)_x$-phenyl--;

At column 118, claim number 2, lines 31-32: please replace "—O—$CF_2$—O—, di(($C_1-C_4$)-alkyl)N—$S(O)_2$—," with -- —O—$CF_2$—O—, $(C_1-C_6)$-alkyl-$S(O)_m$—, di(($C_1-C_4$)-alkyl)N—$S(O)_2$—,--;

At column 118, claim number 2, line 34: please replace "ring;" with --ring; and--;

At column 118, claim number 3, lines 52-53: please replace
   "by a phenyl ring or $(C_3-C_2)$-cycloalkyl ring; and"
with   --by a phenyl ring or $(C_3-C_7)$-cycloalkyl ring; and--;

At column 119, claim number 5, lines 2-8: please replace

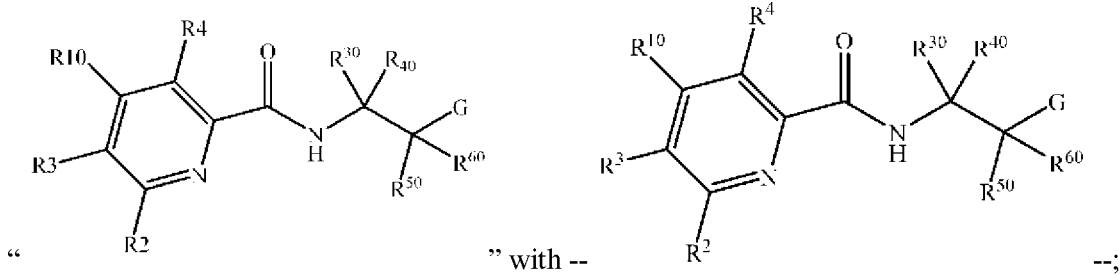

" with -- --;

CERTIFICATE OF CORRECTION (continued)

In the Claims:

At column 119, claim number 5, lines 10-16: please replace

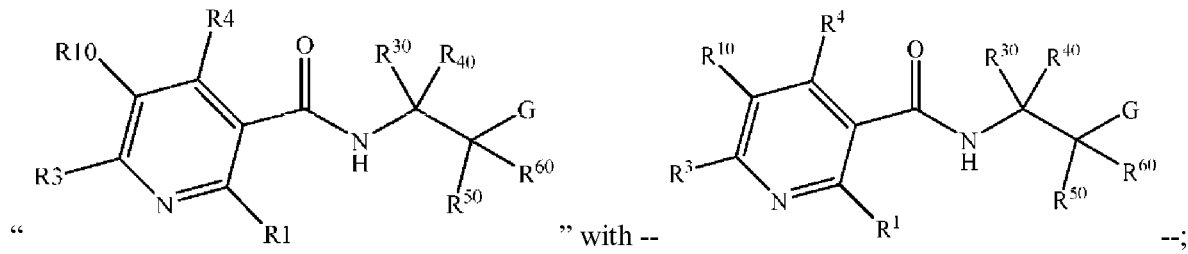

" with --  --;

At column 119, claim number 9, line 43: please replace "selected from:" with --selected from the group consisting of:--;

At column 121, claim number 9, lines 6-7: please replace "(S)-3-[(3,2'-Dimethoxy-[2,3]bipyridinyl-6-carbonyl)-amino]-3-(2-fluoro-phenyl)-propionic acid" with --(S)-3-[(3,2'-Dimethoxy-[2,3']bipyridinyl-6-carbonyl)-amino]-3-(2-fluoro-phenyl)-propionic acid--;

At column 121, claim number 9, lines 46-47: please replace "(S)-3-{[6-(4-Chloro-phenyl)-5-methoxy-pyridine-2-carbonyl]}-3-o-tolyl-propionic acid" with --(S)-3-{[6-(4-Chloro-phenyl)-5-methoxy-pyridine-2-carbonyl]-amino}-3-o-tolyl-propionic acid--;

At column 123, claim number 9, lines 10-11: please replace "(S)-3-(2-Chloro-phenyl)-3-[(3'-fluoro-3-methoxy-[2,4]bipyridinyl-6-carbonyl)-amino]-propionic acid" with --(S)-3-(2-Chloro-phenyl)-3-[(3'-fluoro-3-methoxy-[2,4']bipyridinyl-6-carbonyl)-amino]-propionic acid--;

At column 123, claim number 10, line 28: please replace "selected from:" with --selected from the group consisting of:--;

At column 124, claim number 11, lines 19-20: please replace "physiologically solvate" with --physiologically acceptable solvate--;

CERTIFICATE OF CORRECTION (continued)
U.S. Pat. No. 8,669,370 B2

In the Claims:

At column 124, claim number 11, lines 25-29: please replace

" 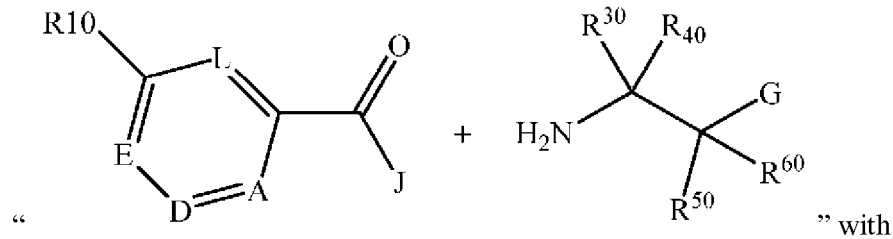 " with

-- 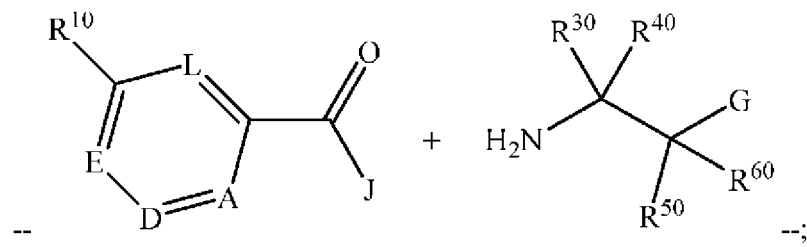 --;

At column 124, claim number 11, lines 31-35: please replace

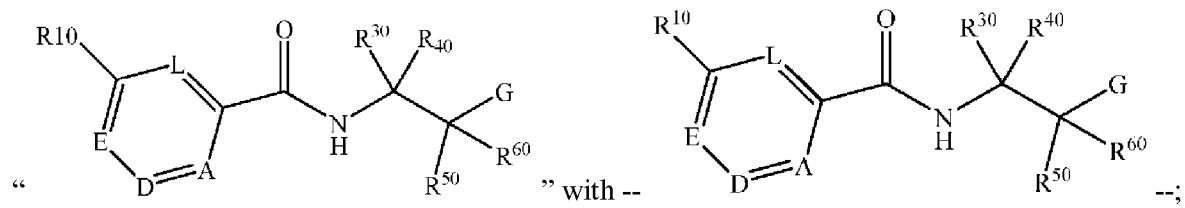

At column 124, claim number 11, lines 42-43: please replace "the group 3" with --the group J--.